US009808434B2

(12) United States Patent
Rahbar et al.

(10) Patent No.: US 9,808,434 B2
(45) Date of Patent: Nov. 7, 2017

(54) COMPOUND FOR TREATING CANCER AND DIABETES

(71) Applicant: CITY OF HOPE, Duarte, CA (US)

(72) Inventors: Samuel Rahbar, Beverly Hills, CA (US); James L. Figarola, West Covina, CA (US); Christopher Lincoln, La Canada, CA (US); David Horne, Altadena, CA (US); Rachael Mooney, Duarte, CA (US); Monika Polewski, Duarte, CA (US); George Somlo, Seal Beach, CA (US); Lixin Yang, Arcadia, CA (US); Sanjay Awasthi, San Marino, CA (US); Sharad Singhal, Duarte, CA (US); Jyotasana Singhal, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 12 days.

(21) Appl. No.: 15/173,628

(22) Filed: Jun. 4, 2016

(65) Prior Publication Data
US 2016/0354327 A1     Dec. 8, 2016

Related U.S. Application Data

(63) Continuation-in-part of application No. 13/953,013, filed on Jul. 29, 2013, which is a continuation of application No. PCT/US2012/023034, filed on Jan. 27, 2012.

(60) Provisional application No. 61/436,958, filed on Jan. 27, 2011.

(51) Int. Cl.
| A61K 31/17 | (2006.01) |
| A61K 45/06 | (2006.01) |
| A61K 31/4745 | (2006.01) |
| A61K 31/513 | (2006.01) |

(Continued)

(52) U.S. Cl.
CPC .......... *A61K 31/17* (2013.01); *A61K 31/4745* (2013.01); *A61K 31/495* (2013.01); *A61K 31/513* (2013.01); *A61K 45/06* (2013.01); *C07D 229/00* (2013.01)

(58) Field of Classification Search
CPC ..... A61K 31/17; A61K 45/06; A61K 31/4745
See application file for complete search history.

(56) References Cited

U.S. PATENT DOCUMENTS

| 4,233,450 A | 11/1980 | Scholz |
| 5,773,459 A | 6/1998 | Tang et al. |
| 6,337,350 B1 | 1/2002 | Rahbar et al. |

(Continued)

FOREIGN PATENT DOCUMENTS

| CA | 2436886 A1 | 6/2002 |
| WO | 2004/031122 A1 | 4/2004 |

(Continued)

OTHER PUBLICATIONS

Adler, V., et al., "Regulation of JNK Signaling by GSTp," EMBO Journal 18(5):1321-1334 (1999).

(Continued)

*Primary Examiner* — San-Ming Hui
(74) *Attorney, Agent, or Firm* — Perkins Coie LLP; Yingli Wang

(57) ABSTRACT

One aspect of the disclosure relates to the use of derivatives of dichlorophenyl urea for treating cancers.

16 Claims, 132 Drawing Sheets

(51) Int. Cl.
C07D 229/00 (2006.01)
A61K 31/495 (2006.01)

(56) References Cited

U.S. PATENT DOCUMENTS

| | | | |
|---|---|---|---|
| 6,589,994 | B1 | 7/2003 | Artman et al. |
| 6,605,642 | B2 | 8/2003 | Rahbar et al. |
| 6,693,106 | B2 | 2/2004 | Rahbar et al. |
| 6,787,566 | B2 | 9/2004 | Rahbar et al. |
| 7,030,133 | B2 | 4/2006 | Rahbar et al. |
| 7,320,988 | B2 | 1/2008 | Rahbar et al. |
| 7,652,037 | B2 | 1/2010 | Rahbar et al. |
| 2009/0202529 | A1 | 8/2009 | Threadgill et al. |
| 2010/0196389 | A1 | 8/2010 | Evans-Freke |

FOREIGN PATENT DOCUMENTS

| | | |
|---|---|---|
| WO | 2007/055966 A2 | 5/2007 |
| WO | 2008/101030 A1 | 8/2008 |
| WO | WO2008/101030 * | 8/2008 |
| WO | 2010/138820 A2 | 12/2010 |

OTHER PUBLICATIONS

Al-Hajj, M., et al., "Prospective Identification of Tumorigenic Breast Cancer Cells," PNAS 100(7):3983-3988 (2003).
Ali-Osman, F., et al., "Prognostic Significance of Glutathione S-Transferase Pi Expression and Subcellular Localization in Human Gliomas," Clin. Cancer Res. 3:2253-2261 (1997).
Auld, C. A., et al., "Skp2-Mediated p27(Kip1) Degradation During S/G2 Phase Progression of Adipocyte Hyperplasia," J. Cell. Physiol. 211:101-111 (2007).
Awasthi, Y.C., et al., "Enzymatic Conjugation of Erythrocyte Glutathione with 1-Chloro-2,4-Dinitrobenzene: The Fate of Glutathione Conjugate in Erythrocytes and the Effect of Glutathione Depletion on Hemoglobin," Blood 58:733-738 (1981).
Badva, S., et al., "Basal-Like and Triple-Negative Breast Cancers: A Critical Review with an Emphasis on the Implications for Pathologists and Oncologists," Modern Pathology 24:157-167 (2011).
Benny, O., et al., "Novel Technologies for Antiangiogenic Drug Delivery in the Brain," Cell Adhesion and Migration 3(2):224-229 (2009).
Berwick, M., et al., "The Current Epidemiology of Cutaneous Malignant Melanoma," Frontiers in Bioscience 11:1244-1254 (2006).
Bosch, A., et al., "Triple-Negative Breast Cancer: Molecular Features, Pathogenesis, Treatment and Current Lines of Research," Cancer Treat. Rev. 36:206-215(2010).
Boyle, J. G., et al., "AMP-Activated Protein Kinase is Activated in Adipose Tissue of Individuals with Type 2 Diabetes Treated with Metformin: A Randomised Glycaemia-Controlled Crossover Study," Diabetologia 54:1799-1809 (2011).
Bray, G. A., et al., "Epidemiology, Trends, and Morbidities of Obesity and the Metabolic Syndrome," Endocrine 29(1):109-117 (2006).
Bray, G. A., et al., "Medicinal Strategies in the Treatment of Obesity," Nature 404:672-677 (2000).
Bruserud, O., et al., "Induction of Differentiation and Apoptosis—A Possible Strategy in the Treatment of Adult Acute Myelogenous Leukemia," The Oncologist 5:454-462 (2000).
Carra, A., et al., "Diphenylurea Derivatives Induce Somatic Embryogenesis in Citrus," Plant Cell Tiss. Organ Cult. 87:41-48 (2006).
Cho, R. W., et al., "Isolation and Molecular Characterization of Cancer Stem Cells in MMTV-Wnt-1 Murine Breast Tumors," Stem Cells 26:364-371 (2008).
Chou, T.C., "Theoretical Basis, Experimental Design, and Computerized Simulation of Synergism and Antagonism in Drug Combination Studies," Pharmacol. Rev. 58:621-681 (2006).

Cool, B., et al., "Identification and Characterization of a Small Molecule AMPK Activator that Treats Key Components of Type 2 Diabetes and the Metabolic Syndrome," Cell Metabolism 3:403-416 (2006).
Davies, G.F., et al., "Troglitazone Inhibits Histone Deacetylase Activity in Breast Cancer Cells," Cancer Letters 288:236-250 (2010).
De Ferranti, S., et al., "The Perfect Storm: Obesity, Adipocyte Dysfunction, and Metabolic Consequences," Clinical Chemistry 54(6):945-955 (2008).
Deangelis, L. M., "Brain Tumors," N. Engl. J. Med. 344(2):114-123 (2001).
Doyle, B. T., et al., "Differentiation-Induced HL-60 Cell Apoptosis: A Mechanism Independent of Mitochondrial Disruption?" Apoptosis 9:345-352 (2004).
Fernandes, K. M., et al., "Helenalin-Mediated Post-Transcriptional Regulation of p21(Cip1) Inhibits 3T3-L1 Preadipocyte Proliferation," J. Cell. Biochem. 105(3):913-921 (2008).
Figarola, J. L., et al., "Novel Dichlorophenyl Urea Compounds Inhibit Proliferation of Human Leukemia HL-60 Cells by Inducing Cell Cycle Arrest, Differentiation and Apoptosis," Invest. New Drugs 30:1413-1425 (2012).
Fischer, H., et al., "Blood-Brain Barrier Permeation: Molecular Parameters Governing Passive Diffusion," J. Membrane Biol. 165:201-211 (1998).
Fogarty, S., et al., "Development of Protein Kinase Activators: AMPK as a Target in Metabolic Disorders and Cancer," Biochim. Biophys. Acta 1804:581-591 (2010).
Fryer, L. G. D., et al., "The Anti-Diabetic Drugs Rosiglitazone and Metformin Stimulate AMP-Activated Protein Kinase Through Distinct Signaling Pathways," J. Biol. Chem. 277:25226-25232 (2002).
Furukawa, S., et al., "Increased Oxidative Stress in Obesity and Its Impact on Metabolic Syndrome," J. Clin. Invest. 114(12):1752-1761 (2004).
Green, C. J., et al., "Elevated NF-kB Activation Is Conserved in Human Myocytes Cultured From Obese Type 2 Diabetic Patients and Attenuated by AMP-Activated Protein Kinase," Diabetes 60:2810-2819 (2011).
Gribble, A. D., et al., "ATP-Citrate Lyase as a Target for Hypolipidemic Intervention. Design and Synthesis of 2-Substituted Butanedioic Acids as Novel, Potent Inhibitors of the Enzyme," J. Med. Chem. 39:3569-3584 (1996).
Guarnieri, G., et al., "Insulin Resistance in Chronic Uremia," J. Ren. Nutr. 19(1):20-24 (2009).
Gupta, P. B., et al., "Cancer Stem Cells: Mirage or Reality?" Nat. Med. 15(9):1010-1012 (2009).
Gupta, P. B., et al., "Identification of Selective Inhibitors of Cancer Stem Cells by High-Throughput Screening," Cell 138:645-659 (2009).
Hansen, L. A., et al., "Retinoids in Chemoprevention and Differentiation Therapy," Carcinogenesis 21(7):1271-1279 (2000).
Hardie, D. G., "AMP-Activated Protein Kinase—An Energy Sensor that Regulates All Aspects of Cell Function," Genes Dev. 25:1895-1908 (2011).
Hatzivassiliou, G., et al., "ATP Citrate Lyase Inhibition Can Suppress Tumor Cell Growth," Cancer Cell 8:311-321 (2005).
Hayes, J. D., et al., "The Glutathione S-Transferase Supergene Family: Regulation of GST* and the Contribution of the Isoenzymes to Cancer Chemoprotection and Drug Resistance," Crit. Rev. Biochem. Mol. Biol. 30(6):445-600 (1995).
Hayes, J. D., et al., "Glutathione Transferases," Annu. Rev. Pharmacol. Toxicol. 45:51-88 (2005).
Heintz, D., et al., "Rapid Alteration of the Phosphoproteome in the Moss Physcomitrella Patens After Cytokinin Treatment," J. Proteome Res. 5:2283-2293 (2006).
Huang, G., et al., "Solid Lipid Nanoparticles of Temozolomide: Potential Reduction of Cardial and Nephric Toxicity," Int. J. Pharm. 355:314-320 (2008).
Huang, D. W., et al., "Bioinformatics Enrichment Tools: Paths Toward the Comprehensive Functional Analysis of Large Gene Lists," Nucleic Acids Research 37(1):1-13 (2009).
Hurt, E. M., et al., "Cancer Stem Cells: The Seeds of Metastasis?" Mol. Interv. 8:140-142 (2008).

(56) References Cited

OTHER PUBLICATIONS

Jakoby, W. B., "The Glutathione S-Transferases: A Group of Multifunctional Detoxification Proteins," Adv. Enzymol. Relat. Areas Mol. Biol. 46:383-414 (1978).

Kahn, B. B., et al., "Obesity and Insulin Resistance," J. Clin. Invest. 106(4):473-481 (2000).

Kantor, P. F., et al., "The Antianginal Drug Trimetazidine Shifts Cardiac Energy Metabolism From Fatty Acid Oxidation to Glucose Oxidation by Inhibiting Mitochondrial Long-Chain 3-Ketoacyl Coenzyme A Thiolase," Circ. Res. 86:580-588 (2000).

Kenwood, B. M., et al.,"Identification of a Novel Mitochondrial Uncoupler That Does Not Depolarize the Plasma Membrane," Mol. Metab. 3:114-123 (2014).

Kim, G.Y., et al., "Mechanisms of Signal Transduction: The Stress-Activated Protein Kinases p38alpha and JNK1 Stabilize p21 CIP1 by Phosphorylation," J. Biol. Chem. 277:29792-29802 (2002).

Kim, S.H., et al., "Vitisin A Inhibits Adipocyte Differentiation Through Cell Cycle Arrest in 3T3-L1 Cells," Biochem. Biophys. Res. Commun. 372:108-113 (2008).

Kim, S.N., et al., "Regulation of Adipocyte Differentiation by Histone Deacetylase Inhibitors," Arch. Pharm. Res. 32(4):535-541 (2009).

Kitange, G. J., et al., "Induction of MGMT Expression is Associated with Temozolomide Resistance in Glioblastoma Xenografts," Neuro-Oncology 11:281-291 (2009).

Laborde, E., "Glutathione Transferases as Mediators of Signaling Pathways Involved in Cell Proliferation and Cell Death," Cell Death and Differentiation 17:1373-1380 (2010).

Lapidot, T., et al., "A Cell Initiating Human Acute Myeloid Leukaemia After Transplantation into SCID Mice," Nature 367:645-648 (1994).

Leszczyniecka, M., et al., "Differentiation Therapy of Human Cancer: Basic Science and Clinical Applications," Pharmacol. Ther. 90:105-156 (2001).

Li, J. J., et al., "2-Hydroxy-N-Arylbenzenesulfonamides as ATP-Citrate Lyase Inhibitors," Bioorg. Med. Chem. Letters 17:3208-3211 (2007).

Linos, E., et al., "Increasing Burden of Melanoma in the United States," J. Invest. Dermatol. 129(7):1666-1674 (2009).

Liu, H., et al., "Cancer Stem Cells from Human Breast Tumors are Involved in Spontaneous Metastases in Orthotopic Mouse Models," PNAS 107(42):18115-18120 (2010).

Lopez-Bergami, P., et al., "Re-Wired ERK-JNK Signaling Pathways in Melanoma," Cancer Cell 11(5):447-460 (2007).

Lowe, S. W., et al., "Apoptosis in Cancer," Carcinogenesis 21(3):485-495 (2000).

Lyon, R. P., et al., "Novel Class of Bivalent Glutathione S-Transferase Inhibitors," Biochem. 42:10418-10428 (2003).

Mannervik, B., et al., "Expression of Class Pi Glutathione Transferase in Human Malignant Melanoma Cells," Carcinogenesis 8(12):1929-1932 (1987).

Meikle, S. R., et al., "Pharmacokinetic Assessment of Novel Anti-Cancer Drugs Using Spectral Analysis and Positron Emission Tomography: A Feasibility Study," Cancer Chemother. Pharmacol. 42:183-193 (1998).

Nicholls, D. G., et al., "Bioenergetic Profile Experiment Using C2C12 Myoblast Cells," J. Vis. Exp. 6(46):e2511 (2010).

Nowak, D., et al., "Differentiation Therapy of Leukemia: 3 Decades of Development," Blood 113:3655-3665 (2009).

Pardridge, W. M., "The Blood-Brain Barrier: Bottleneck in Brain Drug Development," J. Amer. Soc. Exp. NeuroTher. 2:3-14 (2005).

Petrie, K., et al., "Differentiation Therapy of Acute Myeloid Leukemia: Past, Present and Future," Curr. Top. Hematol. 16:84-91 (2009).

Pilch, P. F., et al., "Pharmacological Targeting of Adipocytes/Fat Metabolism for Treatment of Obesity and Diabetes," Mol. Pharmacol. 70(3):779-785 (2006).

Prat, A., et al., "Deconstructing the Molecular Portraits of Breast Cancer," Mol. Oncol. 5:5-23 (2011).

Proctor, R. A., et al., "Two Diarylurea Electron Transport Inhibitors Reduce *Staphylococcus aureus* Hemolytic Activity and Protect Cultured Endothelial Cells from Lysis," Antimicrobial Agents and Chemotherapy 46(8):2333-2336 (2002).

Pubchem Compound, CID 10994120 Compound Summary, http://pubchem.ncbi.nlm.nih.gov/summary/summary.cgi?cid=10994120, accessed Jul. 24, 2012.

Quartu, M., et al., "Polysialylated-Neural Cell Adhesion Molecule (PSA-NCAM) in the Human Trigeminal Ganglion and Brainstem at Prenatal and Adult Ages," BMC Neurosci. 9:108 (2008) (doi:10.1186/1471-2202-9-108).

Rahbar, S., et al., "Novel Inhibitors of Advanced Glycation Endproducts," Arch. Biochem. Biophys. 419:63-79 (2003).

Rathmell, J. C., et al., "Biochemistry. A Glucose-to-Gene Link," Science 324(5930):1021-1022 (2009).

Ricci, A., et al., "Effect of Cl-Substitution on Rooting- or Cytokinin-Like Activity of Diphenylurea Derivatives," J. Plant Growth Regul. 23:261-268 (2005).

Ricci, A., et al., "Urea Derivatives on the Move: Cytokinin-Like Activity and Adventitious Rooting Enhancement Depend on Chemical Structure," Plant Biol. 11:262-272 (2009).

Riester, D., et al., "Histone Deacetylase Inhibitors—Turning Epigenic Mechanisms of Gene Regulation Into Tools of Therapeutic Intervention in Malignant and Other Diseases," Appl. Microbiol. Biotechnol. 75:499-534 (2007).

Rogers, G. W., et al., "High Throughput Microplate Respiratory Measurements Using Minimal Quantities of Isolated Mitochondria," PLoS One 6(7):e21746 (2011).

Roy, R., et al., "Differentiation Therapy: Targeting Breast Cancer Stem Cells to Reduce Resistance to Radiotherapy and Chemotherapy," Breast Cancer Res. 12(Suppl. 1):05 (2010) (doi.10.1186/bcr2496).

Schmittgen, T. D., et al., "Analyzing Real-Time PCR Data by the Comarative CT Method," Nat. Protoc. 3(6):1101-1108 (2008).

Sell, S., "Stem Cell Origin of Cancer and Differentiation Therapy," Crit. Rev. Oncol. Hematol. 51:1-28 (2004).

Shchepinova, M. M., et al., "Dodecyl and Octyl Esters of Fluorescein as Protonophores and Uncouplers of Oxidative Phosphorylation in Mitochondria at Submicromolar Concentrations," Biochim. Biophys. Acta 1837:149-158 (2014).

Shea, T. C., et al., "Identification of an Anionic Form of Glutathione Transferase Present in Many Human Tumors and Human Tumor Cell Lines," Cancer Res. 48:527-533 (1998).

Singhal, S. S., et al., "Hsf-1 and POB1 Induce Drug Sensitivity and Apoptosis by Inhibiting Ralbp1," J. Biol. Chem. 283(28):19714-19729 (2008).

Spitzer, M., et al., "BoxPlotR: A Web Tool for Generation of Box Plots," Nat. Methods 11(2):121-122 (2014).

Storz, P., "Reactive Oxygen Species in Tumor Progression," Frontiers in Bioscience 10:1881-1896 (2005). Stupp, R., et al., "Radiotherapy Plus Concomitant and Adjuvant Temozolomide for Glioblastoma," N. Engl. J. Med. 352:987-996 (2005).

Tew, K. D., et al., "Glutathione-Associated Enzymes in the Human Cell Lines of the National Cancer Institute Drug Screening Program," Mol. Pharmacol. 50:149-159 (1996).

Thangasamy, T., et al., "Quercetin Selectively Inhibits Bioreduction and Enhances Apoptosis in Melanoma Cells That Overexpress Tyrosinase," Nutrition and Cancer 59(2):258-268 (2007).

U.S. International Search Report and Written Opinion dated Jul. 17, 2012 for PCT/US2012/023034.

Van Lenten, L., et al., "Chemistry and Metabolism of Macromolecules: Studies on the Chemical and Enzymatic Modification of Glycoproteins: A General Method for the Tritiation of Sialic Acid-Containing Glycoproteins," J. Biol. Chem. 246:1889-1894 (1971).

Wald, D. N., et al., "Identification of 6-Benzylthioinosine as a Myeloid Leukemia Differentiation-Inducing Compound," Cancer Res. 68:4369-4376 (2008).

Wang, W., et al., "AMP-Activated Protein Kinase and Cancer," Acta Physiol. 196:55-63 (2009).

Waxman, D. J., "Glutathione S-Transferases: Role in Alkylating Agent Resistance and Possible Target for Modulation Chemotherapy—A Review," Cancer Res. 50:6449-6454 (1990).

(56) References Cited

OTHER PUBLICATIONS

Wellen, K, E., et al., "ATP-Citrate Lyase Links Cellular Metabolism to Histone Acetylation," Science 324(5930):1076-1080 (2009).
Yu, L.F., et al., "AMPK Activators as Novel Therapeutics for Type 2 Diabetes," Curr. Top. Med. Chem. 10:397-410 (2010).
Yun, H., et al., "AMP-Activated Protein Kinase Modulators: A Patent Review (2006-2010)," Expert Opin. Ther. Patents 21(7):983-1005 (2011).
Zhuang, Y., et al., "Cell Cycle Arrest in Metformin Treated Breast Cancer Cells Involves Activation of AMPK, Downregulation of Cyclin D1, and Requires p27Kip1 or p21Cip1," J. Mol. Signaling 3:18 (2008) (doi:10.1186/1750-2187-3-18).
United States Patent and Trademark Office, non-final Office Action dated May 4, 2017 for U.S. Appl. No. 13/953,013.

\* cited by examiner

COH-SR1                               COH-SR2

COH-SR3                               COH-SR4

COH-SR5                               COH-SR6

COH-SR7                               COH-SR8

COH-SR9

COH-SR10

COH-SR11

COH-SR12

COH-SR13

COH-SR14

COH-SR16

COH-SR18

LR23

LR59

LR-90

C75

Annexin-FITC Log
Control

MCF-7

MDA-MB-231

[COH-SR4] (µM)

Days after administration of COH-SR4

Days after administration of COH-SR4

Fig. 44A
Fig. 44B
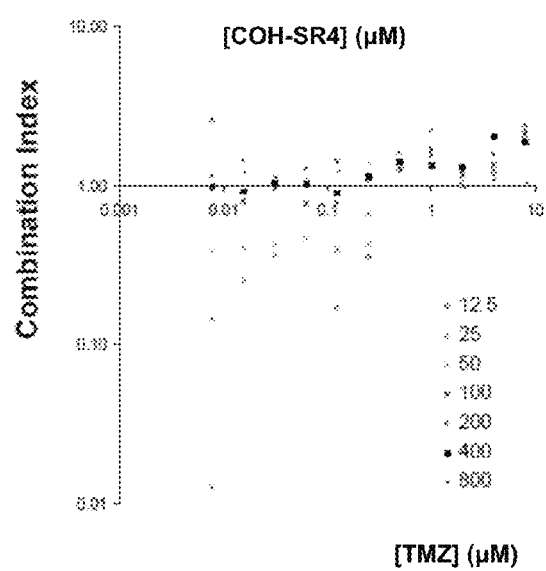
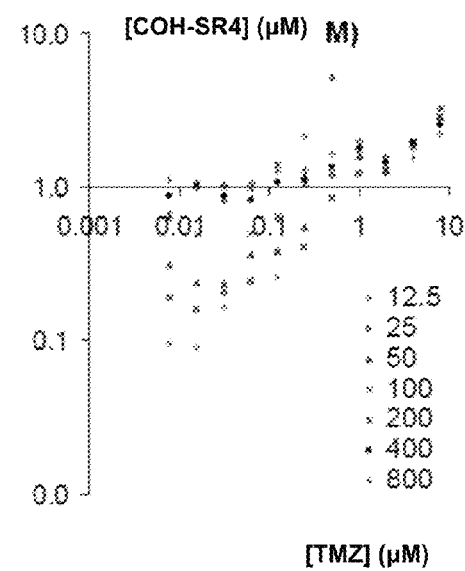

COH-SR4  GSH  GSR4

Fig. 67A

| Cell lines | BRAF mutation | NRAS mutation | LKB1 mutation | SR4 IC50 (µM) 24 h | SR4 IC50 (µM) 48 h | Elesclomol IC50 (µM) 24 h | Elesclomol IC50 (µM) 48 h |
|---|---|---|---|---|---|---|---|
| Malignant | | | | | | | |
| A101D | V600E | WT | positive | 3.8 ± 0.2 | 1.7 ± 0.3 | > 20 µM | 12.2 ± 0.7 |
| A2058 | V600E | WT | deficient | 6.3 ± 0.8 | 2.9 ± 0.4 | > 20 µM | 12.4 ± 1.1 |
| A375 | V600E | WT | positive | 3.4 ± 0.3 | 1.9 ± 0.2 | > 20 µM | 9.2 ± 0.6 |
| Mewo | WT | WT | positive | 5.5 ± 0.6 | 2.8 ± 0.3 | > 20 µM | > 20 µM |
| SK-MEL-2 | WT | Q61R | positive | 6.5 ± 0.4 | 4.8 ± 0.4 | > 20 µM | 14.6 ± 1.2 |
| SK-MEL-5 | V600E | WT | deficient | 2.7 ± 0.4 | 1.2 ± 0.2 | 8.8 ± 0.6 | 5.8 ± 0.64 |
| SK-MEL-28 | V600E | WT | positive | 5.4 ± 0.6 | 3.1 ± 0.2 | > 20 µM | > 20 µM |
| SK-MEL-31 | WT | WT | positive | 6.2 ± 0.5 | 3.3 ± 0.3 | > 20 µM | 15.6 ± 1.2 |
| Normal | | | | | | | |
| NHDF | WT | WT | positive | > 25 µM | > 25 µM | > 25 µM | > 25 µM |
| HAVSMC | WT | WT | positive | > 25 µM | > 25 µM | > 25 µM | > 25 µM |
| Melanocytes | WT | WT | positive | > 25 µM | no data | no data | no data |

Fig. 67B

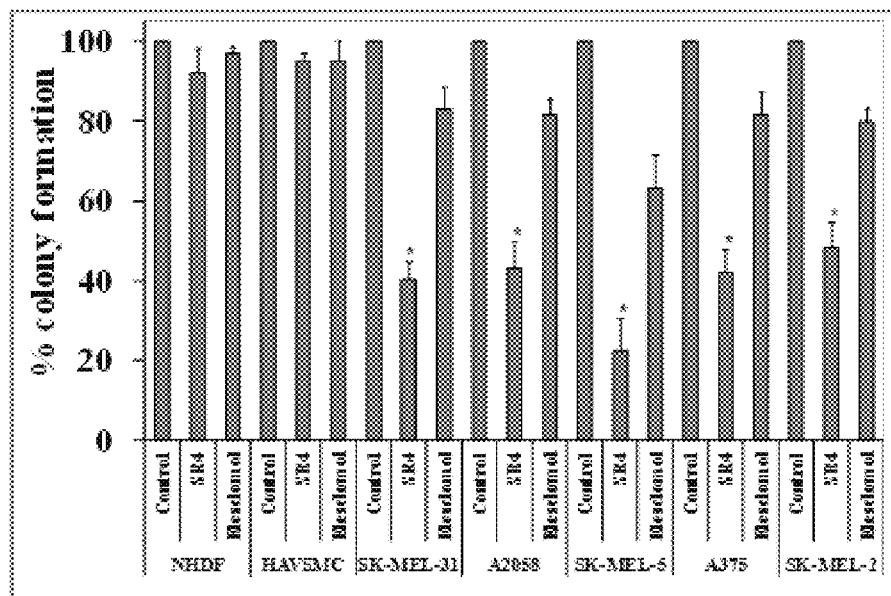

B16-F0 mouse melanoma

A2058 human melanoma

B16-F0 mouse melanoma

A2058 human melanoma

Fig. 71A
Fig. 71B
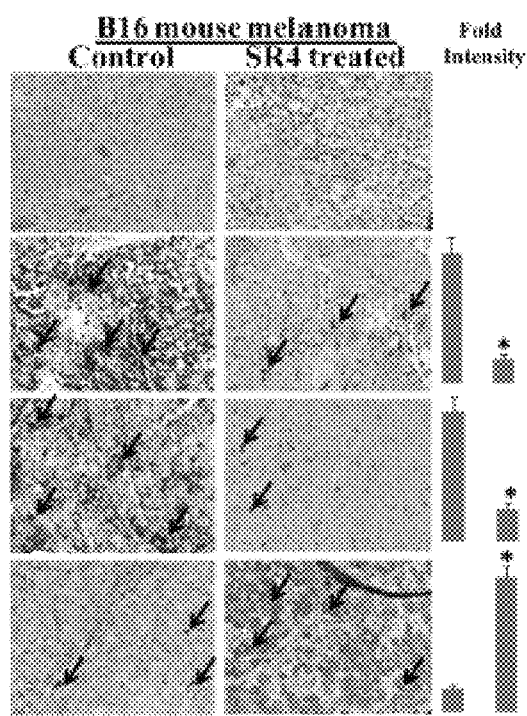
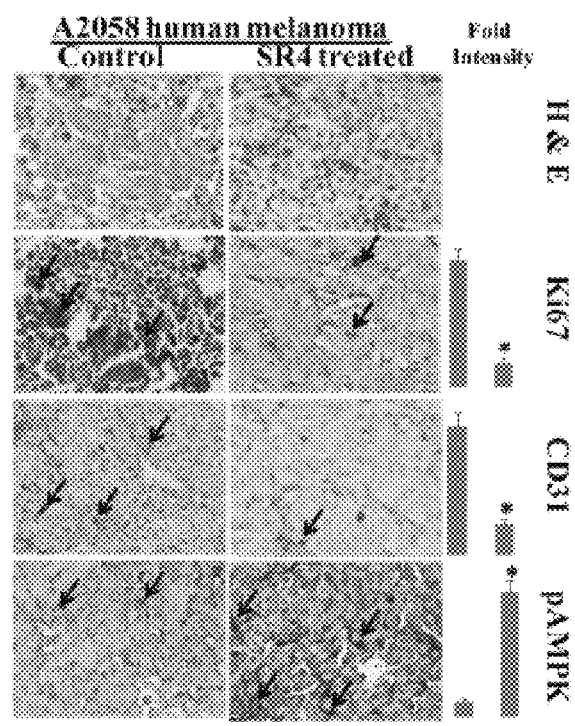

*Indicates SR4 treatment start alternate day by oral gavage after 10 days of H358 cells implantation.

COMPOUND FOR TREATING CANCER AND DIABETES

CROSS-REFERENCE TO RELATED APPLICATIONS

The present application is a continuation-in-part of U.S. patent application Ser. No. 13/953,013, filed on Jul. 29, 2013, which is a continuation of International Application No. PCT/US2012/023034, filed Jan. 27, 2012, which claims priority to U.S. Provisional Application No. 61/436,958, filed Jan. 27, 2011. The contents of all prior, related applications are incorporated herein by reference in their entireties.

FIELD OF THE INVENTION

This invention relates to the field of new compounds and pharmaceutical compositions thereof, and methods of using these new compounds to provide treatment/prevention of diabetes, obesity and/or cancers.

BACKGROUND OF THE INVENTION

The intake of calorie-rich fast food and sedentary lifestyles of developed countries has sharply increased the incidence of obesity. The obesity pandemic is thought to be associated with a sedentary lifestyle and the overconsumption of energy-rich food. Obesity is not only a serious health and economic burden, but also predisposes a person to a variety of metabolic diseases (i.e., the coexistence of several risk factors for atherosclerosis, hyperglycemia, dyslipidemia, and hypertension). Obesity occurs when adipose cells increase excessively in size (hypertrophy) and/or number (hyperplasia). Animal studies suggest that hyperplasia occurs in 2 steps: an increase in numbers of preadipocytes and differentiation of preadipocytes into mature (adipokine-secreting) adipocytes.

Anti-obesity strategies are classified into four categories: reducing food intake, blocking nutrient absorption, increasing thermogenesis, and modulating fat or protein metabolism or storage. There are currently two drugs approved by the FDA for the treatment of obesity. These include orlistat that blocks the absorption of dietary fat, and sibutramine, a specific re-uptake inhibitor for norepinephrine and serotonin that acts in the central nervous system (CNS) to reduce energy intake. These drugs have limited efficacies and side effects are commonly reported, which are further confounded by diminishing response in the long-term treatment of obesity. Moreover, anti-obesity drug development strategy continues to focus on either central or peripheral acting inhibitors of food intake, which will likely encounter similar problems.

Adipocyte differentiation has often been a target of anti-obesity strategies, because obesity is caused not only by hypertrophy of adipocytes, but also by adipocyte hyperplasia. Blocking of adipocytes differentiation is one of the anti-obesity strategies falling under the category of modulating fat storage.

Furthermore, modulation of the state of differentiation and growth of cancer cells, i.e. differentiation therapy may be beneficial to cancer treatments.

The current drugs used in cancer treatment are highly toxic and often non-specific. Current anticancer therapy strategies are more focused on rapid proliferating cells, which can shrink primary and metastatic tumors, but such effects are usually transient and tumor relapse of most metastatic cancers frequently occur. One possible reason for failure is the existence of cancer stem cells. Unlike most cells within the tumor, cancer stem cells are resistant to well-defined chemotherapy, and after treatment, they can regenerate all the cell types in the tumor through their stem cell-like behavior of largely quiescent nature and their abundant expression of drug transporters.

Therefore, there exists a need to find new compounds that can modulate cell cycle of adipocyte and/or cancer cells to provide treatment or prevention of obesity and/or cancers.

SUMMARY OF THE INVENTION

One aspect of the disclosure relates to a COH-SR compound selected from the group consisting of COH-SR1, COH-SR2, COH-SR3, COH-SR4, COH-SR5, COH-SR6, COH-SR7, COH-SR8, COH-SR9, COH-SR10, COH-SR11, COH-SR12, COH-SR13, COH-SR14, COH-SR16, COH-SR18, LR23, LR59, and the pharmaceutically acceptable derivative, solvates, salts and stereoisomers thereof, including mixtures thereof in all ratios.

Another aspect of the disclosure relates to a pharmaceutical composition comprising a therapeutically effective amount of a COH-SR compound.

Another aspect of the disclosure relates to a method of treating or preventing obesity in a subject comprising administering to the subject a pharmaceutical composition disclosed herein.

Another aspect of the disclosure relates to a method of treating cancer in a subject comprising administering to the subject a pharmaceutical composition disclosed herein. In certain embodiments, the method entails administering to the subject a pharmaceutical composition comprising a therapeutically effective amount of COH-SR4, a salt thereof, or stereoisomers thereof. In some embodiments, the cancer is lung cancer (e.g., small cell lung cancer and non-small cell lung cancer), melanoma, ovarian cancer, leukemia, colon cancer, hepatocarcinoma, CNS cancer, renal cancer, prostate cancer, breast cancer, and/or brain cancer. In some embodiments, the cancer is metastatic cancer. In certain embodiments, the cancer treatment methods disclosed herein comprise administering COH-SR4, a salt thereof, or stereoisomers thereof, in combination with one or more second therapeutic agents. COH-SR4 and the second therapeutic agent(s) may be administered in one pharmaceutical composition or in separate pharmaceutical compositions at their respective therapeutically effective amount. In certain embodiments, the cancer treatment methods disclosed herein further comprise one or more additional therapies disclosed herein, e.g., chemotherapy, radiation therapy, immunotherapy, hormone therapy, stem cell transplant to the subject diet, etc.

Another aspect of the disclosure relates to a method of treating or preventing diabetes in a subject comprising administering to the subject a pharmaceutical composition disclosed herein. In certain embodiments, the method entails administering to the subject a pharmaceutical composition comprising a therapeutically effective amount of COH-SR4, a salt thereof, or stereoisomers thereof. In certain embodiments, the diabetes treatment methods disclosed herein comprise administering COH-SR4, a salt thereof, or stereoisomers thereof, in combination with one or more second therapeutic agents. COH-SR4 and the second therapeutic agent(s) may be administered in one pharmaceutical composition or in separate pharmaceutical compositions at their respective therapeutically effective amount. In certain embodiments, the diabetes treatment methods disclosed herein further comprise one or more additional therapies disclosed herein, e.g., diet, etc.

In certain embodiments, the pharmaceutical composition disclosed herein comprises COH-SR4, a salt thereof, or stereoisomers thereof. The pharmaceutical composition exhibits no or minimal undesirable cytotoxicity to normal cells upon administration to a subject at a therapeutically effective amount.

BRIEF DESCRIPTION OF DRAWINGS

FIG. 14A: NBT-stained cells; FIG. 14B: quantity of NBT positive cells; FIG. 14C: effects on surface antigen expression of CD11 b; and FIG. 14D: effects on surface antigen expression of CD14.

FIG. 15A: Dose-dependent effects of COH-SR4 and COH-SR9 on the cell cycle progression in HL-60; FIG. 15B: Kinetics of G0/G1 phase arrest induced by COH-SR4 and COH-SR9; and FIG. 15C: Representative Western blots showing the effects of COH-SR4 and COH-SR9 on cell cycle regulatory proteins.

FIG. 16A: Representative cytograms of HL-60 treated by control; FIG. 16B: Representative cytograms of HL-60 treated by ATRA (2 μM); FIG. 16C: Representative cytograms of HL-60 treated by SR4 (1 μM); FIG. 16D: Representative cytograms of HL-60 treated by SR9 (1 μM); FIG. 16E: Representative cytograms of HL-60 treated by SR4 (2 μM); FIG. 16F: Representative cytograms of HL-60 treated by SR9 (2 μM); FIG. 16G: Representative cytograms of HL-60 treated by SR4 (3 μM); FIG. 16H: Representative cytograms of HL-60 treated by SR9 (3 μM).

FIG. 17A: Representative photographs of DNA fragments obtained from HL-60 cells treated with or without COH-SR4 or COH-SR9; FIG. 17B: Depolarization of the mitochondrial membrane as a consequence of treatments with COH-SR4; and FIG. 17C: Depolarization of the mitochondrial membrane as a consequence of treatments with COH-SR9.

FIG. 18A: Effects of COH-SR4 and COH-SR9 on caspase activation; and FIG. 18B: COH-SR4 and COH-SR9 triggered cytochrome c release and PARP degradation in HL-60 cells.

(FIG. 29B) concentrations of test compounds are 1 μM or lower (uM also represents μM in the figure).

FIG. 31A: FACS analysis for identification of CD44+CD24− cancer stem cells in breast tumor and CD44−/EpCAM+ regular breast cancer cells; FIG. 31B: effects of COH-SR3, COH-SR4, COH-SR9, doxorubicin, paclitaxel or cisplatin on viabilities of CD44+CD24− cancer stem cells in breast tumor; and FIG. 31C: effects of COH-SR3, COH-SR4, COH-SR9, doxorubicin, paclitaxel or cisplatin on viabilities of CD44+CD24−cancer stem cells in breast tumor and CD44−/EpCAM+ regular breast cancer cells.

FIG. 33A: Effects of COH-SR4 on SKOV3, MADH 2744 and A2780 DPPr cells; and FIG. 33B: Inhibition of COH-SR4 in phosphorylation of Stat3 protein and HIF-1α protein expression in SKOV3 cells.

FIG. 37A: Absolute cell numbers of PBT-017 glioma cells decreased after four day of incubation with COH-SR4; and FIG. 37B: Fractions of apoptotic cells of PBT-017 glioma cells increased after four day of incubation with COH-SR4 (uM also represents μM in the figures).

FIGS. 44A-B: COH-SR4 showed synergism with TMZ in treating glioma cells (FIG. 44A) U251 and (FIG. 44B) PBT-017.

FIG. 54A: Dose-dependent effect of COH-SR4 on cell viabilities; and FIG. 54B: $IC_{50}$ of COH-SR4.

FIG. 55A: Dose-dependent effect of COH-SR4 on cell viabilities; and FIG. 55B: $IC_{50}$ of COH-SR4.

(FIG. 59B) changes of tumor cross-sectional area.

FIG. 65A: Effects of COH-SR4 on cell viability of mouse (B16-F0) and human (A2058 and Hs600T) melanoma cell lines, and normal human aortic vascular smooth muscle cells (HAVSMC) (as the non-tumor control) (MTT assay, n=16, 96 h post-treatment). FIG. 65B: Effects of COH-SR4 on cell survival of mouse (B16-F0) and human (A2058 and Hs600T) melanoma cell lines, and normal human aortic vascular smooth muscle cells (HAVSMC) (as the non-tumor control) evaluated using a standard colony-forming assay, *p<0.001 compared with control (n=3). FIG. 65C: Effects of COH-SR4 on cell apoptosis of mouse (B16-F0) and human (A2058) melanoma cell lines evaluated by TUNEL apoptosis assay, apoptotic cells showed green fluorescence. FIG. 65D: COH-SR4 induced cell cycler arrest in mouse (B16-F0) and human (A2058) melanoma cell lines.

FIGS. 67A-67D: Anti-proliferative and pro-apoptotic effects of COH-SR4 and elesclomol in melanoma. FIG. 67A: Cytotoxic effects of COH-SR4 and elesclomol on mouse (B16-F0) melanoma cell lines and human melanoma cell lines with various genetic background/driver mutations (RAS, BRAF, and LKB1 mutations), HAVSMC, melanocytes and normal human dermal fibroblasts (NHDF) were used as control non-tumor cells control) (MTT assay, n=8-16, 24 h and 48 h post-treatments). FIG. 67B: Effects of COH-SR4 and elesclomol on cell survival of human (A375, A2058, SK-MEL-2, SK-MEL-5, and SK-MEL-31) melanoma cell lines, and NHDF and HAVSMC (as the non-tumor control) evaluated using a standard colony-forming assay, *p<0.001 compared with control (n=3). FIG. 67C: Effects of COH-SR4 and elesclomol on cell apoptosis of mouse (B16-F0) and human (A2058) melanoma cell lines evaluated by TUNEL apoptosis assay, apoptotic cells showed green fluorescence. FIG. 67D: Quantification of apoptosis effects of COH-SR4 on human (A2058) melanoma cell lines evaluated by Annexin V-PI double staining method.

FIG. 68A: Effects of COH-SR4 to GST activity towards 1-chloro 2,4-dinitro benzene (CDNB) in mouse (B16-F0) and human (A2058 and Hs600T) melanoma cell lines, human liver purified GST was used as a control (inset). FIG. 68B: Depletion of GSTπ by siRNA in mouse (B16-F0) and human (A2058 and Hs600T) melanoma cell lines transfected with a scrambled control siRNA (C) and GSTπ siRNA (T), β-actin as a loading control. FIG. 68C: Effects of GSTπ depletion on cell survival in mouse (B16-F0) and human (A2058 and Hs600T) melanoma cell lines (inset), and effects of COH-SR4 to mouse (B16-F0) and human (A2058 and Hs600T) melanoma cell lines transfected with GSTπ siRNA or a scrambled control (MTT assay, *p<0.01 compared to control).

FIG. 69A: Multiple reaction monitoring (MRM) mode chromatograms of 6D-SR4 standard 5 pg/μL. FIG. 69B: MRM mode chromatograms of mice serum from control C57 B mice. FIG. 69C: MRM mode chromatograms of mice serum from C57 B mice treated with 0.1 mg/mice (4 mg/kg b.w.) of COH-SR4 on alternate day by oral gavage for 8 weeks, blood collected within 2 h of final dosage. FIG. 69D: Quantification (mean±SD) of COH-SR4 in control and treated mice serum (n=3), ND, not detectable.

FIG. 70A: COH-SR4 treatment did not result in additional weight loss in mice treated. FIG. 70B: Tumor weights and photographs at day 20 (for syngeneic model), and at day 51 (for xenograft model). FIG. 70C: Time-course analysis of tumor regression measured by cross-section area.

FIGS. 71A-71B: Histopathologic analyses of effects of COH-SR4 in.B16-F0 and A2058 melanoma tumor sections. FIG. 71A: Histopathology of resected B16-F0 syngeneic mouse melanoma tumors. FIG. 71B: Histopathology of resected A2058 human melanoma tumors. The intensity of antigen staining was quantified by digital image analysis. Bars represent mean±S.E. (n=5); *p<0.001 compared with control.

FIG. 72A: Western-blot analyses of signaling proteins showing effects of COH-SR4 in B16-F0 syngeneic mouse melanoma tumor tissue lysates. FIG. 72B: Western-blot analyses of signaling proteins showing effects of COH-SR4 in nu/nu nude mice xenograft model melanoma tumor tissue lysates.

FIG. 73A: COH-SR4 stimulated oxygen consumption rate (OCR) in human (SK-MEL28, A2058, and A101 D) melanoma cells. FIG. 73B: Effect of mitochondria recoupler 6-KCH (200 μM) on COH-SR4-induced uncoupling in A101D cells. FIG. 73C: OCR of A2058 cells treated with COH-SR4 or FCCP in the presence of ATP synthase inhibitor oligomycin. FIG. 73D: OCR of isolated mouse liver mitochondria respiring on pyruvate/malate in the presence of rotenone following treatment with increasing concentrations of COH-SR4 or FCCP. FIG. 73E: OCR of isolated mouse liver mitochondria respiring on succinate in the presence of rotenone following treatment with increasing concentrations of COH-SR4 or FCCP. FIG. 73F: Time-dependent depolarization of the mitochondrial membrane of mouse liver mitochondria as a consequence of exposure to 5 μM COH-SR4 or FCCP. FIG. 73G: Mitochondrial swelling in the presence of either COH-SR4 or the classical protonophore FCCP.

FIG. 74A: COH-SR4 and rotenone induced mitochondrial ROS formation in A2058 cells, fluorescence intensity quantified by digital analysis of images obtained from confocal microscopy. FIG. 74B: Mitochondrial ROS formation in A2058 cells induced by COH-SR4, and elesclomol in A2058, A1-1D, and SK-MEL28 cell lines quantified by flow cytometry.

FIG. 75A: Kinetics of intracellular ATP production in SK-MEL2 cells after 5 μM COH-SR4 treatment was measured using ATP luminescence kit (Abcam). FIG. 75B: Loss of ATP production in melanoma (A010D, A2058, Mewo, SK-MEL2, SK-MEL5 and SK-MEL28) cell lines after 1 h exposure to COH-SR4. Melanoma cell lines were plated at 10,000 cells/well and incubated overnight prior to addition of COH-SR4. Intracellular ATP levels measured as % relative to DMSO control over the same time points from two independent experiments.

FIG. 76A: Dose-dependent effects of COH-SR4 on phosphorylation levels of p38 MAPK ($T^{180}/Y^{182}$), ERK1/2 ($T^{202}/Y^{204}$), and pJNK ($T^{183}/Y^{185}$) in various melanoma cells. FIG. 76B: Time-dependent effects of COH-SR4 on phosphorylation levels of p38 MAPK ($T^{180}/Y^{182}$), ERK1/2 ($T^{202}/Y^{204}$), and pJNK ($T^{183}/Y^{185}$) in various melanoma cells.

FIG. 77A: Heirarchical sample clustering map analysis of COH-SR4-treated and untreated B16 melanoma cells showed tight clustering. FIG. 77B: Bar graph and corresponding ontology results for differentially expressed genes in B16 melanoma cells exposed to COH-SR4 for 4 h or 24 h. FIG. 77C: Gene ontology of B16 melanoma cells treated with SR4 for 24 h.

FIG. 78A: Dose-dependent growth inhibition of various lung cancer cell lines by COH-SR4 (NIH/NCI DTP60 screening data). FIG. 78B: Dose-dependent effects of COH-SR4 on cell viability of various lung cancer cell lines (H1417, H1618, H358, and H520) (MTT assay, n=16, 48 h post-treatment). FIG. 78C: Effects of COH-SR4 on cell survival of several lung cancer cells evaluated using a standard clonogenic assay, *p<0.001 compared with control (n=3). FIG. 78D: Effects of COH-SR4 on cell apoptosis of various lung cancer cell lines evaluated by TUNEL apoptosis assay, apoptotic cells showed green fluorescence.

FIG. 79A: Cell cycle distribution determined by fluorescence activated cell sorting (FACS) analysis. FIG. 79B: Effects of COH-SR4 to GST activity towards 1-chloro 2,4-dinitro benzene (CDNB) in lung cancer cell lines (H1417, H1618, H358 and H520), human liver purified GST was used as a control (inset).

FIG. 80A: Dose-dependent effects of COH-SR4 on cell cycle proteins. FIG. 80B: Dose-dependent effects of COH-SR4 on AMPK-mTOR pathway. FIG. 80C: Dose-dependent effects of COH-SR4 on expression of AMPK and ACC following siRNA mediated knock-down of AMPK. FIG. 80D: Effects of COH-SR4 on cell survival (XTT assay) following siRNA mediated knock-down of AMPK, numbers below the blots represent the fold change in the levels of proteins after COH-SR4 treatment as compared to control.

FIG. 81A: COH-SR4 treatment did not result in additional weight loss in mice treated with the compound. FIG. 81B: Tumor weights and photographs at day 60 in COH-SR4 treated and control groups. FIG. 81C: Time-course analysis of tumor regression measured by cross-section area. FIG. 81D: Photographs of animals in COH-SR4 treated and control groups at day 1, 10, 14, 18, 30, and 60, after subcutaneous injection.

FIG. 82A: Immunohistochemical analyses for Ki67 (marker of cellular proliferation), CD31 (angiogenesis marker), E-cadherin (tumor suppressor) and pAMPK (cellular regulator of lipid and glucose metabolism) expressions from tumors in mice of control and COH-SR4 treated groups. FIG. 82B: Western-blot analyses of signaling proteins in tumor tissue lysates in control and COH-SR4 treated experimental groups.

FIG. 83A: COH-SR4 dose- and time dependently increased the OCR in mouse C2C12 myotubes. FIG. 83B: COH-SR4 dose- and time dependently increased the OCR in human HepG2 cells. FIG. 83C: COH-SR4 dose- and time dependently increased the OCR in mouse 3T3-L1 cells.

FIG. 84A: Total intracellular ATP production in HepG2 cells treated with either 5 µM COH-SR4 or FCCP was measured by Luminescent ATP Detection Assay (Abcam) and expressed as percentage of time matched vehicle (DMSO) control. FIG. 84B: hepatic steatosis AMP:ATP ratios increased in HepG2 cells following 1 h treatment with either 5 µM COH-SR4 or FCCP. FIG. 84C: Intracellular AMP:ATP ratios increased in liver of db/db mice treated with COH-SR4 (5 mg/kg B.W.) for 5 weeks. Levels of AMP and ATP were quantified using HPLC analysis. FIG. 84D: Dose-dependent modulation of AMPK-ACC signaling pathways in HepG2 cells by COH-SR4 and FCCP. FIG. 84E: Time-dependent modulation of AMPK-ACC signaling pathways in HepG2 cells by COH-SR4 (5 µM) and FCCP (5 µM). FIG. 84F: Treatment with the AMPK inhibitor Compound C diminished AMPK activation and ACC phosphorylation by COH-SR4. FIG. 84G: AMPK and ACC phosphorylations increased in liver of db/db mice treated with COH-SR4 for 5 weeks. All data represented are mean±SEM, *P<0.05.

FIGS. 85H-85N show metabolic effects of COH-SR4 in Type 2 diabetic db/db mice. FIG. 85A: Representative mice in each treatment group depicting gross images of whole body shape (top) and abdominal fat (bottom). FIG. 85H: Representative mice in each treatment group depicting gross images of whole body shape (top) and abdominal fat (bottom). FIG. 85I: Five weeks of COH-SR4 treatment resulted in decreased body weight. FIG. 85J: Five weeks of COH-SR4 treatment resulted in improved fasting blood glucose. FIG. 85K: Five weeks of COH-SR4 treatment resulted in improved glucose tolerance. FIG. 85L: Five weeks of COH-SR4 treatment resulted in lower HbA1c levels. FIG. 85M: Representative histological image of mouse livers showing reduction in hepatic steatosis in animals treated with COH-SR4. FIG. 85N: COH-SR4 reduced hepatic triglycerides in db/db mice.

FIG. 84A: Relative mRNA expression (mean±SEM) of lipogenic and gluconeogenic genes in HFD obese mice treated with vehicle and COH-SR4. FIG. 86B: Hierarchical clustering of COH-SR4-treatment associated differential gene expression in hepatic steatosis mice. FIG. 86C: Top biological processes and pathways affected by COH-SR4 in db/db mice. FIG.

86D: Key hepatic genes associated with lipid/fatty acid synthesis and glucose and amino acid metabolism regulated by COH-SR4 in db/db mice.

DETAILED DESCRIPTION

Figure 1:
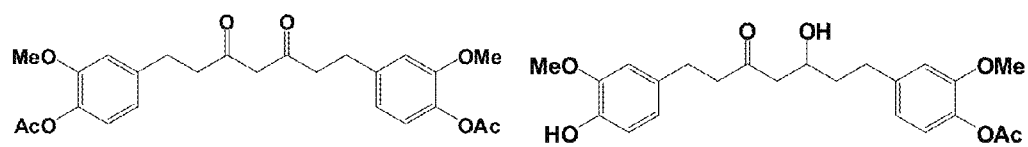
FIG. 1: Chemical structures of COH-SR1, COH-SR2, COH-SR3, COH-SR4, COH-SR5, COH-SR6, COH-SR7 and COH-SR8.
Figure 1:
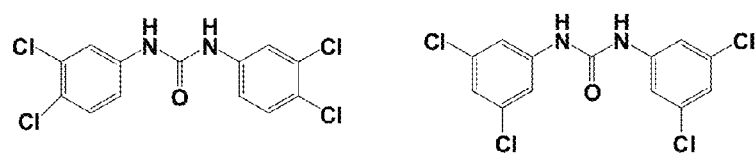
Figure 1:
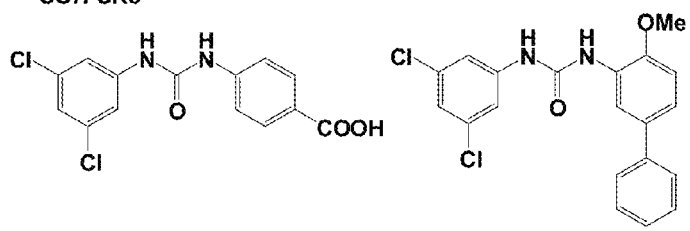
Figure 1:
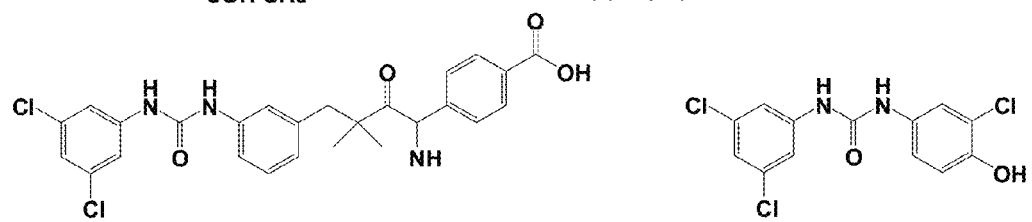
Figure 2:
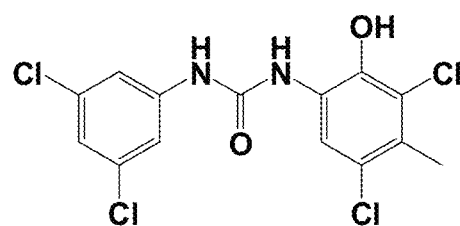
FIG. 2: Chemical structures of COH-SR9, COH-SR10, COH-SR11, COH-SR12, COH-SR13, COH-SR14, COH-SR16, and COH-SR18.
Figure 2:
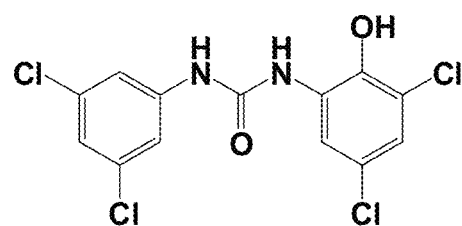
Figure 2:
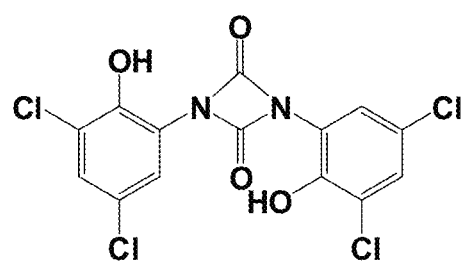
Figure 2:
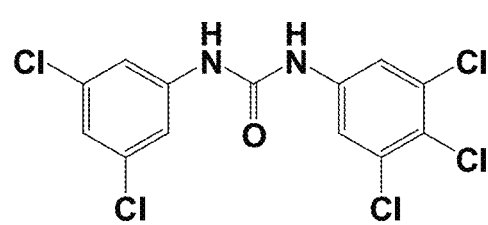
Figure 2:
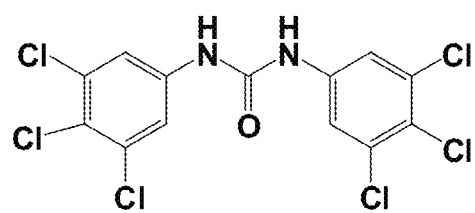
Figure 2:
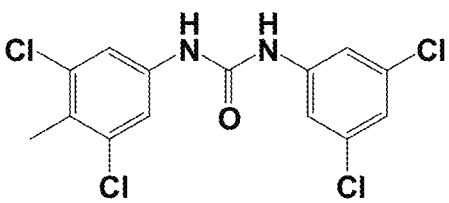
Figure 2:
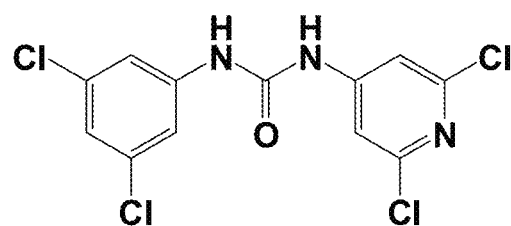
Figure 2:
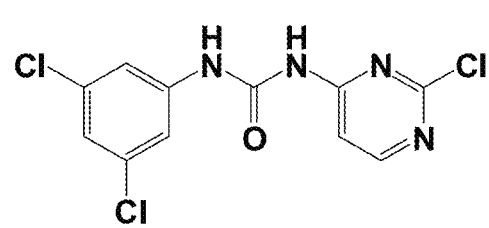
Figure 3:
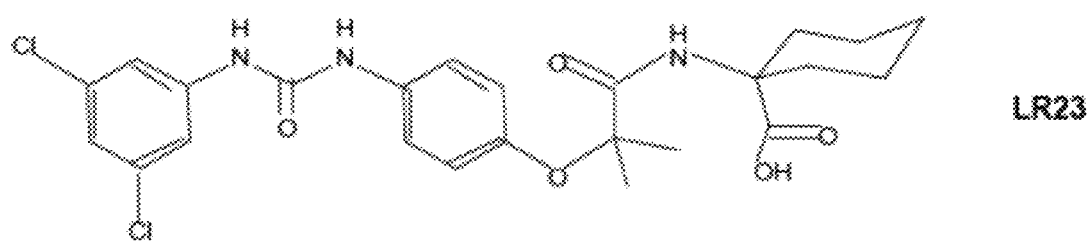
FIG. 3: Chemical structures of LR23, LR59, LR-90 and C75.
Figure 3:
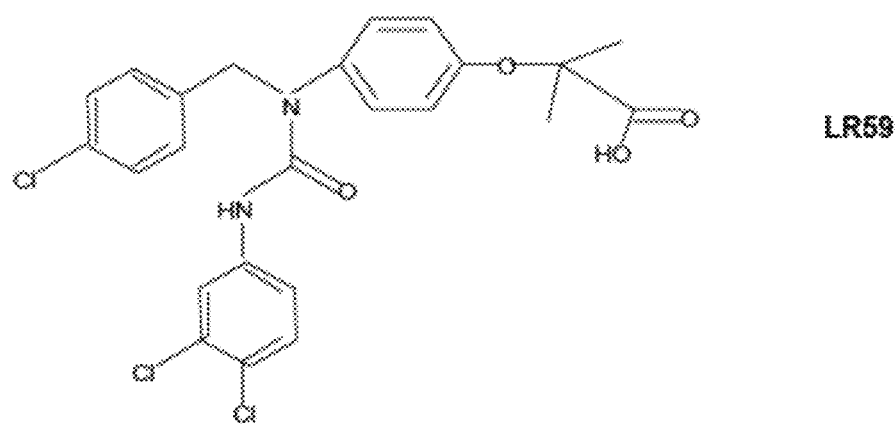
Figure 3:
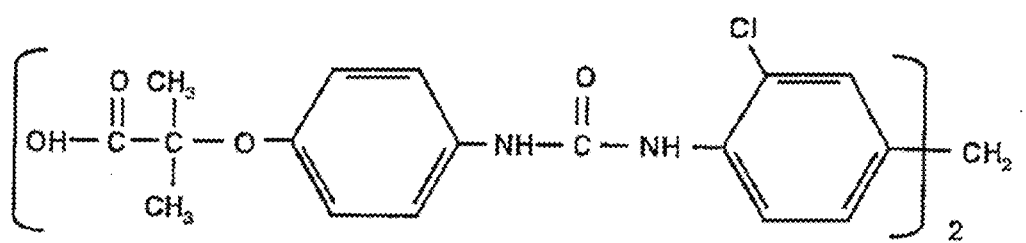
Figure 3:
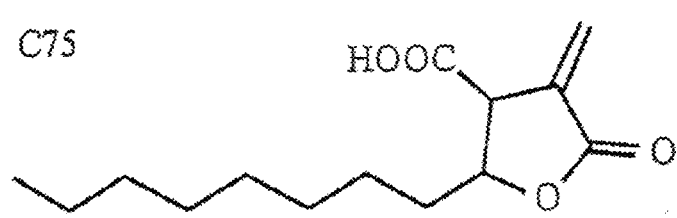

One aspect of the present disclosure relates to derivatives of aryl and heterocyclic ureido aryl and heterocyclic carboxamido isobutyric acids, dichlorophenyl urea, curcumin, and 1,3-diazetidine-2,4-dione (FIGS. 1~3).

Examples of the derivatives of aryl and heterocyclic ureido aryl and heterocyclic carboxamido isobutyric acids include, without limitation, COH-SR7 [4-[(3,5-dichlorophenylureido) phenoxyisobutyril]-4-aminobenzoic acid] (also referred to as LR-99, LR99 or SR7), LR23 [4-(3,5-dichlorophenylureido)phenoxyisobutyryl-1-amidocyclohexane-1carboxylic acid] (also referred to as LR-23), and LR59 [1-(4-chlorobenzyl)-3-dichlorophenyeureido)-4-phenoxyisobutyric acid] (also referred to as LR-59) (FIGS. 1 and 2).

Examples of the derivatives of dichlorophenyl urea include, without limitation, COH-SR3 [1,3-bis(3,4-dichlorophenyl)urea] (also referred to as SR3), COH-SR4 [1,3-bis (3,5-dichlorophenyl) urea] (also referred to as SR4), COH-SR5 [1-(3,5-dichlorophenyl)-3-(4-carboxyphenyl) urea] (also referred to as SR5), COH-SR6 [1-(3,5-dichlorophenyl)-3-(4-methoxy-[1,1'-biphenyl]-3-yl) urea] (also referred to as SR6), COH-SR7, COH-SR8 [1-(3,5-dichlorophenyl)-3-(3-chloro-4-hydroxyphenyl) urea] (also referred to as SR8), COH-SR9 [1-(3,5-dichlorophenyl)-3-(3,5-dichloro-2-hydroxy-4-methyphenyl) urea] (also referred to as SR9), COH-SR10 [1-(3,5-dichlorophenyl)-3-(3,5-dichloro-2-hydroxyphenyl) urea] (also referred to as SR10), COH-SR12 [1-(3,5-dichlorophenyl)-3-(3,4,5-trichlorophenyl) urea] (also referred to as SR12), COH-SR13 [1,3-bis(3,4,5-trichlorophenyl)-3-(2,3,5-trichlorophenyl) urea] (also referred to as SR13), COH-SR14 [1-(3,5-dichloro-4-methylphenyl)-3-(3,5-dichlorophenyl) urea] (also referred to as SR14), COH-SR16 [1-(2,6-dichloropyridin-4-yl)-3-(3,5-dichlorophenyl) urea] (also referred to as SR16), and COH-SR18 [1-(2-chloropyrimidin-4-yl)-3-(3,5-dichlorophenyl) urea] (also referred to as SR18) (FIGS. 1 and 2).

Examples of curcumin derivatives include, without limitation, COH-SR1 [1,7-bis(4'-acetoxy-3'-methoxyphenyl)-3,5-heptadione] (also referred to as SR1) and COH-SR2 [(1E,4Z,6E)-7-(4'''-acetoxy-3'''-methoxyphenyl)-5-hydroxy-1-(4'-hydroxy-3'-methoxyphenyl)hepta-1,4,6-trien-3-one] (also referred to as SR2) (FIG. 1).

Examples of 1,3-diazetidine-2,4-dione derivatives include, without limitation, COH-SR11 [1,3-bis(3,5-dichloro-2-hydroxyphenyl) 1,3-diazetidine-2,4-dione] (also referred to as SR11) (FIG. 2).

As used herein, the COH-SR compound(s) refer to one or more compounds selected from the group consisting of COH-SR1, COH-SR2, COH-SR3, COH-SR4, COH-SR5, COH-SR6, COH-SR7, COH-SR8, COH-SR9, COH-SR10, COH-SR11, COH-SR12, COH-SR13, COH-SR14, COH-SR16, COH-SR18, LR23, LR59, and the pharmaceutically acceptable derivative, solvates, salts and stereoisomers thereof, including mixtures thereof in all ratios.

In one embodiment, the COH-SR compounds modulate differentiation in adipocytes and cancer cells. The preferred COH-SR compounds are COH-SR1, COH-SR2, COH-SR3, COH-SR4, COH-SR6, COH-SR7, COH-SR9, COH-SR14, COH-SR16, COH-SR18, LR23, LR59, and the pharmaceutically acceptable derivative, solvates, salts and stereoisomers thereof, including mixtures thereof in all ratios.

In certain embodiments, under conditions that normally promote differentiation of preadipocytes to adipocytes, the COH-SR compounds (1) inhibit differentiation and accumulation of lipid droplets in preadipocytes and (2) reduce intracellular triglyceride contents. The COH-SR compounds show similar effects to preadipocytes compared to certain known HDAC inhibitors (e.g. TSA and apicidin) and fatty acid synthase inhibitor (e.g. C75).

In certain embodiments, the COH-SR compounds inhibit the earlier stage of the adpogenic process (preadipocyte proliferation) in preadipocytes.

In certain embodiments, the COH-SR compounds induce dedifferentiation of fully differentiated adipocytes.

In certain embodiments, the COH-SR compounds are cytotoxic to cancer cells including cancer stem cells. Examples of the cancer treated include, without limitation, leukemia (e.g. acute myeloid leukemia (AML) and monocytic leukemia), lung cancer (e.g. non-small cell lung cancer), colon cancer, CNS cancer, melanoma, ovarian cancer, renal cancer, prostate cancer, breast cancer, and brain cancer (e.g. glioma, glioblastoma multiforme (GBM)). Examples of cancer cells include, without limitation, leukemia cell (e.g. THP1, CCRF-CEM, HL-60, HL-60 (TB), K-562, MOLT-4, RPMI-8226, SR, and R937); non-small cell lung cancer (e.g. A-549, A549/ATCC, EKVX, HOP-62, HOP-92, NCI-H226, NCI-H23, NCI-H322M, NCI-H460, and NCI-H522); colon cancer (e.g. COLO 205, HCT-116, HCT-15, HT29, KM12, and SW-620); CNS cancer (e.g. SF-268, SF-295, SF-539, SNB-19, SNB-75, and U251); melanoma (e.g. LOX IMVI, MALME-3M, M14, MDA-MB-435, SK-MEL-2, SK-MEL-28, SK-MEL-5, UACC-257, UACC-62, B16F10, and B16-F0); ovarian cancer (e.g. Hela, IGROV1, OVCAR-3, OVCAR-4, OVCAR-5, OVCAR-8, NCI/ADR-RES, MADH2744, A2780 DPPr and SKOV-3); renal cancer (e.g. 786-0, A498, ACHN, CAKI-1, RXF 393, SN12C, TK-10, and UO-31); prostate cancer (PC-3 and DU-145); breast cancer (e.g. 4T1, HMLE, MDA-MB-231, MDA-MB-231/ATCC, HS 578T, BT-549, T-47D, MDA-MB-468, and MCF7, and breast tumor cancer stem cells (e.g. CD44+/CD24– breast cancer cells)), and brain cancer (e.g. glioma cells such as U251, U87, PBT-017, PBT018, PBT003 and PBT028).

In certain embodiments, the COH-SR compounds prevent cellular proliferation and arrest growth via G0/G1 arrest. Cyclins (e.g. cyclin D1 and E2) and cyclin dependent kinases (CDKs, e.g. CDK2 and CDK4) play critical roles in promoting G1 phase progression. The COH-SR compounds modulate various cyclin-dependent kinases (CDKs), and/or induction of p21 and p27 in cancer cells and preadipocytes. A preferred cancer is leukemia and melanoma. The preferred COH-SR compounds are COH-SR4 and COH-SR9, and the pharmaceutically acceptable derivative, solvates, salts and stereoisomers thereof, including mixtures thereof in all ratios.

In certain embodiments, the COH-SR compounds activate AMP-activated protein kinase (AMPK) in cancer cells and adipocytes. The preferred cancers are ovarian cancer and leukemia. The preferred COH-SR compounds are COH-SR4, COH-SR9, COH-SR16 and COH-SR18, and the pharmaceutically acceptable derivative, solvates, salts and stereoisomers thereof, including mixtures thereof in all ratios. The more preferred COH-SR compound is COH-SR4, and the pharmaceutically acceptable derivative, solvates, salts and stereoisomers thereof, including mixtures thereof in all ratios.

AMPK is an energy-sensing serine/threonine kinase present in all eukaryotes that is activated by metabolic stresses that either inhibit ATP synthesis or accelerate ATP consumption. Phosphorylated activation of AMPK in response to an increase in the cellular AMP:ATP ratio increases glucose uptake, fatty acid oxidation, and mitochondrial biogenesis, and decreases synthesis of fatty acids, sterols, glycogen and proteins. Without being bound by a specific mechanism, such alterations in lipid and glucose metabolism would be expected to ameliorate the pathogenesis of obesity, type 2 diabetes and other metabolic disorders. AMPK has also been identified as a potential target for cancer prevention and/or treatment. Cell growth and proliferation are energetically demanding, and AMPK may act as an "energy checkpoint" that permits growth and proliferation only when energy reserves are sufficient. Thus, activators of AMPK such as the COH-SR compounds are therapeutic for metabolic disorders (e.g. diabetes and obesity) and for cancers.

In certain embodiments, the COH-SR compounds induce apoptosis in cancer cells. The preferred cancer is leukemia, brain cancer and melanoma. The preferred COH-SR compounds are COH-SR4 and COH-SR9, and the pharmaceutically acceptable derivative, solvates, salts and stereoisomers thereof, including mixtures thereof in all ratios.

In certain embodiments, the COH-SR compounds are substrates of glutathione S-transferases (GSTs). A conjugate of GSH and a COH-SR compound is formed in the presence of GST, and the conjugate is a product-inhibitor of GSTs.

GSTs are a multi gene family of isoenzymes ubiquitously expressed in most living organisms. These enzymes catalyze the conjugation of glutathione (GSH) to a variety of electrophilic compounds, thus establishing the now widely accepted role of GSTs as cell housekeepers involved in the detoxification of endogenous as well as exogenous substances. The GSTs comprises of three major class of proteins: cytosolic, mitochondrial and microsomal referred to as membrane-associated proteins of which the cytosolic GSTs (class A (alpha), M (mu), P (pi), T (theta), S (sigma), O (Omega) and Z(zeta) constitute the largest family.

Without being bound by a specific mechanism, it is proposed that GSTs could confer drug-resistance to alkylating agents as well as oxidants. The high over-expression of GSTs in many cancer tissues, particularly melanoma, along with the ability of GSTs to activate MAPK in the presence of glutathione-conjugates indicate a critical role of GSTs in providing cancer cells resistance to apoptosis caused by electrophilic toxins during anti-cancer therapy. Therefore, targeting GSTs may be an effective strategy to design the drugs for treatment for malignant melanoma.

The majority of human tumor cell lines, including those selected in vitro for resistance to chemotherapeutic agents, over-express GSTP-1-1, referred herein as GST-P or GSTP. GSTP is the predominant isoenzyme (up to 2.7% of the total cytosolic protein) in all but 2 of 60 tumor cell lines used in the Drug Screening Program of the National Cancer Institute (NCI). Significant quantitative correlations among enzymatic activity, total enzyme protein, and mRNA were shown, particularly in those cell lines selected for resistance to alkylating agents such as melphalan, chlorambucil, cyclophosphamide, BCNU (N, N-bis (2-chloroethyl)-N-nitrosourea), and cisplatin. A variety of human cancers (e.g. breast, colon, kidney, lung and ovarian cancer) usually express high levels of GSTP1-1 compared with the surrounding tissues. Without being bound by a specific mechanism, GSTP1-1 expression may be a marker for cancer development. High expression levels may be associated not only with disease progression but also with drug resistance in patients undergoing chemotherapy. GSTs are known to be overexpressed in malignant tumors suggesting that they may play a role in acquired resistance to anticancer agents.

In certain embodiments, the COH-SR compounds are substrates for GSTP. A conjugate of GSH and a COH-SR compound is product-inhibitor of GSTPs. Therefore, the co-administration of a COH-SR compound as an adjuvant therapy for chemotherapy may restore drug sensitivity of resistant cancer cells.

In certain embodiments, the COH-SR compounds show no or low cytotoxicity to normal cells. COH-SR compounds have little effect on the viability of HUVECs, HAVSMC, NHDF and 3T3-preadipocytes. In certain embodiments, the IC50's on these normal cells are >25 µM or above, compared with <5 µM in almost all cancer cells tested.

Another aspect of the present disclosure relates to a pharmaceutical composition comprising a therapeutically effective amount of a COH-SR compound and a pharmaceutically acceptable carrier.

As used herein, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Pharmaceutically acceptable carrier is a pharmaceutically-acceptable material, composition or vehicle, such as a liquid or solid filler, diluent, excipient, solvent or encapsulating material, involved in carrying or transporting an active ingredient from one location, body fluid, tissue, organ (interior or exterior), or portion of the body, to another location, body fluid, tissue, organ, or portion of the body.

Each carrier is "pharmaceutically acceptable" in the sense of being compatible with the other ingredients, e.g., the COH-SR compounds or other ingredients, of the formulation and suitable for use in contact with the tissue or organ of a biological subject without excessive toxicity, irritation, allergic response, immunogenicity, or other problems or complications, commensurate with a reasonable benefit/risk ratio.

Examples of materials which can serve as pharmaceutically-acceptable carriers include, without limitation, (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of an active ingredient in these formulations can vary widely, and will be selected primarily based on fluid volumes, viscosities, body weight and the like in accordance with the particular mode of administration selected and the biological subject's needs. For example, the concentration can be 0.0001% to 100%, 0.001% to 50%, 0.01% to 30%, 0.1% to 20%, 1% to 10% wt.

The compositions of the invention can be administered for prophylactic, therapeutic, and/or hygienic use. Such administration can be topical, mucosal, e.g., oral, nasal, vaginal, rectal, parenteral, transdermal, subcutaneous, intramuscular, intravenous, via inhalation, ophthalmic and other convenient routes. The pharmaceutical compositions can be administered in a variety of unit dosage forms depending upon the method of administration. For example, unit dosage forms suitable for oral administration include powder, tablets, pills, capsules and lozenges and for transdermal administration include solution, suspension and gel.

In another embodiment, the composition disclosed herein further comprises a second therapeutic agent. In certain embodiments, the second therapeutic agent is another COH-SR compound or a known anticancer drug. Examples of the known anticancer drugs include, without limitation, abiraterone acetate, ado-trastuzumab emtansine, afatinib dimaleate, aldesleukin, alectinib, alemtuzumab, anastrozole, arsenic trioxide, asparaginase Erwinia chrysanthemi, axitinib, belinostat, bendamustine hydrochloride, bevacizumab, bicalutamide, bleomycin, blinatumomab, bortezomib, bosutinib, brentuximab vedotin, busulfan, cabazitaxel, capecitabine, carboplatin, carmustine, carmustine implant, ceritinib, cetuximab, chlorambucil, cisplatin, clofarabine, cobimetinib, crizotinib, cyclophosphamide, cytarabine, cytarabine liposome, dabrafenib, dacarbazine, dasatinib, daunorubicin hydrochloride, degarelix, denileukin diftitox, dexamethasone, docetaxel, doxorubicin hydrochloride, doxorubicin hydrochloride liposome, enzalutamide, epirubicin hydrochloride, eribulin mesylate, erlotinib hydrochloride, etoposide, etoposide phosphate, everolimus, exemestane, fludarabine phosphate, fluorouracil injection, flutamide, fulvestrant, gefitinib, gemcitabine hydrochloride, goserelin acetate, hydroxyurea, ibritumomab tiuxetan, ibrutinib, idarubicin hydrochloride, idelalisib, imatinib mesylate, ipilimumab, irinotecan hydrochloride, ixabepilone, lapatinib ditosylate, lenalidomide, letrozole, leucovorin calcium, leuprolide acetate, lomustine, mechlorethamine hydrochloride, megestrol acetate, melphalan, mercaptopurine, methotrexate, mitoxantrone hydrochloride, necitumumab, nelarabine, nilotinib, nivolumab, obinutuzumab, ofatumumab, olaparib, omacetaxine mepesuccinate, osimertinib, oxaliplatin, paclitaxel, paclitaxel albumin-stabilized nanoparticle formulation, palbociclib, pamidronate disodium, panitumumab, pazopanib hydrochloride, pegaspargase, peginterferon α-2b, pembrolizumab, pemetrexed disodium, pertuzumab, plerixafor, ponatinib hydrochloride, pralatrexate, prednisone, radium 223 dichloride, ramucirumab, recombinant interferon α-2b, regorafenib, rituximab, romidepsin, sipuleucel-T, sorafenib tosylate, sunitinib malate, talimogene laherparepvec, tamoxifen citrate, temozolomide, temsirolimus, thioguanine, thiotepa, topotecan hydrochloride, toremifene, tositumomab and iodine I 131 tositumomab, trametinib, trastuzumab, trifluridine and tipiracil hydrochloride, vemurafenib, venetoclax, vinblastine sulfate, vincristine sulfate, vincristine sulfate liposome, vinorelbine tartrate, vorinostat, and ziv-aflibercept. In certain embodiments, the second therapeutic agent can be one or more chemotherapy drugs (e.g. TMZ, SN38, CPT-11, and 5-FU).

In the methods disclosed below, optimal dosages to be administered to a subject may be determined by those skilled in the art, and will vary with the particular compound in use, the strength of the preparation, the mode of administration, and the advancement of the condition treated. Additional factors depending on the particular subject being treated, including subject age, weight, gender, diet and time of administration, will result in a need to adjust dosages. Administration of the pharmaceutical composition may be effected continuously or intermittently. In any treatment regimen, the composition may be administered to a subject either singly or in a cocktail containing a COH-SR compound and other therapeutic agent (e.g. another COH-SR compound and/or other anti-cancer drugs). In certain embodiments, an appropriate dosage level will generally be about 0.001 to 50 mg per kg subject body weight per day that can be administered in single or multiple doses. Preferably, the dosage level will be about 0.005 to about 25 mg/kg, per day; more preferably about 0.01 to about 10 mg/kg per day; and even more preferably about 0.05 to about 1 mg/kg per day.

The exact dosage will be determined in light of factors related to the subject. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the therapeutic agents in the pharmaceutical composition (e.g. a COH-SR compound) used. Typically, a pharmaceutical composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

Another aspect of the present disclosure relates to a method of treating or preventing obesity in a subject comprising administrating a pharmaceutical composition disclosed supra to the subject. The pharmaceutical composition comprises a COH-SR compound selected from the group consisting of COH-SR1, COH-SR2, COH-SR3, COH-SR4, COH-SR5, COH-SR6, COH-SR7, COH-SR8, COH-SR9, COH-SR10, COH-SR12, COH-SR13, COH-SR14, COH-SR16, COH-SR18, LR23 and LR59, and preferably from the group consisting of COH-SR1, COH-SR2, COH-SR3, COH-SR4, COH-SR6, COH-SR7, LR23 and LR59.

In one embodiment, the treatment/prevention of obesity includes, without limitation, reducing fat mass and lowering body weights.

In another embodiment, the method further comprises administering to the subject a pharmaceutical composition disclosed herein to (1) inhibit differentiation and/or accumulation of lipid droplets and/or (2) to reduce intracellular triglyceride contents and/or (3) inhibit proliferation in pre-adipocyte cells of the subject.

In another embodiment, the method further comprises administering to the subject a pharmaceutical composition disclosed herein to induce dedifferentiation of fully differentiated adipocytes in the subject.

In another embodiment, the method further comprises administering to the subject a pharmaceutical composition disclosed herein to activate AMPK in preadipocyte cells of the subject.

Another aspect of the present disclosure relates to a method of treating a cancer in a subject comprising administering a pharmaceutical composition disclosed herein to the subject. The pharmaceutical composition comprises a COH-SR compound selected from the group consisting of COH-SR1, COH-SR2, COH-SR3, COH-SR4, COH-SR5, COH-SR6, COH-SR7, COH-SR8, COH-SR9, COH-SR10, COH-SR12, COH-SR13, COH-SR14, COH-SR16, COH-SR18, LR23 and LR59, preferably from the group consisting of COH-SR2, COH-SR3, COH-SR4, COH-SR6, COH-SR7, COH-SR9, COH-SR14, COH-SR16, and COH-SR18, and more preferably COH-SR4 and COH-SR9.

Examples of the cancer treated include, without limitation, leukemia (e.g. acute myeloid leukemia (AML) and monocytic leukemia), lung cancer (e.g. non-small cell lung cancer), colon cancer, CNS cancer, melanoma, ovarian cancer, renal cancer, prostate cancer, breast cancer, and brain cancer (e.g. glioma and GBM).

In one embodiment, the method further comprises administering to the subject a pharmaceutical composition disclosed herein to (1) modulate differentiation and/or (2) promote cell cycle arrest and/or apoptosis in the cancer cells in the subject.

In another embodiment, the method further comprises administering to the subject a pharmaceutical composition disclosed herein to activate AMPK in the cancer cells of the subject.

In another embodiments, the method further comprises administering to the subject a pharmaceutical composition disclosed herein to inhibit a GST, preferably GSTP, in the cancer cells of the subject.

In another embodiment, the cancer treated in the method described herein is a malignant and/or resistant cancer, examples include, without limitation, chemotherapy resistant ovarian cancer (e.g. cisplatin resistant ovarian cancer), TMZ resistant GBM, and malignant melanoma.

In another embodiment, the pharmaceutical composition administered in the method further comprising a second therapeutic agent, which is a second COH-SR compound or an anticancer drug that is not a COH-SR compound. In certain embodiments, the combination of a COH-SR compound and a second therapeutic agent can show synergistic or additive effects in the treatment. The optimal dosages of each ingredient in the pharmaceutical composition can be determined as described supra.

Examples of the anticancer drugs that are not the COH-SR compounds include, without limitation, abiraterone acetate, ado-trastuzumab emtansine, afatinib dimaleate, aldesleukin, alectinib, alemtuzumab, anastrozole, arsenic trioxide, asparaginase Erwinia chrysanthemi, axitinib, belinostat, bendamustine hydrochloride, bevacizumab, bicalutamide, bleomycin, blinatumomab, bortezomib, bosutinib, brentuximab vedotin, busulfan, cabazitaxel, capecitabine, carboplatin, carmustine, carmustine implant, ceritinib, cetuximab, chlorambucil, cisplatin, clofarabine, cobimetinib, crizotinib, cyclophosphamide, cytarabine, cytarabine liposome, dabrafenib, dacarbazine, dasatinib, daunorubicin hydrochloride, degarelix, denileukin diftitox, dexamethasone, docetaxel, doxorubicin hydrochloride, doxorubicin hydrochloride liposome, enzalutamide, epirubicin hydrochloride, eribulin mesylate, erlotinib hydrochloride, etoposide, etoposide phosphate, everolimus, exemestane, fludarabine phosphate, fluorouracil injection, flutamide, fulvestrant, gefitinib, gemcitabine hydrochloride, goserelin acetate, hydroxyurea, ibritumomab tiuxetan, ibrutinib, idarubicin hydrochloride, idelalisib, imatinib mesylate, ipilimumab, irinotecan hydrochloride, ixabepilone, lapatinib ditosylate, lenalidomide, letrozole, leucovorin calcium, leuprolide acetate, lomustine, mechlorethamine hydrochloride, megestrol acetate, melphalan, mercaptopurine, methotrexate, mitoxantrone hydrochloride, necitumumab, nelarabine, nilotinib, nivolumab, obinutuzumab, ofatumumab, olaparib, omacetaxine mepesuccinate, osimertinib, oxaliplatin, paclitaxel, paclitaxel albumin-stabilized nanoparticle formulation, palbociclib, pamidronate disodium, panitumumab, pazopanib hydrochloride, pegaspargase, peginterferon α-2b, pembrolizumab, pemetrexed disodium, pertuzumab, plerixafor, ponatinib hydrochloride, pralatrexate, prednisone, radium 223 dichloride, ramucirumab, recombinant interferon α-2b, regorafenib, rituximab, romidepsin, sipuleucel-T, sorafenib tosylate, sunitinib malate, talimogene laherparepvec, tamoxifen citrate, temozolomide, temsirolimus, thioguanine, thiotepa, topotecan hydrochloride, toremifene, tositumomab and iodine I 131 tositumomab, trametinib, trastuzumab, trifluridine and tipiracil hydrochloride, vemurafenib, venetoclax, vinblastine sulfate, vincristine sulfate, vincristine sulfate liposome, vinorelbine tartrate, vorinostat, and ziv-aflibercept. In certain embodiments, the anticancer drugs may be chemotherapeutics such as TMZ, SN38, CPT-11, or 5-FU. In certain embodiments, the pharmaceutical composition comprising COH-SR4 and a second therapeutic agent selected from the group consisting of abiraterone acetate, ado-trastuzumab emtansine, afatinib dimaleate, aldesleukin, alectinib, alemtuzumab, anastrozole, arsenic trioxide, asparaginase Erwinia chrysanthemi, axitinib, belinostat, bendamustine hydrochloride, bevacizumab, bicalutamide, bleomycin, blinatumomab, bortezomib, bosutinib, brentuximab vedotin, busulfan, cabazitaxel, capecitabine, carboplatin, carmustine, carmustine implant, ceritinib, cetuximab, chlorambucil, cisplatin, clofarabine, cobimetinib, crizotinib, cyclophosphamide, cytarabine, cytarabine liposome, dabrafenib, dacarbazine, dasatinib, daunorubicin hydrochloride, degarelix, denileukin diftitox, dexamethasone, docetaxel, doxorubicin hydrochloride, doxorubicin hydrochloride liposome, enzalutamide, epirubicin hydrochloride, eribulin mesylate, erlotinib hydrochloride, etoposide, etoposide phosphate, everolimus, exemestane, fludarabine phosphate, fluorouracil injection, flutamide, fulvestrant, gefitinib, gemcitabine hydrochloride, goserelin acetate, hydroxyurea, ibritumomab tiuxetan, ibrutinib, idarubicin hydrochloride, idelalisib, imatinib mesylate, ipilimumab, irinotecan hydrochloride, ixabepilone, lapatinib ditosylate, lenalidomide, letrozole, leucovorin calcium, leuprolide acetate, lomustine, mechlorethamine hydrochloride, megestrol acetate, melphalan, mercaptopurine, methotrexate, mitoxantrone hydrochloride, necitumumab, nelarabine, nilotinib, nivolumab, obinutuzumab, ofatumumab, olaparib, omacetaxine mepesuccinate, osimertinib, oxaliplatin, paclitaxel, paclitaxel albumin-stabilized nanoparticle formulation, palbociclib, pamidronate disodium, panitumumab, pazopanib hydrochloride, pegaspargase, peginterferon α-2b, pembrolizumab, pemetrexed disodium, pertuzumab, plerixafor, ponatinib hydrochloride, pralatrexate, prednisone, radium 223 dichloride, ramucirumab, recombinant interferon α-2b, regorafenib, rituximab, romidepsin, sipuleucel-T, sorafenib tosylate, sunitinib malate, talimogene laherparepvec, tamoxifen citrate, temozolomide, temsirolimus, thioguanine, thiotepa, topotecan hydrochloride, toremifene, tositumomab and iodine I 131 tositumomab, trametinib, trastuzumab, trifluridine and tipiracil hydrochloride, vemurafenib, venetoclax, vinblastine sulfate, vincristine sulfate, vincristine sulfate liposome, vinorelbine tartrate, vorinostat, and ziv-aflibercept. In certain embodiments, the pharmaceutical composition comprising COH-SR4 and a second therapeutic agent selected from the group consisting of TMZ, SN38, CPT-11, and 5-FU. In certain embodiments, the combination of COH-SR4 and a chemotherapeutic can show synergistic or additive effect in treating cancer. The optimal dosage of each composition can be determined as described supra. Low dosages of COH-SR4 and a chemotherapeutic show a synergistic effect to cancer cells. Thus, low dosage of COH-SR compound can improve the therapeutic effects of the chemotherapeutics.

Certain cancers, (e.g. GBMs) can repair TMZ-induced damages and therefore develop resistance to TMZ. Thus there is a need to potentiate therapeutic effects of TMZ. Without being bound by a specific mechanism, TMZ may generate intracellular reactive oxygen species (ROS) in cancer cells, which in turn caused apoptosis of the cancer cells. In certain embodiments, treatment of COH-SR4 or a pharmaceutical composition thereof increase ROS in cancer cells (e.g. glioma cells). In certain embodiments, COH-SR4 or a pharmaceutical composition thereof shows more potent cytotoxicity to cancer cells (e.g. glioma cells) than certain known chemotherapy drugs such as TMZ, 5-FU, and CPT-11.

In another embodiment, the method comprises administering to the subject a first pharmaceutical composition comprising a first COH-SR compound, and administering to the subject a second pharmaceutical composition comprising a second therapeutic agent, wherein the two pharmaceutical compositions are administered at the same time or separate times.

The second therapeutic agent can be a second COH-SR compound or an anticancer drug that is not a COH-SR compound. In certain embodiments, the combination of administering the first and the second pharmaceutical compositions can show synergistic or additive effects in the treatment. In certain embodiments, the combination of administering the first and the second pharmaceutical compositions potentiates the cytotoxicity of the first COH-SR compound or the second therapeutic agent. The optimal dosages of each ingredient in the pharmaceutical compositions can be determined as described supra.

Examples of the anticancer drugs that are not the COH-SR compounds include, without limitation, abiraterone acetate, ado-trastuzumab emtansine, afatinib dimaleate, aldesleukin, alectinib, alemtuzumab, anastrozole, arsenic trioxide, asparaginase Erwinia chrysanthemi, axitinib, belinostat, bendamustine hydrochloride, bevacizumab, bicalutamide, bleomycin, blinatumomab, bortezomib, bosutinib, brentuximab vedotin, busulfan, cabazitaxel, capecitabine, carboplatin, carmustine, carmustine implant, ceritinib, cetuximab, chlorambucil, cisplatin, clofarabine, cobimetinib, crizotinib, cyclophosphamide, cytarabine, cytarabine liposome, dabrafenib, dacarbazine, dasatinib, daunorubicin hydrochloride, degarelix, denileukin diftitox, dexamethasone, docetaxel, doxorubicin hydrochloride, doxorubicin hydrochloride liposome, enzalutamide, epirubicin hydrochloride, eribulin mesylate, erlotinib hydrochloride, etoposide, etoposide phosphate, everolimus, exemestane, fludarabine phosphate, fluorouracil injection, flutamide, fulvestrant, gefitinib, gemcitabine hydrochloride, goserelin acetate, hydroxyurea, ibritumomab tiuxetan, ibrutinib, idarubicin hydrochloride, idelalisib, imatinib mesylate, ipilimumab, irinotecan hydrochloride, ixabepilone, lapatinib ditosylate, lenalidomide, letrozole, leucovorin calcium, leuprolide acetate, lomustine, mechlorethamine hydrochloride, megestrol acetate, melphalan, mercaptopurine, methotrexate, mitoxantrone hydrochloride, necitumumab, nelarabine, nilotinib, nivolumab, obinutuzumab, ofatumumab, olaparib, omacetaxine mepesuccinate, osimertinib, oxaliplatin, paclitaxel, paclitaxel albumin-stabilized nanoparticle formulation, palbociclib, pamidronate disodium, panitumumab, pazopanib hydrochloride, pegaspargase, peginterferon α-2b, pembrolizumab, pemetrexed disodium, pertuzumab, plerixafor, ponatinib hydrochloride, pralatrexate, prednisone, radium 223 dichloride, ramucirumab, recombinant interferon α-2b, regorafenib, rituximab, romidepsin, sipuleucel-T, sorafenib tosylate, sunitinib malate, talimogene laherparepvec, tamoxifen citrate, temozolomide, temsirolimus, thioguanine, thiotepa, topotecan hydrochloride, toremifene, tositumomab and iodine I 131 tositumomab, trametinib, trastuzumab, trifluridine and tipiracil hydrochloride, vemurafenib, venetoclax, vinblastine sulfate, vincristine sulfate, vincristine sulfate liposome, vinorelbine tartrate, vorinostat, and ziv-aflibercept. In certain embodiments, the anticancer drugs are chemotherapeutics such as TMZ, SN38, CPT-11, and 5-FU, and an antibody against RLIP76 (anti-RLIP76, e.g. anti-RLIP76 IgG).

In certain embodiments, the first COH-SR compound is COH-SR4 and the second therapeutic agent is selected from the group consisting of abiraterone acetate, ado-trastuzumab emtansine, afatinib dimaleate, aldesleukin, alectinib, alemtuzumab, anastrozole, arsenic trioxide, asparaginase Erwinia chrysanthemi, axitinib, belinostat, bendamustine hydrochloride, bevacizumab, bicalutamide, bleomycin, blinatumomab, bortezomib, bosutinib, brentuximab vedotin, busulfan, cabazitaxel, capecitabine, carboplatin, carmustine, carmustine implant, ceritinib, cetuximab, chlorambucil, cisplatin, clofarabine, cobimetinib, crizotinib, cyclophosphamide, cytarabine, cytarabine liposome, dabrafenib, dacarbazine, dasatinib, daunorubicin hydrochloride, degarelix, denileukin diftitox, dexamethasone, docetaxel, doxorubicin hydrochloride, doxorubicin hydrochloride liposome, enzalutamide, epirubicin hydrochloride, eribulin mesylate, erlotinib hydrochloride, etoposide, etoposide phosphate, everolimus, exemestane, fludarabine phosphate, fluorouracil injection, flutamide, fulvestrant, gefitinib, gemcitabine hydrochloride, goserelin acetate, hydroxyurea, ibritumomab tiuxetan, ibrutinib, idarubicin hydrochloride, idelalisib, imatinib mesylate, ipilimumab, irinotecan hydrochloride, ixabepilone, lapatinib ditosylate, lenalidomide, letrozole, leucovorin calcium, leuprolide acetate, lomustine, mechlorethamine hydrochloride, megestrol acetate, melphalan, mercaptopurine, methotrexate, mitoxantrone hydrochloride, necitumumab, nelarabine, nilotinib, nivolumab, obinutuzumab, ofatumumab, olaparib, omacetaxine mepesuccinate, osimertinib, oxaliplatin, paclitaxel, paclitaxel albumin-stabilized nanoparticle formulation, palbociclib, pamidronate disodium, panitumumab, pazopanib hydrochloride, pegaspargase, peginterferon α-2b, pembrolizumab, pemetrexed disodium, pertuzumab, plerixafor, ponatinib hydrochloride, pralatrexate, prednisone, radium 223 dichloride, ramucirumab, recombinant interferon α-2b, regorafenib, rituximab, romidepsin, sipuleucel-T, sorafenib tosylate, sunitinib malate, talimogene laherparepvec, tamoxifen citrate, temozolomide, temsirolimus, thioguanine, thiotepa, topotecan hydrochloride, toremifene, tositumomab and iodine I 131 tositumomab, trametinib, trastuzumab, trifluridine and tipiracil hydrochloride, vemurafenib, venetoclax, vinblastine sulfate, vincristine sulfate, vincristine sulfate liposome, vinorelbine tartrate, vorinostat, and ziv-aflibercept. In certain embodiments, the first COH-SR compound is COH-SR4 and the second therapeutic agent is a chemotherapeutic (e.g. TMZ, SN38, CPT-11, 5-FU) or anti-RLIP76. In certain embodiments, the first pharmaceutical composition is administered before the second pharmaceutical composition is applied. In certain embodiments, the first pharmaceutical composition is administered after the second pharmaceutical composition is applied. The optimal time difference between the administrations of the two pharmaceutical compositions can be minutes, hours, or days, which can be determined by those skilled in the art, and will vary with the particular compound in use, the strength of the preparation, the mode of administration, and the advancement of the condition treated. Additional factors depending on the particular subject being treated, including subject age, weight, gender, diet and time of administration, will result in a need to adjust dosages.

In certain embodiments, the first COH-SR compound is COH-SR4 and the second therapeutic agent is anti-RLIP76. The second pharmaceutical composition comprising anti-RLIP76 is administered to the subject first, and then the first pharmaceutical composition comprising COH-SR4 is administered after a first time period. The first time period is about 24 hours.

Without being bound by a specific mechanism, GST can be inhibited by the product formed by conjugation of GSH (GS-E). Thus, GS-E is actively transported out of cells to avoid product inhibition of GSTs (e.g. in a mercapturic acid pathway). The majority of GS-E transport is carried out by the non-ABC transporter, RLIP76. Thus, administering to the subject a pharmaceutical composition comprising anti-RLIP76 improves the therapeutic effects of the first COH-SR compound.

The use of the pharmaceutical composition comprising COH-SR4 disclosed herein for treating various types of cancer and diabetes are further described in the following embodiments.

Certain embodiments of the anticancer methods disclosed herein comprises administering to the subject a pharmaceutical composition comprising a therapeutically effective amount of COH-SR4, a salt thereof, or stereoisomers thereof, wherein the cancer is melanoma (e.g., metastatic melanoma) and lung cancer (e.g., small cell lung cancer, non-small cell lung cancer, metastatic lung cancer). The anticancer methods disclosed herein may further comprise administering to the subject a pharmaceutical composition comprising a therapeutically effective amount of one or more second anticancer agents as disclosed supra. The second anticancer agent(s) may be administered with COH-SR4 in one pharmaceutical composition, or in separate pharmaceutical compositions. The second anticancer agent(s) and COH-SR4 may be administered simultaneously or sequentially.

For methods for treating melanoma, the one or more second anticancer agents may be selected from the group consisting of aldesleukin, cobimetinib, dabrafenib, dacarbazine, ipilimumab, nivolumab, peginterferon α-2b, pembrolizumab, recombinant interferon α-2b, talimogene laherparepvec, trametinib, and vemurafenib. For methods for treating small cell lung cancer, the one or more second anticancer agents may be selected from the group consisting of doxorubicin hydrochloride, etoposide, etoposide phosphate, everolimus, mechlorethamine hydrochloride, methotrexate, and topotecan hydrochloride. For methods for treating non-small cell lung cancer, the one or more second anticancer agents may be selected from the group consisting of afatinib dimaleate, alectinib, bevacizumab, carboplatin, ceritinib, crizotinib, docetaxel, erlotinib hydrochloride, everolimus, gefitinib, gemcitabine hydrochloride, mechlorethamine hydrochloride, methotrexate, necitumumab, nivolumab, osimertinib, paclitaxel, paclitaxel albumin-stabilized nanoparticle formulation, pembrolizumab, pemetrexed disodium, ramucirumab, and vinorelbine tartrate.

Certain embodiments of the anticancer (e.g. melanoma and lung cancer) methods disclosed herein further comprises administering an additional therapy selected from the group consisting of chemotherapy, radiation therapy, immunotherapy, hormone therapy, and stem cell transplant to the subject, wherein the additional therapy may be administered simultaneously or sequentially.

In certain embodiments, the pharmaceutical composition is administered by oral administration, intravenous injection, intraperitoneal injection, topical administration, subcutaneous administration, intraventricular/intrathecal administration, intra-arterial administration, intravesicular administration, intrapleural administration or intramuscular injection.

In certain embodiments, the pharmaceutical composition is administered three times a day, twice a day, once a day, once every two days, or once every three days over a period of up to 1 week, up to 2 weeks, up to 4 weeks, up to 6 weeks, up to 8 weeks, up to 10 weeks, or up to 12 weeks.

In certain embodiments, the pharmaceutical composition is administered at a daily dose of about 0.005 to about 25 mg/kg, about 0.01 to about 10 mg/kg, about 0.05 to about 1 mg/kg, or 4 mg/kg body weight of COH-SR4, a salt thereof, or stereoisomers thereof. The daily dose may be administered in a single administration or multiple administrations. The dose does not cause significant cytotoxic effects in the subject.

Treatment for Melanoma

Despite increased awareness and surveillance, melanoma incidence continues to rise. Although early detection and surgery is curative for early stages, metastatic melanoma has a dismal prognosis with 5 year survivals of less than 15%. New immuno- and targeted therapies are promising but have severe dose-limiting toxicities, thus, newer alternative therapeutic approaches are needed.

The current clinical interventions in malignant melanomas are met with poor response to therapy due to dynamic regulation of multiple melanoma signaling pathways consequent to administration of single target agents. In this context of limited response to single target agents, novel candidate molecules capable of effectively inducing tumor inhibition along with targeting multiple critical nodes of melanoma signaling assume translational significance. As demonstrated in the working examples, the COH-SR4 treatment decreased the survival and inhibited the clonogenic potential of melanomas along with inducing apoptosis in vitro in cell cultures. COH-SR4 treatments resulted in inhibition of GST activity along with causing cell cycle arrest. Oral administration of 4 mg/kg COH-SR4 resulted in effective inhibition of tumor burdens in both syngeneic and nude mouse models of melanoma. COH-SR4 treatment was well tolerated and no overt toxicity was observed. The histopathological examination of resected tumor sections revealed decreased blood vessels, decrease in the levels of angiogenesis marker, CD31, and proliferation marker, Ki67. The Western blot analyses of resected tumor lysates revealed increased PARP cleavage, Bim, increased phosphorylation of AMPK along with decreased phosphorylation of Akt, and higher vimentin, fibronectin, CDK4 and cyclin B1 protein staining. Thus, COH-SR4 can be used in mono and combinatorial therapies to effectively target aggressive and therapeutically refractory melanomas.

In recent years, the mitochondria provides a novel targeting site for new anticancer drugs (known as "mitocans") which can selectively kill cancer cells without affecting normal cells. COH-SR4 possessed significant anti-tumor activity against melanoma in the NCI 60-DTP panel. COH-SR4 treatment decreased the survival and inhibited the clonogenic potential of melanomas along with inducing apoptosis, highly potent to elesclomol, a drug that has received fast track and orphan drug status from the U.S. FDA and is currently in ongoing clinical trials for metastatic melanoma and a known regulator of oxidative phosphorylation. To test the effect of COH-SR4 on the mitochondria, real-time mitochondrial respiration was performed using the Seahorse XFe96 flux analyzer. As shown in the working examples, COH-SR4 treatments demonstrated uncoupling effects on mitochondrial respiration, as shown by an increase in oxygen consumption rate (OCR) and mitochondria swelling, and caused a rapid loss of transmembrane potential ($\Delta\psi m$). COH-SR4 also increased intracellular ROS production in cancer cells which appeared to be related to the increased activity of certain MAPK proteins in human melanoma cells. RNA sequencing analyses showed that COH-SR4 treatment upregulated a number of genes involved in apoptosis and cellular energetic stress pathways such as protein metabolism, mTOR and MAPK, while downregulating genes involved in DNA replication and cell cycle, suggesting that the antitumor activity of COH-SR4 is at least partially due to inhibition of these pathways in human melanoma cells.

As disclosed herein and demonstrated in the working examples, COH-SR4 treatment effectively inhibited melanoma cell proliferation and induced apoptosis of melanoma cells without causing any significant cytotoxicity in normal cells. The therapeutic effect of COH-SR4 was independent of the genetic background (or driver mutations) of melanoma cells or models. These include BRAF, RAS, and LKB-1 mutations, as well as PTEN and p53. These mutations are known to increase the metastatic and bioenergetic potentials, as well as confer resistance to some chemotherapeutic agents used for melanoma therapy. Administration of COH-SR4 was effective in reducing tumor burden, inhibiting tumor progression and prolonging survival in melanoma animal models. Thus, COH-SR4 can be used for treating melanoma, particularly aggressive, malignant melanoma of various mutations.

Treatment for Lung Cancer

Lung cancer remains the most prominent cause of cancer mortality in the developed world. According to recent estimates in 2012, there will be 226,000 new cases and 160,000 deaths yearly from lung cancer in the United States. A dynamic interplay between host and environmental factors is responsible for the development, progression and the acquisition of drug-resistance in lung cancer. The major risk factor for the development of lung cancer is tobacco smoking and about 90% of all lung cancer patients are current or previous smokers indicating tobacco smoke and associated oxidative-stress in both incidence and progression of lung tumors. Also, a significant fraction of the remaining patients have other risk factors, such as passive smoking, certain genetic factors or exposure to other environmental pathogens. This calls for development of novel agents for the treatment of small-cell and non-small cell lung cancers.

The chronic oxidant-stress induced by tobacco smoking as well as oxidative-stress prevalent in lung tumors leads to up-regulation of the cellular defense pathways that enhance detoxification of toxic products of lipid peroxidation resulting from oxidant-stress. Mercapturic acid pathway (MAP) represents a central axis of the detoxification of toxic end-products of lipid peroxidation. The products of lipid peroxidation like 4-hydroxynonenal (4-HNE) which are formed due to oxidative-stress are conjugated by cellular glutathione S transferases (GSTs) leading to formation of glutathione-conjugate of 4-HNE (GS-HNE) which is rapidly effluxed by the MAP transporter RLIP76, thereby simultaneously preventing the cellular cytotoxicity and feedback product inhibition of GST. Previous studies have revealed that small molecule inhibitors of RLIP76 and RLIP76 targeted antibody are effective choices for targeting lung cancer progression and drug-resistance, which reinforces the mechanistic significance of these first two rate limiting steps in MAP.

The loss of tumor suppressor p53 has not only been implicated as an early molecular event in the development of lung cancer in smokers, but also enables the acquisition of drug-resistant and metastatic phenotypes. Activating mutations in intracellular signal transduction pathways like $KRAS^{G12V}$ lead to constitutive activation of proliferative signals which further enhance the aggressive behavior of p53 null lung tumors. The onset of epithelial-to-mesenchymal transition that accompanies the malignant transformation of normal cells is associated with increased expression of fibronectin and vimentin. Tumor cells also modulate the intracellular energy sensor pathways mediated by the AMPK pathway. Suppression of AMPK activation allows for tumor cell survival in energy depleted conditions. In addition, LKB1, a primary upstream kinase of AMPK, have been shown to modulate lung cancer differentiation and metastasis. Thus, novel agents that can collectively target the critical nodes of adaptations to oxidative-stress, low energy status and enhanced proliferative signaling in lung cancer cells would immensely contribute to the development of more effective therapies for lung cancer. The working examples disclosed herein demonstrated effects of COH-SR4 on critical signaling proteins in lung cancer.

As disclosed herein and demonstrated in the working examples, COH-SR4 treatment effectively inhibited lung cancer cell proliferation and induced apoptosis of lung cancer cells without causing any significant cytotoxicity in normal cells. Similar to its effects on melanoma, COH-SR4 treatment modulated the AMPK-mTOR signaling pathways in cells as well as resected tumor sections of xenograft animals. Admission of COH-SR4 resulted in significant reduction in tumor burdens and inhibited tumor progression in lung cancer animal models.

Treatment for Type 2 Diabetes Mellitus

The number of people suffering from Type 2 diabetes mellitus (T2DM) is skyrocketing worldwide. T2DM, which is characterized by high plasma glucose levels and insulin resistance, if left untreated, can cause severe and sometimes fatal complications. Most current treatments ameliorate the hyperglycemic symptom of the disease but are not effective in correcting its underlying cause. Development of new drugs with new mechanisms of action, in particular those targeting the cause of insulin resistance, is important to improve diabetes therapy. As disclosed herein, COH-SR4 was a novel mitochondrial uncoupler with anti-diabetic properties. COH-SR4 increased oxygen consumption, dissipated mitochondrial membrane potential, induced mitochondrial swelling, and decreased intracellular ATP in cultured cells and isolated liver mitochondria.

As demonstrated in the working examples, oral feeding of COH-SR4 significantly reduced body weight gain, improved glycemic control and insulin resistance, and prevented dyslipidemia in both high fat-diet (HFD) induced obese and diabetic db/db mice. Mitochondrial uncoupling of COH-SR4 resulted to activation of AMP-activated protein kinase (AMPK), leading to the phosphorylation and inhibition of acetyl-CoA carboxylase (ACC). Gene analyses by RT-PCR showed COH-SR4 significantly suppressed the mRNA expression of several lipogenic genes and gluconeogenic genes in the liver of HFD obese mice. RNA sequencing analysis showed that 642 genes were differentially expressed in liver of db/db mice after COH-SR4 treatment (217 upregulated, 425 downregulated). Gene ontology analysis by DAVID indicated COH-SR4 upregulated amino acid metabolism and downregulated lipid and fatty acid synthesis and glucose metabolism.

Thus, COH-SR4 may act as an uncoupler of oxidative phosphorylation and activates AMPK, which can lead to reduction in lipogenesis and cholesterol synthesis and a simultaneous increase in fatty acid oxidation and glucose utilization in obese and diabetic animals. These studies demonstrate that COH-SR4 is a promising compound for treatment of T2DM.

As disclosed herein, a method of treating diabetes (e.g., Type 2 diabetes mellitus (T2DM)) in a subject comprising administering to the subject a pharmaceutical composition comprising a therapeutically effective amount of COH-SR4, a salt thereof, or a stereoisomer thereof.

In certain embodiments of the diabetes treatment methods, the method further comprises administering a pharmaceutical composition comprising one or more secondary therapeutic agents selected from the group consisting of ranibizumab, empagliflozin, linagliptin, duglaglutide, canagliflozin, metformin, abliglutide, dapaglifozin, canagliflozin, alogliptin benzoate, pioglitazone, glimepiride, sitagliptin, simvastatin, saxagliptin, liraglutide, repaglinide, exenatide, pramlintide, glipizide, rosiglitazone maleate, and insulin. The second therapeutic agent(s) may be administered with COH-SR4 in one pharmaceutical composition, or in separate pharmaceutical compositions. The second therapeutic agent(s) and COH-SR4 may be administered simultaneously or sequentially.

Certain embodiments of the methods of treating diabetes disclosed herein further comprises administering an additional therapy e.g., diet to the subject, wherein the additional therapy may be administered simultaneously or sequentially.

In certain embodiments, the pharmaceutical composition is administered by oral administration, intravenous injection, intramuscular injection, subcutaneous injection, intranasal administration, pulmonary administration, transdermal administration, buccal administration, sublingual administration.

In certain embodiments, the pharmaceutical composition is administered three times a day, twice a day, once a day, once every two days, or once every three days over a period of up to 1 week, up to 2 weeks, up to 4 weeks, up to 6 weeks, up to 8 weeks, up to 10 weeks, or up to 12 weeks.

In certain embodiments, the pharmaceutical composition is administered at a daily dose of about 0.005 to about 25 mg/kg, about 0.01 to about 10 mg/kg, about 0.05 to about 1 mg/kg, or 4 mg/kg body weight of COH-SR4, a salt thereof, or stereoisomers thereof. The daily dose may be administered in a single administration or multiple administrations. The dose does not cause significant cytotoxic effects in the subject.

EXAMPLES

The following examples are provided to better illustrate the claimed invention and are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Materials and Methods

Reagents

COH-SR4 ($C_{13}H_8Cl_4N_2O$ Mr 350.03) was synthesized according to a previously validated protocol by Dr. Christopher Lincoln, Director of Chemical GMP Synthesis Facility, Beckman Research Institute of the City of Hope, Duarte, Calif. (88). Elesclomol ($C_{19}H_{20}N_4O_2S_2$ Mr 400.52) was procured from MedChem Express (Monmouth Junction, N.J.). Terminal deoxynucleotidyl-transferase deoxyuridine triphosphate nick-end labeling (TUNEL) fluorescence and avidin/biotin complex (ABC) detection kits were purchased from Promega (Madison, Wis.) and Vector (Burlingame, Calif.), respectively. FCCP, antimycin A, rotenone, 6-ketocholestanol (6-KCH), cyclosporin A (CSA), valinomycin, MitoTempo, tetramethylrhodamine ester (TMRE), MTT, Horseradish peroxidase (HRP)-conjugated anti-mouse, and anti-rabbit secondary antibodies were procured from Sigma (St. Louis, Mo.). PARP, β-actin, pAkt ($S^{473}$), fibronectin, vimentin, Bim, Bcl2, cyclin B1, CDK4, Akt, Ki67, CD31, GAPDH, p38 MAPK ($T^{180}/Y^{182}$), pERK1/2 ($T^{202}/Y^{204}$), pJNK ($T^{183}/Y^{185}$), and pAMPK ($T^{172}$) antibodies were purchased from Invitrogen, Santa Cruz Biotechnology (Columbus, Ohio) and Cell Signaling Technologies (Danvers, Mass.). GSTπ siRNA (GSTP1_1 FlexiTube siRNA; SI00300349) was purchased from Qiagen (Valencia, Calif.). Universal Mycoplasma Detection Kit was procured from ATCC (Manassas, Va.). AMPK and scrambled siRNA were obtained from Invitrogen (San Diego, Calif.). XTT proliferation assay kit was purchased from American Type Culture Collection (ATCC, Manassas, Va.). Antibodies against CDK2, CDK4, cyclin A, cyclin B1, cyclin E1, p27$^{Kip1}$, AMPK, pAMPK ($T^{172}$), ACC, pACC ($S^{79}$), Raptor, p-Raptor ($S^{792}$), TSC2, and pTSC2 ($S^{1387}$) were purchased from Cell Signaling Technology (Danvers, Mass., USA).

Cell Lines and Cultures

Mouse (B16-F0), human (A2058, Hs600T and A101D) melanoma cell lines and the H1417, H1618, H520 and H358 lung cancer cell lines were purchased from the American Type Culture Collection (ATCC, Manassas, Va.). SK-Mel-2, SK-Mel-5, SK-Mel-28, SK-Mel-31, MeWo, A375 human melanoma cells were kindly provided by Dr. Ralf Buettner, Beckman Research Institute of the City of Hope, Duarte, Calif. Normal human dermal fibroblasts (NHDF) and normal human aortic vascular smooth muscle cells (HAVSMC) were kindly authenticated and donated by Dr. Jun Wu, Tumor Biology Core, Beckman Research Institute of the City of Hope, Duarte, Calif., and Dr. Paul Boor, University of Texas Medical Branch, Galveston, Tex., respectively. The cells were immediately expanded and frozen after being obtained and restarted every 3 to 4 months from a frozen vial of the same batch of cells and no additional authentication was done on these cells. All cells were cultured at 37° C. in a humidified atmosphere of 5% $CO_2$ in the appropriate medium: RPMI-1640 (A2058, SK-Mel-2, SK-Mel-5, SK-Mel-28, SK-Mel-31, MeWo, A375, H1417, H1618, H520, and H358) and DMEM (NHDF, HAVSMC, B16-F0, and Hs600T) medium supplemented with 10% heat-inactivated FBS and 1% penicillin/streptomycin solution. All cells lines were free of Mycoplasma infection tested by Universal Mycoplasma Detection kit.

siRNA Mediated Knock-Down of GSTπ

Cells were transfected with scrambled and GSTπ siRNA at the concentration of 10 µg/ml in serum free medium, using Lipofectamine 2000 (Invitrogen, Carlsbad, Calif.) for 3 h, according to the manufacturer's instructions. Excess siRNA was washed off with PBS and complete medium (i.e. with FBS) was added. After 24 h silencing, cells were exposed with COH-SR4. After 96 h incubation, MTT assays as well as Western blot analyses for GSTπ expression were performed.

Mitochondria Isolation

Mitochondria were isolated from the livers of 10 week old male C57BL/6 mice. Mice were euthanized by $CO_2$ inhalation followed by cervical dislocation. Livers were removed, minced with scissors, and immediately placed in ~10 volumes of ice-cold mitochondria isolation medium (250 mM sucrose, 10 mM Tris-HCl, 1 mM EGTA, 1% fatty acid/endotoxin-free BSA, pH 7.4). The presence of BSA in the medium allowed the endogenous free fatty acids to be chelated from the homogenate suspension. The tissues were homogenized using 25-30 strokes in Potter-Elvehjem tissue grinder. Following centrifugation at 800×g for 10 min at 4° C., the fats/lipids were carefully aspirated, and the remaining supernatant was filtered through sterile 0.40 micron nylon mesh membrane and centrifuged at 8,000×g for 10 min at 4° C. The supernatant and any white debris were removed and the mitochondrial pellet were resuspended in ice-cold mitochondrial assay solution (MAS buffer, 70 mM sucrose, 220 mM mannitol, 10 mM $KH_2PO_4$, 5 mM $MgCl_2$, 2 mM HEPES, 1 mM EGTA, 0.2% fatty acid free BSA, pH 7.2) and the centrifugation repeated. The final pellet was resuspended in a minimal volume of MAS buffer. The mitochondrial protein concentration was determined by the DC Protein Assay kit (Bio-Rad, Hercules, Calif.) with BSA as a standard. The isolated mitochondria were placed on ice and used within 3 h.

Measurements of Mitochondrial Respiration in Whole Cells

Oxygen consumption rate (OCR), a measure of OxPhos, and extracellular acidification rate (ECAR), a measure of lactate production by glycolysis, were measured using a Seahorse Xf°96 Flux Analyzers (Seahorse Biosciences, North Billerica, Mass.). Cells were seeded in DMEM media in Seahorse 96-well tissue culture plates at a density of 5×10³ cells/well and allowed to adhere for 24 h. Prior to the assay, the media was changed to unbuffered DMEM containing 25 mM glucose, 1 mM pyruvate and 1 mM glutamine, with 0.2% fatty acid/endotoxin-free BSA (w/v) (pH 7.4) and the cells were equilibrated for 30 min at 37° C. Test compounds were injected during the assay and OCR and ECAR were measured using 2-3 min measurement periods. Similar sets of experiments were performed in the presence of the mitochondria recoupler agent 6-KCH or the mitochondrial permeability transition (MPT) pore blocker CSA, where each compound was injected into the assay media prior to COH-SR4 or FCCP injection. In separate experiments with A2058 and A2058 p° cells, a modified Mitostress test was performed accordingly per Seahorse protocols (89, 90). Briefly, test compounds were injected after oligomycin (ATP synthase inhibitor) treatment followed by injection of rotenone/Antimycin A (Complex 1 and III inhibitor, respectively). OCR was measured throughout the different injections of the stressors and test compounds (indicated by arrows in the figures).

Measurements of Mitochondrial Respiration in Isolated Mitochondria

Isolated mouse liver mitochondria (2 µg/well or 5 µg/well) were seeded on Seahorse 96-well plate, and respiration (OCR) was measured on mitochondria respiring either on pyruvate (10 mM) and malate (2 mM) or succinate (10 mM) and rotenone (2 µM) using a Seahorse 96 Flux Analyzers according to Rogers et al (90).

Mitochondrial Membrane Depolarization Measurements

Cells (4×10⁵/well in 6-well plates) cultured overnight were pre-incubated with the fluorescent indicator of MMP tetramethylrhodamine ester (TMRE, 200 nM) or DMSO control for 30 min at 37° C. in $CO_2$ incubator. Cells were washed with pre-warmed normal DMEM media, and test compounds were added with fresh media for the indicated times. Cells were then trypsinized, collected, centrifuged for 5 min at 800×g, and washed once in pre-warmed PBS-0.2% BSA. Cells were then resuspended in the same buffer prior to flow cytometric analysis. A total of 30,000 cells were counted per sample and data was analyzed by Cyan ADP flow cytometer with excitation/emission of 488 nm/572 nm (Beckman Coulter, Inc., Brea, Calif.). For measurements of membrane potential in isolated mouse liver mitochondria, the organelles were pre-incubated with 200 nM TMRE in $MAS_{SRO}$ buffer (MAS buffer supplemented with 10 mM succinate, 1 µM rotenone, and 1 µM oligomycin) for 20 min at 25° C. The mitochondria were centrifuged for 5 min at 3000×g and resuspended in $MAS_{SRO}$ buffer. Mitochondria were then added to $MAS_{SRO}$ buffer containing the indicated concentrations of COH-SR4, FCCP or DMSO vehicle control and incubated at room temperature for 15 min. The mitochondria were then centrifuged for 5 min at 3000×g. The supernatant was then removed and placed into a black clear bottom 96-well plate (100 µL/well). TMRE fluorescence was measured with a microplate reader (Tecan Infinite M200 Pro, Tecan Group Ltd., Switzerland) using an excitation emission of 545ex/580em.

Mitochondrial Swelling Assay

Mitochondrial swelling was measured in non-respiring mouse liver mitochondria incubated in buffered isotonic potassium acetate in the presence of valinomycin (24,25). Briefly, isolated liver mitochondria were added to 1 mL isotonic acetate buffer (145 mM potassium acetate, 5 mM Tris-HCl, 0.5 mM EDTA, 5 µM valinomycin, and 1 µM rotenone, pH 7.4) in a cuvette at a final concentration of 0.5 mg/mL mitochondrial protein. Absorbance of the mitochondrial suspension before and after addition test compounds was measured every 10 seconds using a Varian Cary 300 spectrophotometer (Agilent Technologies, Santa Clara, Calif.). Swelling was recorded from the decrease in absorbance at 600 nm and expressed as percentage from initial reading after addition of mitochondria.

Adenine Nucleotide Measurement

ATP production from cells treated with test compounds were measured using the Luminescent ATP Detection Assay Kit. AMP, ATP and ADP were measured by UV-HPLC.

Cell viability (MTT) Assay

Cell density measurements were performed using a hemocytometer to count reproductive cells resistant to staining with trypan blue. Approximately 20,000 cells were plated into each well of 96-well flat-bottomed micro-titer plates. After 12 h or 24 h incubation at 37° C., medium containing either COH-SR4 (ranging 0-200 µM) or elesclomol (ranging 0-20 µM) were added to the cells. After 24 h, 48 h or 96 h incubation, 20 µL of 5 mg/mL MTT were introduced to each well and incubated for 2 h. The plates were centrifuged and medium was decanted. Cells were subsequently dissolved in 100 µl DMSO with gentle shaking for 2 h at room temperature, followed by measurement of $OD_{570}$ (91).

Cell Proliferation (XTT) Assay

The effects of COH-SR4 on cell viability were assessed in quadruplicate samples using the 2,3-bis (2-methoxy-4-nitro-5-sulfophenly)-5-[(phenylamino) carbonyl]-2H-tetrazolium hydroxide (XTT) assay. Briefly, 20,000 cells were seeded and incubated in 96-well, flat-bottomed plates in 10% FBS-supplemented culture medium 24 h before drug treatment. After 24 h incubation at 37° C., cells were then exposed to the indicated concentrations of drug at 37° C. in 5% $CO_2$ for 48 h. The medium was removed and replaced with 100 µL fresh medium containing 50 µL of the activated-XTT solution to each well, and the cells were further cultured in the $CO_2$ incubator at 37° C. for 4 h. Absorbance was determined on a plate reader at 475 nm.

Colony Formation Assay

Cell survival was evaluated using a standard colony-forming assay. In total, $1\times10^5$ cells/mL were incubated with COH-SR4 (1.5 µM or 5 µM) or elesclomol (5 µM) for 24 h, and aliquots of 50 or 100 µL were added to 60 mm size petri dishes, containing 4 mL culture medium. After 7 or 10 days, adherent colonies were fixed, stained with 0.5% methylene blue for 30 min and colonies were counted using the Innotech Alpha Imager HP (91).

TUNEL Apoptosis Assay

For TUNEL assay, $1\times10^5$ cells were grown on the cover slips for ~12 h followed by treatment with COH-SR4 (5 µM or 10 µM) or elesclomol (5 µM) for 24 h. Apoptosis was determined by the labeling of DNA fragments with terminal deoxynucleotidyl-transferase dUTP nick-end labeling (TUNEL) assay using Promega fluorescence apoptosis detection system, and examined using Zeiss LSM 510 META laser scanning fluorescence microscope with filters 520 and 620 nm according to the protocol described previously (91). Photographs taken at identical exposure at ×400 magnification are presented. Apoptotic cells showed green fluorescence.

Flow Cytometry Analysis of Cell Cycle Regulation $2\times10^5$ cells were treated with COH-SR4 (0 µM, 5 µM or 10 µM) for 18 h at 37° C. After treatment, floating and adherent cells were collected, washed with PBS, and fixed with 70% ethanol. On the day of flow analysis, cell suspensions were centrifuged; counted and same numbers of cells were resuspended in 500 µL PBS in flow cytometry tubes. Cells were then incubated with 2.5 µL of RNase (stock 20 mg/mL) at 37° C. for 30 min after which they were treated with 10 µL of propidium iodide (stock 1 mg/mL) solution and then incubated at room temperature for 30 min in the dark. The stained cells were analyzed using the Beckman Coulter Cytomics FC500, Flow Cytometry Analyzer. Results were processed using CXP2.2 analysis software from Beckman Coulter.

Apoptosis Detection by Annexin V-FITC

Apoptosis of cells were measured based on loss of membrane integrity using Annexin V-FITC Apoptosis Detection Kit as described by the supplier (BD Biosciences Pharmingen, San Diego, Calif.), in which the early- and late-death cells were stained with Annexin V-FITC and propidium iodide. Cells were analyzed using a CyAn ADP cytometer (Beckman Coulter Inc) to quantify fluorescence. Apoptotic cells were defined as Annexin V-FITC positive.

Mitochondrial ROS Production

Mitochondrial ROS generation in melanoma cells were assessed by MitoSox™ Red (Thermo Fisher), a fluorogenic dye developed and validated for highly selective detection of superoxide in the mitochondria of living cells. Briefly, cells ($4\times10^5$ well) were seeded in a 6-well plate and incubated overnight. Twenty-four hours after plating, cells were treated with test compounds as indicated in each experiment. After washing with pre-warmed PBS, cells were incubated with fresh medium containing 5 µM MitoSox Red for 15 min at 37° C. The fluorescence intensity was measured at of $530_{ex}/590_{em}$ using flow cytometry (Cyan ADP). The cells only sample (no MitoSox dye added) was used as the background. Approximately 30,000 counts were made for each sample. Experiments were repeated for three times and at least duplicate samples were included in each experiment.

RNA Isolation and Sequencing for Melanoma Studies

B16-F0 cells ($4\times10^5$/well in 6-well plates) were treated with 5 µM COH-SR4 or vehicle (DMSO) and RNA isolated 4 and 24 h post treatment. Three biological replicates were prepared for each time point as well as control untreated cells. After treatment, total RNA was prepared using RNeasy Mini Kit (Qiagen) according to the manufacturer's instructions, eluted in 50 µL of RNase/DNase-free water, and initial concentration and purity assessed by NanoDrop ND-1000 spectrophotometer (NanoDrop Technologies, Wilmington, Del.). Prior to sequencing, RNA quality was also assessed by microfluidic capillary electrophoresis using an Agilent 2100 Bioanalyzer and the RNA 6000 Nano Chip kit (Agilent Technologies, Santa Clara, Calif.). Sequencing libraries were prepared with the TruSeq RNA Sample Prep Kit V2 (Illumina, San Diego, Calif.) according to manufacturer's protocol with minor modifications. Briefly, ribosomal RNA was removed from 500 ng of total RNA using RiboZero kit (Illumina) and the resulting RNA was ethanol precipitated. Pellets were resuspended in 17 µL of Elute/Prime/Fragment Mix (Illumina) and first-strand cDNA synthesis performed using DNA polymerase I and RNase H. cDNA was end repaired, 3' end adenylated, and universal adapter ligated followed by 10 cycles of PCR using Illumina PCR Primer Cocktail and Phusion DNA polymerase (Illumina). Libraries were purified with Agencourt AMPure XP beads, validated with Agilent Bioanalyzer 2100, and quantified with Qubit (Life Technologies). Libraries were sequenced on Illumina Hiseq 2500 with single end 40 bp reads. Reads were aligned using TopHat (2.0.8b) to human genome hg19.

Quantitative Real-Time PCR (qRT-PCR) Validation

To confirm the results obtained from RNA-seq analysis, several up- and down-regulated genes at 24 h post COH-SR4 treatment were selected and analyzed by qRT-PCR. First strand cDNA was prepared using the High Capacity cDNA Reverse Transcription Kit (Life Technologies). Pre-validated primer pairs were purchased from Bio-Rad Laboratories (PrimePCR™ PCR Primers). qRTPCR was performed on three independent samples per treatment using the ABI-7500 Fast Real Time PCR system (Life Technologies) and Power SYBR Green master mix. After initial incubation for 2 min at 50° C., the cDNA was denatured at 95° C. for 10 min followed by 40 cycles of PCR (95° C. for 15 s, 60° C. for 60 s).

Quantitative Real Time PCR and RNA Sequence Analysis for Diabetes/Obesity Studies Total RNA was isolated from livers of lean, vehicle or COH-SR4-treated HFD mice using standard protocols and subjected to quantitative RT-PCR using primers for key genes associated with lipid and fatty acid synthesis (Acaca, Pparg, Acly, Scd1, Srebf1, Hmgcr, Cpt1, Fasn) and gluconeogenesis (G6pc, Pck1). Livers of db/+ and db/db mice treated with vehicle or COH-SR4 were used for RNA-seq analysis. RNA isolation, purification, sequencing, library preparation and read alignments were done at the City of Hope Functional Genomics Core facility. Differential gene expression was identified from standard Partek workflow (Partek Genomics Suite v6.6, Partek, Inc) using ANOVA, with step-up FDR multiple testing correction p-value of <0.05 and 1.5× fold change. Gene ontology for COH-SR4 treatment up- or downregulated genes were analyzed for functional enrichment using the Database for Annotation, Visualization, and Integrated Discovery (DAVID, v6.7). Databases utilized included GOTERM_BP_FAT (biological process) and Kyoto Encyclopedia of Genes and Genomes (KEGG_PATHWAY).

Western Blotting

Cell or tissue proteins were extracted with cell lysis buffer (Cell Signaling Technology) and protein concentration was determined using the DC Protein Assay kit (Bio-Rad, Hercules, Calif., USA). Equal amount of proteins (~40 μg) were loaded onto 4-15% Criterion TGX gels (Bio-Rad, Hercules, Calif.), resolved by SDS-PAGE electrophoresis, and then transferred onto nitrocellulose membranes for immunoblotting. Membranes were blocked with 5% skimmed milk in Tris-buffered saline containing 0.05% Tween 20 before incubation overnight at 4° C. with desired primary antibodies. Immuno-reactive proteins were visualized by peroxidase-labeled secondary antibodies and ECL system (Western Lightning Chemiluminescence Reagent, Perkin-Elmer, Mass., USA). Equal loading of proteins was confirmed by stripping and re-probing the membranes with either β-actin or GAPDH antibodies. Band intensities were quantified using a densitometer (Quantity One, Bio-Rad, Hercules, Calif.).

Analysis of COH-SR4 in Serum by Mass Spectrometry

Mice (n=3 each for control and COH-SR4 treatment) were administered either 0.2 mL corn oil or 100 μg COH-SR4/0.2 mL corn oil/mice (4 mg/kg b.w.) by oral gavage on alternate days for 8 weeks. On the last day, the blood was collected within 2 h after final dosage. To 50 μL serum was added 0.5 μL 5 μg/μL 6D-SR4 standard in DMSO and 500 μL ethyl acetate. The samples were vortexed for 1 min and then spun down in a bench-top centrifuge for 2 min. Then 400 μL of the organic layer was collected, evaporated to dryness and redisolved in 500 μL methanol for analysis. After an initial concentration test, 50 μL were taken and diluted to 2 mL with methanol for final analysis. A calibration curve was built using a serial dilution of COH-SR4 (from 0.1 μg/μL to 1 ng/μL) in 125 pg/μL 6D-SR4.

COH-SR4 and 6D-SR4 were separated by HPLC using an Agilent Zorbax 0.5×150 mm C18, 5 μm column with a flow rate of 50 μL/min and a gradient of 65% B to 95% B over 4 min, then 2 min at 95% B and 1 min back to 65% B. Buffer A was 5 mM ammonium formate and buffer B was 5 mM ammonium formate in methanol. The elute from the column was introduced into an Agilent 6410 triple quadrupole tandem mass spectrometer by electrospray ionization (ESI) through a capillary maintained at 4 kV, using 6 L/min nitrogen nebulizing gas at 350° C. and 15 psi, fragmentor voltage=190 V. The following transitions were monitored in positive ion mode: 344>127.1 and 355>130.1 (collision energy=28 V), 344>161.9 and 355>164.9 (C.E.=20 V) for COH-SR4 and 6dSR4. Quantification was achieved using Masshunter Quantitative Analysis 5 (Agilent Technologies) using a linear calibration curve.

In Vivo Xenograft Studies

Figure 63:
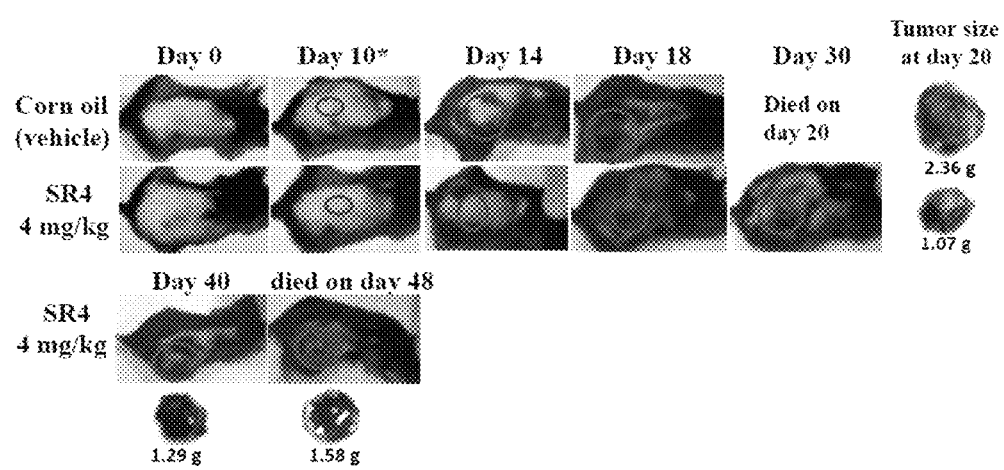
FIG. 63: Effect of COH-SR4 on syngeneic B16-F0 mouse melanoma model.
Figure 64:
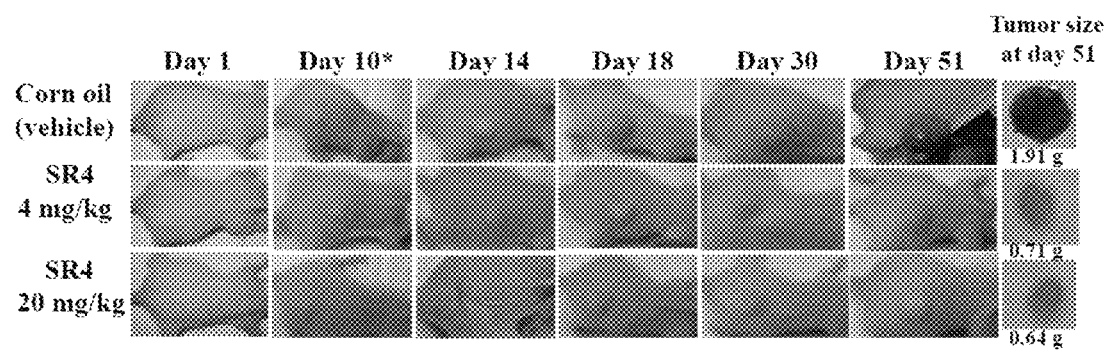
FIG. 64: Effect of COH-SR4 on A2058 human melanoma nude mice xenografts model.

For melanoma studies, C57B mice (for syngeneic B16-F0 mouse melanoma model) and Hsd: Athymic nude nu/nu mice (for A2058 human melanoma mouse xenografts model), were obtained from Harlan, Indianapolis, Ind. All animal experiments were carried out in accordance with a protocol approved by the Institutional Animal Care and Use Committee (IACUC). In each model, ten 10-weeks-old mice were divided into two groups of 5 animals (treated with corn oil (vehicle), and COH-SR4 compound 4 mg/kg b.w.). All animals were injected with 2×10$^6$ melanoma cells suspensions in 100 μL of PBS, subcutaneously into one flank of each mouse. At the same time, animals were randomized into treatment groups as indicated in the figures (FIGS. 63 and 64). Treatment was started 10 days after the implantation to see palpable tumor growth. Treatment consisted of 0.1 mg of COH-SR4/mice in 200 μL corn oil by oral gavage alternate day. Control groups were treated with 200 μL corn oil by oral gavage alternate days. Animals were examined daily for signs of tumor growth. Tumors were measured in two dimensions using calipers. Photographs of animals were taken at day 1, day 10, day 14, day 18, day 20, day 30, and day 51 after subcutaneous injection, are shown for all groups. Photographs of tumors were also taken at day 20 (for syngeneic model), and at day 51 (for xenograft model).

For lung cancer studies, twelve 10-weeks-old mice were divided into two groups of 6 animals (treated with corn oil (vehicle), and COH-SR4 compound 4 mg/kg b.w.). All animals were injected with 2×10$^6$ H358 cells suspensions in 100 μL of PBS, subcutaneously into one flank of each mouse. At the same time, animals were randomized treatment groups as well as control groups. Treatment was started 10 days after the implantation to see palpable tumor growth. Treatment consisted of 0.1 mg of COH-SR4/m ice in 200 μL corn oil by oral gavage alternate day. Control groups were treated with 200 μL corn oil by oral gavage alternate day. Animals were examined daily for signs of tumor growth. Tumors were measured in two dimensions using calipers. Photographs of animals were taken at day 1, day 10, day 14, day 18, day 30, and day 60 after subcutaneous injection.

Animal Experiments for Diabetes/Obesity Studies

All animal experiments were carried out in accordance with the protocols approved by the Institutional Animal Care and Use Committee of the City of Hope. Nine-week old male C57BL/6J mice fed on high fat diet (HFD, 60% fat) and 10-week old db/db mice were given COH-SR4 (5 mg/kg B.W.) or vehicle (corn oil) via oral gavage every other day for six and five weeks, respectively. Oral glucose tolerance test was performed on animals after an overnight fast. All other metabolic parameters were measured at the end of study. Liver samples were stained with H&E and Oil Red O.

Histopathological Examination of Tumors for Angiogenic, Proliferative and Differentiation Markers For melanoma studies, control and COH-SR4 treated B16-F0 and A2058 melanoma bearing mice tumor sections were used for histopathologic analyses. Immuno-histochemistry analyses were performed for Ki-67 expression (marker of cellular proliferation), CD31 (angiogenesis marker), and pAMPK (cellular regulator of lipid and glucose metabolism) from tumors in mice of control and COH-SR4-treated groups. Statistical significance of difference was determined by two-tailed Student's t test, p<0.001, COH-SR4-treated compared with control. Immuno-reactivity was evident as a dark brown stain, whereas non-reactive areas displayed only the background color. Sections were counterstained with Hematoxylin (blue). Photomicrographs at 40× magnification were acquired using Olympus DP 72 microscope. Percent staining was determined by measuring positive immuno-reactivity per unit area. Arrows represent the area for positive staining for an antigen. The intensity of antigen staining was quantified by digital image analysis using DP2-BSW software. Bars represent mean±S.E. (n=5); *p<0.001 compared with control.

For lung cancer studies, control and COH-SR4 treated H358 lung cancer bearing mice tumor sections were used for histopathologic analyses. Immuno-histochemistry analyses were performed for Ki67, CD31, E-cadherin, and pAMPK expressions. Immuno-reactivity was evident as a dark brown stain, whereas non-reactive areas displayed only the background color. Sections were counterstained with Hematoxylin (blue). Photomicrographs at 40× magnification were acquired using Olympus DP 72 microscope and were processed with DP2-BSW software. Percent staining was determined by measuring positive immuno-reactivity per unit area. The intensity of antigen staining was quantified by digital image analysis using Image Pro plus 6.3 software.

Statistical Analysis

All data were evaluated with a two-tailed unpaired student's t test and are expressed as the mean±SD. The statistical significance of differences between control and treatment groups was determined by ANOVA followed by multiple comparison tests. Changes in tumor size and body weight during the course of the experiments were visualized by scatter plot. Differences were considered statistically significant when the p value was less than 0.05.

RNA-Seq, qRTPCR, and Gene Ontology

Differential gene expression was identified from standard Partek workflow (Partek Genomics Suite v6.6, Partek, Inc) using ANOVA, with step-up FDR multiple testing correction p-value <0.05 and requiring a >1.5× fold change between each time point and control samples. Gene ontology for the 24 h COH-SR4 treatment up- or down-regulated genes were analyzed for functional enrichment using the Database for Annotation, Visualization, and Integrated Discovery (DAVID, v6.7) (92). Databases included: GOTERM_BP_FAT (biological process), and Kyoto Encyclopedia of Genes and Genomes (KEGG_PATHWAY). For inclusion, terms required an EASE score of p<0.005. Fold-changes in gene expression between control and 24 h COH-SR4 treatment were derived from the comparative CT method (93) with β-actin as an internal control. Correlation between the expression values detected by RNA-seq (normalized log 2 RPKM fold-change) and qRTPCR (mean fold change) for the 9 genes tested was estimated by calculating Spearman's Rho correlation in the Prism 6.0 software (GraphPad, San Diego, Calif.). For expression distribution via box plots, average RPKM values for genes falling within each ontology term were log 2 converted and box plots generated with BoxPlotR software (94). Mann-Whitney U-tests were used to assess statistical significance between time points (two-tailed,*p<0.05).

Mitochondrial Measurements, ROS, Intracellular ATP Levels, AMP:ATP Ratios, and MTT Assays Data are presented as mean±SEM. At least 2 independent biological replicates with triplicate measurements were taken. Additional details can be found in corresponding figure legends. Statistical significance from control samples was assessed with a two-way ANOVA, Sidak's post test (*p<0.05). Unpaired student t-tests were also used for TMRE and intracellular AMP:ATP ratios (*p<0.05). Statistical tests were conducted using Prism 6.0 software.

Example 1. Modulation of COH-SR1, COH-SR2, COH-SR3, COH-SR4, COH-SR6, COH-SR7, LR23 and LR59 on Development of Preadipocyte Cells and Adipocyte Cells A) Effects of COH-SR1, COH-SR2, COH-SR3, COH-SR4, COH-SR6, COH-SR7, LR23 and LR59 on Adipocyte Differentiation of 3T3-L 1 Cells (FIGS. 4 and 5)

Figure 4:
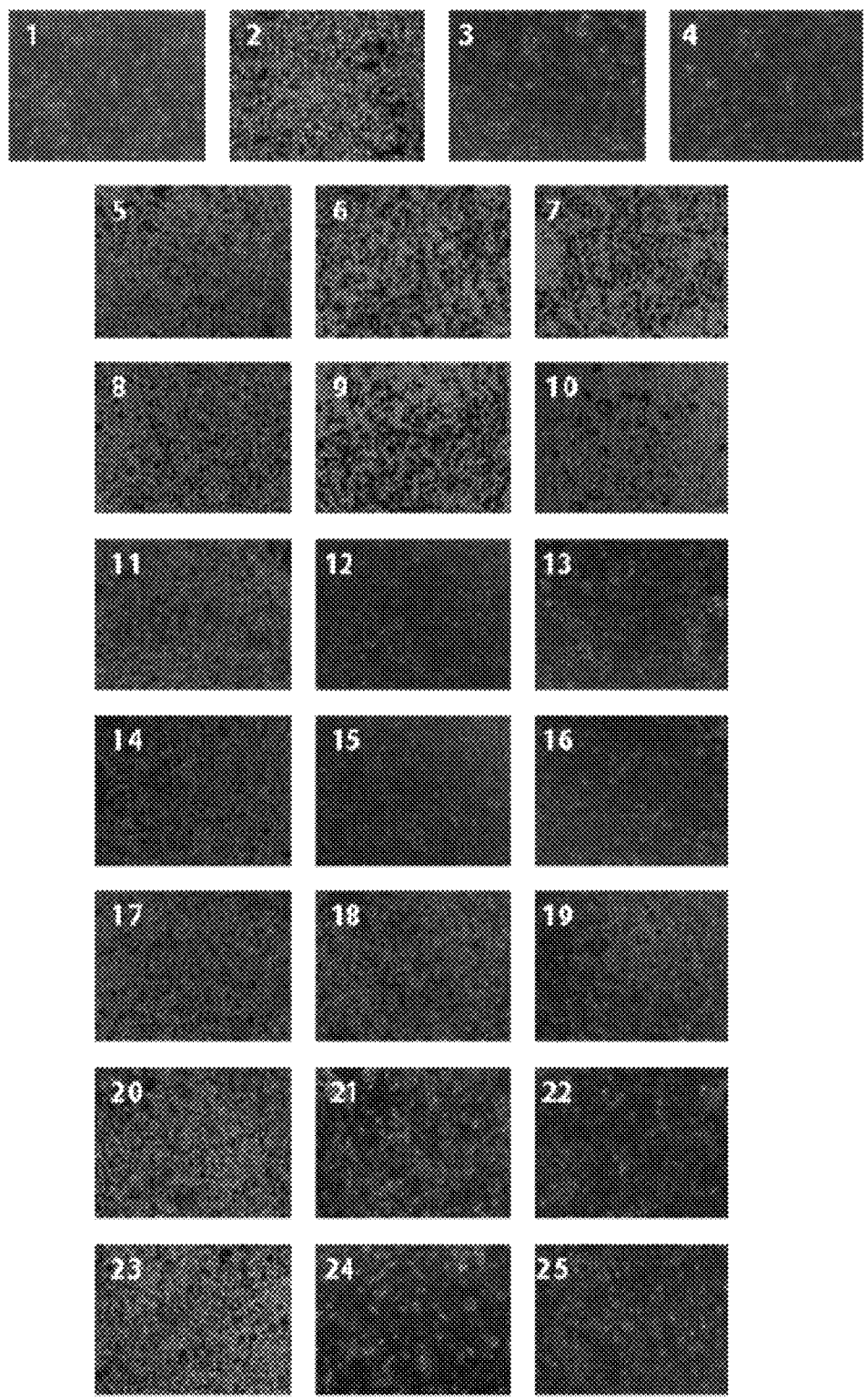
FIG. 4: Effects of COH-SR1, COH-SR2, COH-SR3, COH-SR4, COH-SR7, LR23 and LR59 on adipocyte differentiation of 3T3-L1 cells shown by morphological changes associated with adipogenesis using Oil Red O staining. 1=control (preadipocytes); 2=DM (preadipocytes treated with differentiating media); 3=DM+0.5 μM Trichostatin A (TSA); 4=DM+1 μM Apicidin; 5~7=DM+5, 10, 25 μM COH-SR1; 8~10=DM+5, 10, 15 μM COH-SR2; 11~13=DM+2.5, 5, 10 μM COH-SR3; 14~16=DM+1, 2.5, 5 μM COH-SR4; 17~19=DM+5, 10, 15 μM COH-SR7; 20~22=DM+10, 25, 50 μM LR23; and 23~25=DM+10, 25, 50 μM LR59.
Figure 5:
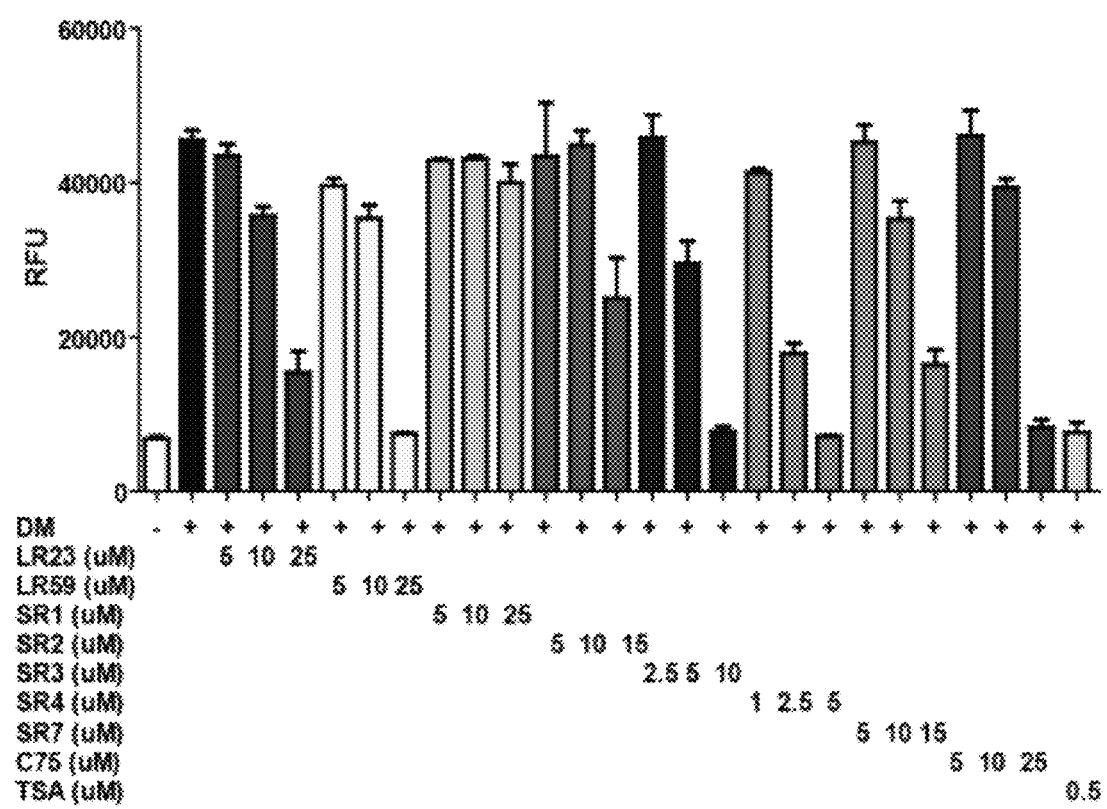
FIG. 5: Effects of COH-SR1, COH-SR2, COH-SR3, COH-SR4, COH-SR7, LR23 and LR59 on adipocyte differentiation of 3T3-L1 cells, shown by intracellular triglyceride contents (AdipoRed Assay™).

In a 3T3-L1 cell model, under conditions that normally promoted differentiation of preadipocyte to adipocytes, all seven test compounds (COH-SR1, COH-SR2, COH-SR3, COH-SR4, COH-SR7, LR23 and LR59) dose-dependently inhibited differentiation and accumulation of lipid droplets, similar to TSA and apicidin, two known HDAC inhibitors, as well as C75, a known inhibitor of fatty acid synthase (FAS) (FIGS. 4 and 5).

Two-day post-confluent 3T3-L1 preadipocyte cells were allowed to differentiate for 7 days in the presence of nothing, DM only, DM+ a test compound (COH-SR1, COH-SR2, COH-SR3, COH-SR4, COH-SR7, LR23 or LR59), or DM+ a positive control (TSA, C75, or Apicidin). Morphological changes associated with adipogenesis were assessed by Oil Red O Staining and shown in FIG. 4.

Intracellular triglyceride contents were measured using AdipoRed Assay™ and the results were shown in relative fluorescence units (RFU) in FIG. 5.

Figure 6:
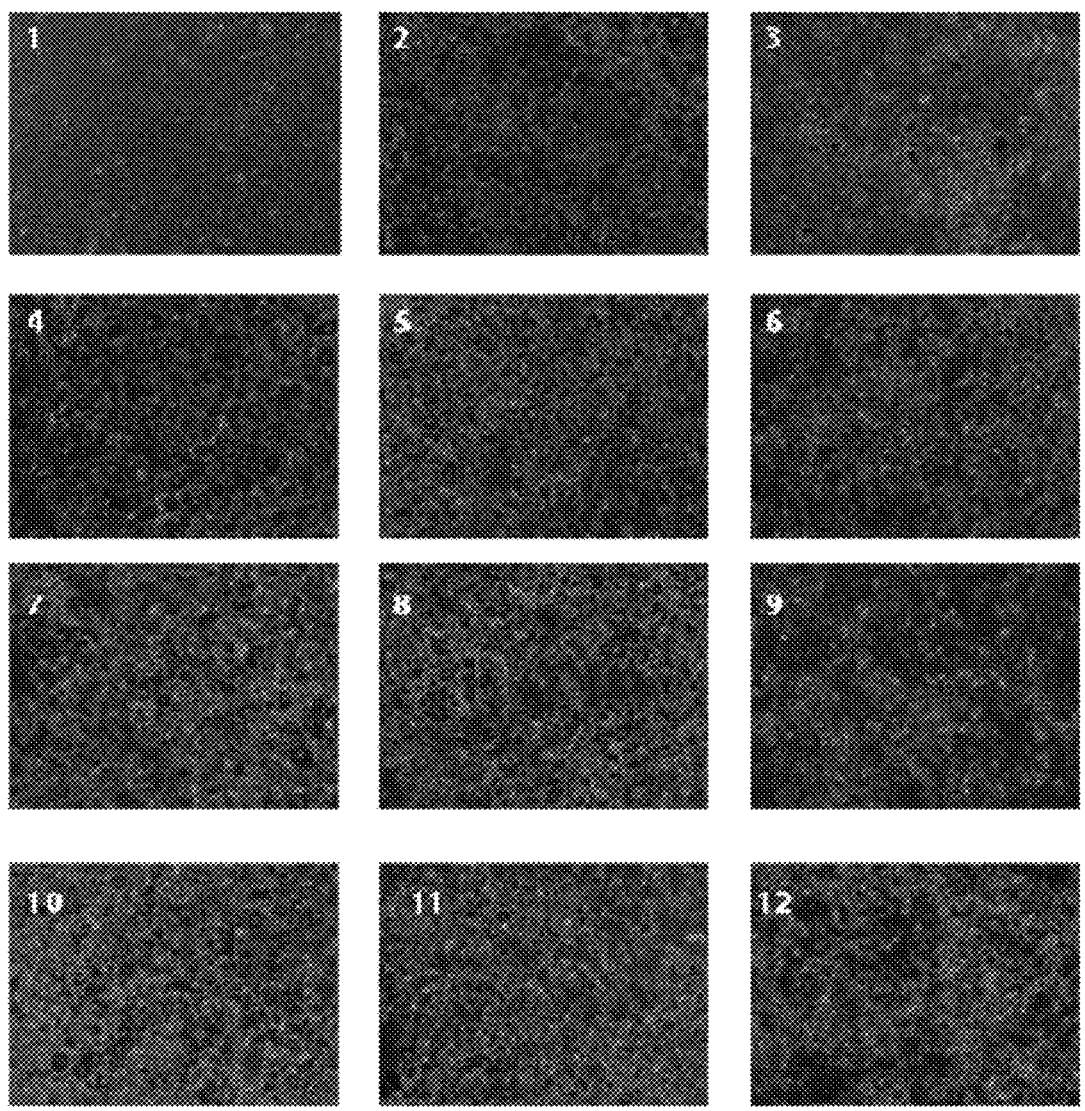
FIG. 6: Effects of COH-SR3, COH-SR7 and LR59 on the dedifferentiation of fully differentiated adipocytes, shown by the morphological change associated with adipogenesis using Oil Red O staining. 1=control, 2=DM, 3=DM+1 μM Apicidin, 4~6=DM+2.5, 5, 10 μM COH-SR3, 7~9=DM+10, 25, 50 μM COH-SR7, 10~12=DM+10, 25, 50 μM LR59.

B) Effects of COH-SR3, COH-SR7 and LR59 on Dedifferentiation of Fully Differentiated Adipocytes (FIG. 6)

Fully differentiated adipocyte cells were differentiated for 7 days and were treated for additional 3 days with DM+ a test compound (COH-SR3, COH-SR7, or LR59), DM+ a positive control (Apicidin, TSA or C75), DM, or nothing (control).

Morphological changes associated with adipogenesis were assessed by Oil Red O Staining (FIG. 6), and showed that COH-SR3, COH-SR7, and LR59 induced dedifferentiation of fully differentiated adipocytes.

Figure 7:
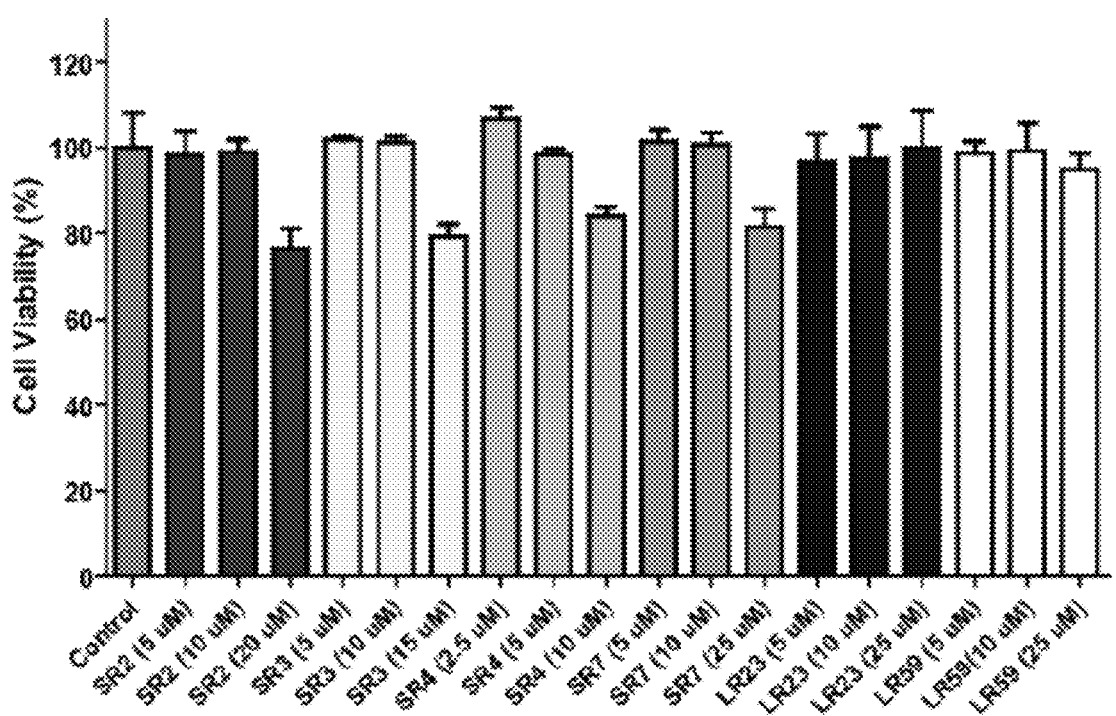
FIG. 7: Effects of COH-SR2, COH-SR3, COH-SR4, COH-SR7, LR23, and LR59 on cell viability of preadipocytes (MTT assay).

C) Effects of COH-SR2, COH-SR3, COH-SR4, COH-SR7, LR23 and LR59 on Preadipocytes (FIG. 7)

Undifferentiated 3T3-LI cells were treated with COH-SR2, COH-SR3, COH-SR4, COH-SR7, LR23 or LR59 for 3 days at a concentration of 2.5 µM, 5 µM, 10 µM, 15 µM, 20 µM, or 25 µM. The cell viability for each treatment was determined by MTT assay (FIG. 7). The result showed that COH-SR2, COH-SR3, COH-SR4 and COH-SR7 inhibited the earlier stage of the adipogenic process (preadipocyte proliferation) as all four compounds inhibited growth of undifferentiated 3T3-L1 cells.

Figure 8:
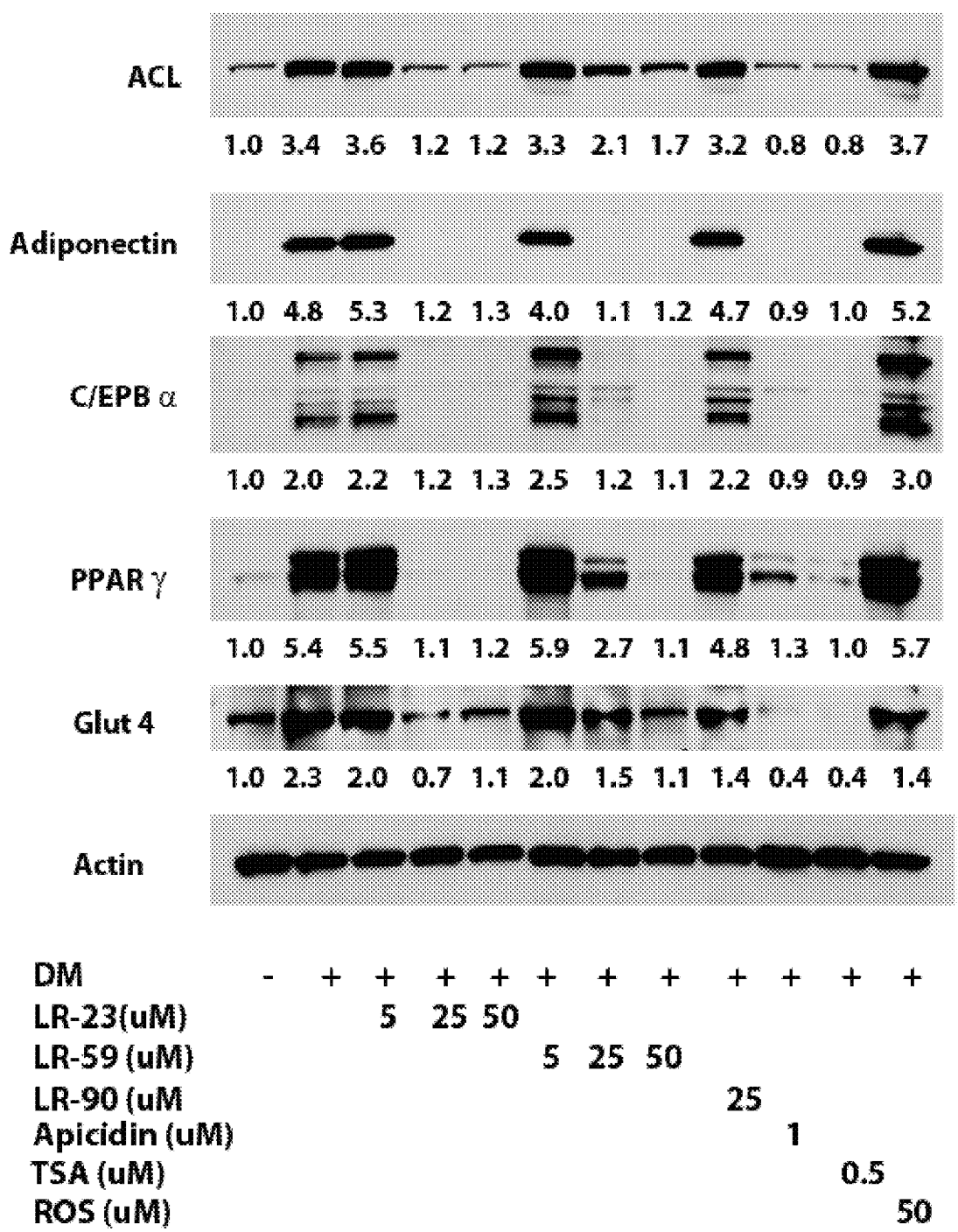
FIG. 8: Effects of LR23, LR59 and LR-90 on protein expression of selected adipogenic markers ACL, adiponectin, C/EBPα, Glut4, and PPARγ. DM=preadipocytes treated with differentiating media, TSA, Ros (Rosiglitazone, positive control).

D) Effects of LR23 and LR59 on Protein Expression of Selected Adipogenic Markers ACL, Adiponectin, C/EBPα, Glut4, and PPARγ (FIG. 8).

Post-confluent 3T3-L1 preadipocytes were differentiated for 7 days in the presence of differentiating media (DM), or DM+ test compounds (LR23 (5 µM, 25 µM, or 50 µM), LR59 (5 µM, 25 µM, or 50 µM), LR-90 (25 µM), ROS (50 µM), TSA (0.5 µM) or apicidin (1 µM)). Protein levels were analyzed by Western blotting and the relative expression of each protein was quantified using a densitometer and calculated according to the reference bands of β-actin (FIG. 8). Numbers above each blot represent fold increase over control (undifferentiated preadipocytes).

It is shown that the expression of adipogenic marker genes such as PPARγ, C/EBPα, ACL and adiponectin, which are upregulated during adipocyte differentiation, was also inhibited by the test compounds.

Figure 9A:
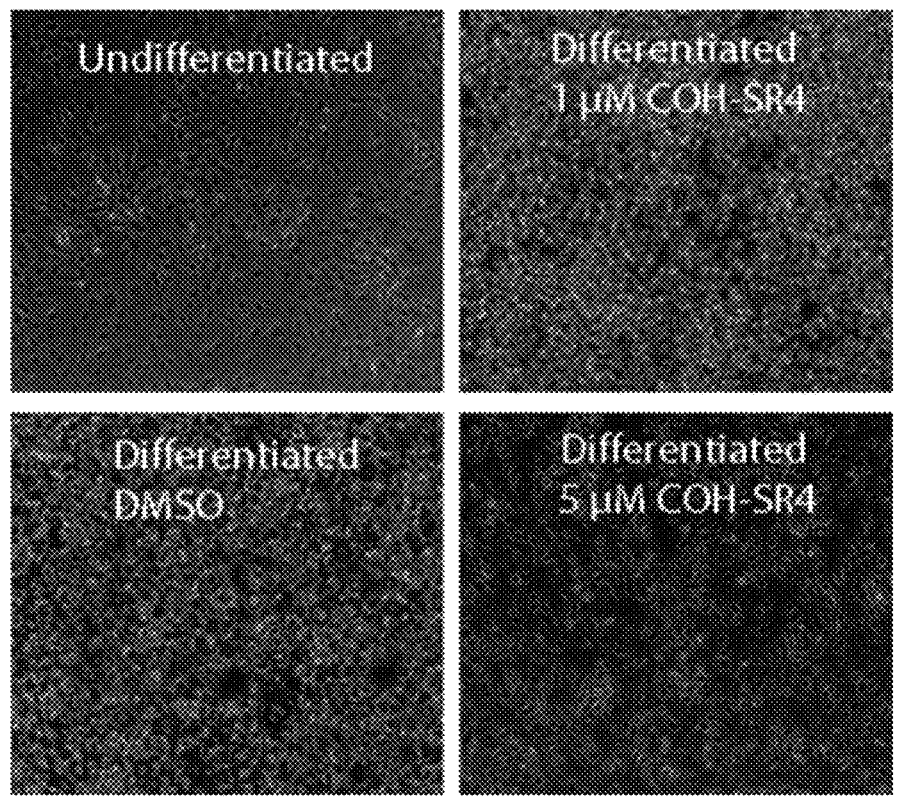
FIGS. 9A-9C: Effects of COH-SR4 on adipocyte differentiation, COH-SR4 prevented accumulation of fat droplets as indicated by (FIG. 9A) reduced Oil Red O staining, (FIG. 9B) decreased intracellular triglyceride contents, and (FIG. 9C) decreased expression of key transcription factors (C/EBPα, PPARγ) and proteins (ACL, adiponectin, FAS) involved in adipocyte development.
Figure 9B:
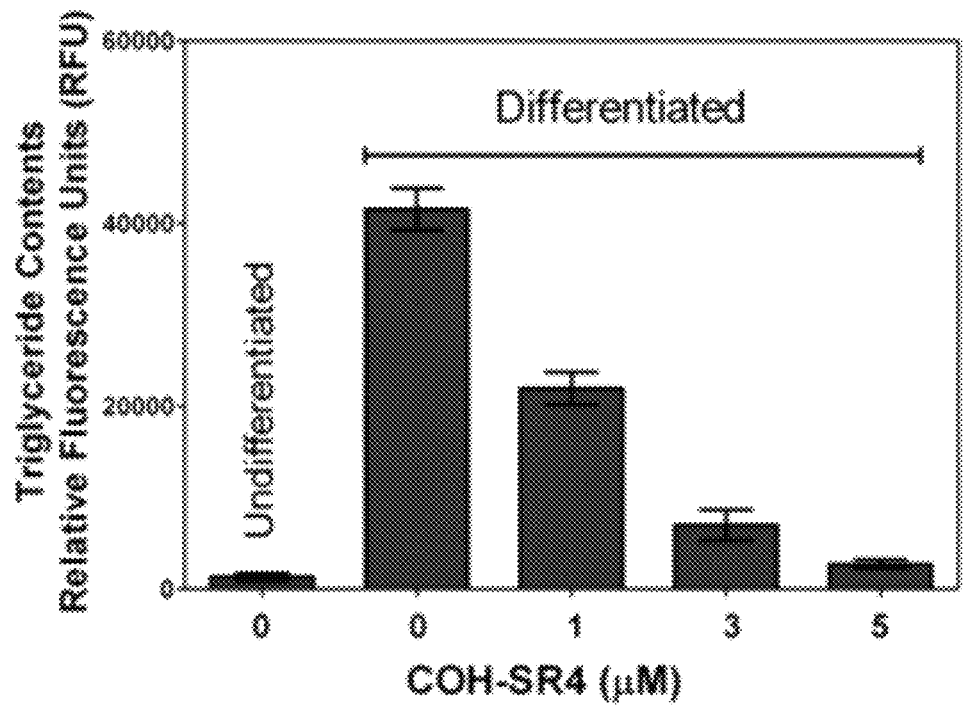
Figure 9C:
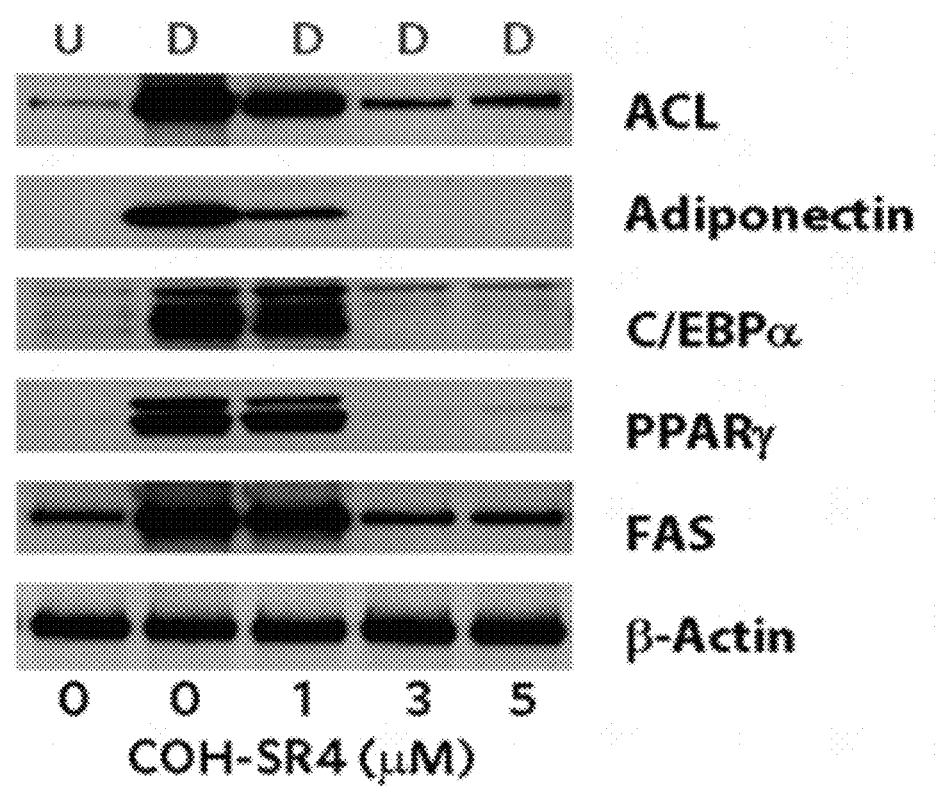

E) Effects of COH-SR4 on Adipocyte Differentiation (FIGS. 9A-C)

3T3-L1 preadipocytes cells were treated with differentiating media (DM) with COH-SR4 (1 µM, 3 µM, or 5 µM) or without for 7 days. COH-SR4 prevented accumulation of fat droplets, as shown by morphological changes associated with adipogenesis using Oil Red O staining (FIG. 9A), decreased intracellular triglyceride contents (FIG. 9B), and decreased expression of key transcription factors (C/EBPα, PPARγ) and proteins (ACL, adiponectin, FAS) involved in adipocyte development (FIG. 9C). As used in FIG. 9C, U=undifferentiated, D=differentiated with cocktail media.

F) Conclusion

The results showed that in the 3T3-L1 cell model, under conditions that normally promote differentiation of preadipocyte to adipocytes, COH-SR1, COH-SR2, COH-SR3, COH-SR4, COH-SR7, LR23 and LR59 attenuated the differentiation and accumulation of lipid droplets, similar to TSA and apicidin, two known HDAC inhibitors, as well as C75, a specific inhibitor of FAS (FIG. 4). In addition, intracellular triglyceride contents were also dose-dependently reduced by all these compounds (FIG. 5). COH-SR3, COH-SR7 and LR59 treatment also induced dedifferentiation of fully differentiated adipocytes, as evidenced by the fact that these compounds decreased Oil Red O-staining in mature adipocytes (FIG. 6).

Undifferentiated 3T3-LI cells treated with COH-SR2, COH-SR3, and COH-SR4 inhibited the earlier stage of the adipogenic process (preadipocyte proliferation) as all three compounds inhibited growth of undifferentiated 3T3-L1 cells (FIG. 7). Such inhibition on preadipocyte proliferation may be associated with cell cycle arrest similar to what were observed in cancer cells such as HL-60 leukemia cells (see Example 3) where COH-SR3 and COH-SR4, as well as all-trans retinoic acid (ATRA, as a control) prevented cellular proliferation and arrested growth via G0/G1 arrest and modulation of various cyclin-dependent kinases (CDKs) and induction of p21 and p27.

Thus the results suggest that treatment of adipocytes with the COH-SR compounds prevented the adipocyte differentiation and accumulation of triglycerides in these cells. The COH-SR compounds may find therapeutic application in the prevention of obesity by reducing fat mass and lowering body weights.

Example 2. Effects of COH-SR Compounds on AMPK Activations in Cancer Cells and Adipose Cells (FIGS. 10A-B)

Figure 10A:
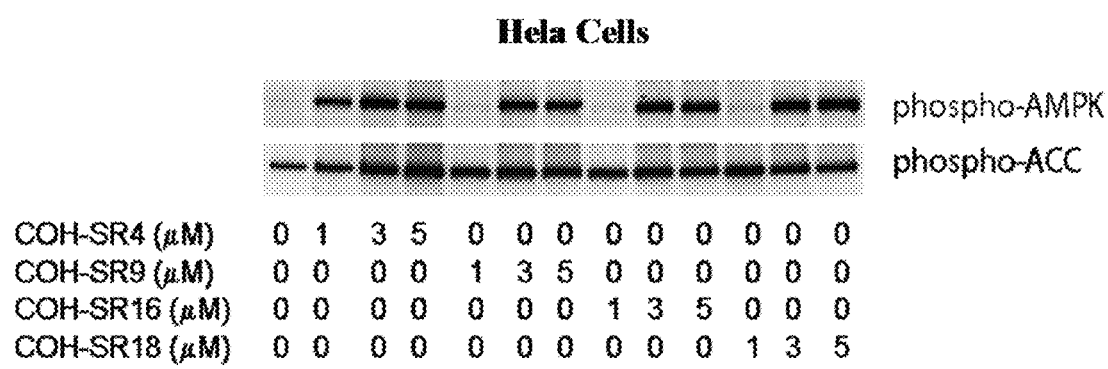
FIG. 10A: Dose-dependent AMPK activation by COH-SR4, COH-SR9, COH-SR16, and COH-SR18 in Hela cells.
Figure 10B:
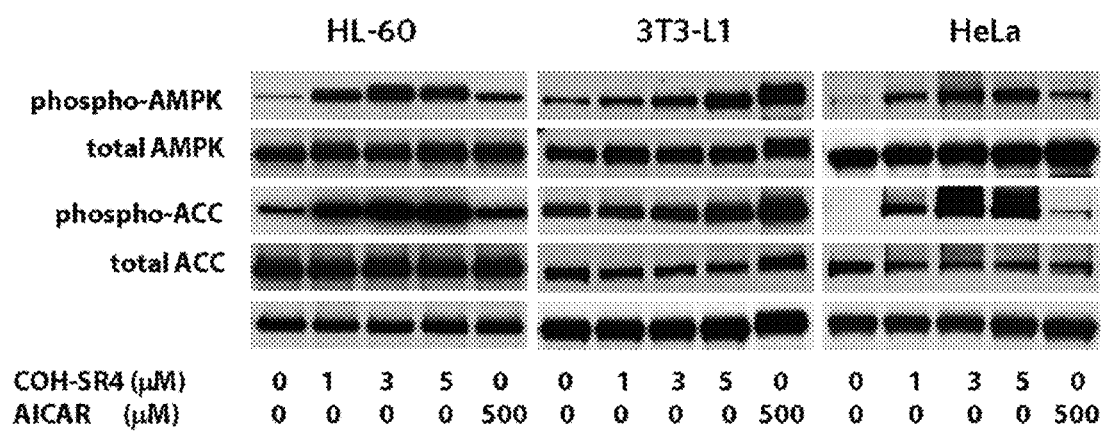
FIG. 10B: Dose-dependent AMPK activation by COH-SR4 in Hela, HL-60 and 3T3-L1 cells.

Activation of AMPK was associated with the phosphorylation of the α-subunit on Thr-172 of as assessed using phospho-specific antibodies (FIGS. 10A-B). AMPK activation also leads to the increased phosphorylation of the target protein acetyl-CoA carboxylase (ACC) (FIG. 10B).

Cells of each cell lines (Hela, HL-60, and 3T3-L1) were treated for 1 hour with a test compound (COH-SR4, COH-SR9, COH-SR16, or COH-SR18) at a concentration of 1 μM, 3 μM, or 5 μM, or AICAR (5-aminoimidazole-4-carboxamideriboside, an AMPK agonist used as positive control) at a concentration of 500 μM, or none of the above (the untreated cells as negative control). Total cell lysates from the untreated cells and the cells treated with a test compound or AICAR were analyzed by Western blot assay using specific antibodies against phospho-AMPK, phospho-ACC, total AMPK and total ACC.

COH-SR compounds activated AMPK in Hela ovarian cancer cell line (FIG. 10A). HeLa cells lack the LKB1 gene and do not express LKB1 mRNA and protein, thus indicating that COH-SR compounds activated AMPK independent of the LKB1 pathway.

COH-SR4 showed the highest potency among the COH-SR compounds tested (FIG. 10A).

FIG. 10B showed that COH-SR4 activated AMPK in human promyelocytic leukemia HL-60 cell lines and adipose cell line 3T3-L1.

Figure 11A:
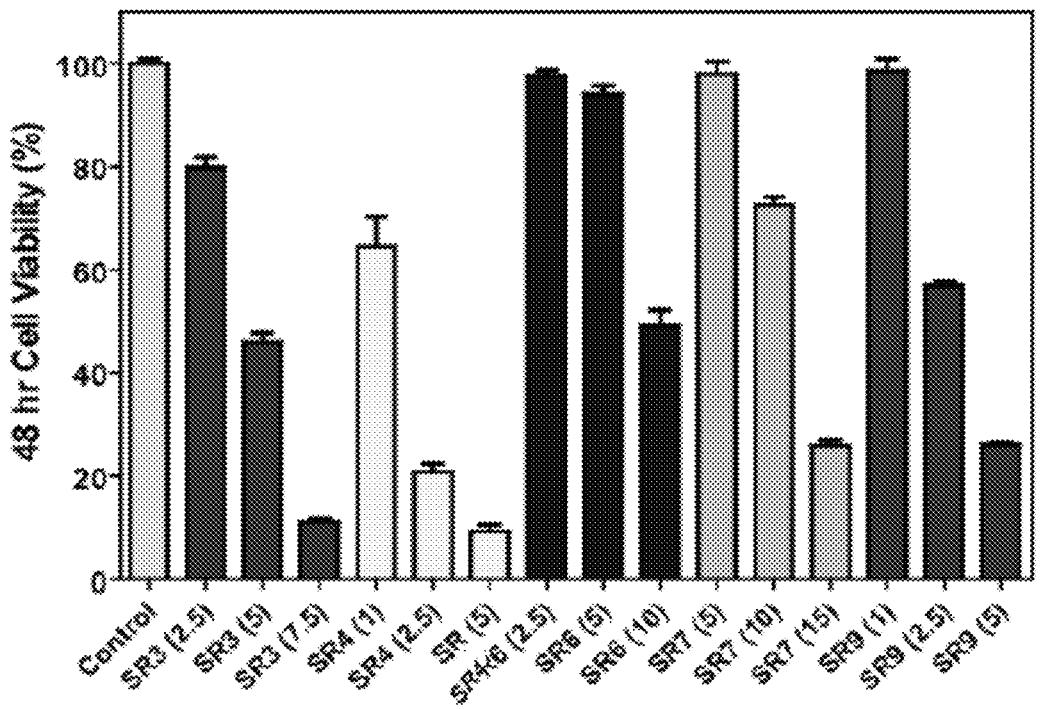
FIG. 11A: COH-SR3, COH-SR4, COH-SR6, COH-SR7, and COH-SR9, inhibited growth and proliferation of HL-60 cells, incubation time was 48 hours.
Figure 11B:
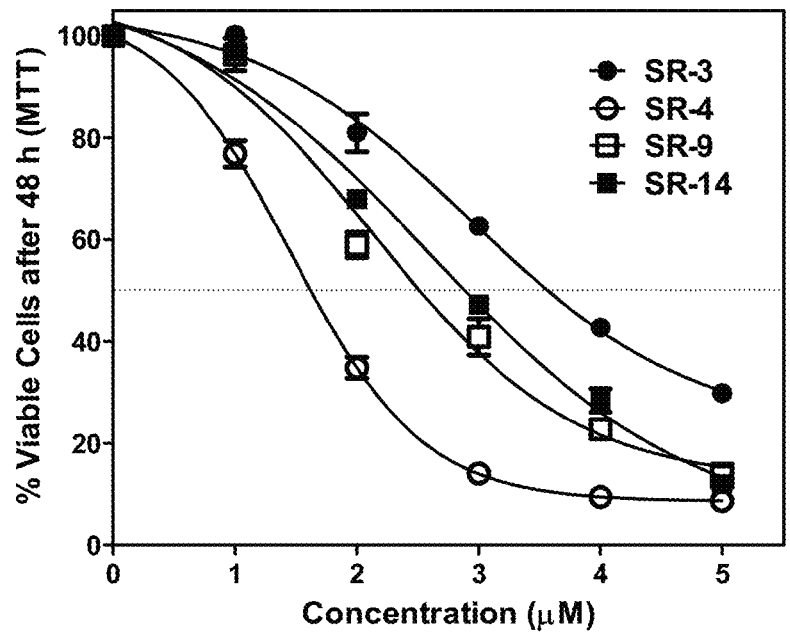
FIG. 11B: Dose-dependent effects of COH-SR3, COH-SR4, COH-SR9, and COH-SR14 on cell viability of HL-60 cells, incubation time was 48 hours.
Figure 13:
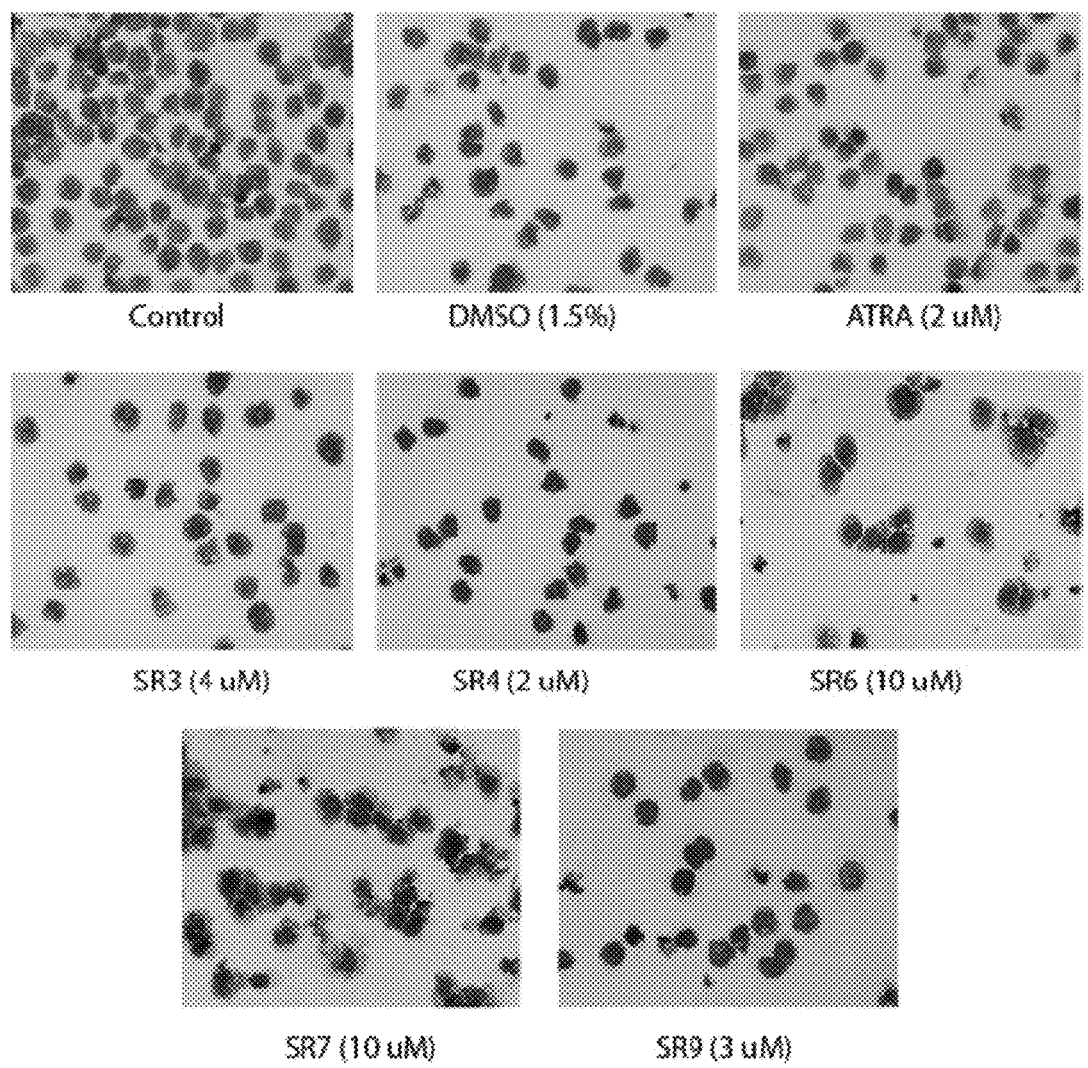
FIG. 13: COH-SR3, COH-SR4, COH-SR6, COH-SR7, and COH-SR9 induced myeloid differentiation of HL-60 cells.

Example 3. COH-SR3, COH-SR4, COH-SR6, COH-SR7, COH-SR9 and COH-SR14 Inhibited Growth and Proliferation of Human Meyoblastic Leukemia Cell Line (HL-60) (FIGS. 11A-B~13)

(A) COH-SR3, COH-SR4, COH-SR9, and COH-SR-14 Inhibited Growth and Proliferation of HL-60 Cells, Shown by Dose and/or Time-Dependent Effects Thereof on Cell Viability of HL-60 Cells (FIGS. 11A-B and 12A-B).

HL-60 is an uncommitted human meyoblastic leukemia cell line that grows avidly in culture. HL-60 cells ($5 \times 10^4$) were incubated with a test compound (COH-SR3, COH-SR4, COH-SR6, COH-SR7, COH-SR9, or COH-SR14) of various concentrations (1~15 μM) or without any test compound for 48 hours. The numbers of viable cells after the incubation periods were measured by the MTT assay and shown in FIGS. 11A and 11B. Numbers after each compound represented the concentration in μM in FIG. 11A. COH-SR3, COH-SR4, COH-SR6, COH-SR7, COH-SR9 exhibited cytotoxicity and prevented cell proliferation of HL-60 leukemia cells (FIG. 11A). COH-SR3, COH-SR4, COH-SR9, and COH-SR14 exhibited cytotoxicity and prevented cell proliferation of HL-60 leukemia cells with $IC_{50}$ of less than 5 μM (FIG. 11B). Three independent experiments were carried out with 3 duplications each, and data are shown as mean±SE.

Figure 12A:
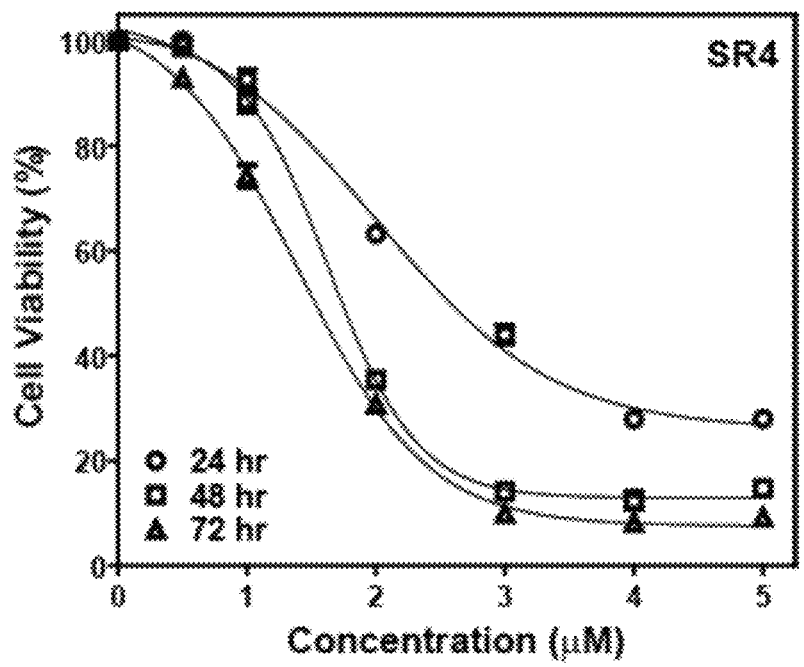
FIG. 12A: Dose and time-dependent effects of COH-SR4 on cell viability of HL-60 cells.
Figure 12B:
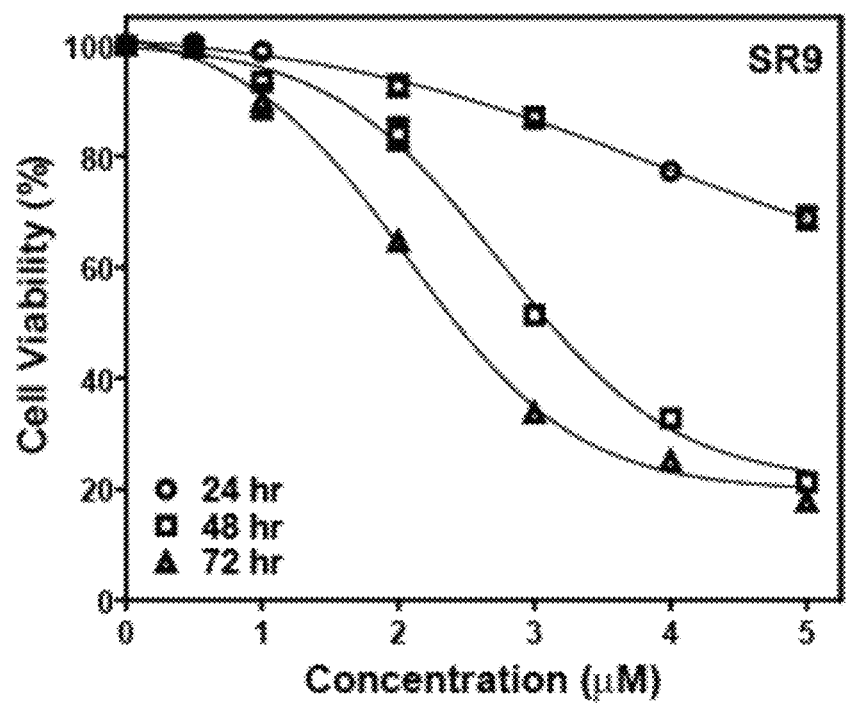
FIG. 12B: Dose and time-dependent effects of COH-SR9 on cell viability of HL-60 cells.

A dose and time-dependent cytotoxic and anti-proliferative effects of COH-SR4 and COH-SR9 on HL-60 cells were observed, as shown in FIG. 12A and FIG. 12B respectively. COH-SR4 and COH-SR9 had an $IC_{50}$ around 1.7 μM and 2.5 μM, respectively, after 72 hours incubation with the test compounds (FIGS. 12A and 12B). Three independent experiments were carried out with 3 duplications each, and data are shown as mean±SE.

(B) Test Compounds (COH-SR3, COH-SR4, COH-SR6, COH-SR7, and COH-SR9) Induced Myeloid Differentiation of HL-60 Cells (FIG. 13).

HL-60 cells are also bipotent cells with the capacity to differentiate either into myeloid or monocytes/macrophages. The effects of the test compounds to induce differentiation in these cells were also tested and shown in FIG. 13.

HL-60 cells were incubated with a test compound at various concentrations (2~10 μM), DMSO, or without any test compound for 48 hours, and then examined for morphologic changes by Giemsa-Wright stain. The results were observed microscopically and shown in FIG. 13 at a magnification of ×400. HL-60 cells treated with COH-SR3, COH-SR4, COH-SR6, COH-SR7, or COH-SR9 exhibited cytoplasmic vacuolation, reduced nucleus-to-cytoplasmic ratio, and absence of prominent nucleoli (FIG. 13). Such results were similar to cells treated with DMSO or all-trans retinoic acid (ATRA), wherein DMSO or ATRA terminally differentiated HL-60 cells into myeloid cells (FIG. 13).

(C) COH-SR4 and COH-SR9 Induced Superoxide Production as Indicated by the Increased Numbers of Nitro Blue Tetrazolium (NBT)-Positive Cells (FIGS. 14A-D).

Figure 14A:
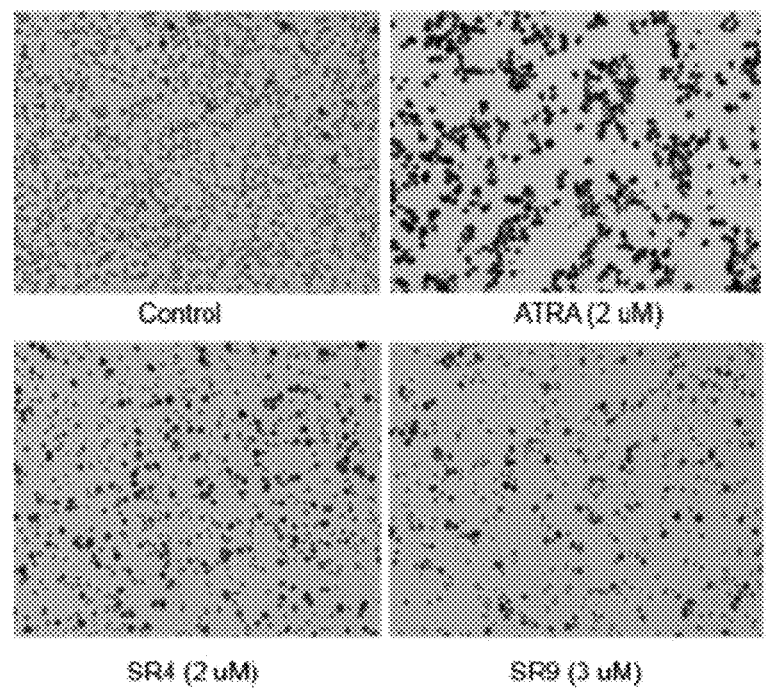
FIGS. 14A-14D: COH-SR4 and COH-SR9 induced superoxide production of HL-60 cells.
Figure 14B:
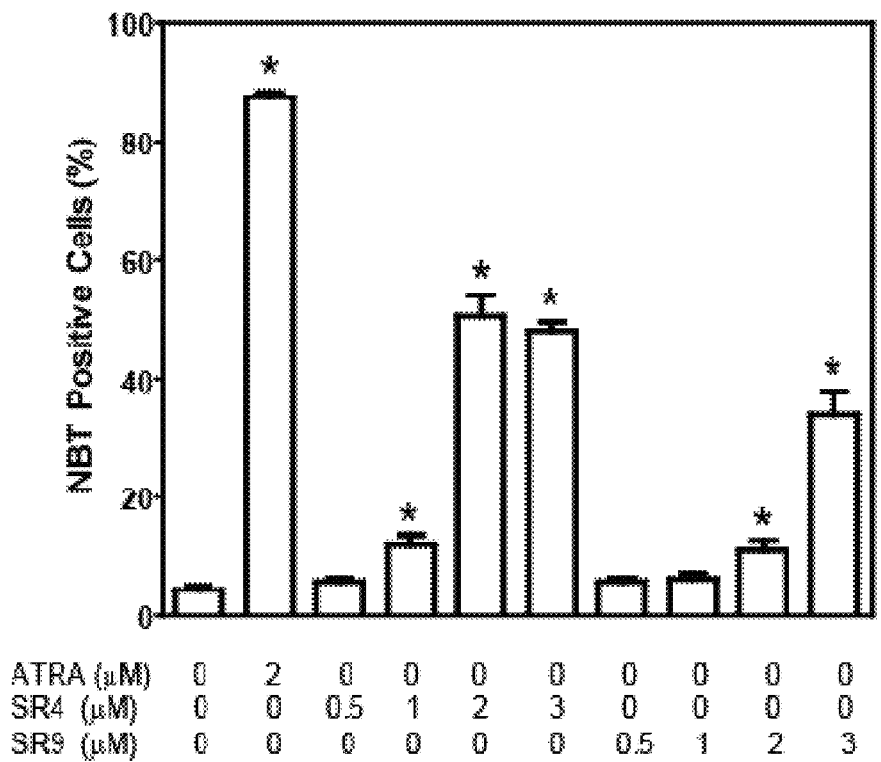

HL-60 cells ($2.5 \times 10^5$) were treated with or without a test compound for 48 hours and then stained with NBT, wherein positively-stained cells appeared as purple black (FIG. 14A). NBT positive cells were counted and the overall percentage was calculated based on 200 total cells counted for each treatment. Three~four independent experiments were carried out, and data are shown as mean±SE (FIG. 14B). This measurement of "oxidative burst" by the NBT assay is a well-known and extensively tested functional marker of HL-60 cell differentiation.

Figure 14C:
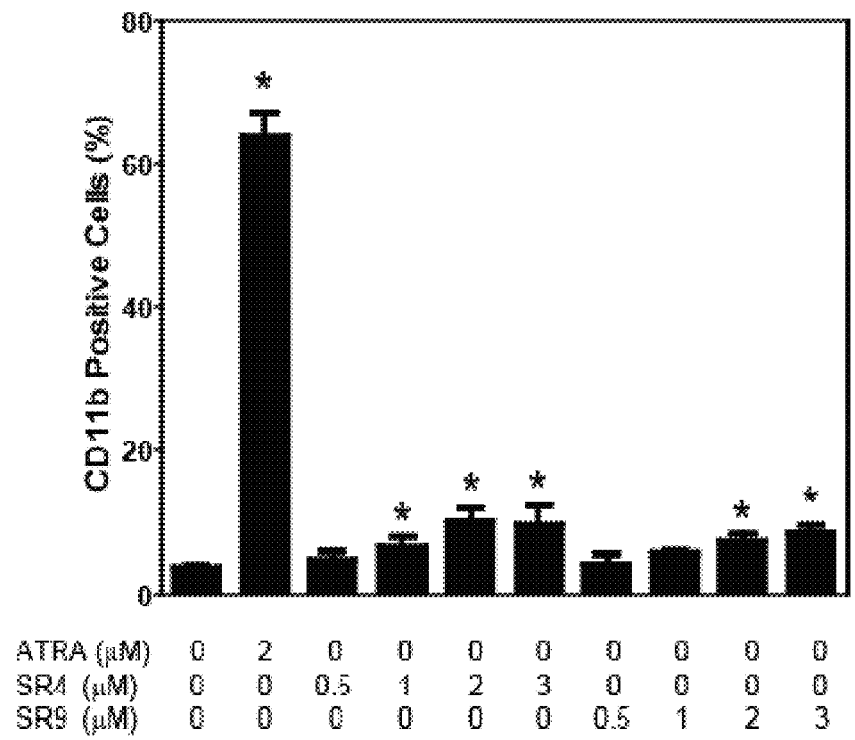
Figure 14D:
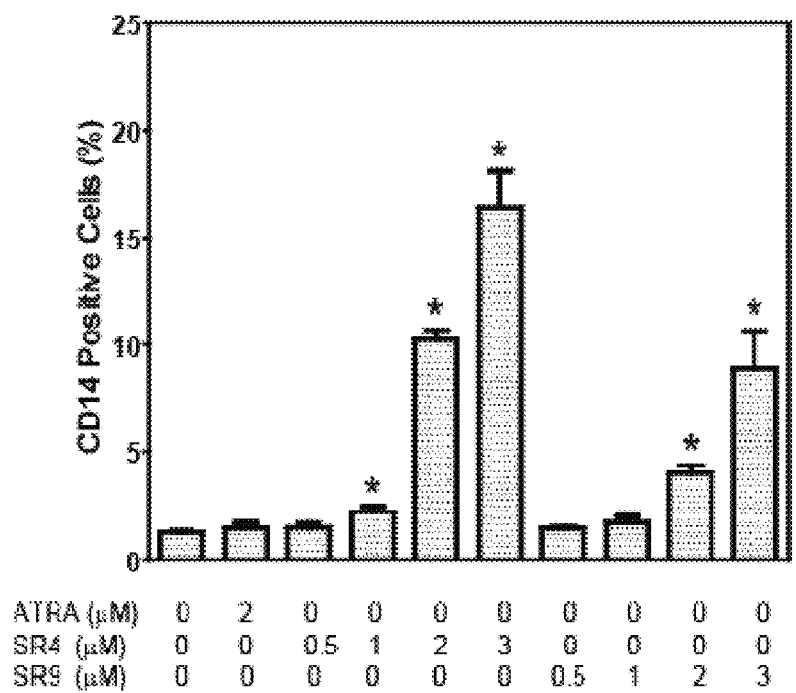

Additionally, using flow cytometry analyses, cell differentiation was further confirmed by dose-dependent increase in expression of both CD11 b and CD14 monocyte/macrophage differentiation markers on the cell surface of HL-60 cells treated with COH-SR4 or COH-SR9 (FIGS. 14C and 14D). HL-60 cells ($2.5 \times 10^5$) were incubated with a test compound (COH-SR4 or COH-SR9) at a concentration of 0.5 μM, 1 μM, 2 μM, or 3 μM, or without any COH-SR compound for 48 hours and then assessed for the surface expression of CD11b (FIG. 14C) and CD14 (FIG. 14D) by flow cytometry, respectively. Three-four independent experiments were carried out, and data are shown as mean±SE (FIGS. 14C and 14D).

Cellular differentiation of HL-60 leukemia cells into mature terminal cells is associated with the inhibition of cell proliferation, followed by programmed cell death or apoptosis. It is known that several anti-cancer agents may alter regulation of the cell cycle machinery, resulting in an arrest of cells in different phases of the cell cycle and thereby reducing the growth and proliferation even inducing apoptosis of cancerous cells. The results showed that COH-SR compounds can do the same.

Figure 15A:
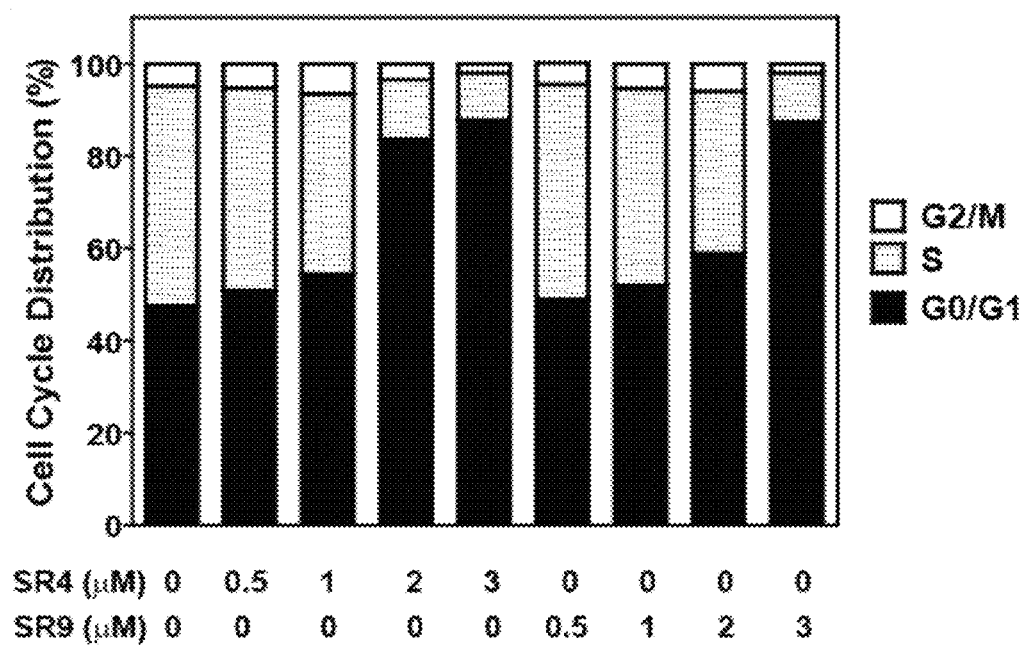
FIGS. 15A-15C: COH-SR4 and COH-SR9 induced a dose and time-dependant G0/G1 phase arrest in HL-60 cells.
Figure 15B:
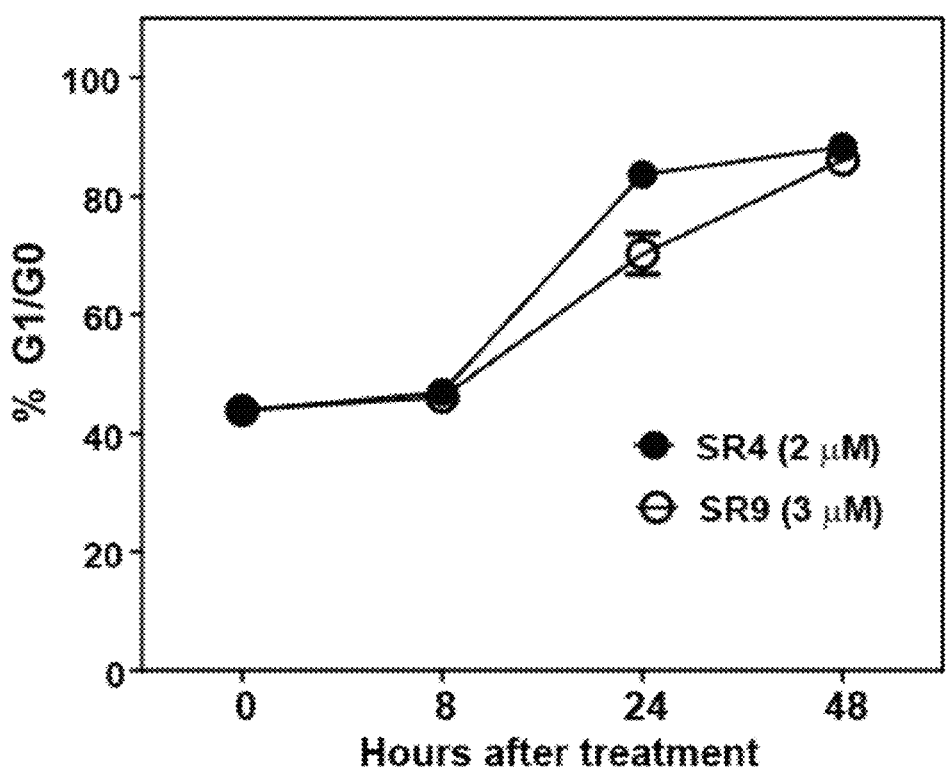
Figure 15C:
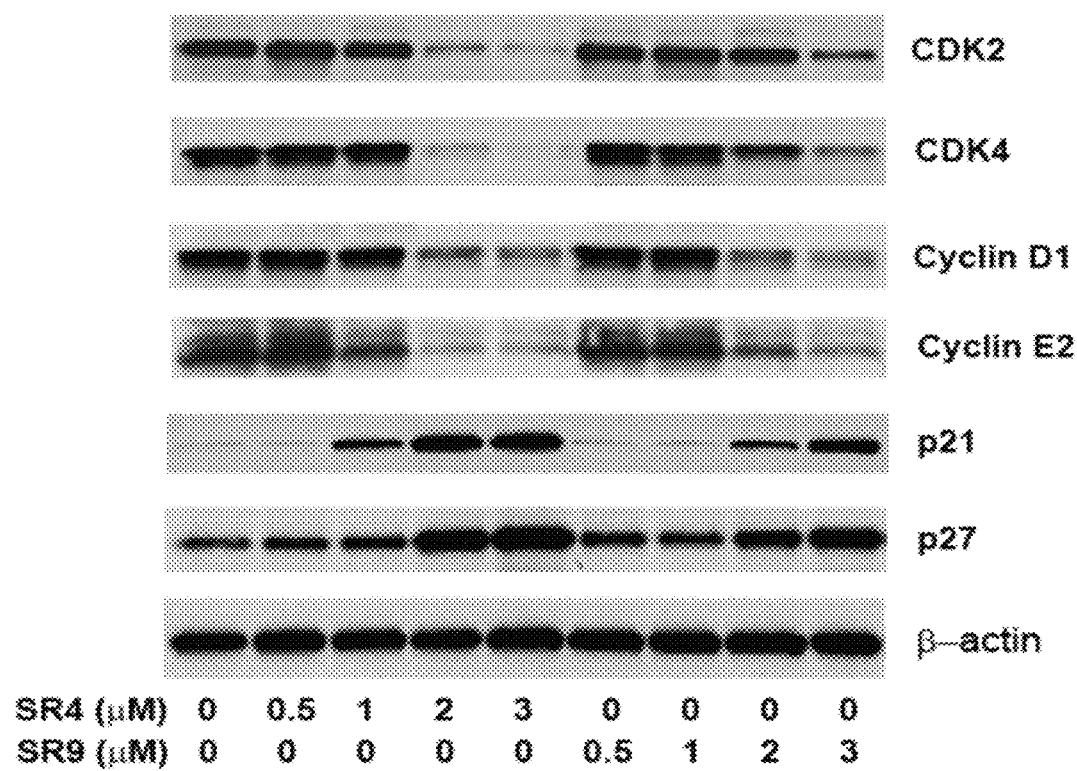
Figure 16A:
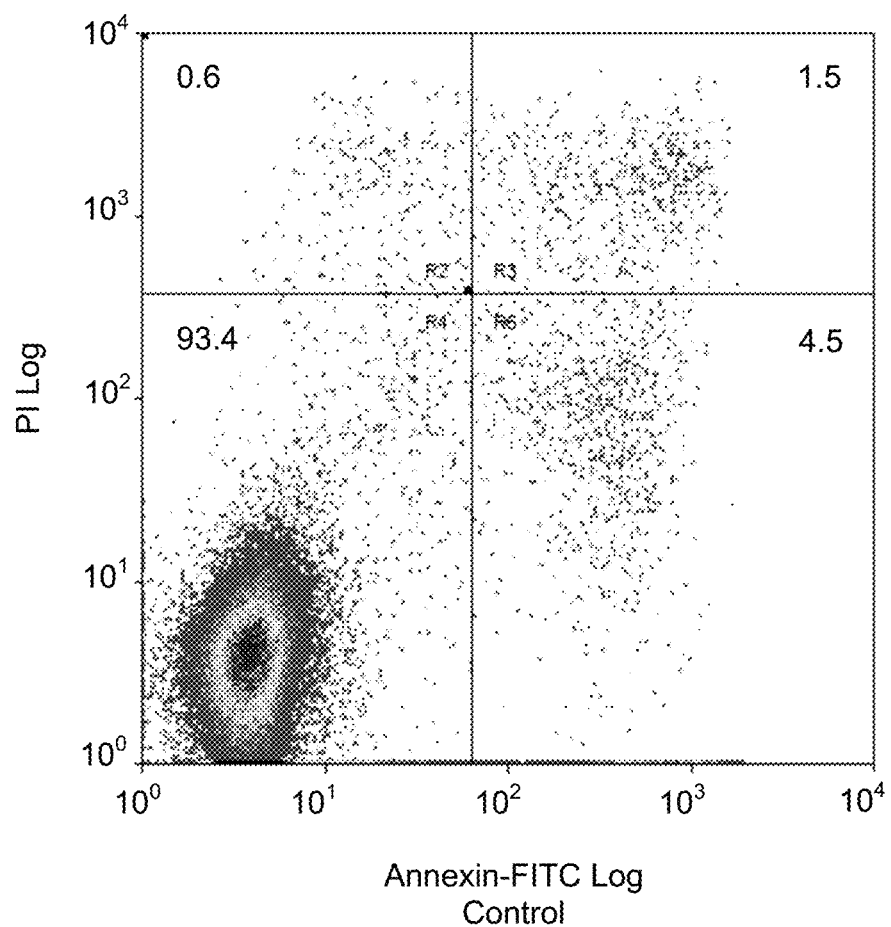
FIGS. 16A-H: COH-SR4 and COH-SR9 induced apoptosis of HL-60 as shown by representative cytograms of Annexin V-PI double staining.
Figure 16B:
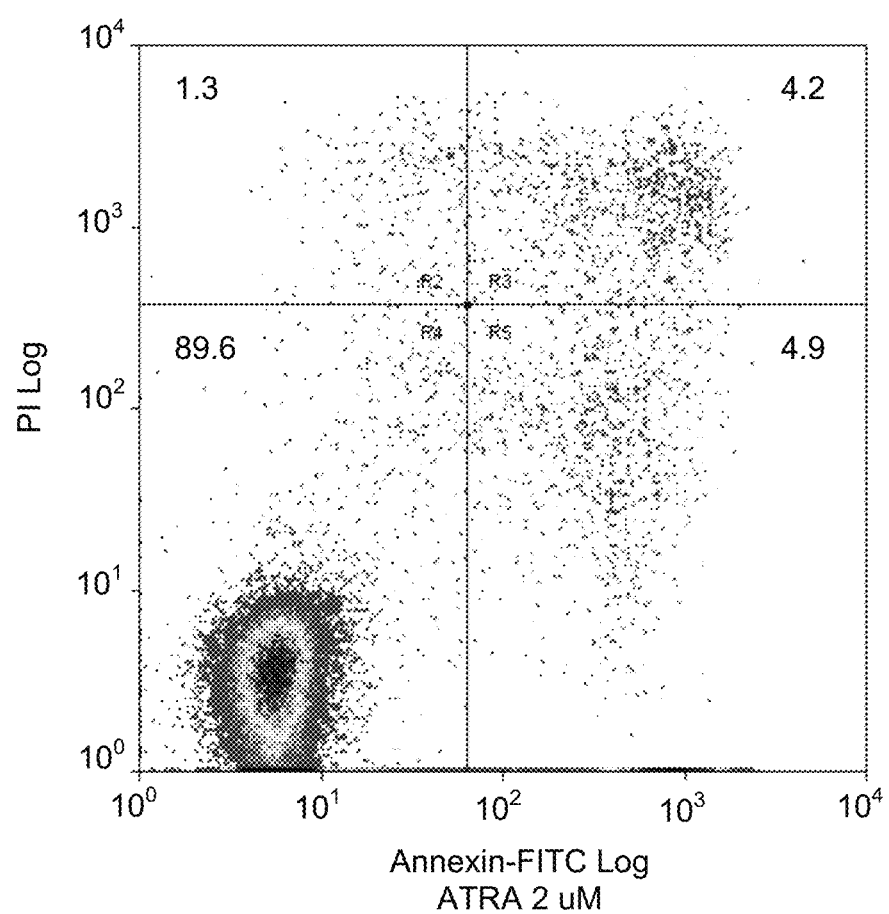
Figure 16C:
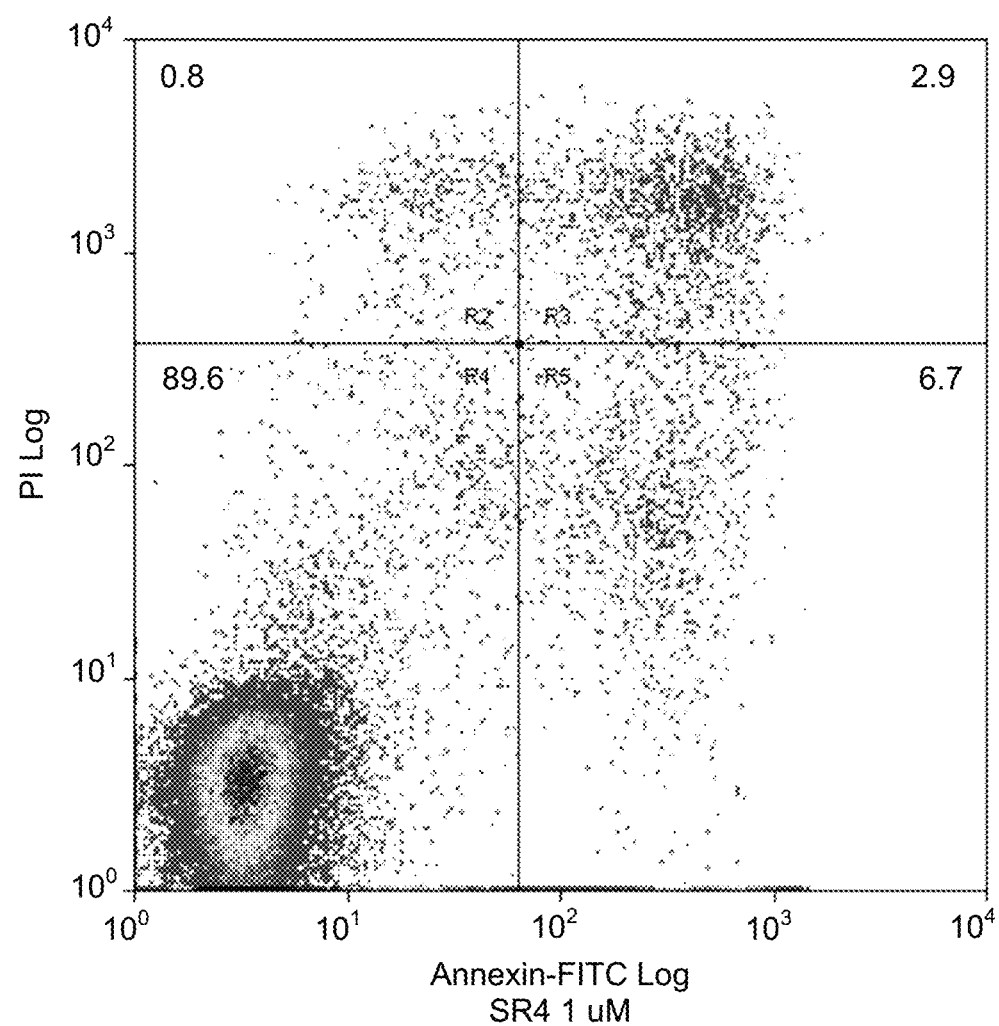
Figure 16D:
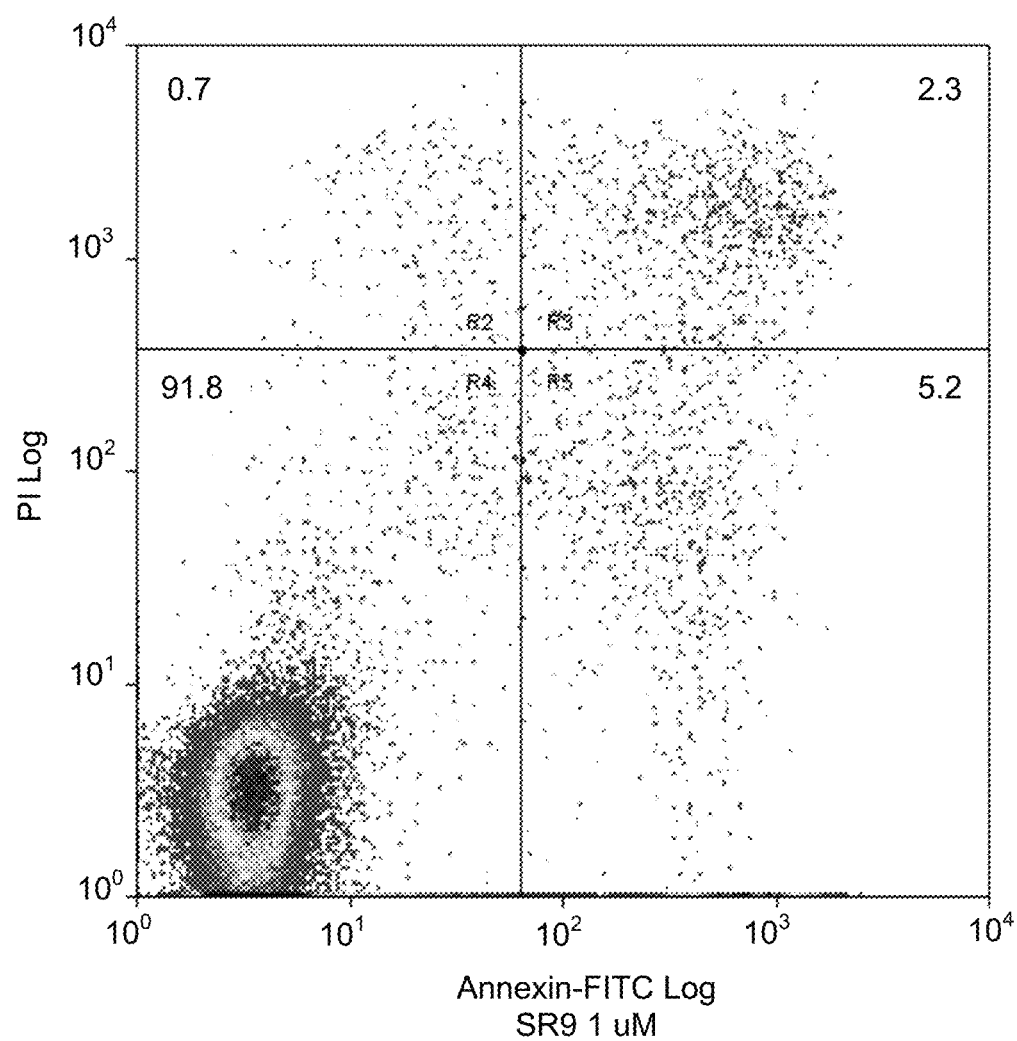
Figure 16E:
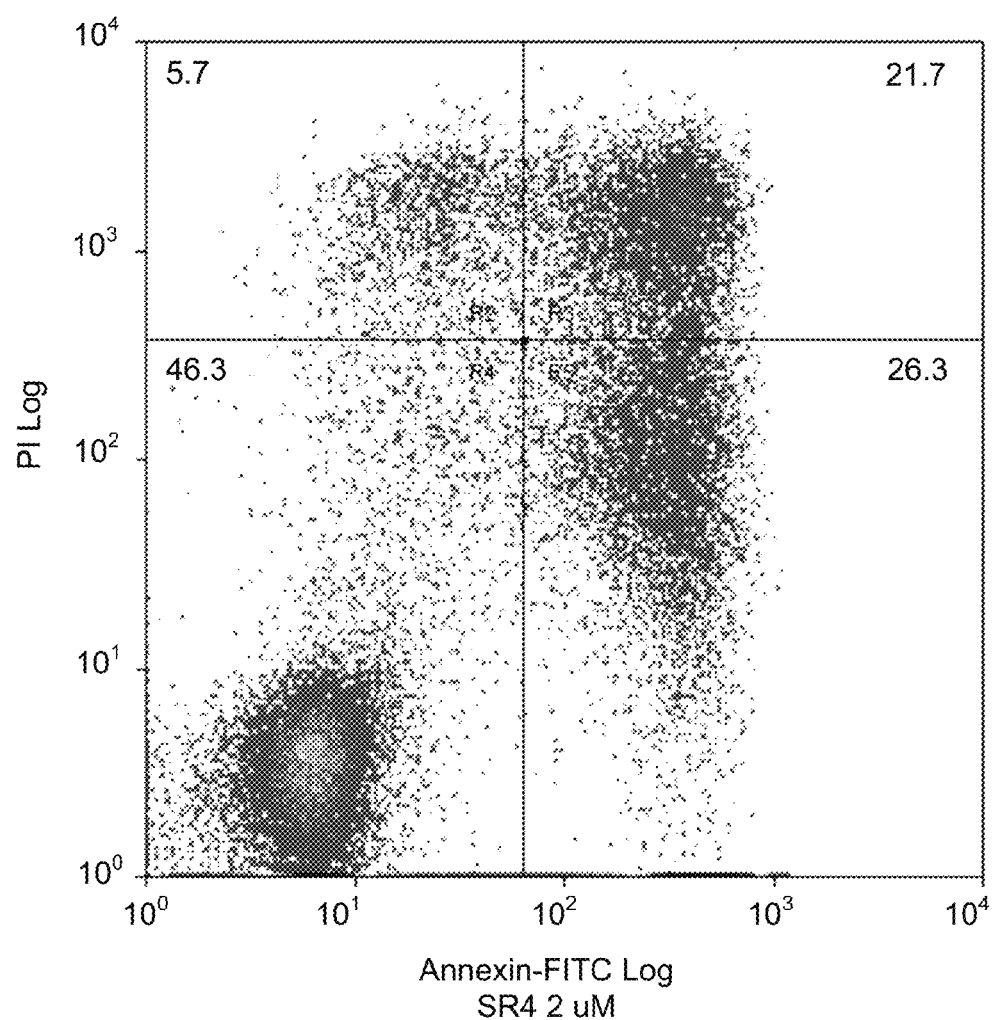
Figure 16F:
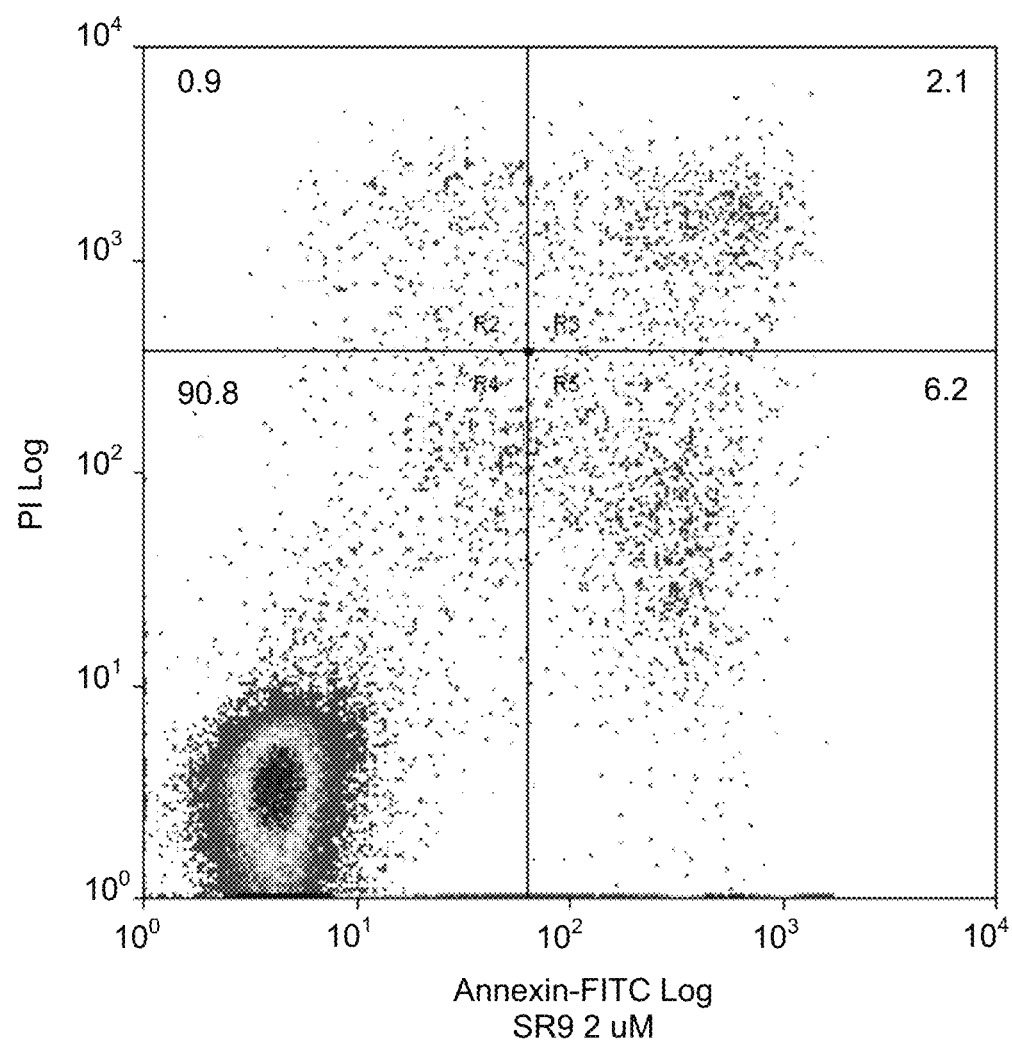
Figure 16G:
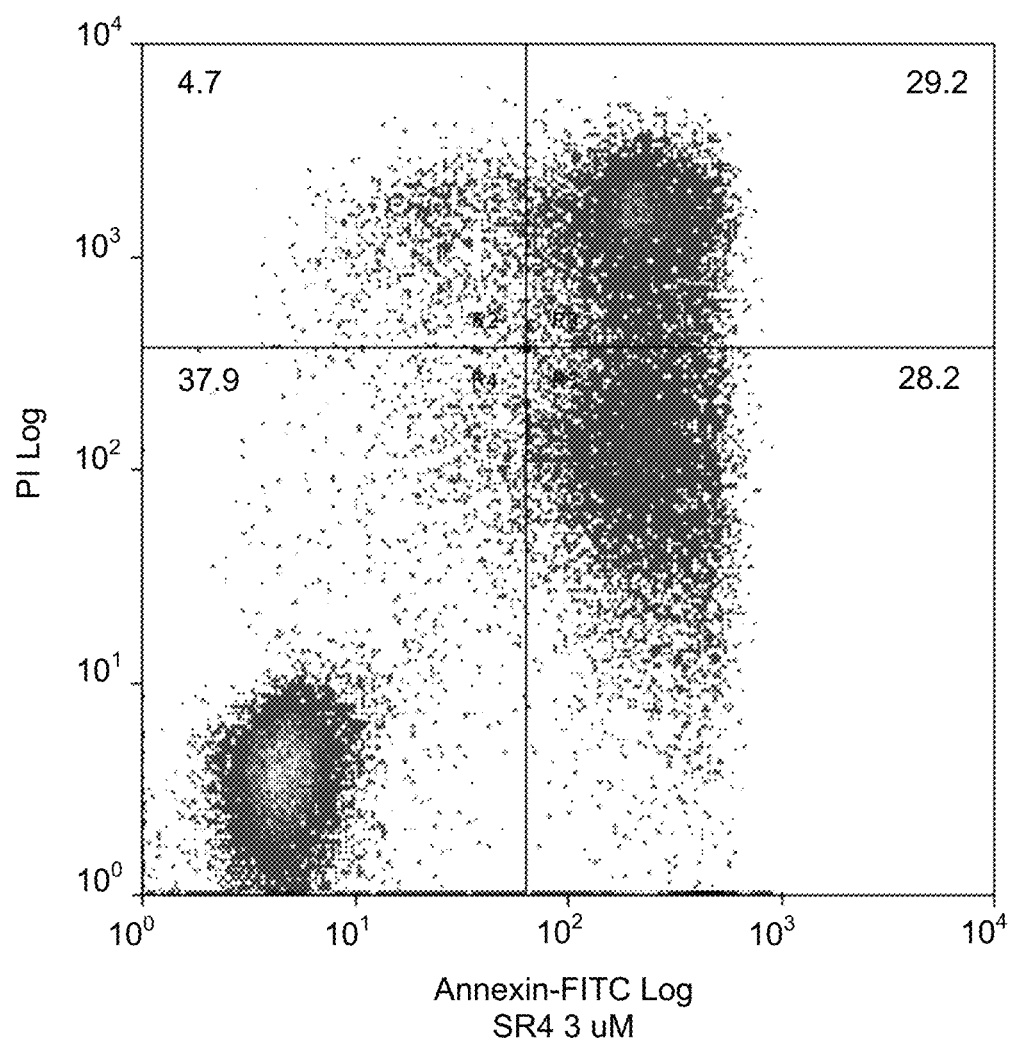
Figure 16H:
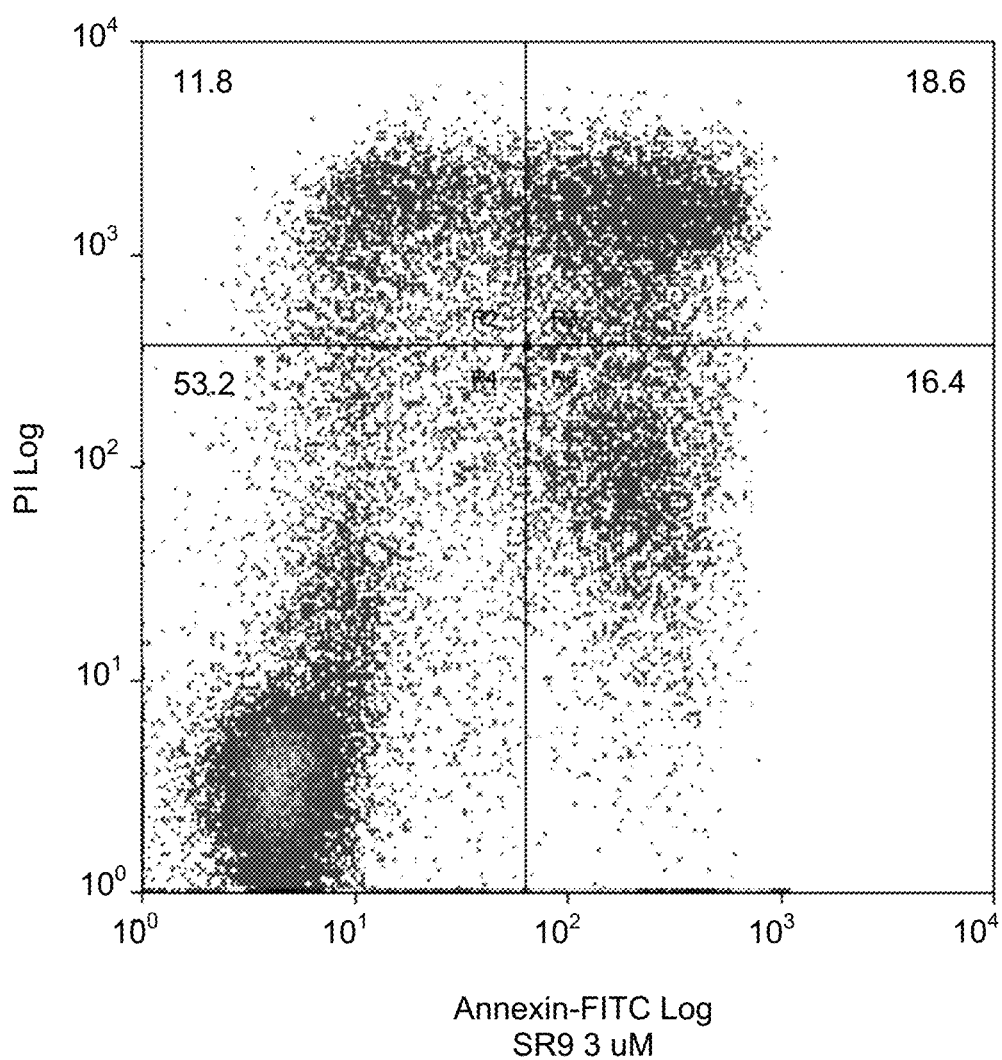

(D) COH-SR4 and COH-SR9 Induced a Dose and Time-Dependent G0/G1 Phase Arrest in HL-60 Cells (FIGS. 15A-C).

As COH-SR compounds induced significant growth inhibition of HL-60 cells, the effects of these compounds on the cell cycle progression of HL-60 cells were investigated using flow cytometry. HL-60 cells ($1 \times 10^6$) were incubated with a test compound (COH-SR4 or COH-SR9) at various concentrations (0.5~3 µM) for 48 hours, washed and harvested. The cells were then fixed and stained with propodium iodide (P1) and the DNA content was analyzed by flow cytometry. Results of each figure were from 3-4 independent experiments. The cell number in each cell cycle phase was calculated and expressed as overall percentage (FIG. 15A). The percentage of cells in G0/G1 were measured from 0-48-hour treatment with test compounds (FIG. 15B), data expressed as mean±SE.

As shown in FIGS. 15A and 15B, HL-60 cells treated with COH-SR4 or COH-SR9 resulted in a dose- and time-dependent G0/G1 phase arrest. After 24-hour treatment with COH-SR4 or COH-SR9, more than 70% of cells were stuck at this phase compared with 46% in the control, and within 48-hour treatment, 85% of the viable cells were arrested at this stage. Concomitant with this increase in percentage of cells in the G0/G1 phase was a significant decrease in the percentage of cells in the S phase (from 47% in the control cells versus 10% and 13% in 3 µM COH-SR4 and 3 µM COH-SR9, respectively). These results suggest that COH-SR compound-induced growth inhibition was strongly associated with its induction of cell cycle arrest.

Because cyclins (e.g. cyclin D1 and E2) and cyclin dependent kinases (CDKs) such as CDK2 and CDK4 play critical roles in promoting G1 phase progression, the effects of the COH-SR compounds on these regulatory proteins were examined.

HL-60 cells were treated without or with COH-SR4 or COH-SR9 at a concentration of 0.5 µM, 1 µM, 2 µM, or 3 µM for 24 hours. Then the total cell lysates from the treated cells or untreated cells were resolved under electrophoresis and immunoblotted with antibodies against cyclin D1, cyclin E2, CDK2, CDK4, p21WAF1/Cip1, p27Kip1, and β-actin. β-actin served as an internal control. Densitometric quantitation was performed on each blot and the arbitrary numbers above each band represent the fold increase/decrease compared with untreated control. Representative Western blot results (FIG. 15C) showed that treatment with either test compound for 24 hours resulted in dose-dependent reduction in the protein levels of cyclin D1, cyclin E2, CDK2 and CDK4. In contrast, the protein levels of the CDK inhibitors p21WAF1/Cip1 and p27Kip1 were both upregulated by either compound. These kinase inhibitors are known to interfere with cell cycle progression to cause phase-specific cycle arrest by perturbing the phosphorylation process through direct interaction with their target proteins (cyclins or CDK). Therefore, these data indicate that the inhibitory effect of both COH-SR compounds on HL-60 proliferation may be a result of the induction of cell cycle arrest at the G0/G1 phase through changes in the expressions of G1 associated regulatory proteins.

(E) COH-SR4 and COH-SR9 Induced Apoptosis of HL-60 (FIGS. 16A-H~18A-B)

Figure 17A:
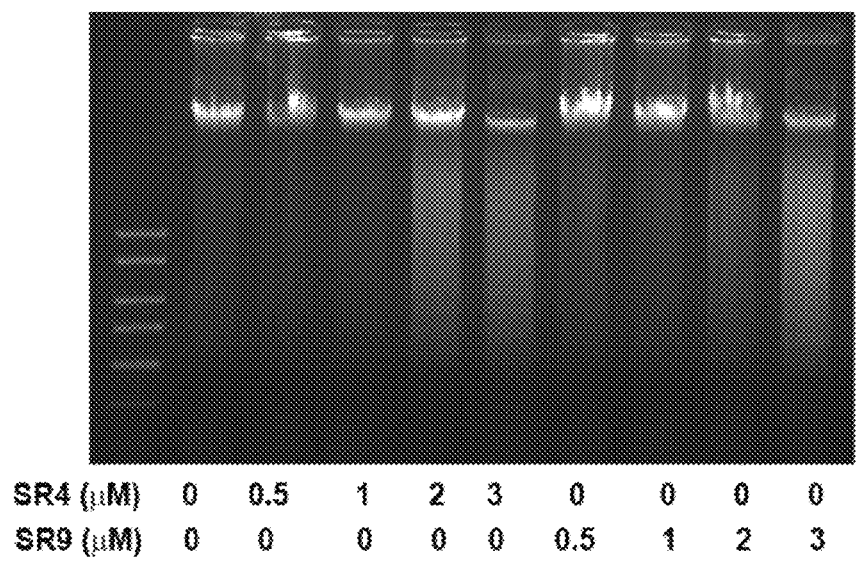
FIGS. 17A-17C: COH-SR4 and COH-SR9 induced apoptosis of HL-60.
Figure 17B:
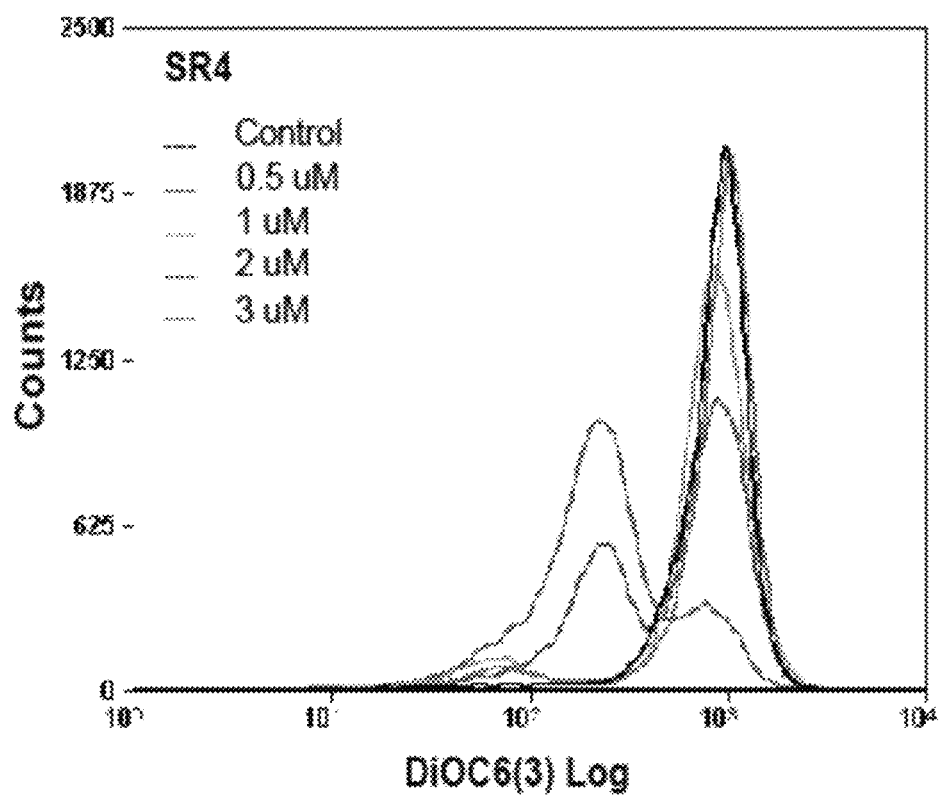
Figure 17C:
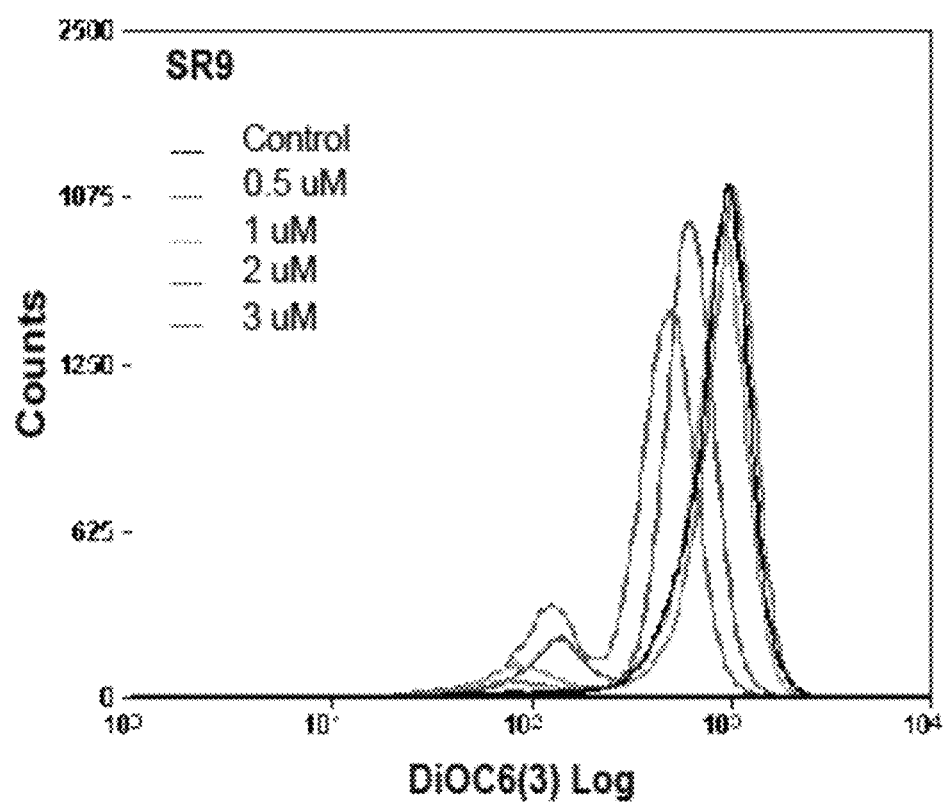
Figure 18A:
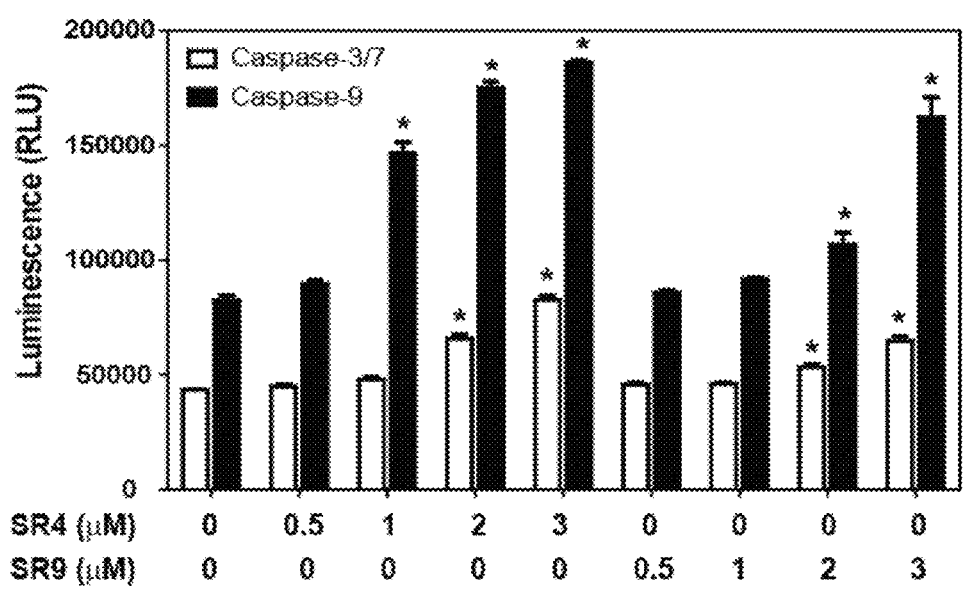
FIGS. 18A-18B: COH-SR4 and COH-SR9 induced apoptosis of HL-60.
Figure 18B:
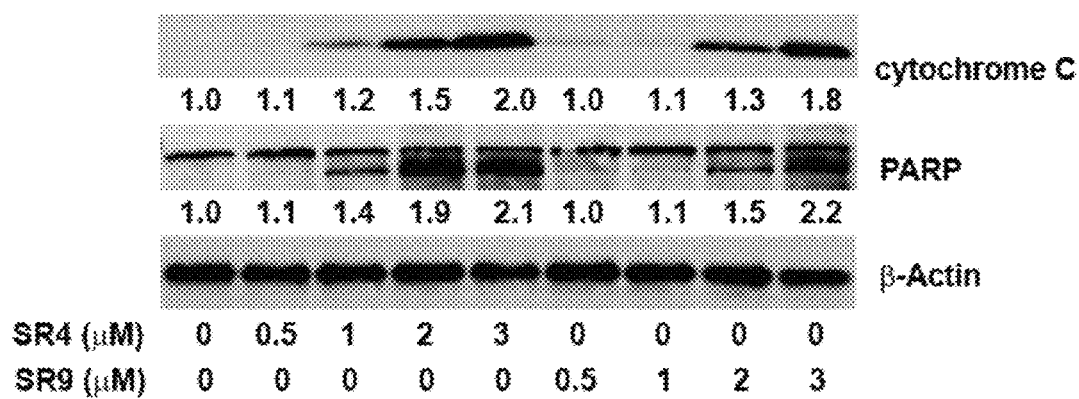

Data showed that after/or during $G_0/G_1$ phase arrest, COH-SR4 and COH-SR9 treated HL-60 cells underwent apoptosis as indicated by increased Annexin V-PI positive stainings (FIGS. 16A-H), dose-dependent increased DNA fragmentation (FIG. 17A), reduced fluorescence intensity of DiOC6(3) (FIG. 17 B and FIG. 17C), higher caspase 3/7 and caspase 9 activity (FIG. 18A), and release of cytochrome c into the cytoplasm and PARP enzyme activation (FIG. 18B).

HL-60 ($5 \times 10^5$) cells were incubated with a test compound (COH-SR4 or COH-SR9), ATRA, or nothing (Control) for 48 hours, washed and harvested. The cells were then fixed and double stained with Annexin V-FITC and propodium iodide (PI) and analyzed by flow cytometry. Conjugation of Annexin V and PI staining was used to identify apoptosis cells (early stage and late stage), normal/viable cells and necrotic cells. The percentage distribution of normal/viable (R3, lower left quadrant), early apoptotic (R4, lower right quadrant), late apoptotic (R2, upper right quadrant) and necrotic cells (R1, upper left quadrant) was calculated using Summit software. The percentages of apoptotic cells after treatment with various doses of each compound are shown in FIGS. 16A-H. Both COH-SR4 and COH-SR9 treatment of HL-60 cells increased the number of early apoptotic and late apoptotic cells in a dose-dependent manner compared with untreated cells. At 3 µM, overall apoptotic cells were ~60% and 40% for COH-SR4 and COHSR9, respectively.

Additionally, exposure of HL-60 cells to COH-SR4 or COH-SR9 led to dose-dependent DNA fragmentation as indicated by the formation of lower molecular weight DNA fragments (DNA ladder) in the agarose gel, whereas control cells contained only high-molecular weight DNA and showed no evidence of DNA ladder (FIG. 17A). DNA was stained with ethidium bromide after electrophoresis on 1.5% agarose gel and then visualized under UV light.

To test whether mitochondrial membrane disruption was involved in the apoptotic effects of COH-SR4 and COH-SR9, fluorescent cationic lipophilic dye DiOC6(3) was used and monitored using flow cytometry. HL-60 cells were exposed to various concentrations of COH-SR4 or COH-SR9 for 4 hours. After incubation, cells were rinsed and stained with the cationic fluorescent dye DiOC6(3) and then the overall fluorescence was analyzed by flow cytometry. HL-60 cells treated with COH-SR4 (FIG. 17B) or COH-SR9 (FIG. 17C) showed decreased overall DiOC6(3) fluorescent intensity compared with control cells, as the fluorescence signals shifted to the left with increasing dose of the test compounds. Reduction of the fluorescence intensity of DiOC6(3) is indicative of the cells undergoing mitochondrial depolarization and loss of $\Delta\psi$mt. This effect, which has been commonly observed with other anticancer drugs irrespective of the cell type, generally defines an early but already irreversible stage of apoptosis.

Moreover, treatment with COH-SR compounds exhibited a dose-dependent activation of both caspase-3/7 and caspase-9 (FIG. 18A). HL-60 ($2.5 \times 10^4$) cells were seeded into 96-well plates and incubated with a test compound (COH-SR4 or COH-SR9) at various concentrations (0.5~3 µM) for 48 hours, then caspase-3/7 or caspase-9 activity was measured with the Caspase Glo kit (Promega), respectively. Data are expressed as mean±SE from 3 independent experiments (FIG. 18A), "*" in the figure means p<0.05 when compared to the untreated control.

Treatment of COH-SR compounds also triggered release of cytochrome c (14 kDa) into the cytoplasm and cleavage of full length PARP (116 kDa) into the 89 kDa fragment, all hallmarks of cells undergoing apoptosis (FIG. 18B). HL-60 cells were treated with COH-SR4 or COH-SR9 at various concentrations (0.5 µM~3 µM) or nothing for 24 hours. Cytochrome c (14 kDa) and cleavage of full length PARP (116 kDa) into the 89 kDa fragment were analyzed in untreated HL-60 cells and HL-60 cells treated with COH-SR4 or COH-SR9 by Western blot. Numbers below each blot represent fold increase in protein expression relative to the control as quantified by densitometry and calculated with reference to β-actin as an internal standard.

Example 4. COH-SR Compounds Inhibited Growth and Proliferation of Cancer Cells Such as Leukemia, Non-Small Cell Lung Cancer, Colon Cancer, CNS Cancer, Melanoma, Ovarian Cancer, Renal Cancer, Prostate Cancer, and Breast Cancer (FIGS. 19~27)

Figure 19:
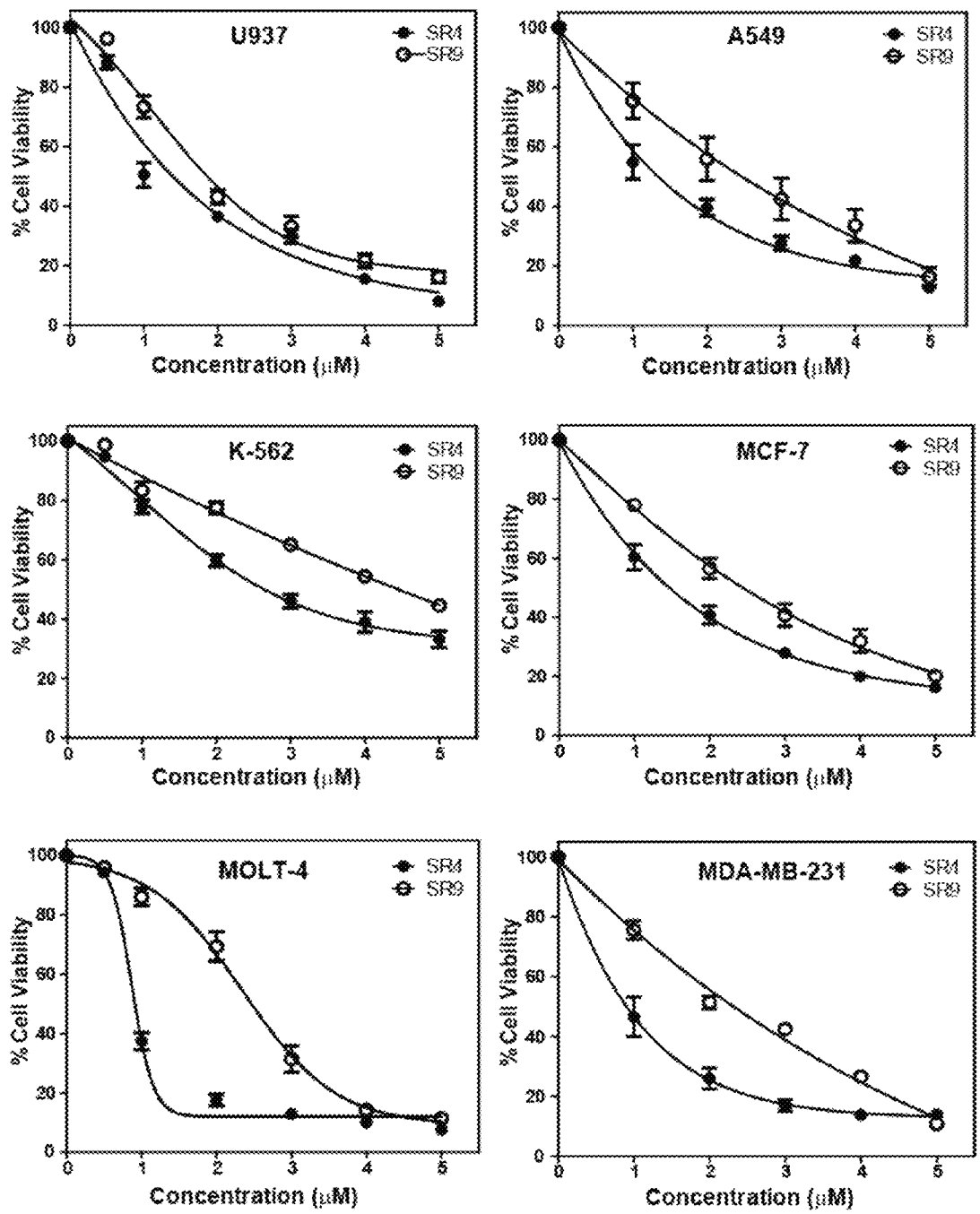
FIG. 19: Anti-proliferative effects of COH-SR4 and COH-SR9 against leukemia (U937, K-562, MOLT-4), breast cancer (MCF-7, MDA-MB-231), and small lung cancer cells (A549).
Figure 20:
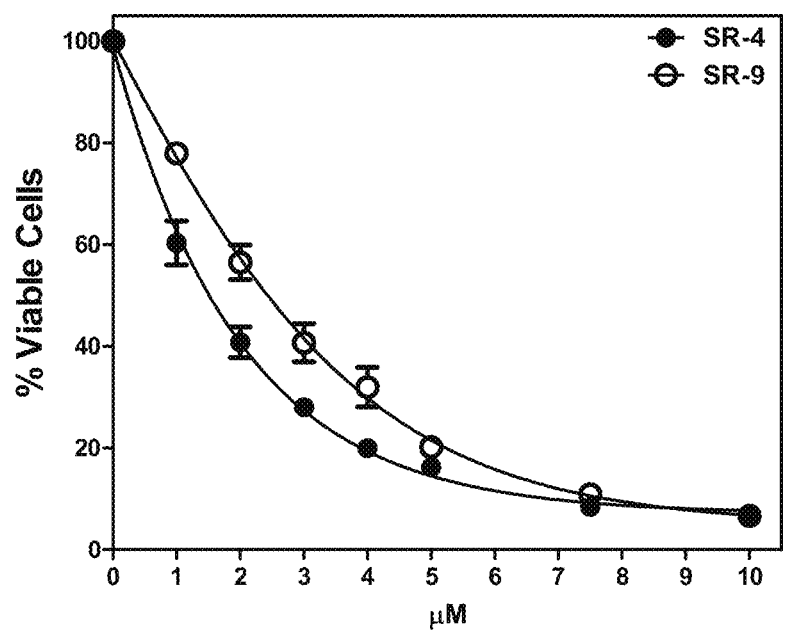
FIG. 20: COH-SR4 and COH-SR9 inhibited growth and proliferation of MCF-7 and MDA-MB-231 breast cancer cells.
Figure 20:
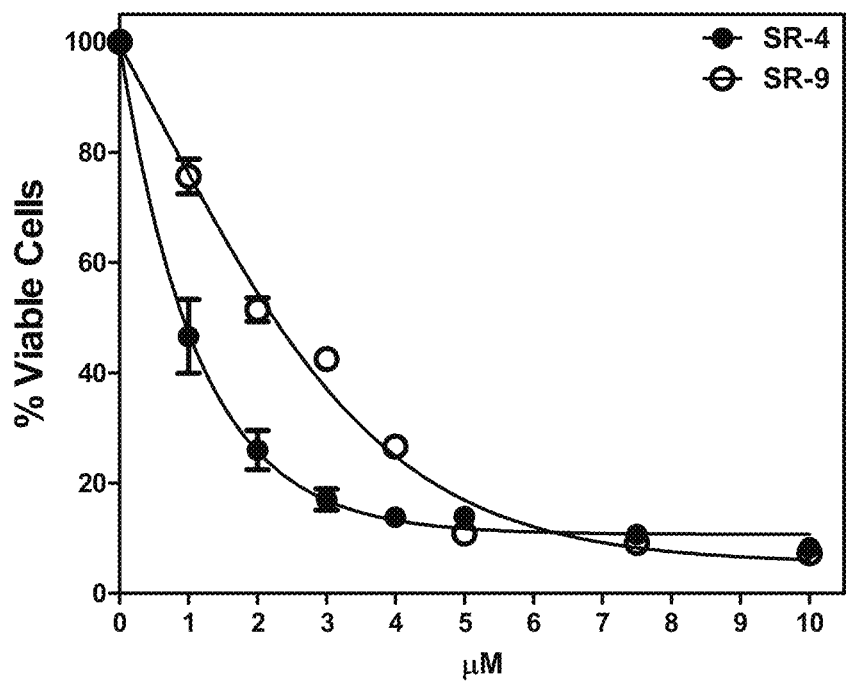
Figure 21:
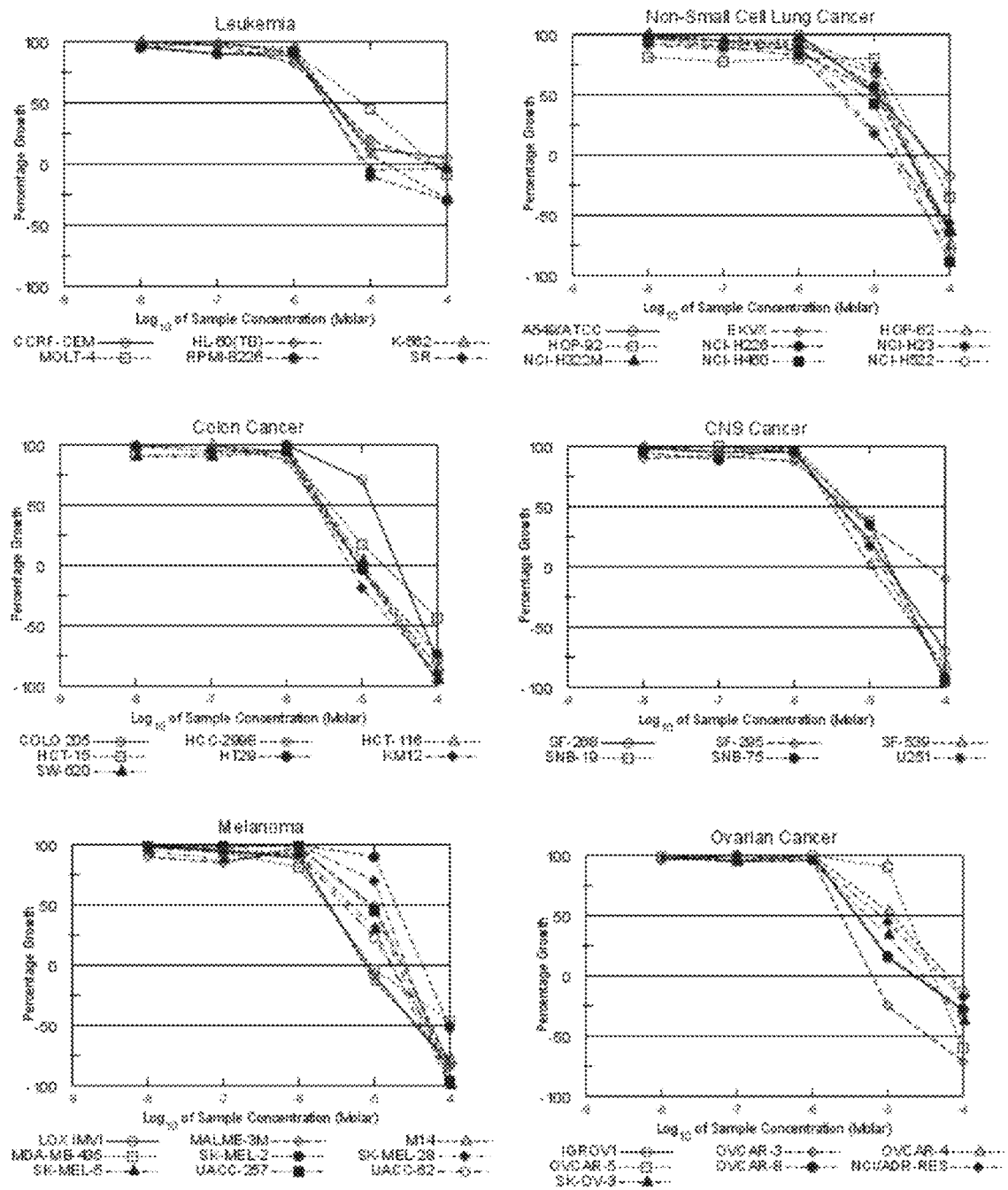
FIG. 21: NIH NCI-60 Developmental Therapeutics Program (DTP) dose response curves for COH-SR2.
Figure 21:
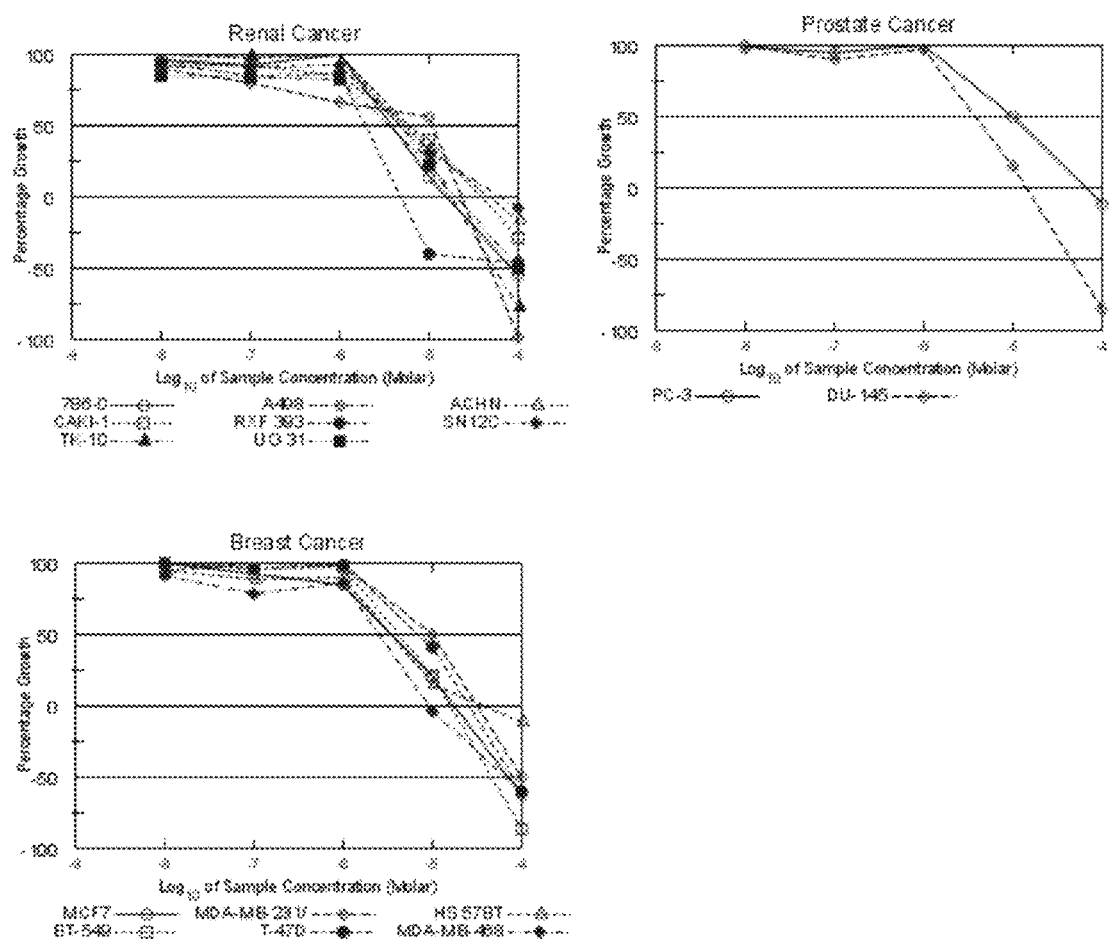
Figure 22:
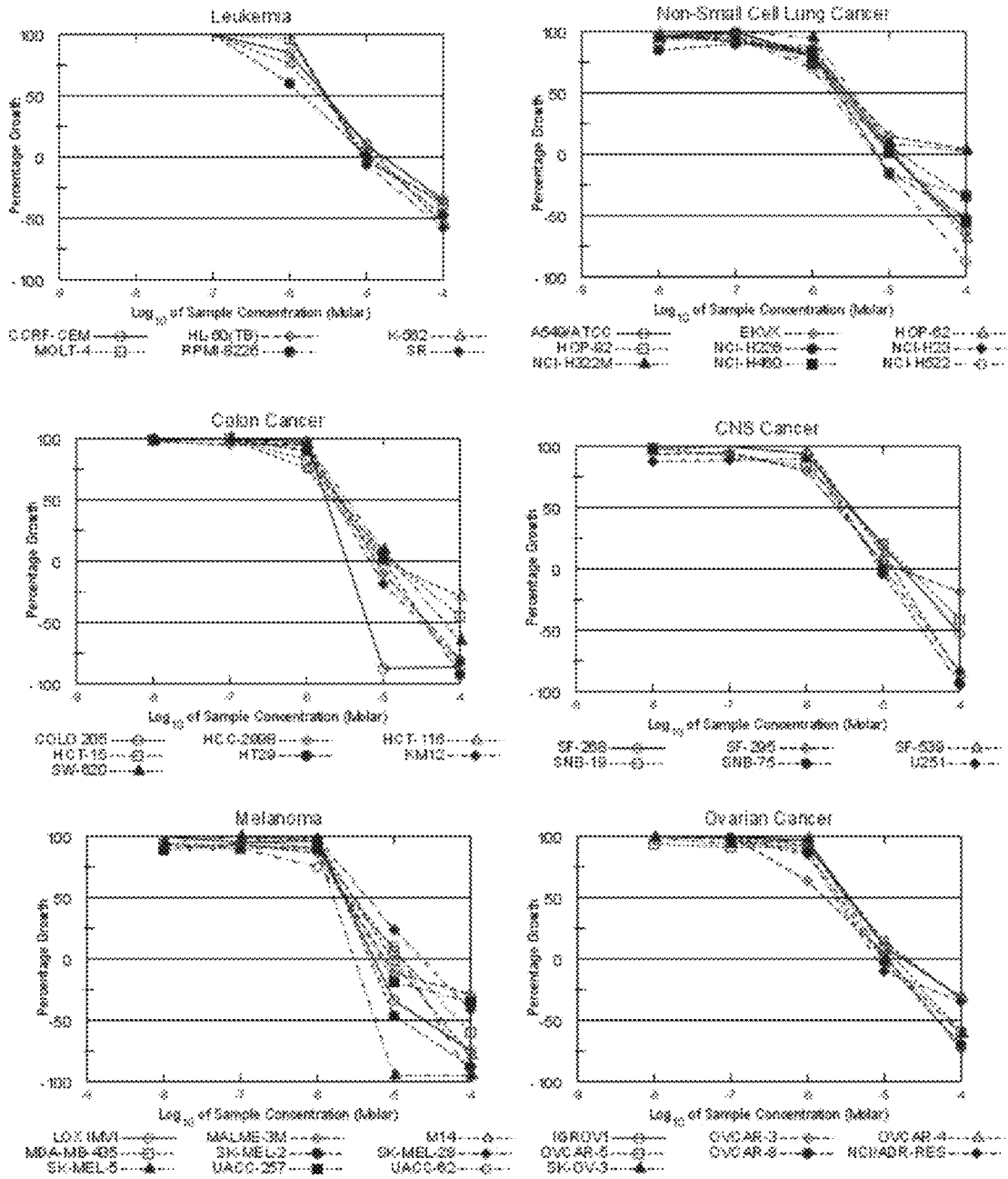
FIG. 22: NIH NCI-60 DTP dose response curves for COH-SR3.
Figure 22:
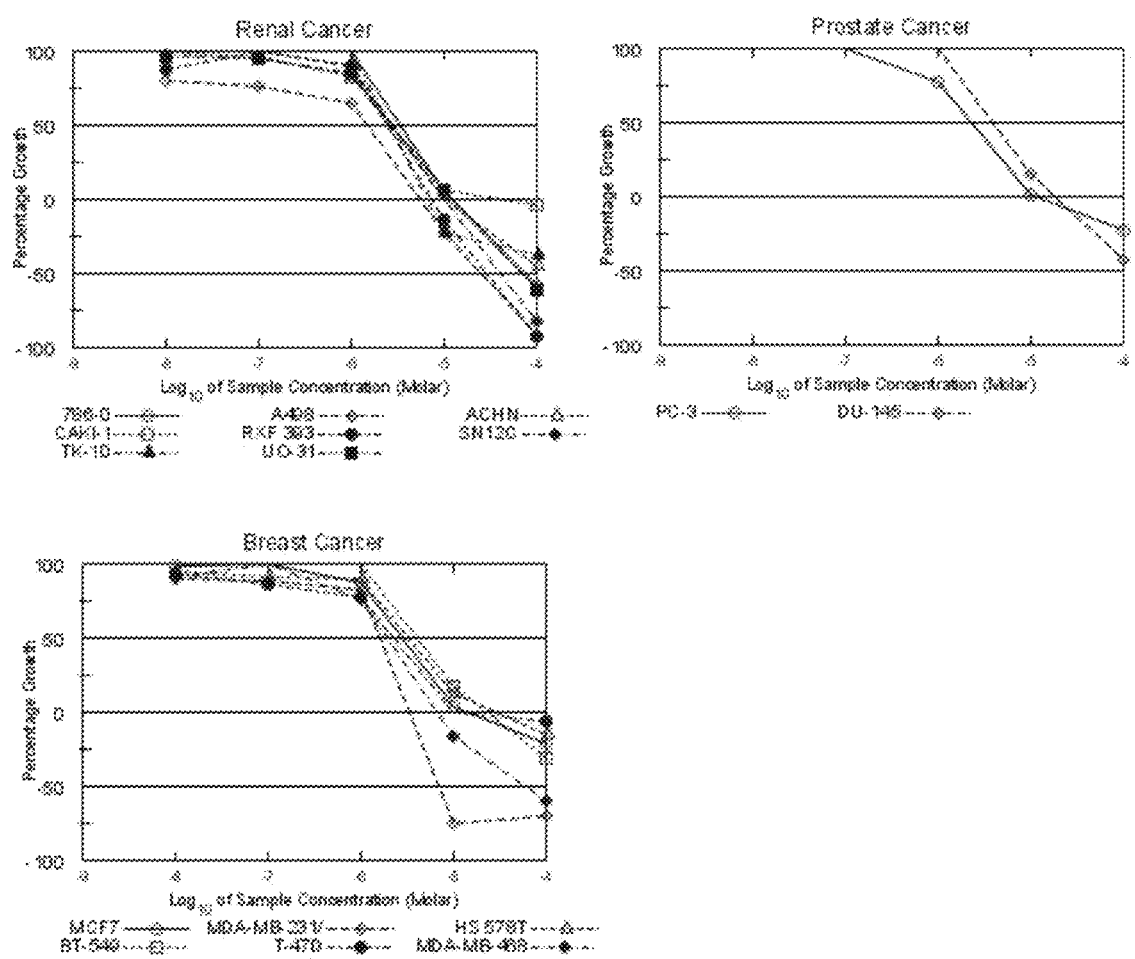
Figure 23:
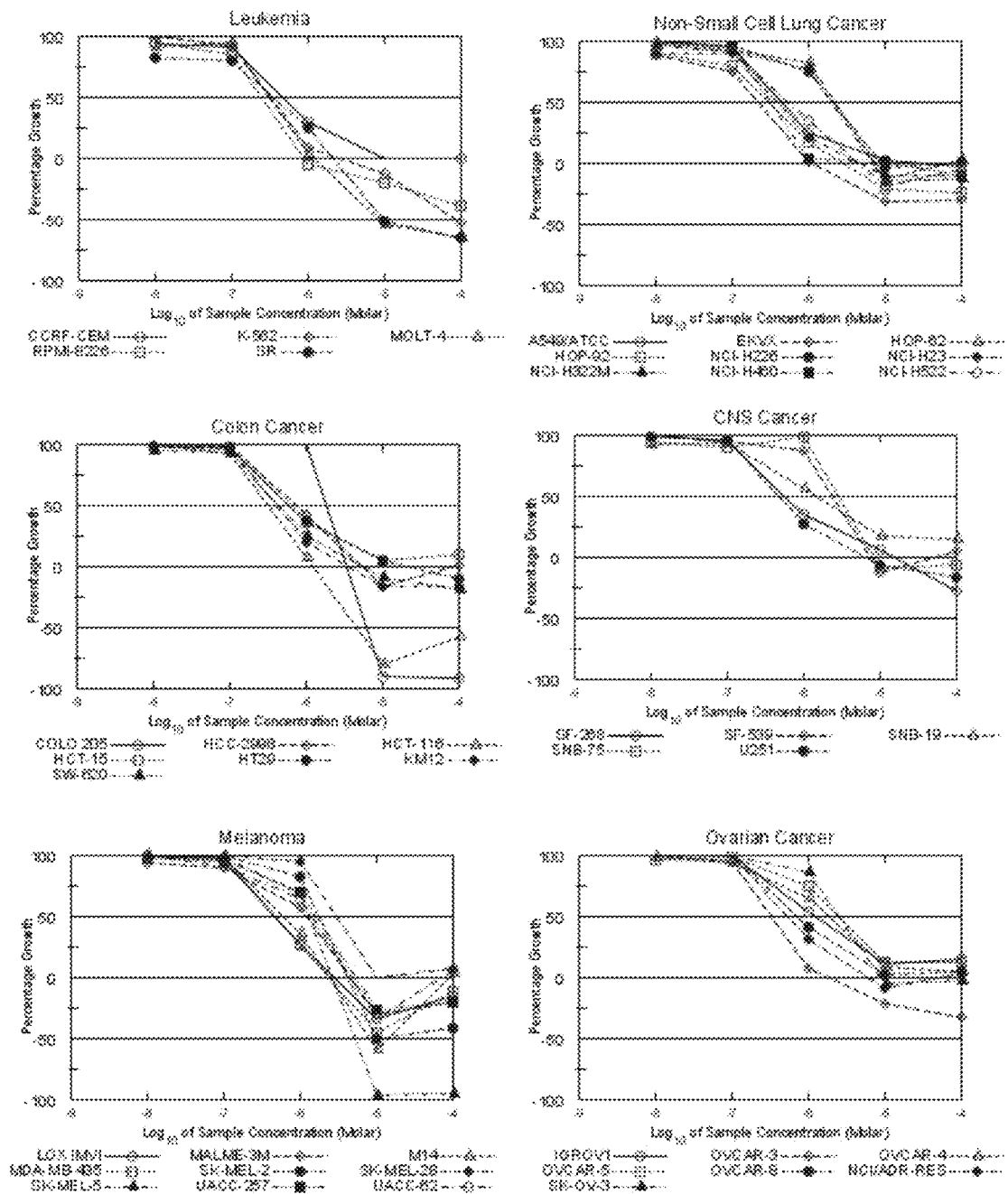
FIG. 23: NIH NCI-60 DTP dose response curves for COH-SR4.
Figure 23:
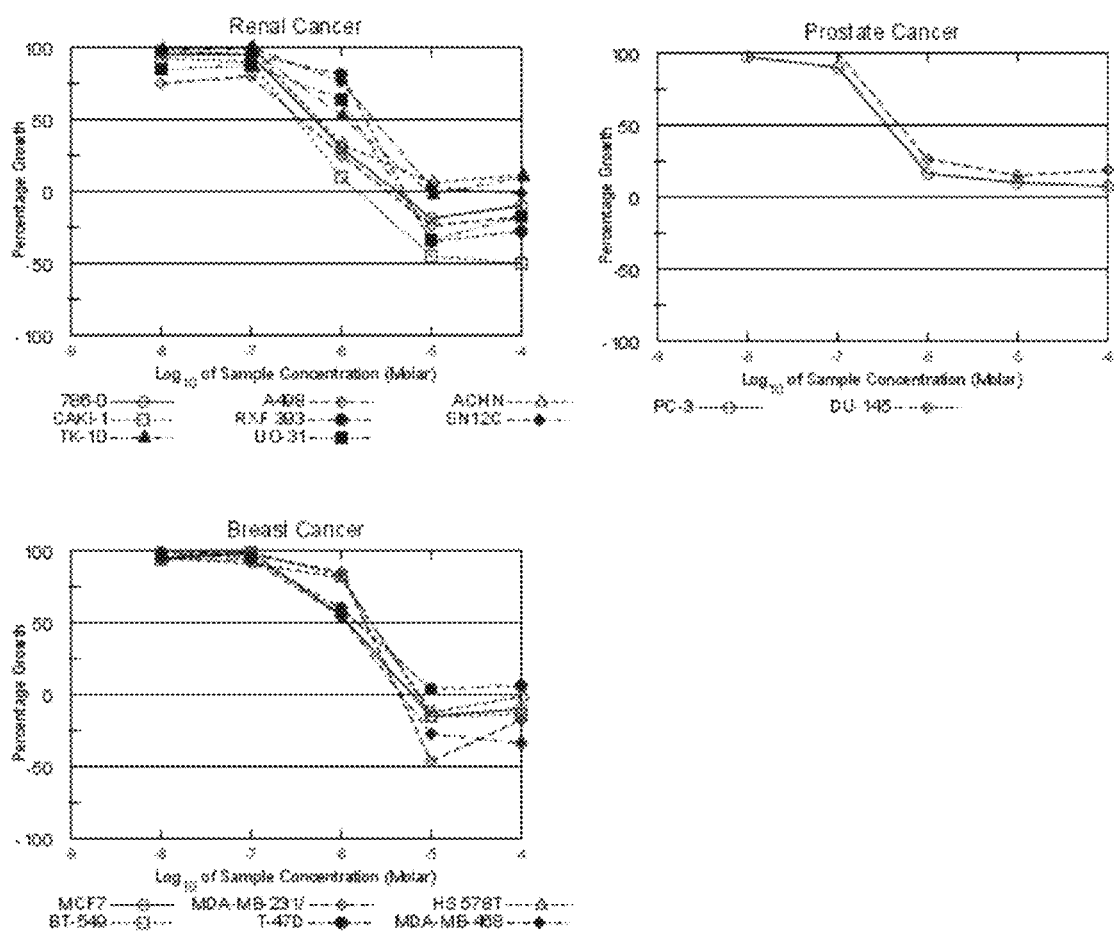
Figure 24:
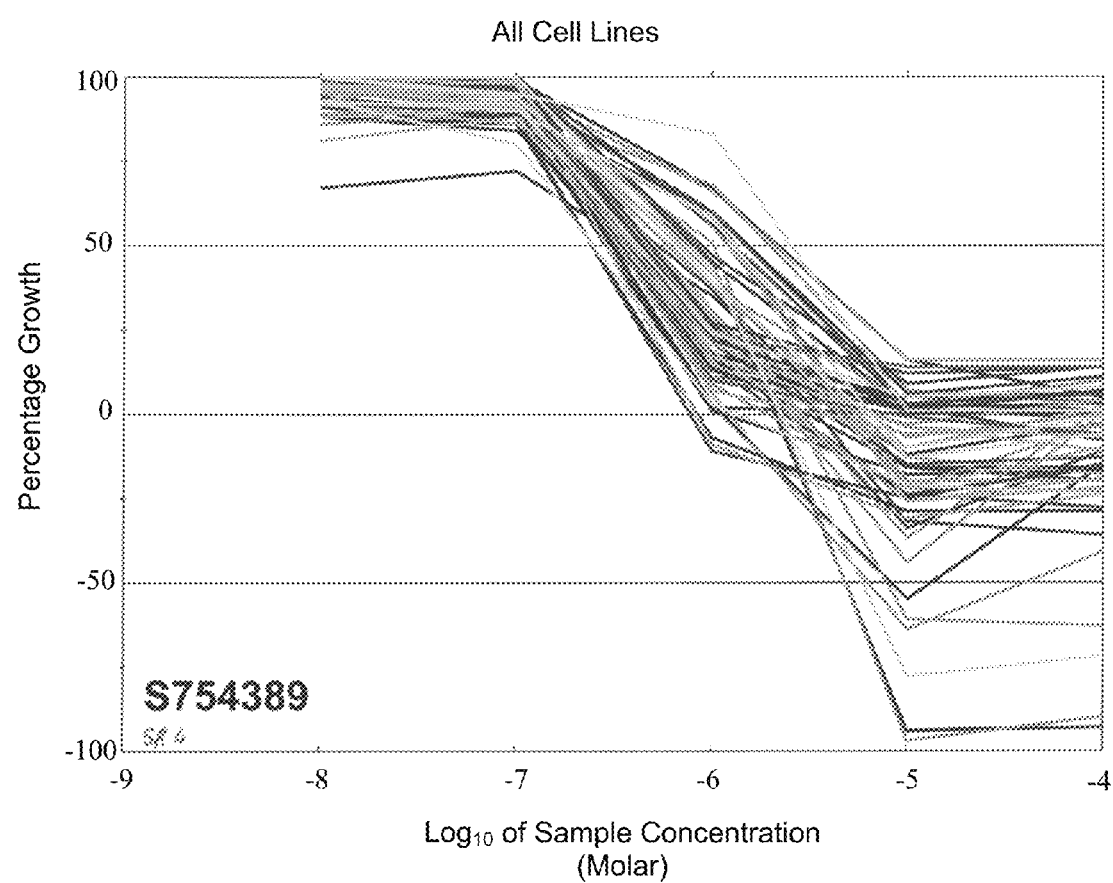
FIG. 24: NIH NCI-60 DTP dose response curves for COH-SR4 shown in one figure.
Figure 25:
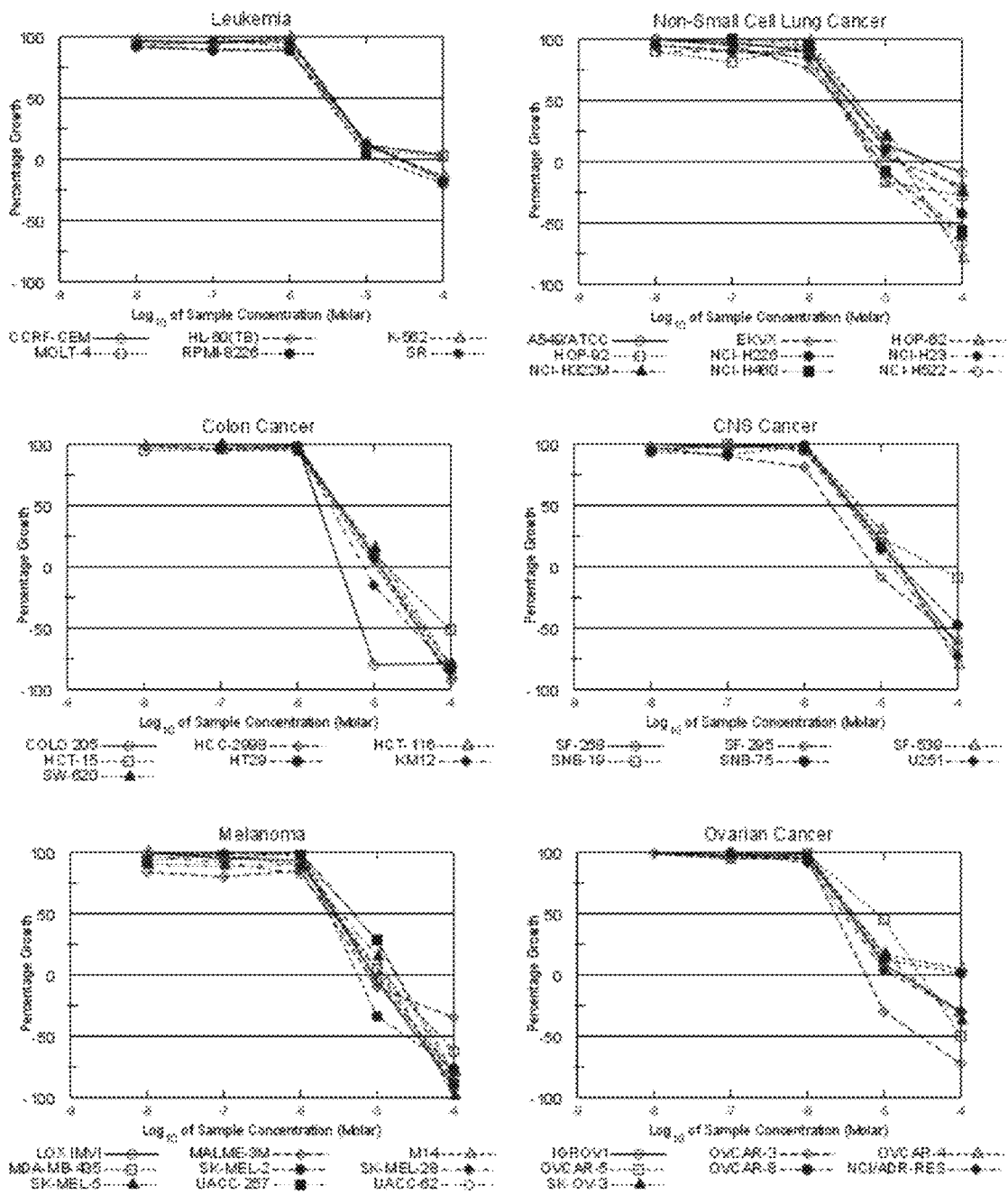
FIG. 25: NIH NCI-60 DTP dose response curves for COH-SR6.
Figure 25:
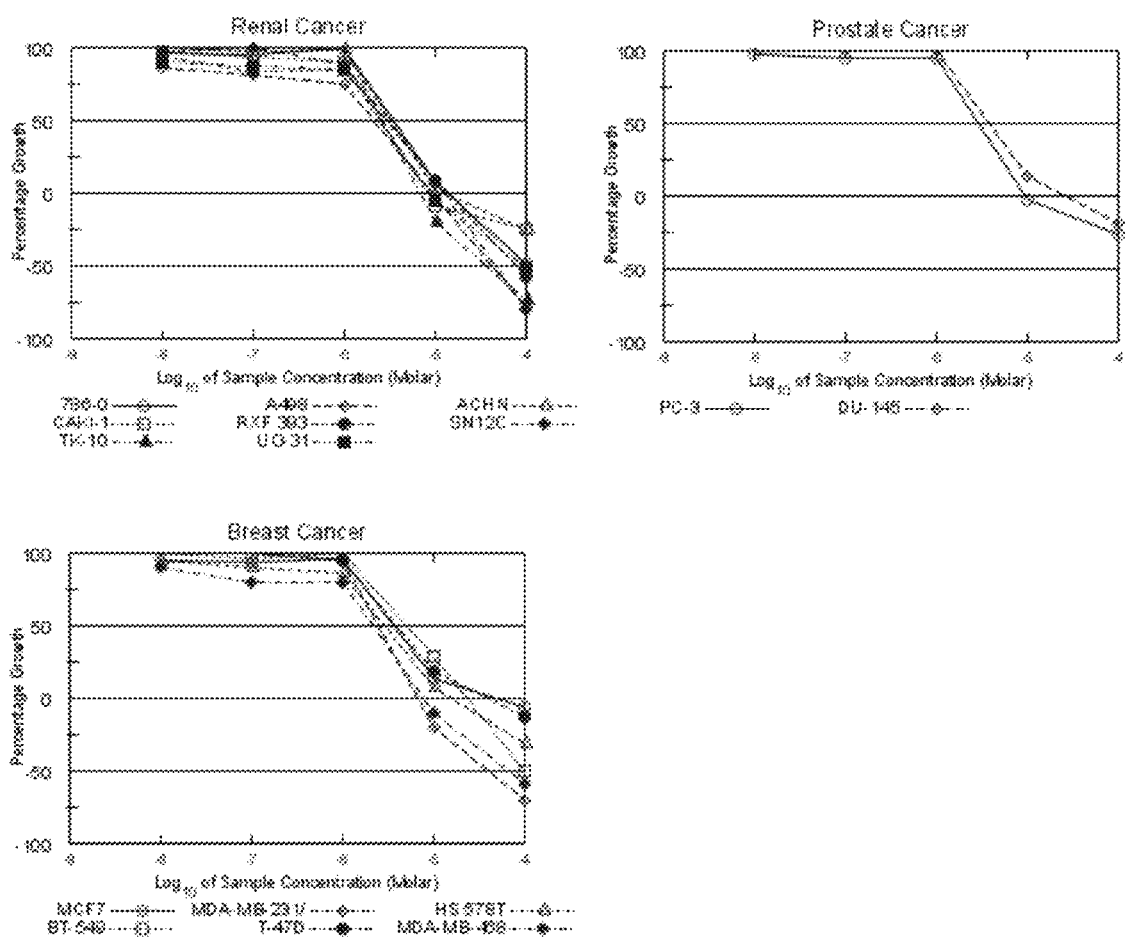
Figure 26:
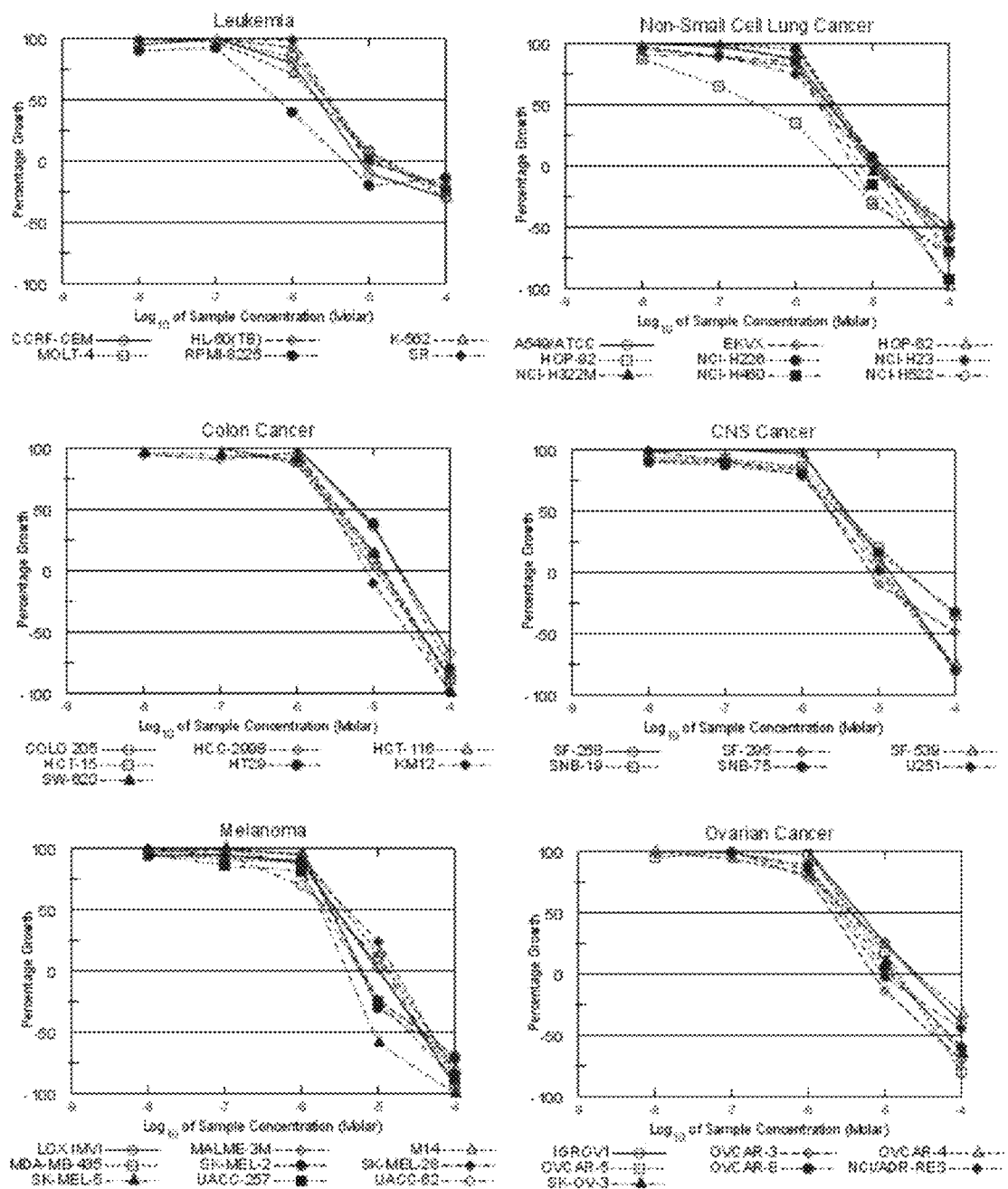
FIG. 26: NIH NCI-60 DTP dose response curves for COH-SR9.
Figure 26:
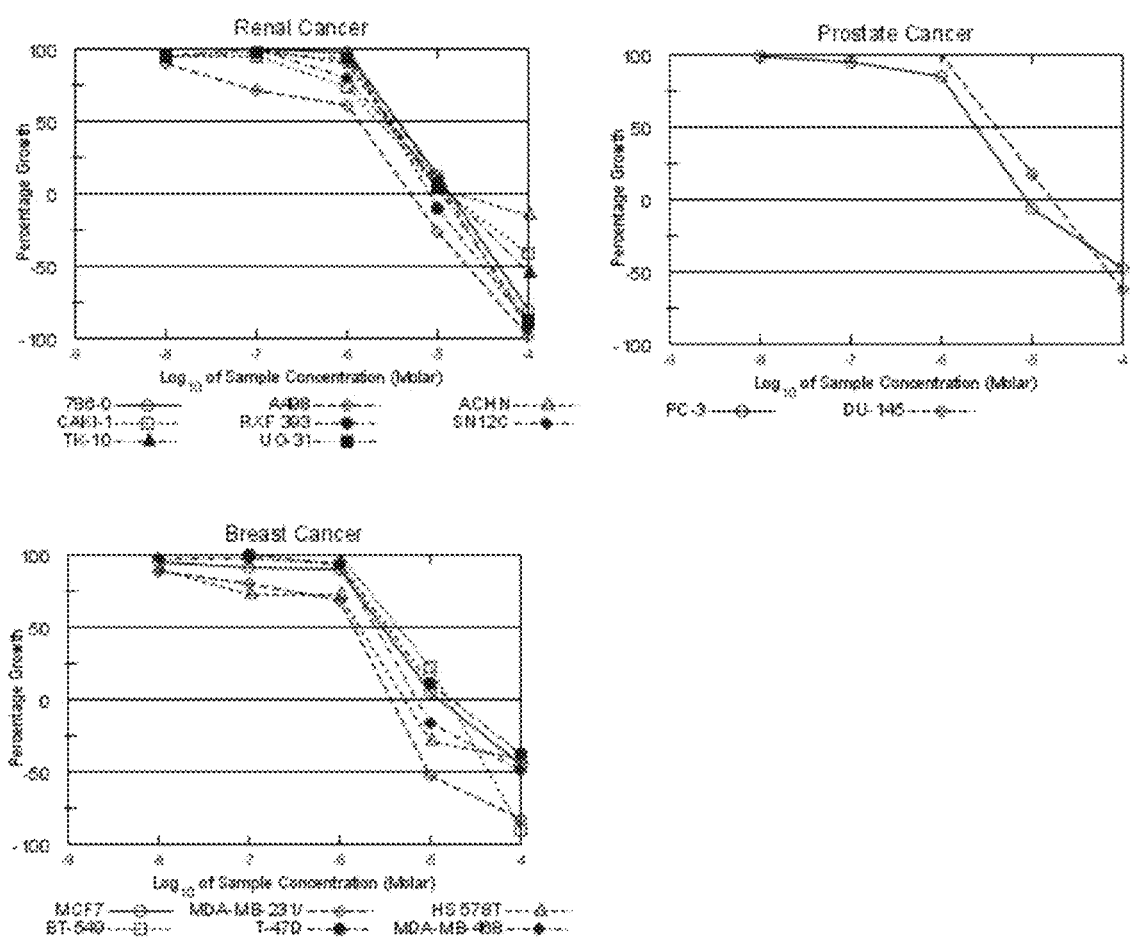
Figure 27:
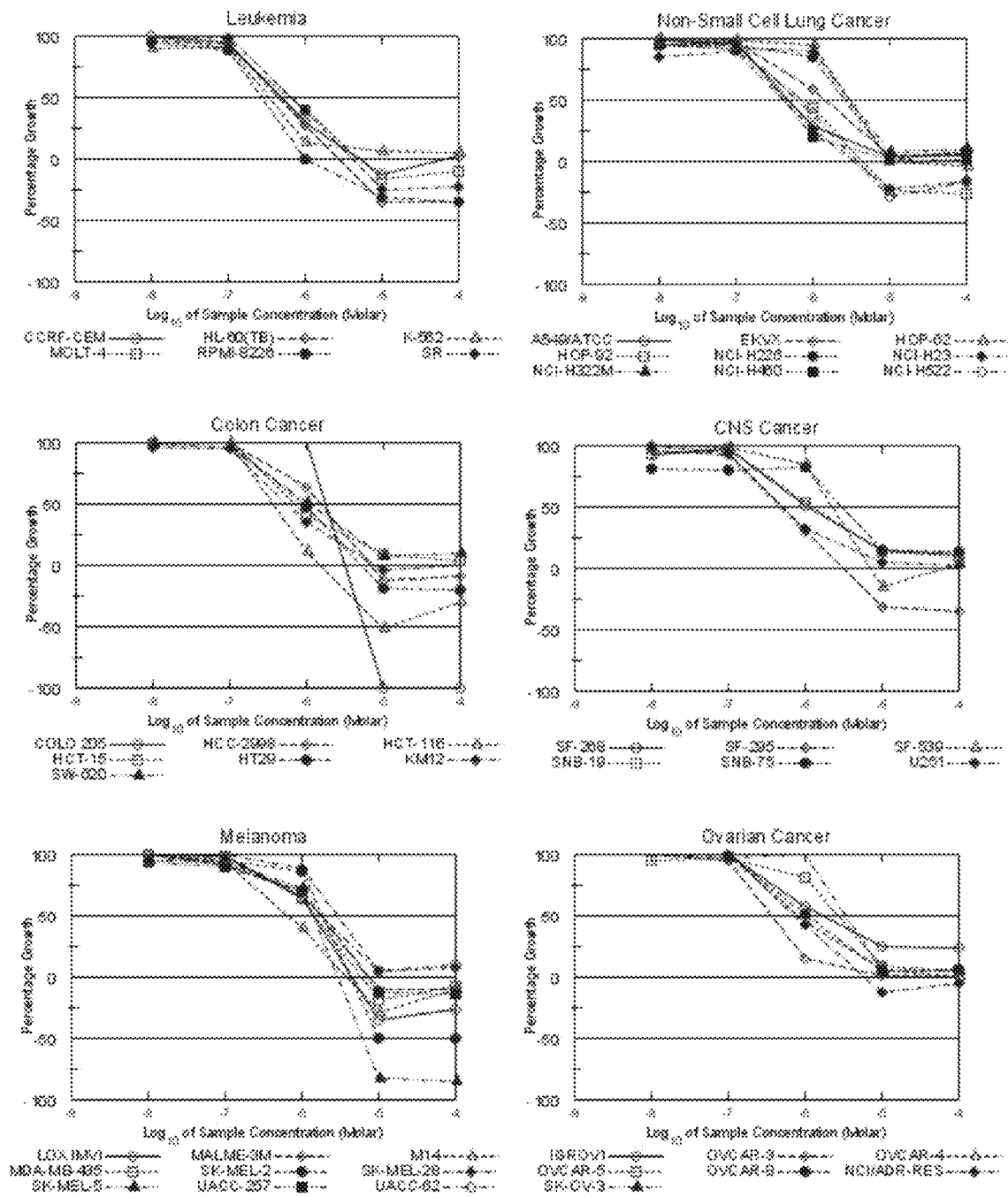
FIG. 27: NIH NCI-60 DTP dose response curves for COH-SR14.
Figure 27:
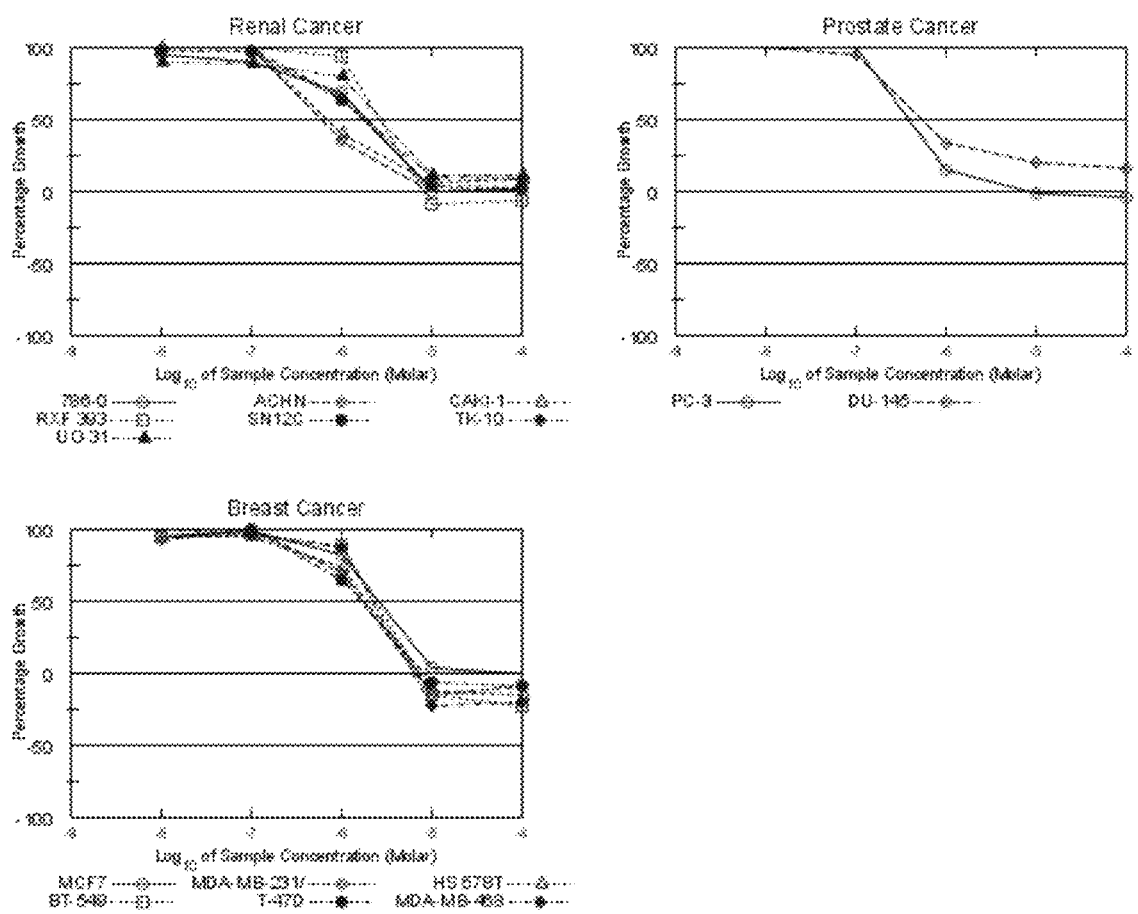

The anti-proliferative and cytotoxic effects of these COH-SR compounds were not only observed in HL-60 amyloid leukemia cells, but was also observed in other types of human cancer lines including leukemia (U937, K-562, MOLT-4), small lung cancer (A549) and breast cancer cells (MCF-7, MDA-MB-231), with $IC_{50}$ of <5 µM after 48-hour treatment (FIG. 19).

Each cancer cells ($2 \times 10^4$) were incubated with a test compound (COH-SR4, or COH-SR9) at various concentrations (0~10 µM) for 48 hours, and the numbers of viable cells were measured by the MTT/XTT assay. Data are expressed as mean±SE from 2 independent experiments with 3 replications each (FIG. 19). Significant anti-proliferative dose-dependent effects of the compounds tested against all cancer cell lines tested were observed (FIG. 19).

Breast cancer cells MCF-7 or MDA-MB-231 ($1 \times 10^4$ cells) were allowed to proliferate for 1 day and then treated with COH-SR4 or COH-SR9 or nothing for 72 hours. The number of viable cells were measured by MTT assay and shown in FIG. 20. Data expressed as mean±SE from 3 independent experiments.

Figure 28:
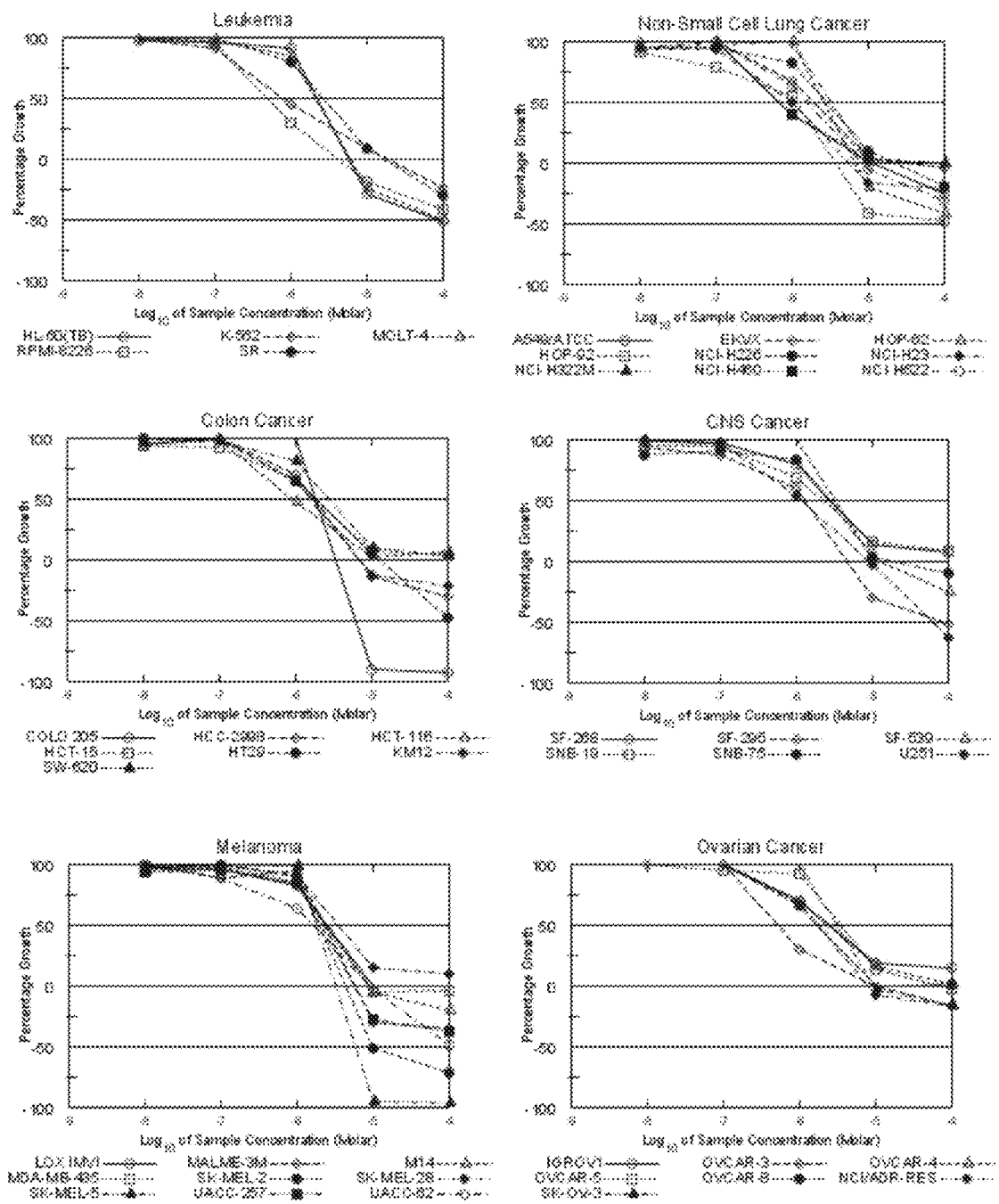
FIG. 28: NIH NCI-60 DTP dose response curves for COH-SR16.
Figure 28:
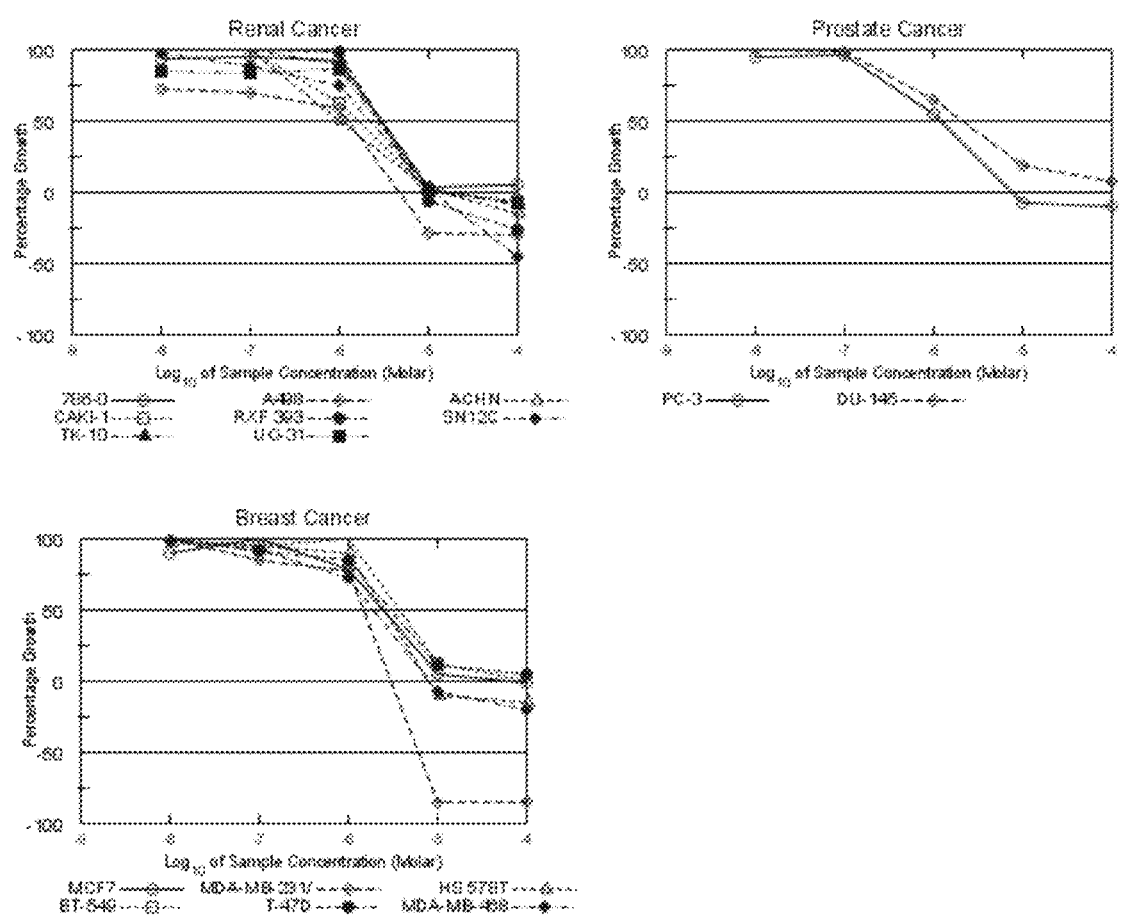

Moreover, preliminary data from the NCI-60 DTP Human Tumor Cell Line Drug Screening (http://dtp.nci.nih.gov/branches/btb/ivclsp.html) further confirmed the observations on these COH-SR compounds. Results showed COH-SR compounds (COH-SR2 (FIG. 21), COH-SR3 (FIG. 22), COH-SR4 (FIGS. 23 and 24), COH-SR6 (FIG. 25), COH-SR9 (FIG. 26), COH-SR14 (FIG. 27), and COH-SR16 (FIG. 28)) were active against various leukemia cells lines (C CRF-CEM, HL-60 (TB), K-562, MOLT-4, RPMI-8226, and SR), non-small cell lung cancer cell lines (A549/ATCC, EKVX, HOP-62, HOP-92, NCI-H226, NCI-H23, NCI-H322M, NCI-H460, and NCI-H522), colon cancer cell lines (COLO 205, HCC-2998, HCT-116, HCT-115, HT29, KM12, and SW-620), CNS cancer cell lines (SF-268, SF-295, SF-539, SNB-19, SNB-75 and U251), melanoma cell line (LOX IMVI, MALME-3M, M14, MDA-MB-435, SK-MEL-2, SK-MEL-28, SK-MEL-5, UACC-257, and UACC-62), ovarian cancer cell lines (IGROV1, OVCAR-3, OVCAR-4, OVCAR-5, OVCAR-8, NCI/ADR-RES, and SK-OV-3), renal cancer cell lines (786-0, A498, ACHN, CAKI-1, RXF 393, SN12C, TK-10, and UO-31), prostate cancer cell lines (PC-3, and DU-145), and breast cancer cell lines (MCF7, MDA-MB-231, HS 578T, BT-549, T-47D, and MDA-MB-468). A value of 100 meant no growth inhibition. A value of 20 meant 80% growth inhibition. A value of 0 meant no net growth over the course of the experiment. A value of −40 meant 40% lethality. A value of −100 meant all cells were dead.

These data suggest that the COH-SR compounds may be used in treating cancers such as leukemia (e.g. acute myeloid leukemia (AML) and monocytic leukemia), lung cancer (e.g. non-small cell lung cancer), colon cancer, CNS cancer, melanoma, ovarian cancer, renal cancer, prostate cancer, and breast cancer.

Figure 29A:
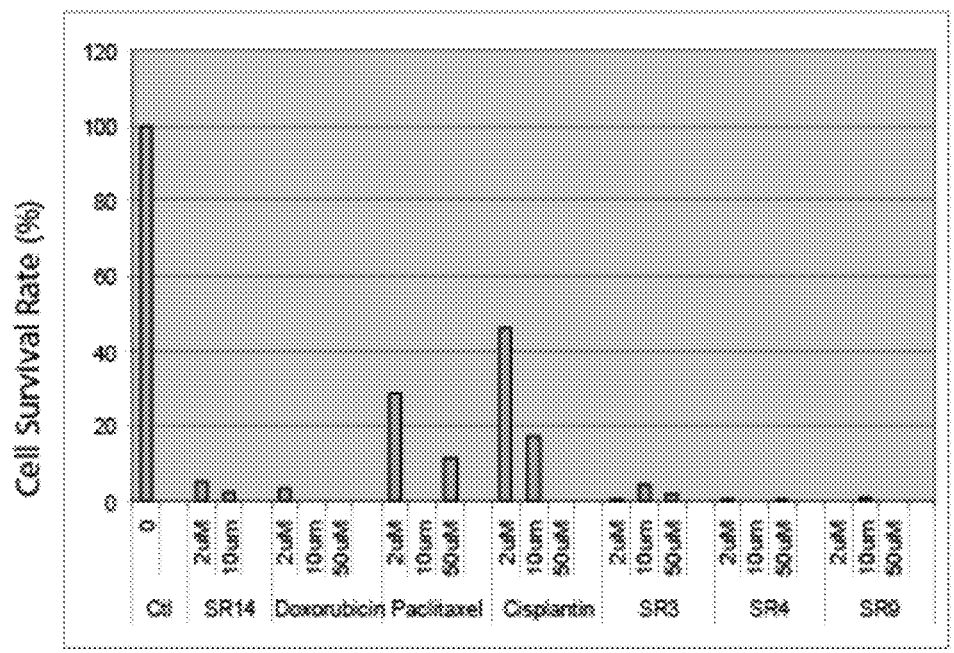
FIGS. 29A-29B: Effects of COH-SR3, COH-SR4, COH-SR9, COH-SR14, doxorubicin, paclitaxel or cisplatin on viabilities of 4T1 breast cancer cells (FIG. 29A) concentrations of test compounds are 2 μM or higher.
Figure 29B:
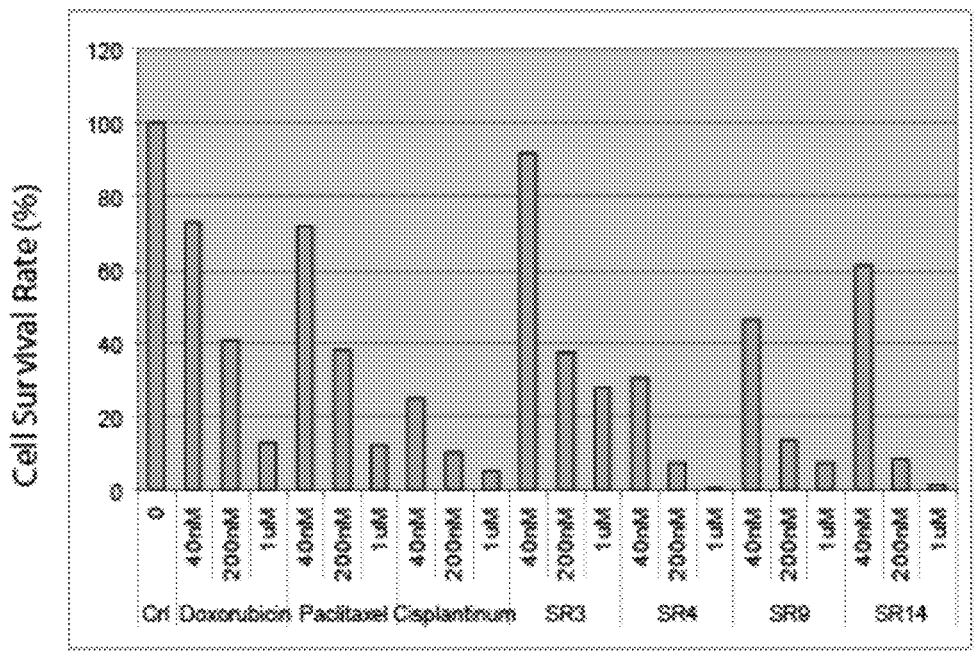
Figure 30:
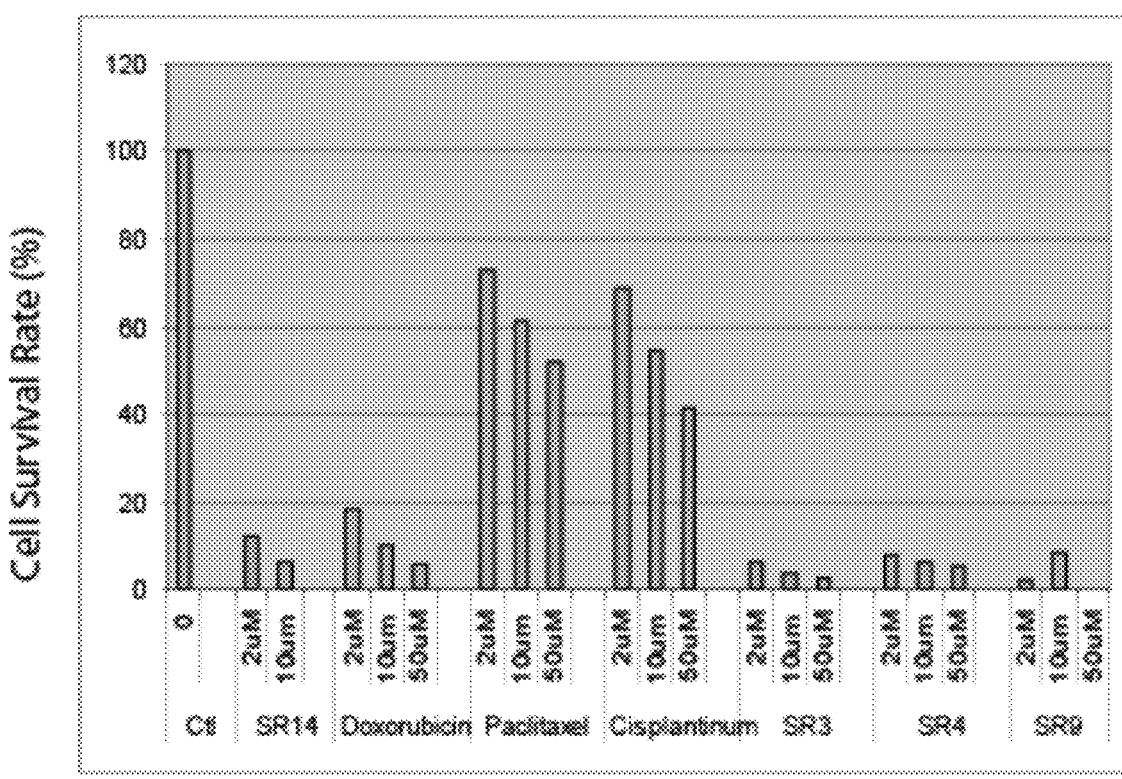
FIG. 30: Effects of COH-SR3, COH-SR4, COH-SR9, COH-SR14, doxorubicin, paclitaxel and cisplatin on viabilities of HMLE breast cancer cells (uM also represents μM in the figure).

Example 5. COH-SR Compounds Inhibited Growth and Proliferation of Breast Cancer Cell Line 4T1 (a Mouse Mammary Tumor Line) (FIGS. 29A-B) and HMLE (Telomerase Immortalized Human Mammary Epithelial Cells) (FIG. 30)

The effects of COH-SR compounds on breast cancer cells were investigated. Cells from 4T1 or HMLE breast cancer cell line were seeded in 96-well plates (about 2000 cells/well), allowed to proliferate for one day, treated with a COH-SR compound, doxorubicin, paclitaxel, cisplatin, or nothing (control) at a specific dose (3 wells for each treatment) and assayed for cell viability 3 days after using DIMSCAN assay. COH-SR3, COH-SR4, COH-SR9, doxorubicin, paclitaxel, and cisplatin were used at a dosage of 40 nM, 200 nM, 1 µM, 2 µM, 10 µM, or 50 µM for 4T1 breast cancer cell lines. COH-SR14 was used at a dosage of 40 nM, 200 nM, 1 µM, 2 µM, or 10 µM for 4T1 breast cancer cell lines. COH-SR3, COH-SR4, COH-SR9, doxorubicin, paclitaxel, and cisplatin were used at a dosage of 2 µM, 10 µM, or 50 µM for HMLE breast cancer cell lines. COH-SR14 was used at a dosage of 2 µM, or 10 µM for HMLE breast cancer cell lines. COH-SR3, COH-SR4, COH-SR9 and COH-SR14 showed similar or better cytotoxic effects on 4T1 breast cancer cell lines compared with current anti-cancer drugs such as doxorubicin, paclitaxel and cisplatin (FIGS. 29A-B). COH-SR3, COH-SR4, COH-SR9 and COH-SR14 showed more potent cytotoxic effects on 4T1 breast cancer cell lines compared with current anti-cancer drugs such as doxorubicin, paclitaxel and cisplatin (FIG. 30).

Example 6. COH-SR Compounds Inhibited Growth and Proliferation of Breast Cancer Stem Cell (BCSC) (CD44+CD24−) (FIGS. 31A-C and 32A-B)

Xenograft preparations from NOD/SCID mice were performed to generate BCSC (CD44+CD24−) using patient tumor specimens derived from primary breast cancer tumors previously exposed to neoadjuvant chemotherapy. Identifications of BCSC (CD44+CD24−) and regular breast cancer cells (CD44−EpCAM+) were performed by FACS analysis (FIG. 31(A)).

Figure 31A:
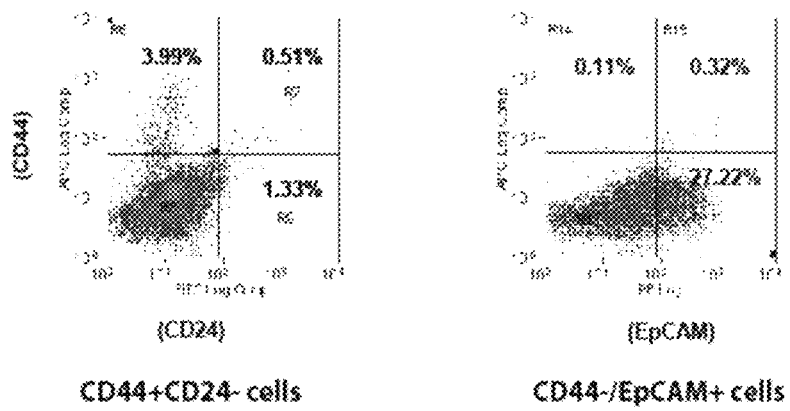
FIGS. 31A-31C: Effects of 20 μM COH-SR3, COH-SR4, COH-SR9, doxorubicin, paclitaxel or cisplatin on viabilities of CD44+CD24− cancer stem cells in breast tumor and CD44−/EpCAM+ regular breast cancer cells.
Figure 31B:
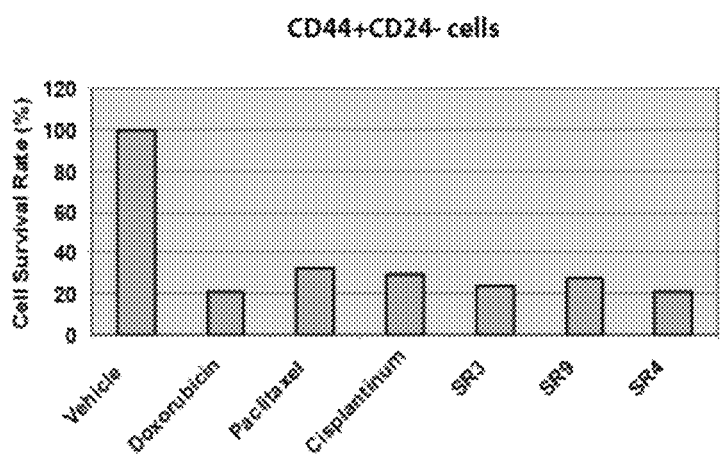
Figure 31C:
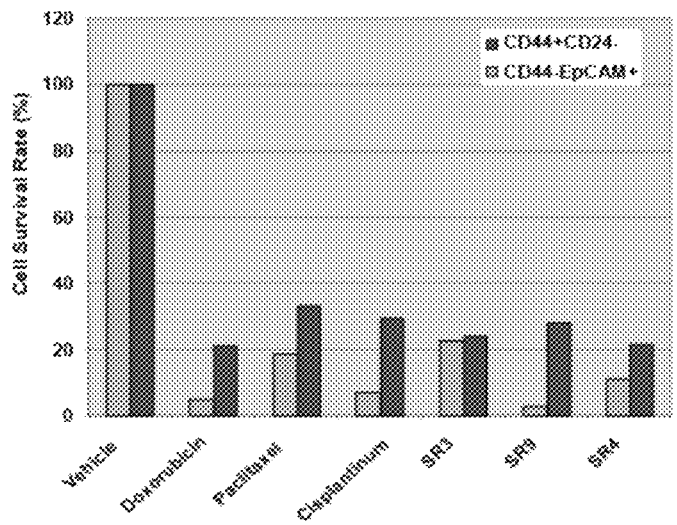

Cells of BCSC (CD44+CD24−) or regular breast cancer cells (CD44−EpCAM+) were isolated and cultured for several passages, and then treated with 20 µM of a COH-SR compound (COH-SR3, COH-SR4, or COH-SR9), or 20 µM of a known anti-cancer drug (adriamycin, paclitaxel or cisplatin) or nothing for 72 hours. Cell survival rates (%) were calculated from MTT assay with triplicate wells for each treatment. COH-SR3, COH-SR4 and COH-SR9 showed a similar or better effect on inhibition of cell growth of BCSC cells (FIGS. 31B and 31C) and regular breast cancer cells CD44−/EpCAM+ (FIG. 31C), but the effects on cell growth of BCSC cells and regular breast cancer cells were different (FIG. 31C).

Figure 32A:
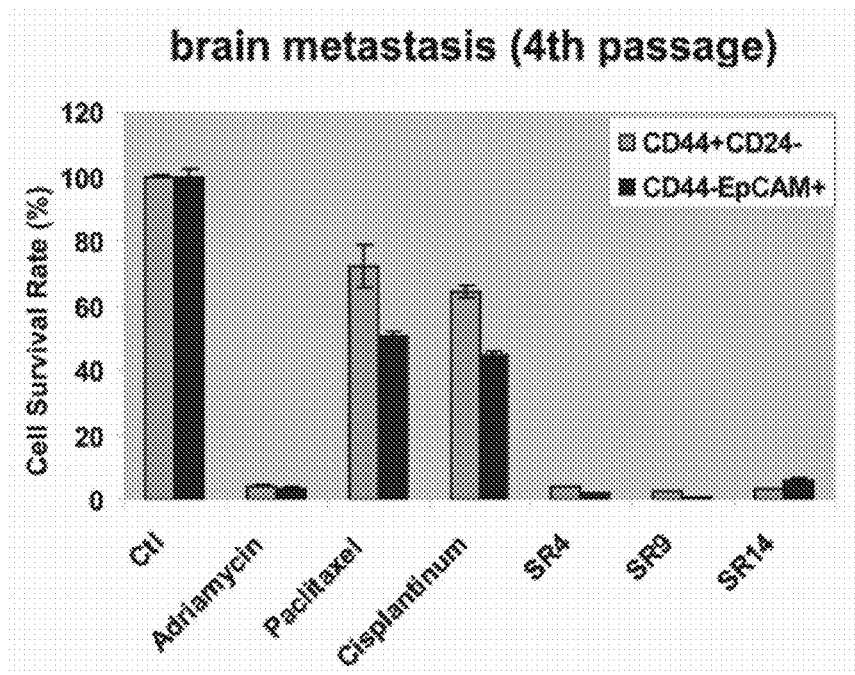
FIGS. 32A-32B: Effects of 20 μM COH-SR4, COH-SR9, COH-SR14, doxorubicin, paclitaxel or cisplatin on viabilities of CD44+CD24− cancer stem cells and CD44−/EpCAM+ regular breast cancer cells (FIG. 32A) metastized in the brain, and (FIG. 32B) in breast tumor.
Figure 32B:
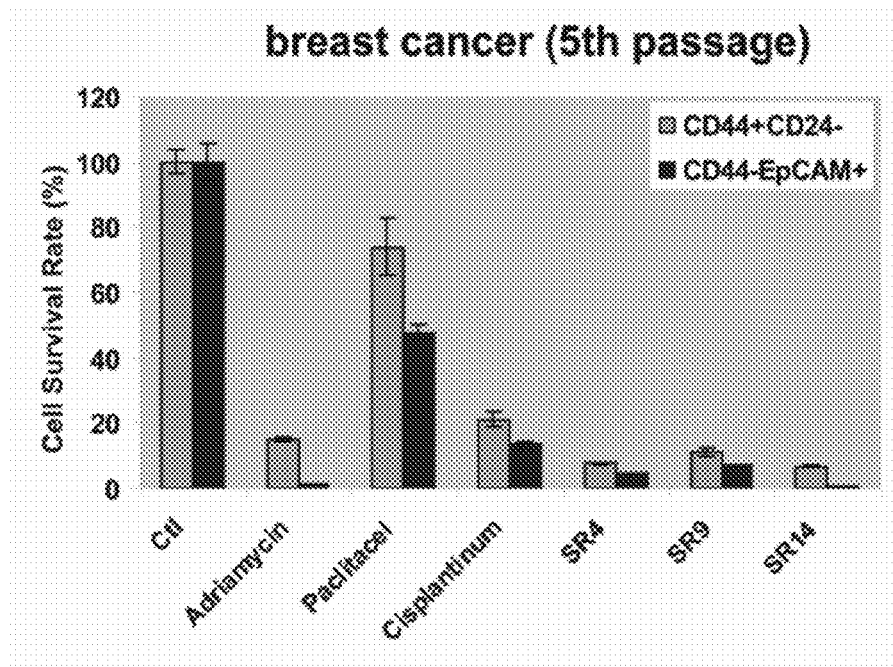

Cells of BCSC (CD44+CD24−) or regular breast cancer cells (CD44−EpCAM+) were isolated from breast tumor or brain metastasis and cultured for several passages, and then treated with 20 μM of a COH-SR compound (COH-SR4, COH-SR9, or COH-SR14), or 20 μM of a known anti-cancer drug (adriamycin, paclitaxel or cisplatin) or nothing for 72 hours. Cell survival rates (%) were calculated from MTT assay with triplicate wells for each treatment. The results showed that COH-SR4, COH-SR9 and COH-SR14 showed a similar or better effect on inhibition of cell growth of BCSC cells and regular breast cancer cells CD44−/EpCAM+, but the effects on cell growth of BCSC cells and regular breast cancer cells were different (FIGS. 32A and 32B).

Example 7. Effects of COH-SR4 in Ovarian Cancer Cells (FIGS. 33A-B)

Figure 33A:
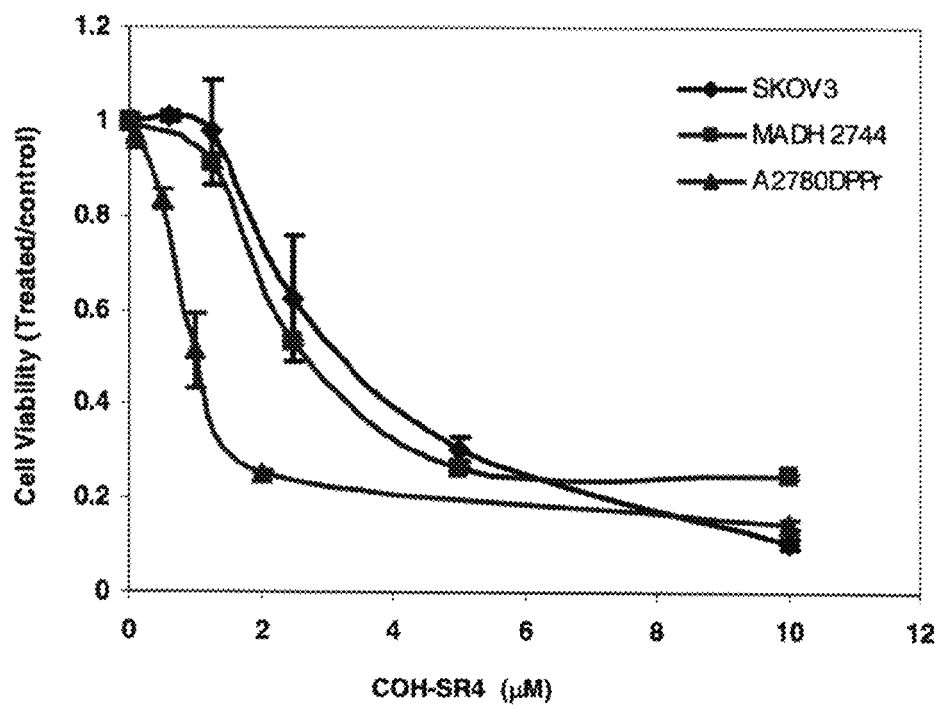
FIGS. 33A-33B: Effects of COH-SR4 in ovarian cancer cells.

(A) COH-SR4 Showed Toxicity Against Ovarian Cancer Cells (e.g. SKOV3, MADH2744, and A2780 DPPr) (FIG. 33A).

SKOV3 is a cisplatin resistant human ovarian cancer cell line. Human ovarian cancer cells (SKOV3, MADH2744, and S2780 DPPr) were incubated with COH-SR4 at various concentrations (0~10 μM) or without COH-SR4 for 48 hours. Cells Viabilities were determined by measuring cellular acid phosphatase activities. Data were represented as a ratio to vehicle (DMSO) control. Data showed a dose-dependent cytotoxicity and anti-proliferative effects of COH-SR4 on both regular and cisplatin-resistant ovarian cancer cells.

Figure 33B:
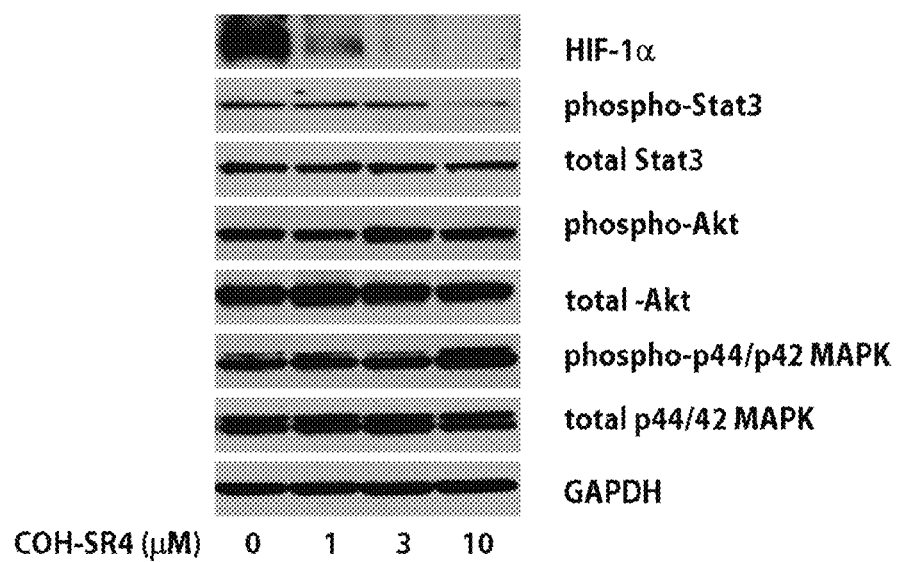

(8) COH-SR4 Inhibited Phosphorylation of Stat3 Protein and HIF-1α Protein Expression in SKOV3 Cells (FIG. 33B).

SKOV3 cells were incubated with various concentrations of COH-SR4 (1~10 μM) for 24 hours. Whole-cell lysates were analyzed by immunoblotting with antibodies against phosphorylated and total form of Stat3, Akt and MAPK, and HIF-1α. GAPDH was used as a loading control. The results showed that COH-SR4 inhibited phosphorylation of Stat3 protein and HIF-1α protein expression in SKOV3 cells (FIG. 33B).

Example 8. Effects of COH-SR4 on Brain Cancer (Glioma Cells)

Figure 34A:
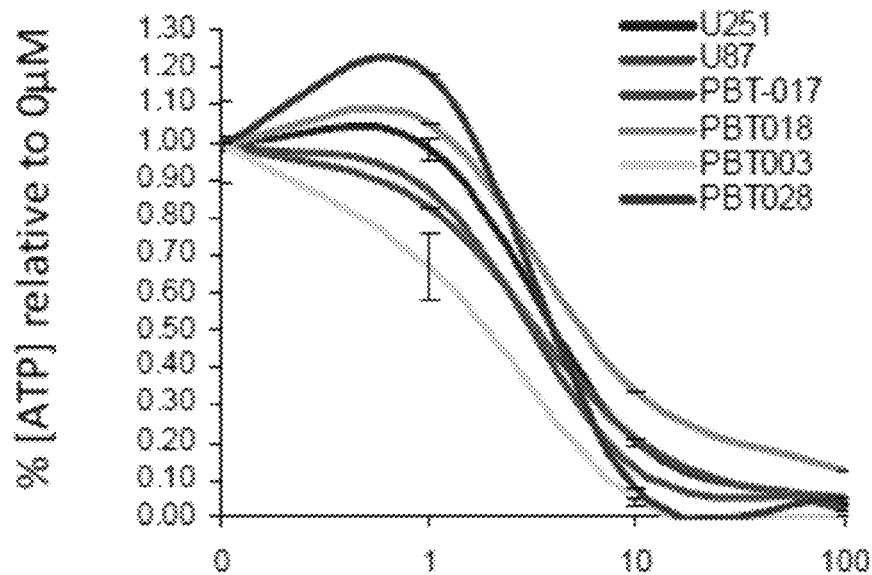
FIG. 34A: Effects of COH-SR4 in U251, U87, PBT-017, PBT018, PBT003 and PBT028 glioma cell lines.
Figure 34B:
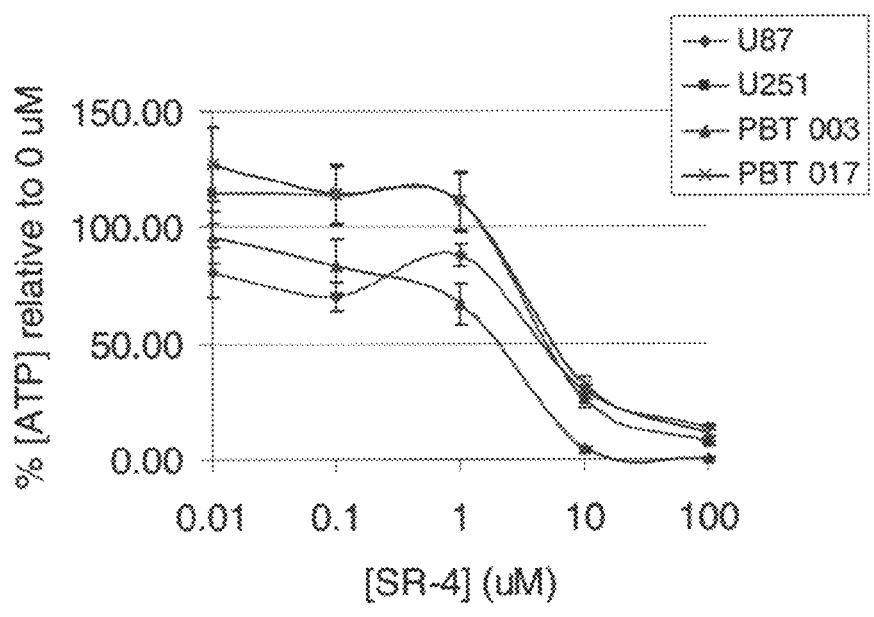
FIG. 34B: Effects of COH-SR4 in U251, U87, PBT-017, and PBT003 glioma cell lines.

(A) COH-SR4 Showed Toxicity Against Glioma Cell Lines (e.g. U251, U87, P8T-017, PT018, P8T003 and P8T028) (FIG. 34A and FIG. 34B).

Cells of each cell line (U251, U87, PBT-017, PBT018, PBT003 and PBT028) were treated with various concentrations (0~100 μM) of COH-SR4 for 72 hours. Cell viabilities were determined by ATP viability assays. Data were represented as a ratio to vehicle (DMSO) control, and plotted as mean±SEM (n=12) obtained from 2~3 experiments (FIG. 34A).

Cells of each cell line (U87, U251, PBT003 and PVT-017) were treated with various concentrations (0~100 μM) of COH-SR4 for 72 hours. Cell viabilities were determined by ATP viability assays. Data were represented as a ratio to vehicle (DMSO) control, and plotted as mean±SEM (n=12) obtained from 2-3 experiments (FIG. 34B).

The $IC_{50}$ of killing each glioma cancer cell lines are summarized in Table 1:

TABLE 1

$IC_{50}$ of COH-SR4 on Glioma Cancer Cell Lines
U251, U87, PBT-017, PBT018, PBT028 and PBT003

| Glioma Cell Line | U251 | U87 | PBT-017 | PBT018 | PBT028 | PBT003 |
|---|---|---|---|---|---|---|
| $IC_{50}$ (μM) | 2.1 | 2.8 | 2.0 | 6.5 | 2.0 | 1.5 |

Figure 34C:
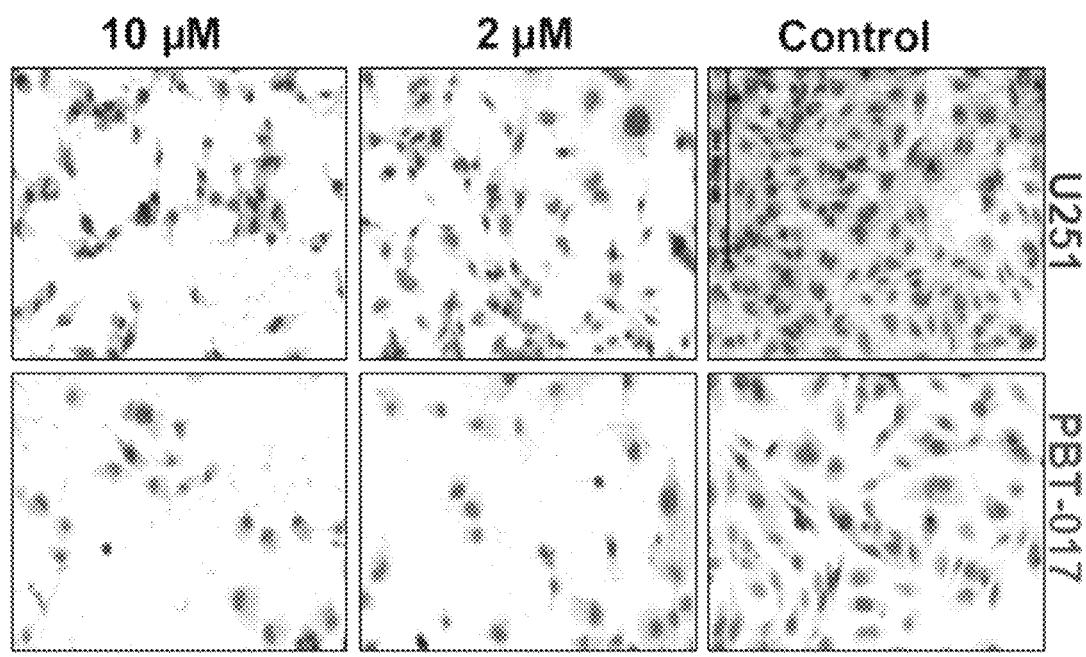
FIG. 34C: COH-SR4 was cytotoxic to U251, and PBT-017 glioma cell lines, wherein scale bar applies to all images (uM also represents μM in the figures).

(B) COH-SR4 was Cytotoxicto Glioma Cells U251 and P8T-017 (FIG. 34C).

Cells of glioma U251 cell line or PBT-017 cell line were incubated with COH-SR4 of 2 μM or 10 μM, or without any treatment for 48 hours, and then examined for morphologic changes by Giemsa-Wright stain. The results were observed microscopically and shown in FIG. 34C. All pictures in FIG. 34C were shown with the same magnification. The cell numbers in glioma cells treated with COH-SR4 decreased compared to cells not treated (FIG. 34C).

Figure 35A:
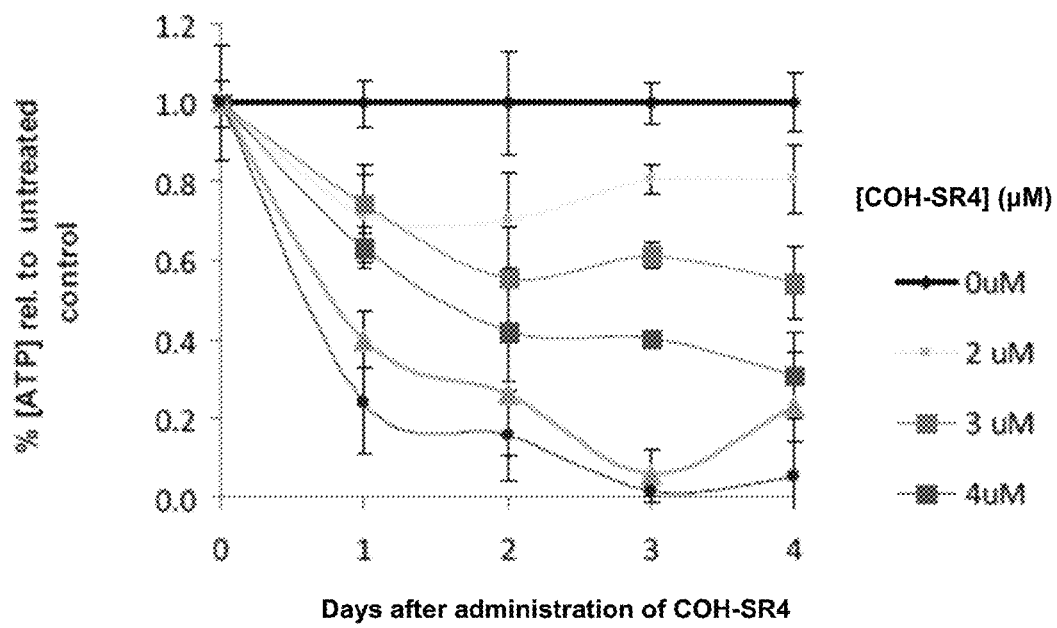
FIGS. 35A-35B: Higher doses of COH-SR4 showed faster killing in glioma cells (FIG. 35A) U251 and (FIG. 35B) PBT-017 (uM also represents μM in the figures).
Figure 35B:
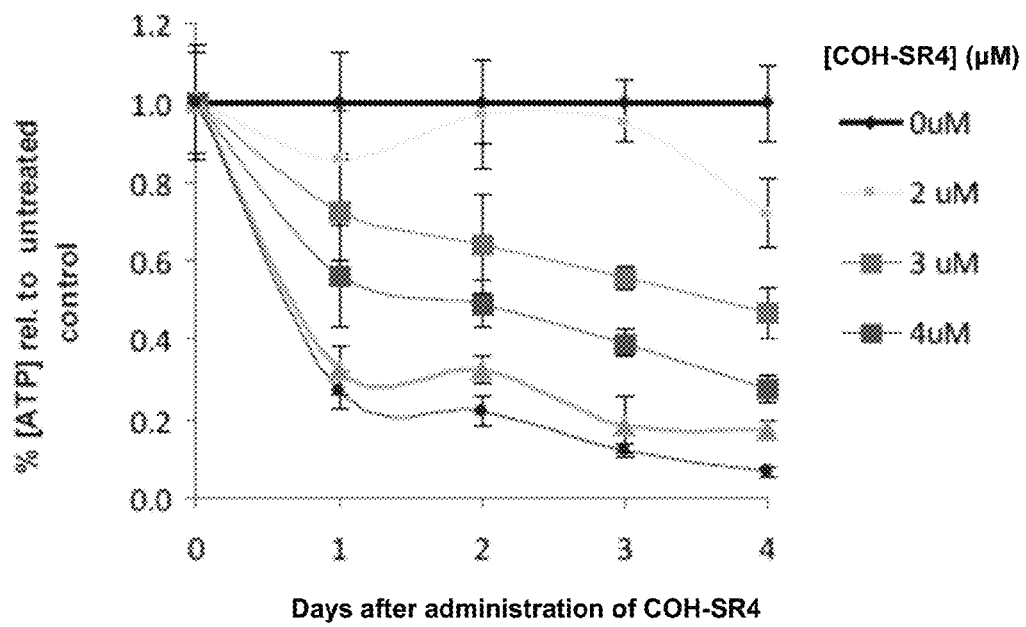

(C) Higher Doses of COH-SR4 Showed Faster Killing in Glioma Cells (FIGS. 35A-B).

Glioma cells U251 (FIG. 35A) and PBT-017 (FIG. 35B) were treated with COH-SR4 having a concentration of 0 μM, 2 μM, 3 μM, or 4 μM and analyzed by the same protocol described supra. Cell viabilities were determined by ATP viability assays. Data were represented as a ratio to untreated control, and plotted as mean±SEM (n=12) obtained from 2-3 experiments. The results showed that higher doses of COH-SR4 killed the glioma cells faster.

Figure 36:
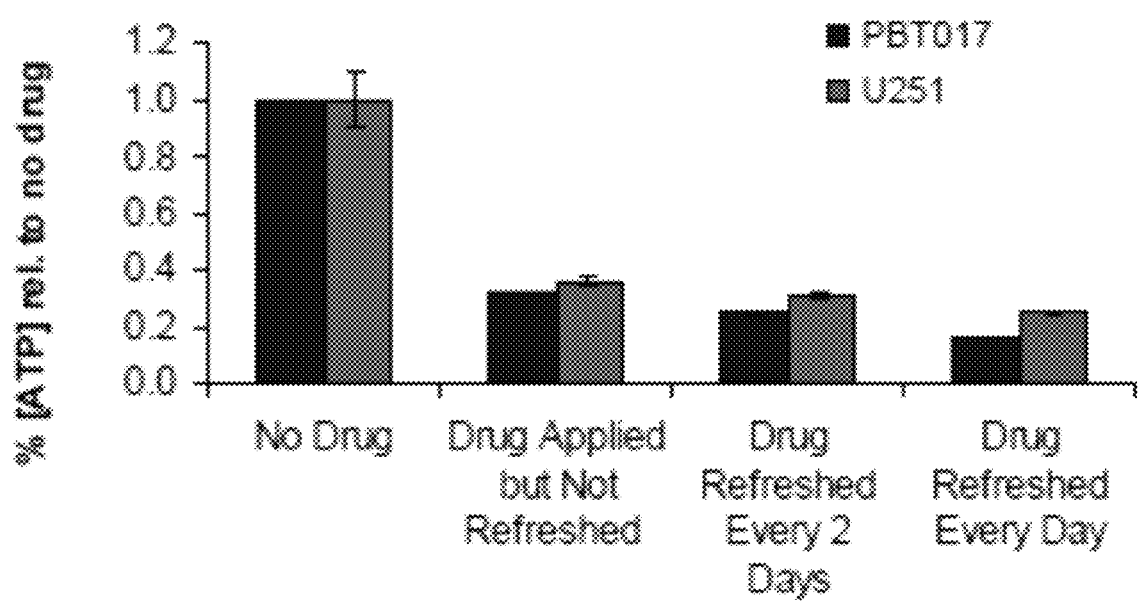
FIG. 36: Treatments of COH-SR4 showed improved killing in glioma cells U251 and PBT-017 when the drugs applied were refreshed.

(D) Treatments of COH-SR4 Showed Improved Killing in Glioma Cells U251 and PBT-017 when the Drugs Applied were Refreshed. (FIG. 36).

Glioma cells U251 and PBT-017 were treated with COH-SR4 with no refreshment of the drug, with refreshment of the drug every 2 days or with refreshment of the drug every day, or without any treatment. The resulting cells were analyzed by the same protocol described supra after treatment of. Data were represented as a ratio to untreated control, and plotted as mean±SEM (n=12) obtained from 2~3 experiments. The results showed that refreshment of the COH-SR4 applied killed the glioma cells faster.

Figure 37A:
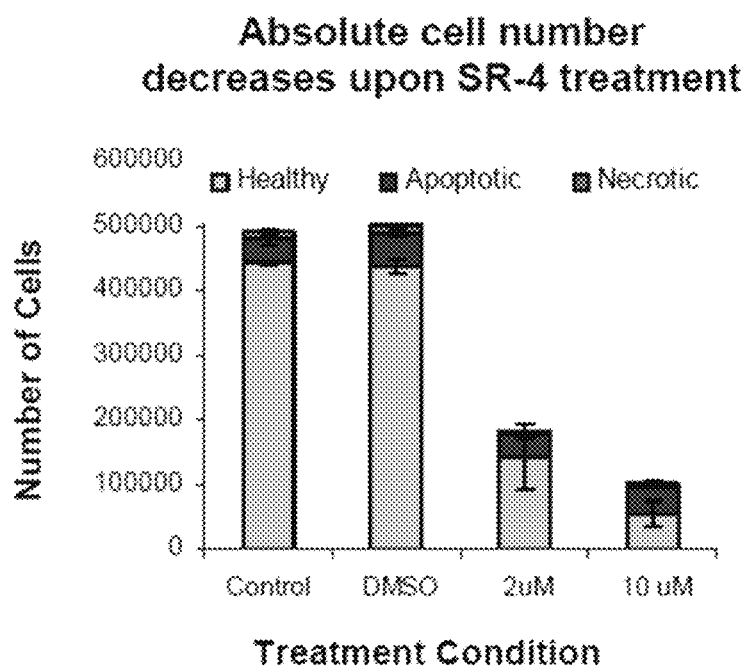
FIGS. 37A-37B: COH-SR4 induced apoptosis of glioma cells.
Figure 37B:
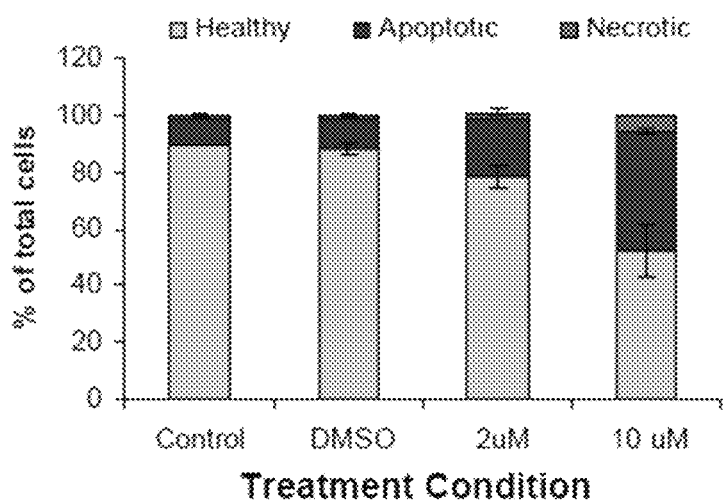

(E) COH-SR4 Induced Apoptosis of Glioma Cells (FIGS. 37A-B).

PBT-017 glioma cells were incubated with nothing (control), DMSO, and COH-SR4 at 2 μM or 10 μM for 4 days. The absolute cell number of the healthy cells, apoptotic cells and necrotic cells were measured and summarized in FIGS. 37A-B.

Treatment of COH-SR4 decreased absolute cell numbers of PBT-017 glioma cells (FIG. 37A). Furthermore, treatment of COH-SR4 increased the fraction of apoptotic cells in the remaining PBT-017 glioma cells (FIG. 37B).

Figure 38:
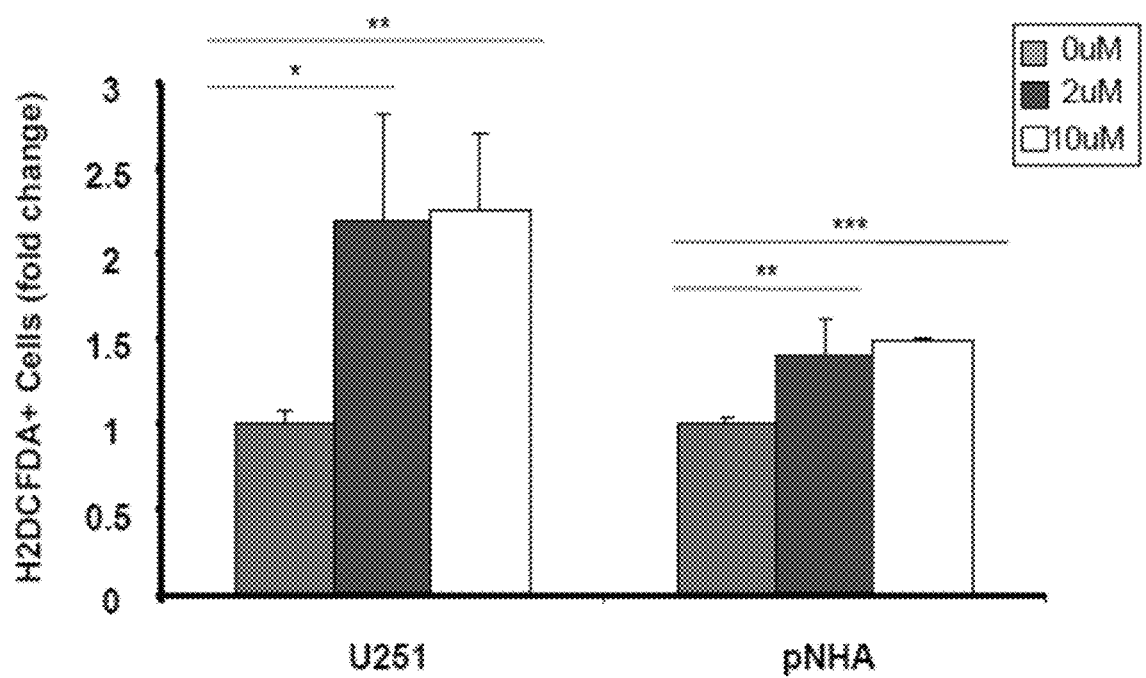
FIG. 38: Effects of COH-SR4 on H2DCFDA+ cells in glioma cells U251 compared to normal human astrocytes (pNHA) cells (uM also represents μM in the figures, "*" means $p<0.05$, "" means $p<0.01$, and "*" means $p<0.001$ regarding the significant differences).

(F) Treatment of COH-SR4 Generated Intracellular ROS in Glioma Cells (FIG. 38).

Cells of U251 glioma cells or pNHA cell lines were treated with COH-SR4 at a concentration of 0 μM, 2 μM or 10 μM for 24 hours before intracellular ROS was assessed by flow cytometry (representative of 3 runs and samples in triplicate). ROS increased in the glioma cells treated with COH-SR4 as indicated by the increased amounts of H2DCFDA+ cells (FIG. 38).

Figure 39A:
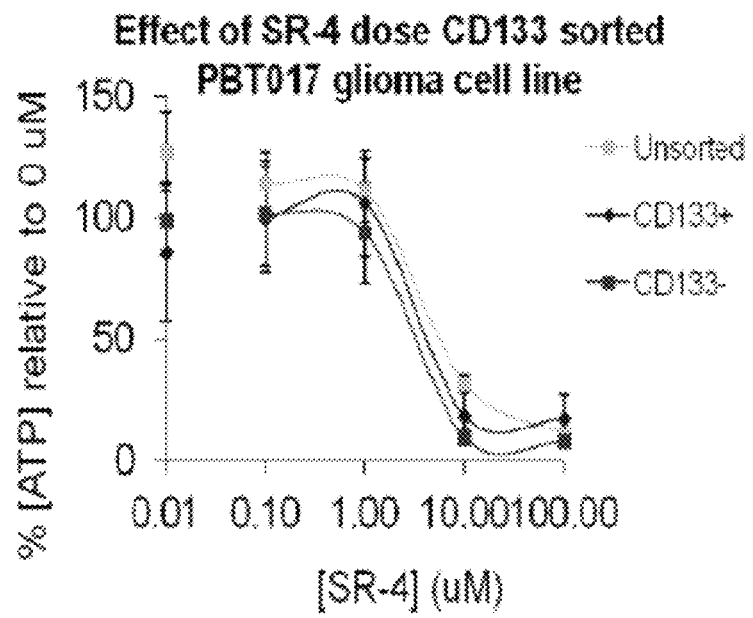
FIG. 39A: Effects of COH-SR4 on CD133 sorted glioma cell PBT-017.

(G) Effects of Dosages of COH-SR4 on CD133 Sorted P8T-017 Glioma Cell Line (FIG. 39A).

CD133 positive glioma stem cells were sorted by FACS. Unsorted cells, CD133 positive cells, and CD133 negative PBT-017 glioma cells were treated with COH-SR4 at various concentrations (0~100 µM) for 4 days, respectively. Data were represented as a ratio to untreated control, and plotted as mean±SEM (n=12) obtained from 2~3 experiments (FIG. 39A). The results showed that COH-SR4 was effective in killing the CD133 positive glioma stem cells as well as the unsorted and CD133 negative glioma cells.

Figure 39B:
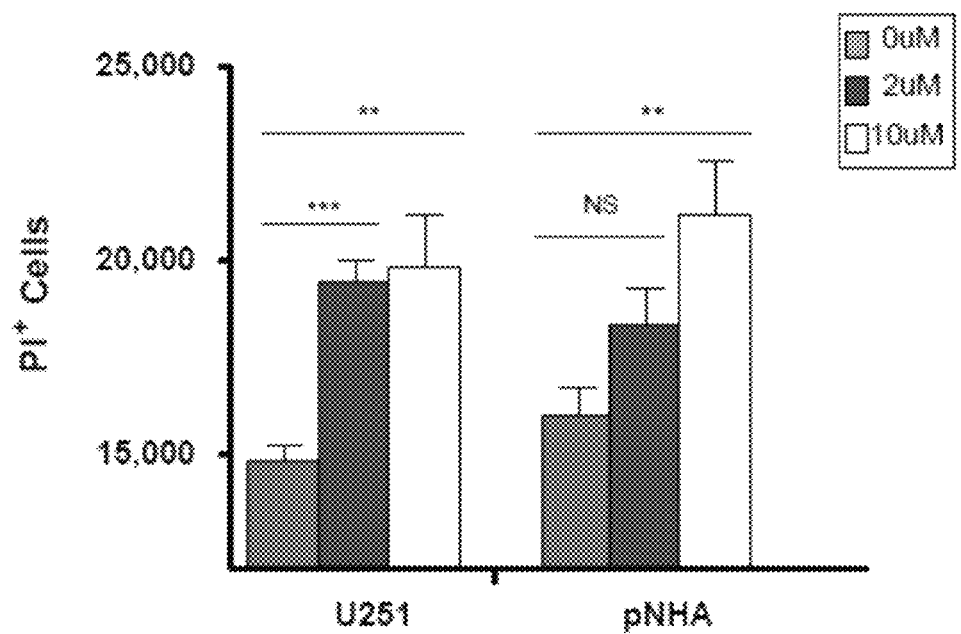
FIG. 39B: Effects of COH-SR4 on amounts of PI+ cells in pNHA and glioma cell U251 (uM also represents μM in the figures, "NS" means no statistically significant difference was observed; "" means $p<0.01$, and "*" means $p<0.001$ regarding the significant differences).

(H) Effects of Dosages of COH-SR4 on PI Positive Cells in U251 Glioma Cell Line (FIG. 39B).

Cells of U251 glioma cells or pNHA cell lines were treated with COH-SR4 at a concentration of 2 µM or 10 µM for four days. The amounts of PI positive (dead) cells were assessed by flow cytometry (representative of 3 runs and samples in triplicate) (FIG. 39B). There was no significant difference in PI positive cells between pNHA and glioma cells without treatment.

Figure 40:
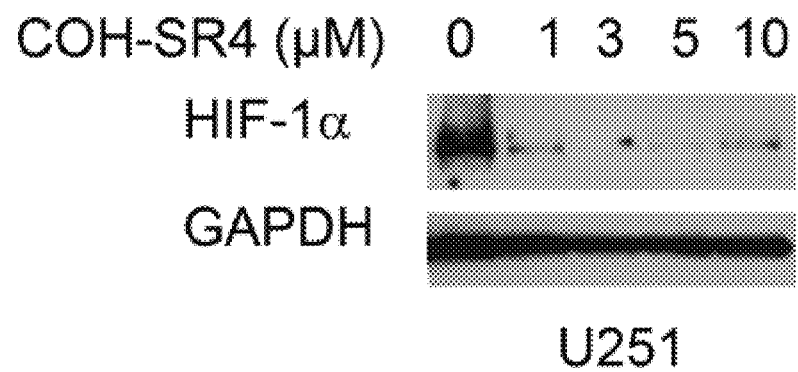
FIG. 40: COH-SR4 inhibited HIF-1α protein expression in U251 (uM also represents μM in the figure).

(I) COH-SR4 Inhibited HIF-1α Protein Expression in U251 Cells (FIG. 40)

U251 cells were incubated with various concentrations of COH-SR4 (1~10 µM). Whole-cell lysates were analyzed by immunoblotting with antibodies against HIF-1α. GAPDH was used as a loading control. The results showed that COH-SR4 inhibited HIF-1α protein expression in U251 cells (FIG. 40).

Figure 41:
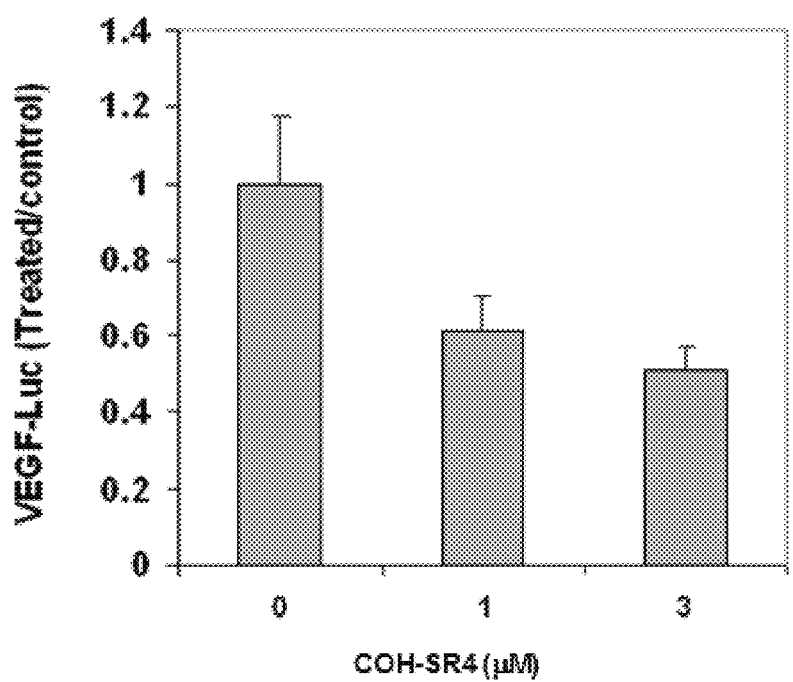
FIG. 41: COH-SR4 inhibited luciferase expression of VEGF protein in U251 cells.

(J) COH-SR4 inhibited luciferase expression of VEGF protein in U251 cells (FIG. 41).

U251 cells expressing luciferase reporter containing human VEGF promoter were incubated with various concentrations of COH-SR4 (0, 1, or 3 µM) for 24 hours. Luciferase activity was determined and normalized to the cell number for each treatment. Data were represented as a ratio to vehicle control that was treated by DMSO. The results showed that COH-SR4 inhibited luciferase expression of VEGF protein in U251 cells (FIG. 41).

Figure 42:
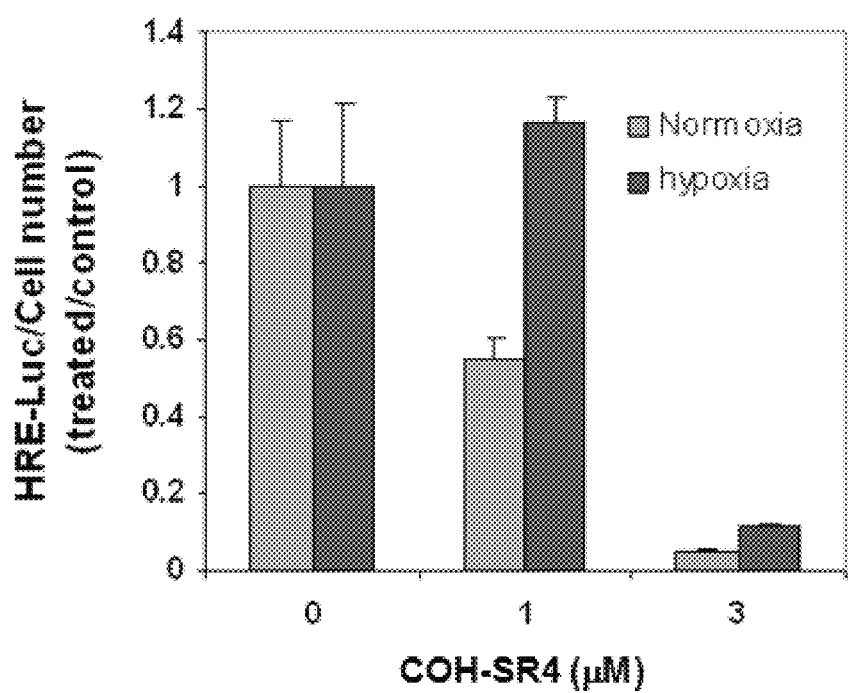
FIG. 42: COH-SR4 inhibited luciferase expression driven by HRE promoter in U251 cells under both normoxia and hypoxia conditions.

(K) COH-SR4 Inhibited Luciferase Expression Driven by HRE Promoter in U251 Cells Under Both Normoxic and Hypoxic Conditions (FIG. 42).

U251 cells were transfected with plasmids expressing luciferase reporter genes driven by a HRE reporter plasmid containing five copies of the HRE site (5xHRE). Transfected cells were then incubated with COH-SR4 at various concentrations (0, 1, or 3 µM) for 24 hours and assayed for luciferase activities. Data were represented as a ratio to vehicle control that was treated by DMSO. The results showed that COH-SR4 inhibited luciferase expression driven by HRE promoter in U251 cells under both normoxic and hypoxic conditions (FIG. 42).

Figure 43A:
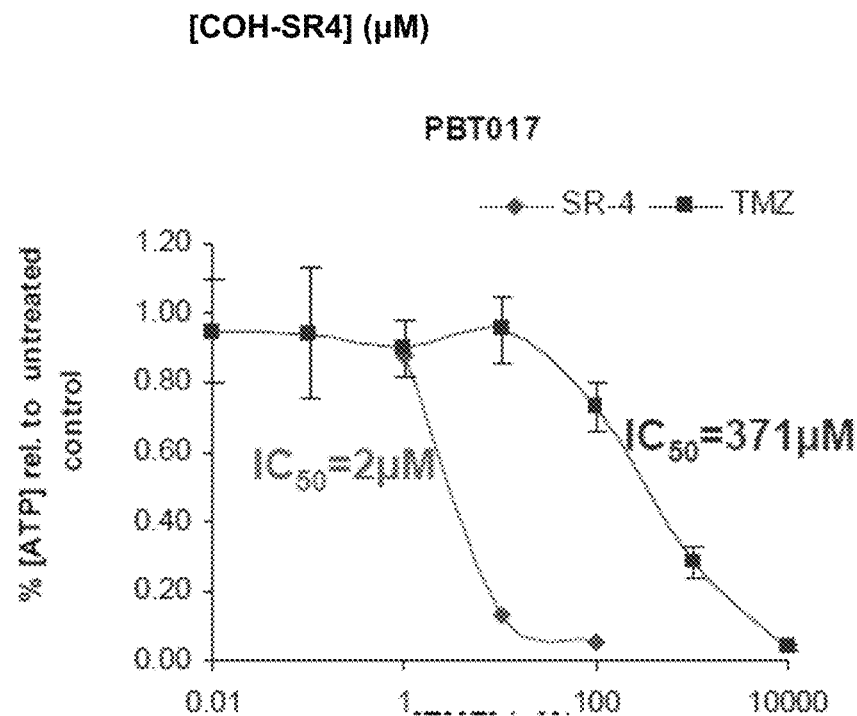
FIGS. 43A-B: Effects of COH-SR4 and TMZ on glioma cells (FIG. 43A) PBT-017 and (FIG. 43B) U251.
Figure 43B:
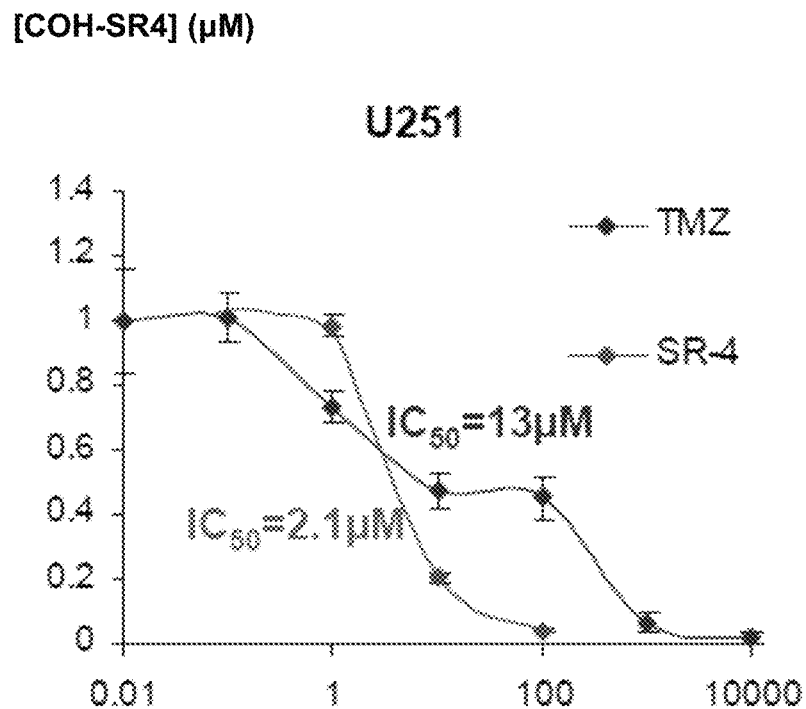

Example 9. Effects of COH-SR4 and TMZ on Glioma Cells PBT-017 and U251 (FIGS. 43A-B)

Cells of each cell line were treated with various concentrations (0~100 µM) of COH-SR4 or various concentrations (0~1000 µM) of TMZ for 72 hours. Cell viabilities were determined by ATP viability assays. Data were represented as a ratio to untreated cells as control, and plotted as mean±SEM (n=12) obtained from 2~3 experiments (FIGS. 43A-B).

The $IC_{50}$ of TMZ and COH-SR4 for each glioma cancer cell lines are summarized in Table 2: Table 2 also includes $IC_{50}$ of other chemotherapy drugs such as 5-FU, CPT-11 and 7-ethyl-10-hydroxy-camptothecin (SN-38, an active metabolite of CPT-11) for glioma cancer cell obtained using the protocol described supra.

TABLE 2

| $IC_{50}$ of COH-SR4 and TMZ on Glioma Cancer Cell Lines U251, and PBT-017 | | |
|---|---|---|
| Glioma Cell Line | U251 | PBT-017 |
| $IC_{50}$ of TMZ (µM) | 371 | 13 |
| $IC_{50}$ of COH-SR4 (µM) | 2 | 2.1 |
| $IC_{50}$ of 5-FU (µM) | 61 | — |
| $IC_{50}$ of CPT-11 (µM) | 41.1 | — |
| $IC_{50}$ of SN-38 (µM) | 0.04 | — |

Thus, COH-SR4 showed higher cytotoxicity potency toward glioma cells compared to TMZ and other chemotherapy drugs 5-FU and CPT-11.

Figure 47:
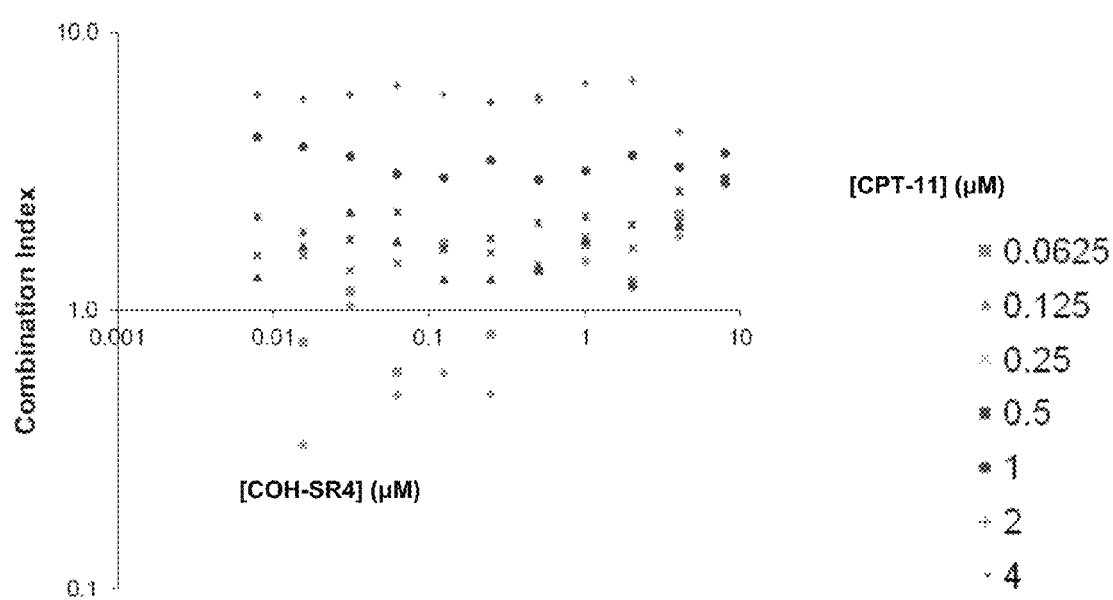
FIG. 47: COH-SR4 showed synergism with irinotecan (CPT-11) in treating glioma cells PBT-017.

Example 10. COH-SR4 Showed Synergism with a Chemotherapy Drug (e.g. TMZ, SN38, CPT-11, or 5-FU) in Treating Glioma Cells PBT-017 and/or U251 (FIGS. 44A-B~47)

Effects of combination of COH-SR4 and a chemotherapy drug such as TMZ, SN38, CPT-11, and 5-FU were studied by combination index (CI) theorem and plot using the method described in Chou ("Experimental Design, and Computerized Simulation of Synergism and Antagonism in Drug Combination Studies," Pharmacological Reviews, Vol. 58, No. 3), which is incorporated herein by reference in its entirety. For a two-drug combination, a CI of less than 1 showed a synergistic effect of the two drugs, a CI of 1 showed an additive effect of the two drugs, and a CI of more than 1 showed an antagonistic effect.

COH-SR4 and a chemotherapy drug (TMZ, SN38, CPT-11, or 5-FU) were dissolved in DMSO individually, and then diluted to the appropriate concentration in the same cell culture media before applying to cells of each cell line. After 4 days, the amount of ATP present in the cell lysates were assessed using Progema's CellGlo kit. The CI of each combination of COH-SR4 and the chemotherapy drug was calculated and plotted against the concentration of COH-SR4 for each concentration of the chemotherapy drug used.

Figure 45A:
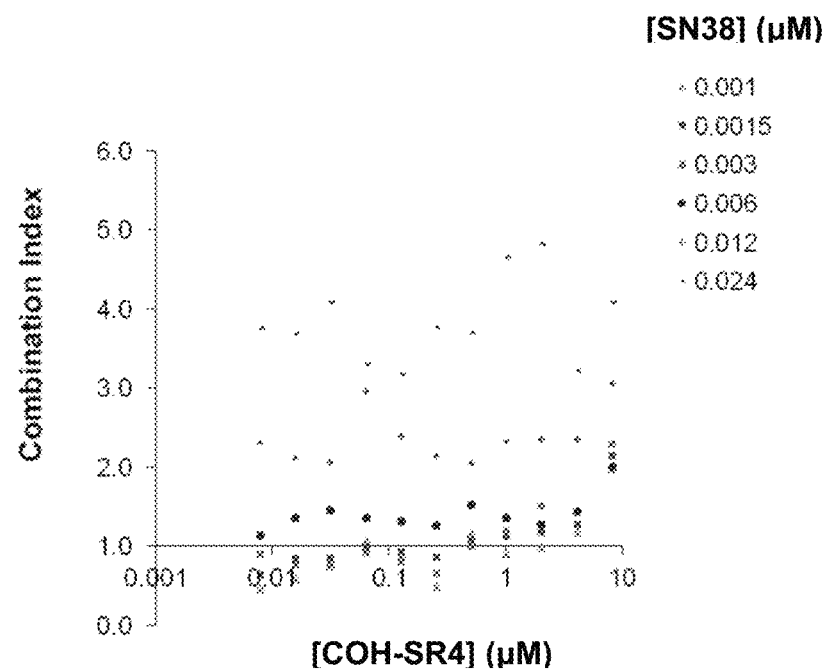
FIGS. 45A-B: COH-SR4 showed synergism with 7-ethyl-10-hydroxy-camptothecin (SN-38, an active metabolite of CPT-11) in treating glioma cells (FIG. 45A) U251 and (FIG. 45B) PBT-017.
Figure 46:
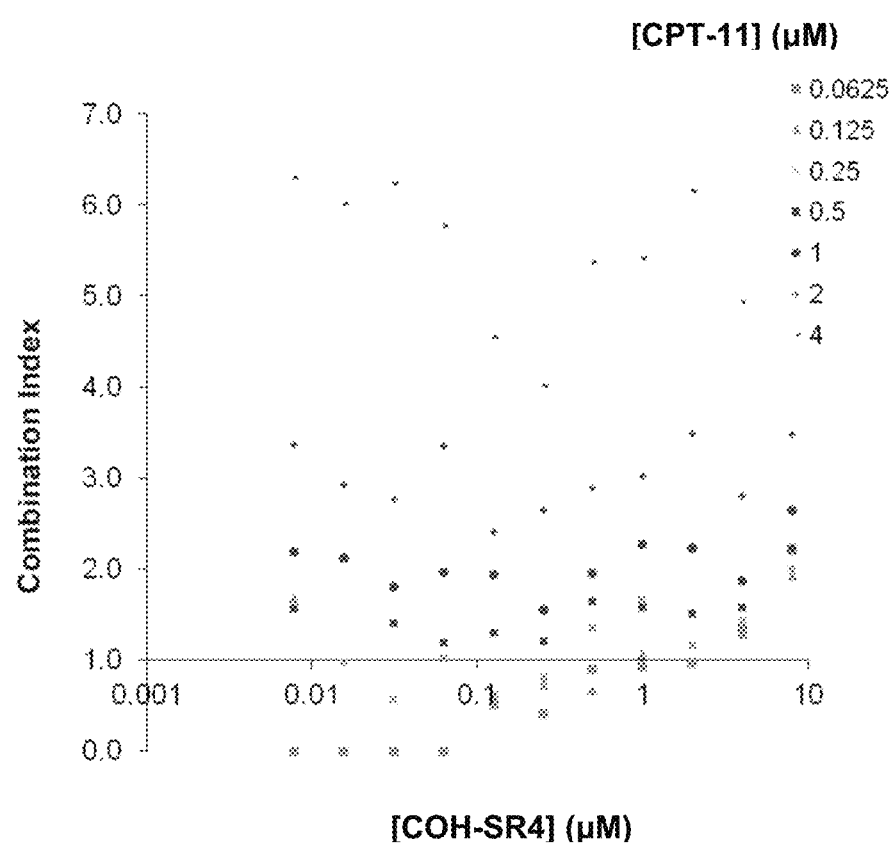
FIG. 46: COH-SR4 showed synergism with irinotecan (CPT-11) in treating glioma cells U251.

The combination indexes of combinations of COH-SR4 and TMZ, SN38, or CPT-11 in U251 glioma cells are shown in FIG. 44A, FIG. 45A, and FIG. 46, respectively. Synergism were observed for COH-SR4 at a concentration of less than 0.5 µM and low concentration of TMZ (12.5 µM), SN-38 (<0.001 µM), or CPT-11 (<0.125 µM). Additive effects were observed for COH-SR4 at a concentration of higher than 0.65 µM and TMZ at a concentration of 100 µM, for COH-SR4 at a concentration of higher than 0.5 µM and SN-38 at a concentration of less than 0.003 µM, and for COH-SR4 at a concentration of higher than 0.675 µM and CPT-11 at a concentration of higher than 0.5 µM.

Figure 45B:
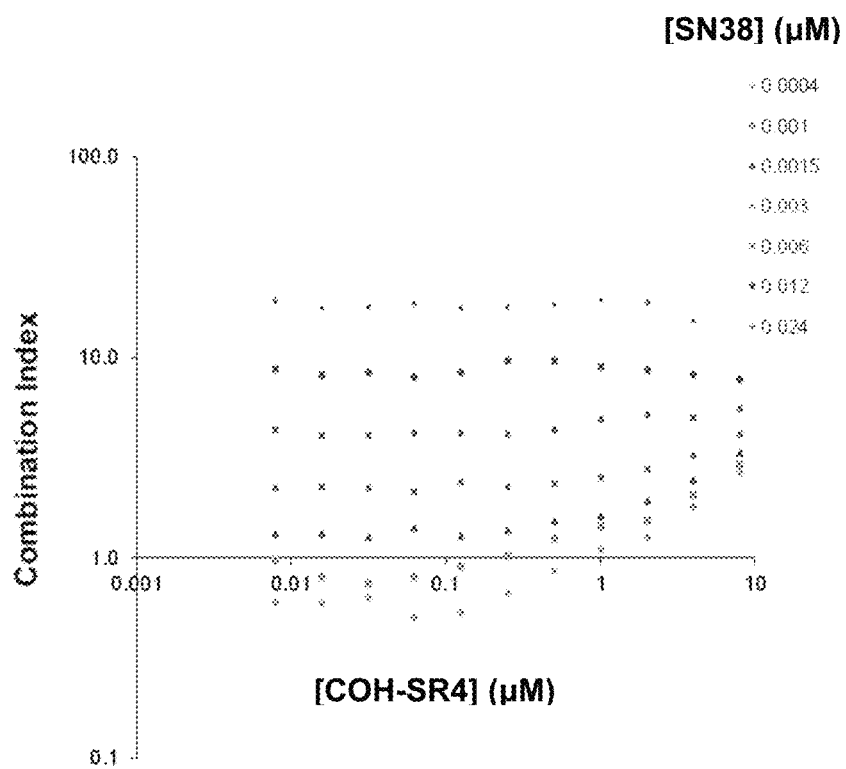

The combination index of COH-SR4 and TMZ, SN38, or CPT-11 in PBT-017 glioma cells are shown in FIG. 44B, FIG. 45B, FIG. 47, respectively. Synergism were observed for COH-SR4 at a concentration of less than 0.5 µM and low concentration of TMZ (25 µM), SN-38 (<0.0004 µM), or CPT-11 (<0.0625 µM). Additive effects were observed for COH-SR4 at a concentration of less than 1.0 µM and TMZ at a concentration of higher than 100 µM, for COH-SR4 at a concentration of higher than 0.5 µM and SN-38 at a concentration of less than 0.001 µM, for COH-SR4 at a concentration of higher than 1.0 µM and CPT-11 at a concentration of less than 0.5 µM, and for COH-SR4 at a concentration of less than 0.05 µM and 5-FU at a concentration of higher than 250 µM.

CI studies of COH-SR4 and 5-FU showed synergism for COH-SR4 at concentration of less than 0.5 µM and 5-FU at a concentration of less than 125 µM.

Thus, the results showed that small amounts of COH-SR4 may be useful to increase the therapeutic effect of another anticancer drug such as TMZ, SN38, CPT-11 and 5-FU.

Example 11. COH-SR4 is a Substrate for GSTP

Prokaryotic Expression of GSTP

The cDNA of GSTP was cloned into the prokaryotic expression plasmid vector, pET30a(+) (Novagen), creating the GSTP-pET30a(+) plasmid free of extraneous sequences. Bam H1 and XhoI restriction sites were used for cloning. This plasmid was transfected into E. coli BL21 (DE3). Protein was expressed in E. coli BL21 (DE3) grown at 37° C. Once the $OD_{600}$ reached 0.6 protein was induced with 0.4 mM IPTG.

Purification of Recombinant GSTP

All purification steps were carried out at 4° C. unless otherwise specified. All buffers were prepared fresh and filter sterilized. Briefly, bacteria was lysed in 10 mM $K-PO_4$ buffer pH 7.0 containing 1.4 mM β-mercaptoethanol (Buffer A) and 100 µM PMSF followed by sonication at 50 rpm for 3 times at 30 sec each. After incubation in the above buffer for 4 hours with gentle shaking lysate was centrifuges at 28,000× g for 45 min at 4° C. and the supernatant was collected for GSH-affinity chromatography. GSH-affinity resin (i.e., epoxy-activated Sepharose 6B) was equilibrated with 22 nM $K-PO_4$ buffer, pH 7.0 containing 1.4 mM β-mercaptoethanol (Buffer B). The supernatant was mixed with GSH-affinity resin for coupling for overnight at 4° C. The unbound proteins were washed with Buffer B until OD at 280 nm is zero. Bound protein (purified GSTP) was eluted with 50 mM Tris-HCl, pH 9.6 containing 1.4 mM β-mercaptoethanol. Elutes protein was dialyzed against Buffer A for overnight and the GSTP protein concentration was checked by Bradford's assay.

Figure 48:
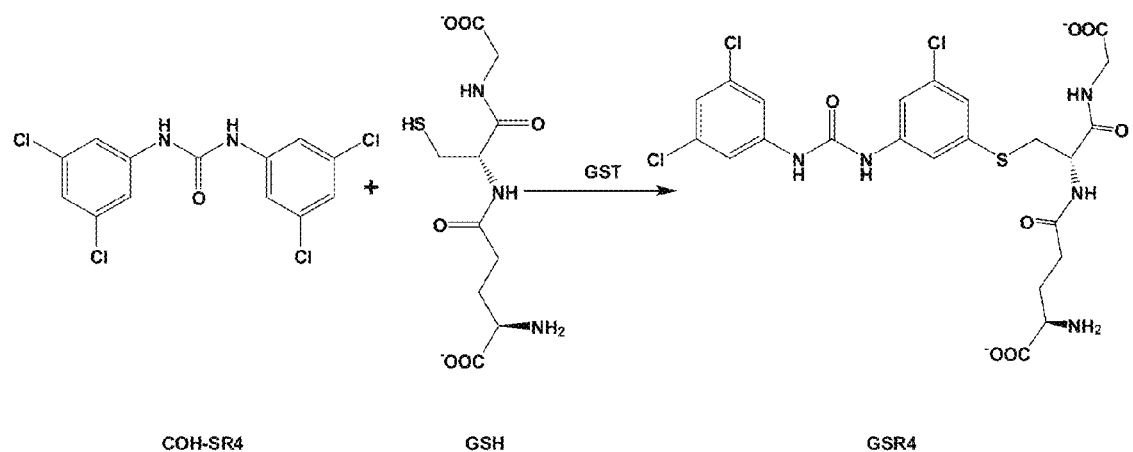
FIG. 48: Formation of COH-SR4 and Glutathione (GSH) conjugate mono-glutationyl-SR4(GSR4) in the presence of GST-P of the glutathione S-transferase family (GSTs).

FIG. 48 shows the formation of COH-SR4 and GSH conjugate (GSR4) in the presence of GSTs.

1-Chloro-2,4-dinitrobenzene (CDNB) is a known substrate of GST-P. Reaction of CDNB and GSH in the presence of GST-P forms a conjugate S-(2,4-dinitrophenol)-glutathione (DNP-SG) (Awasthi, Y. C. et al., Blood, 58: 733-738, 1981, incorporated herein by reference in its entirety).

15 mM GSH in 5 ml of 100 mM $K-PO_4$, pH 7.0 was prepared, degassed by bubbling with nitrogen for about 30 seconds, and added 5 U purified GSTP to provide a GSH-GSTP solution. CDNB (400 mM in 250 µL ethyl alcohol) was added slowly drop-by-drop into the GSH-GSTP solution with stirring in dark to provide a reaction mixture. The reaction mixture was degassed by bubbling with nitrogen for about 30 seconds, and stirred at room temperature in dark for about 12 hours. The reaction mixture was then lyophilized into reaction pellet. The reaction pellet (about 95% DNP-SG, with traces of oxidized glutathione (GSSG)) was washed twice with ethyl alcohol and reconstituted in $dH_2O$ (about 100~200 µL).

The similar protocol was used in preparing GSR4 by replacing CDNB with COH-SR4 (2 mM/250 µL ethanol solution prepared from 20 mM COH-SR4 in DMSO).

Figure 49:
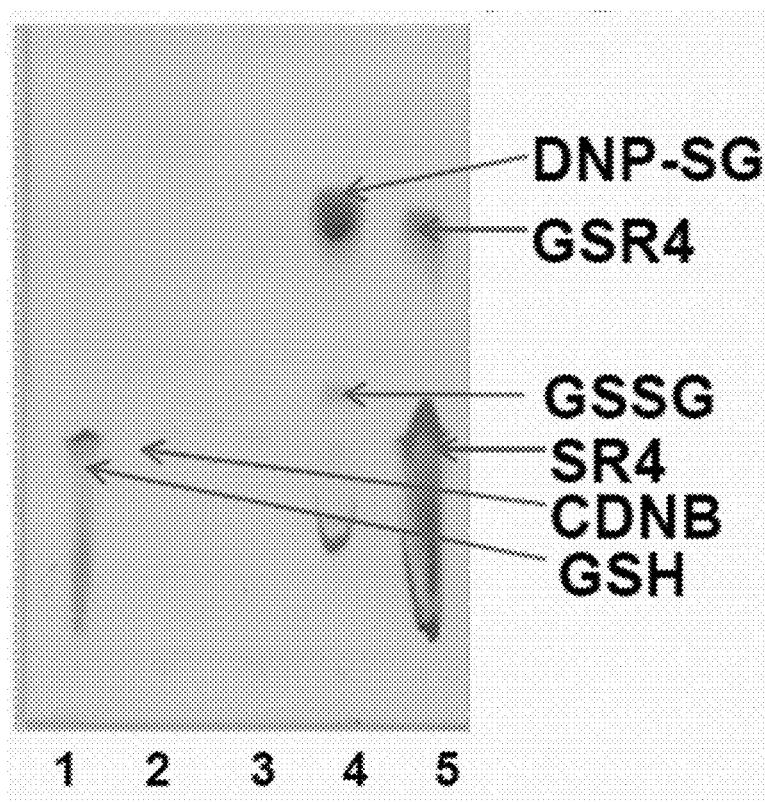
FIG. 49: TLC plate showing the formation of GSR4.

The TLC was run in a TLC silica plate (Whatman, 250 µm) in a TLC solvent of 7 part acetonitrile and 2 part $dH_2O$ for about 60 minutes. The TLC was visualized by spraying the TLC plate with ninhydrin (FIG. 49).

Lane 1 in the figure showed GSH; lane 2 showed CDNB; lane 3 showed COH-SR4; lane 4 showed DNP-SG as an example of GSH conjugate; and lane 5 showed that the GST-P catalyzed reaction of COH-SR4 and GSH formed a conjugate, GSR4.

Figure 50:
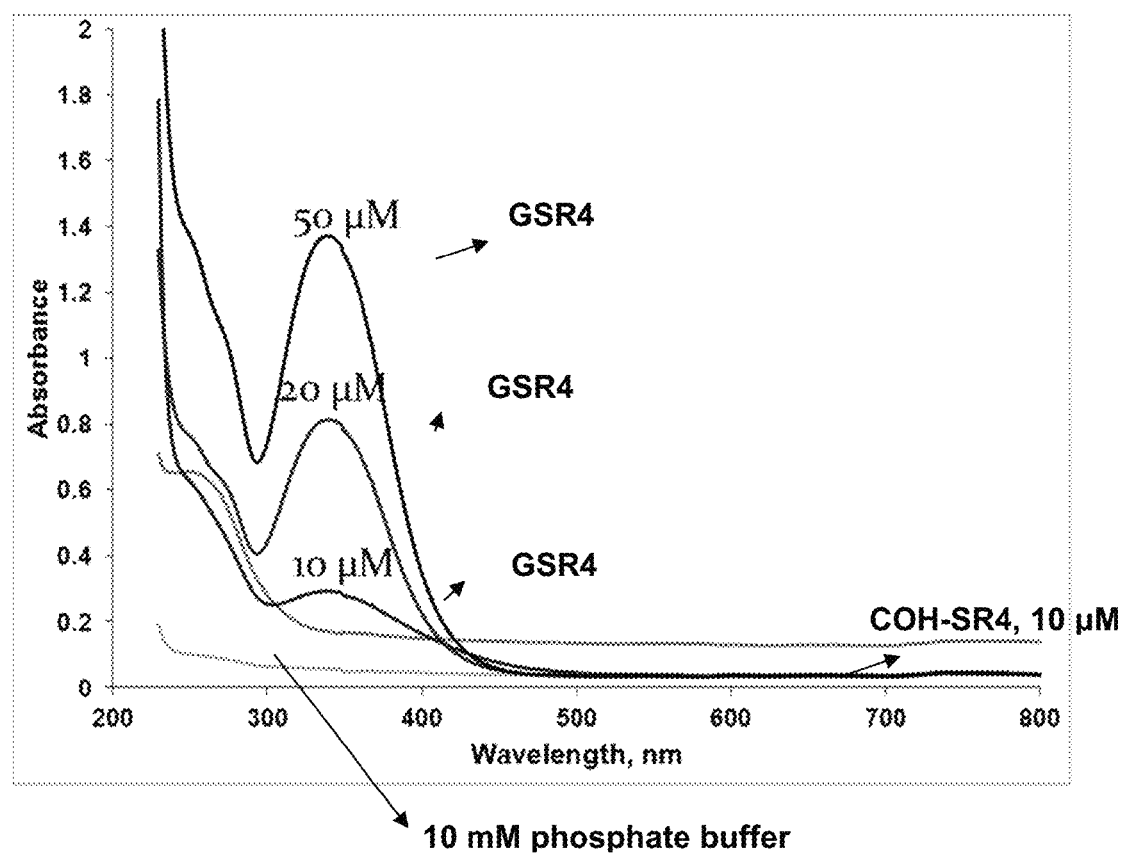
FIG. 50: Visible absorption spectrum of GSR4 and COH-SR4.

UV-VIS spectrums of COH-SR4 and GSR4 were obtained in the wavelength of 800~200 nm. The peaks at the 340 nm were characteristics of GSR4 (at 10, 20 or 50 µM in 10 mM phosphate buffer) compared to COH-SR4 (10 µM in 10 mM phosphate buffer) (FIG. 50).

Figure 51:
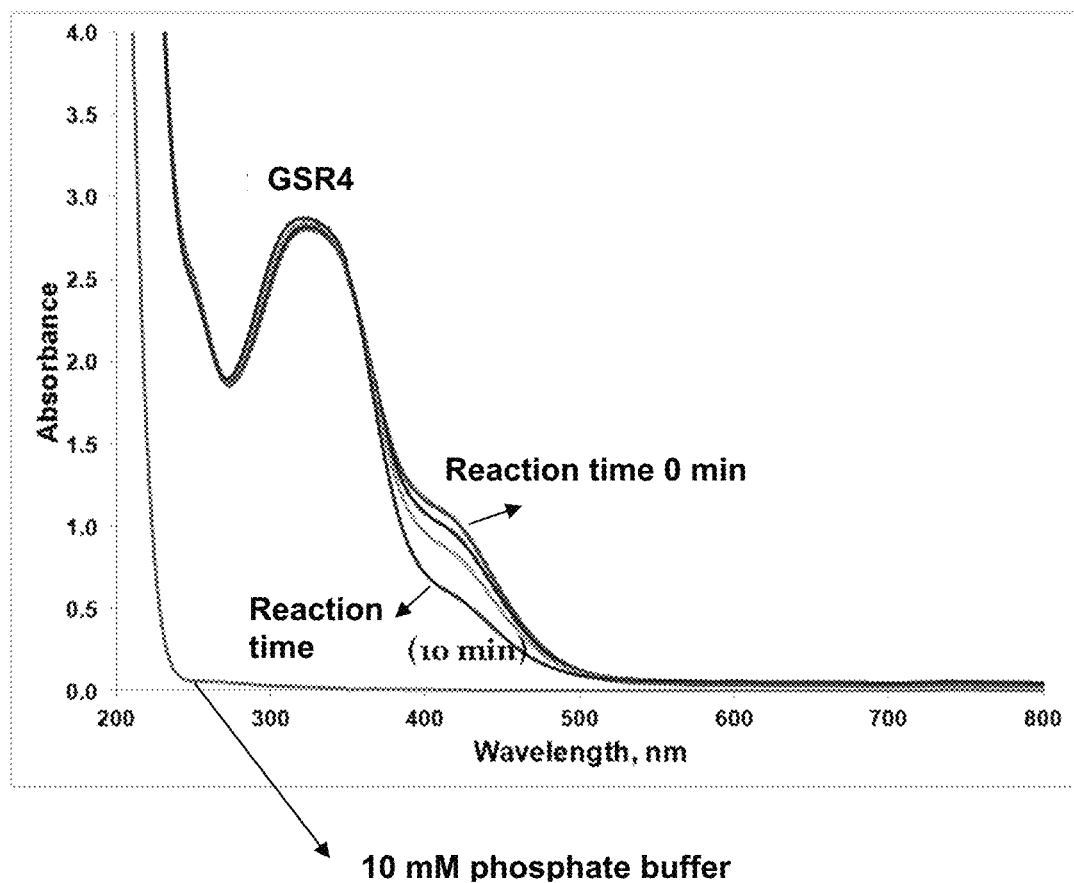
FIG. 51: Visible absorption spectrum showing formation of GSR4.

Furthermore, COH-SR4 significantly decreased the amount of GSH, which coincided with the formation of the conjugate GSR4 in a cell-free system (FIG. 51). A reaction system having 50 µM GSH, 50 µM COH-SR4 and 10 µL GSTP was prepared (Thangasamy, T. et al., Nutrition and Cancer, 59(2), 258-268, which is incorporated herein by reference). Aliquots were removed from the reaction system after certain reaction time (0~10 min) and added into 5, 5' dithiobis 2-nitrobenzoic acid (DTNB). Then UV-VIS spectrophotometers of the reaction aliquots were obtained. Visible absorption spectrum showed consumption of COH-SR4 (~415 nm, COH-SR4 with DTNB) and increased amount of GSR4 (~340 nm) as reaction time increased from about 0 min (the first spectrum from the top) to about 10 min (the first spectrum above the buffer spectrum, the spectrums in between (from the top to the bottom) were reaction mixtures having increasing reaction times).

Figure 52:
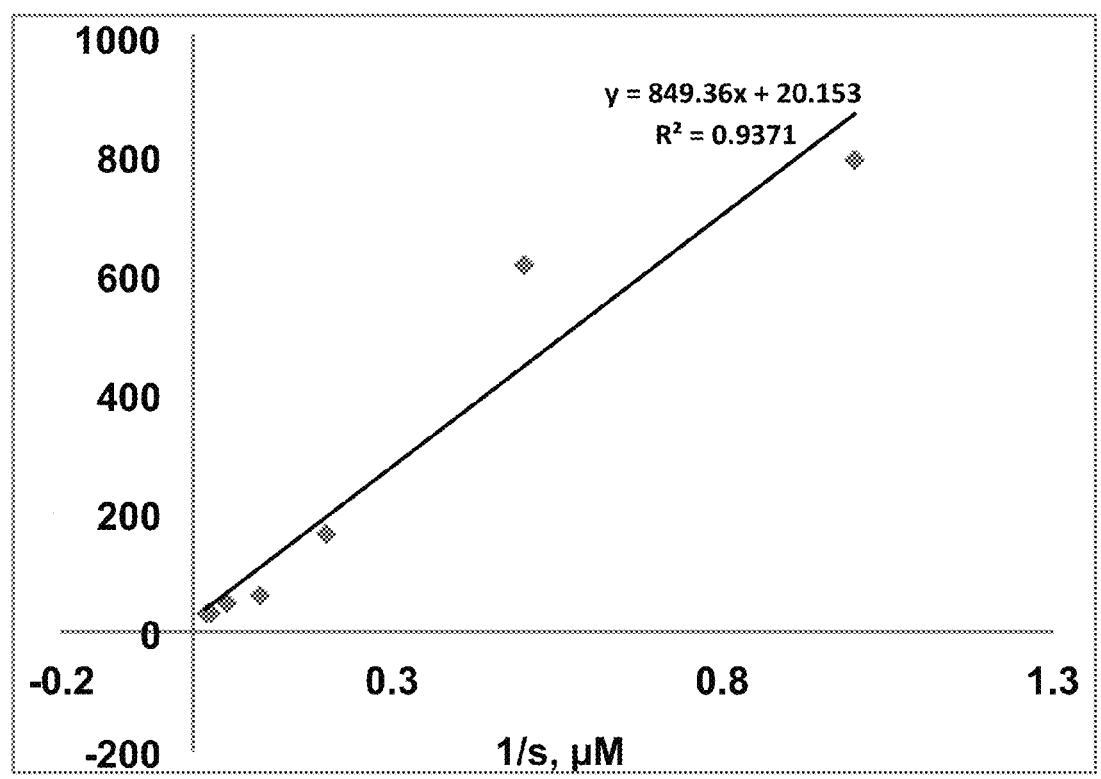
FIG. 52: Kinetics of GST-P using COH-SR4 as a substrate.

FIG. 52 showed kinetics of GST-P using COH-SR4 as a substrate, and the $K_m$ is 40 µM. Reaction systems were prepared by mixing COH-SR4 (50 µL, various final concentrations of 0~10 µM), 100 µL of 10 mM GSH (GSH solution in GST assay buffer, pH 6.5), 10 µL of GSTP enzyme (0.52 mg/mL) and having 840 µL GST assay buffer (100 mM $K-PO_4$ buffer, pH 6.5). Kinetics at 340 nm for 5 min at room temperature using Varian spectrophotometer was obtained.

Furthermore, GSTP activities towards CDNB were assessed in the presence of various concentration of GSR4. The GSTP activities decreased when the concentration of GSR4 increased (Table 3). Thus, COH-SR4 was a product inhibitor of GSTP with an estimated $K_i$ of less than 5 µM.

TABLE 3

| GSTP activity towards CDNB in the presence of GSR4 | |
| --- | --- |
| [GSR4] (µM) | GSTP activity towards CDNB ($K_{cat}$ [s-1]) |
| 0 | 93977 |
| 5 | 36385 |
| 10 | 16115 |

Figure 53A:
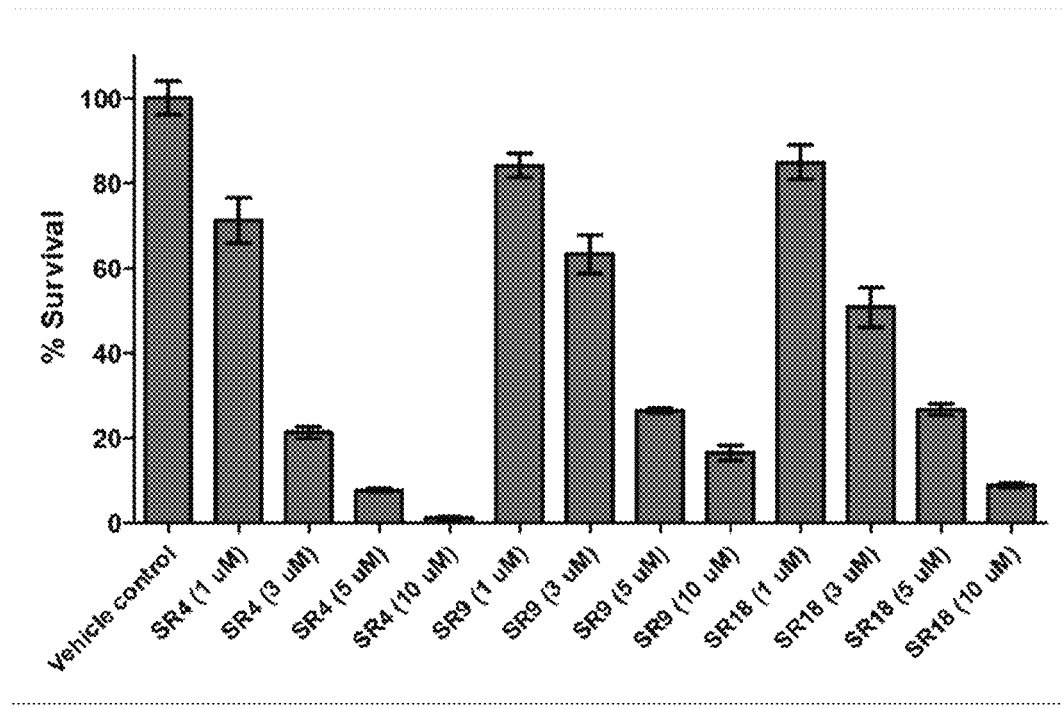
FIG. 53A: Effect of COH-SR4, COH-SR9 and COH-SR18 on B16F10 cells
Figure 53B:
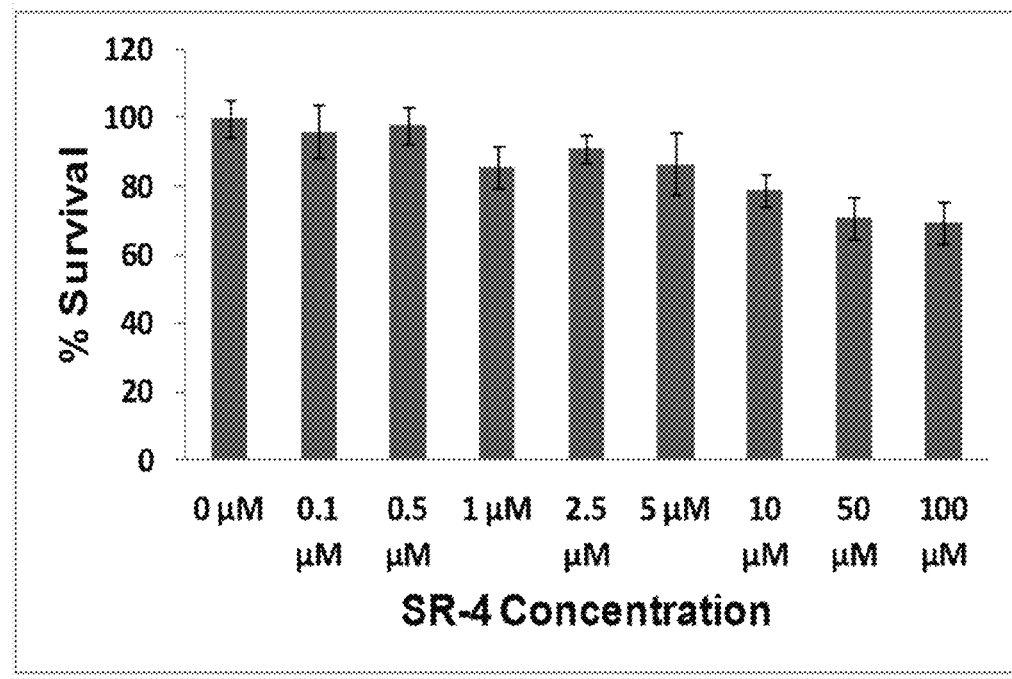
FIG. 53B: Effect of COH-SR4 on HUVEC cells.

Example 12. Effects of COH-SR4, COH-SR9 and COH-SR18 on Melanoma Cell Line B16F10 (FIGS. 53A-B)

Cells of highly aggressive mouse melanoma cell line B16F10 were incubated with various doses of COH-SR4, COH-SR9 and COH-SR18 (1, 3, 5 or 10 µM) for 48 hours. The cell viabilities were measured and summarized in FIG. 53A. COH-SR4 showed the best potency in killing B16F10 cells among the drugs tested.

HUVEC were treated with COH-SR4 at a concentration from 0.1~100 µM for 48 hours. COH-SR4 showed significant lower cytotoxicity to HUVEC cells compared to the melanoma cells. COH-SR4 showed almost no cytotoxicity to HUVEC cells at a concentration of up to 10 μM.

Data presented were representative of at least 4 replicates and the standard deviations were also presented.

Example 13. Effects of COH-SR4 on Mouse Melanoma Cell Line B16-F0 and Human Melanoma Cell Line Hs600T (FIGS. 54A-B and 55A-B)

Figure 54A:
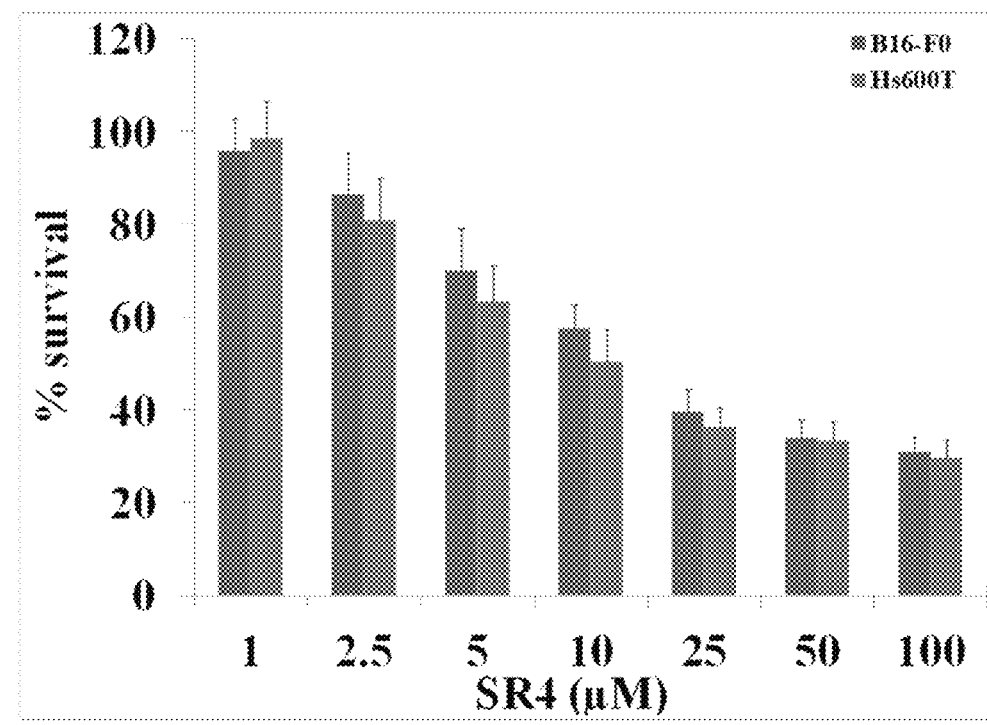
FIGS. 54A-54B: Effect of COH-SR4 on B16-F0 cells and Hs600T cells after 48-hour treatment.
Figure 54B:
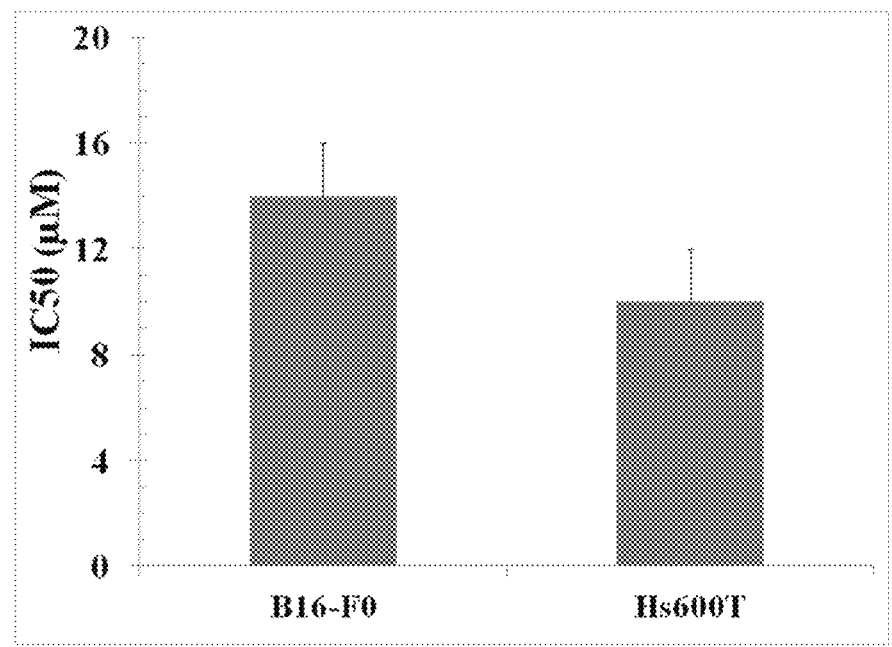
Figure 55A:
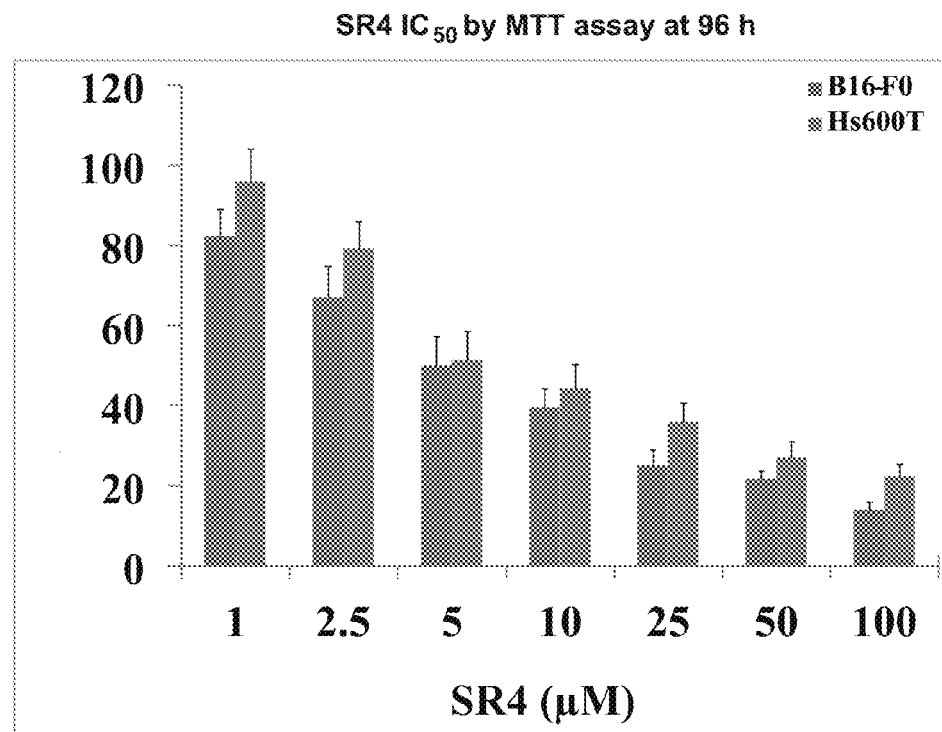
FIGS. 55A-55B: Effect of COH-SR4 on B16-F0 cells and Hs600T cells after 96-hour treatment.
Figure 55B:
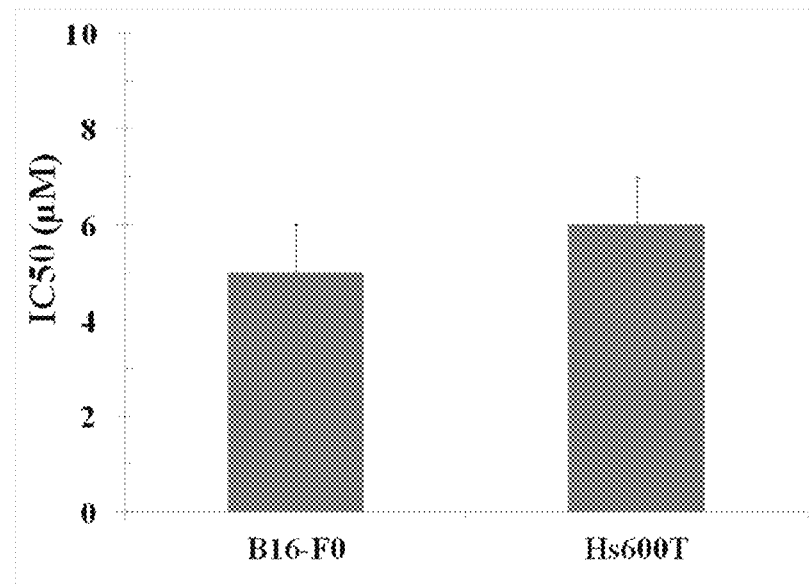

Cells of highly aggressive mouse melanoma cell line B16-F0 or human melanoma cell line Hs600T were incubated with various doses of COH-SR4 (1, 2.5, 5, 10, 25, 50, or 100 μM). The cell viabilities after treatment of 48 hours and 96 hours were measured and summarized in FIGS. 54A and 55A, respectively. The $IC_{50}$ of COH-SR4 in B16-F0 and Hs600T after treatment of 48 hours and 96 hours were measured respectively (FIGS. 54B and 55B). Data were presented as mean±Standard Deviation from two separate determinations with eight replicate each (n=16). The $IC_{50}$ of COH-SR4 in B16-F0 after treatment of 48 hours was about 14 μM; the $IC_{50}$ of COH-SR4 in Hs600T after treatment of 48 hours was about 10 μM; the $IC_{50}$ of COH-SR4 in B16-F0 after treatment of 96 hours was about 5 μM; and the $IC_{50}$ of COH-SR4 in Hs600T after treatment of 96 hours was about 6 μM. COH-SR4 showed cytotoxicities in both cell lines.

Figure 56:
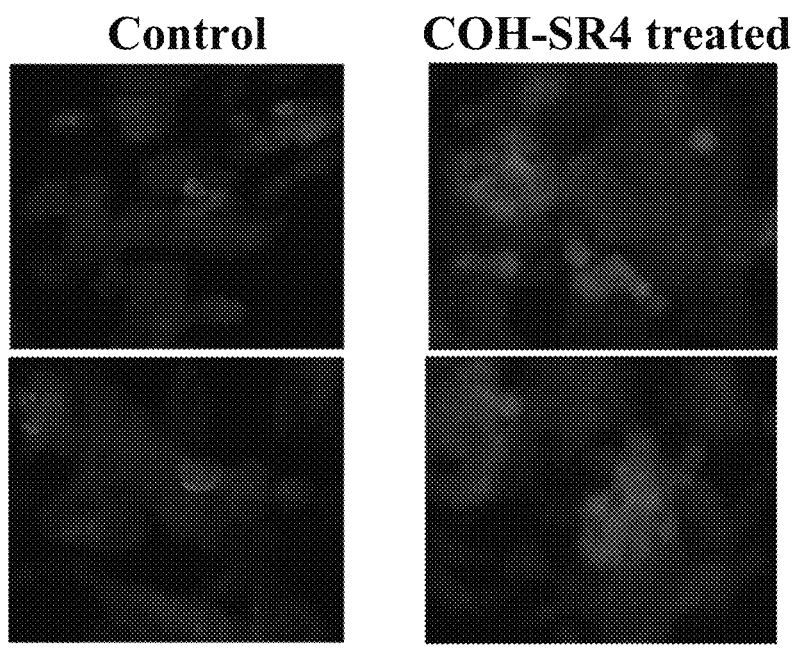
FIG. 56: Effect of COH-SR4 on apoptosis as determined by TUNEL assay in B16-F0 cells and Hs600T cells after 48-hour treatment. Apoptotic cells showed green fluorescence, the pictures shown in the top panels were obtained from one sample, and the pictures shown in the bottom panels were obtained from another sample.

Example 14. Effects of COH-SR4 on Apoptosis in Melanoma Cells (FIG. 56)

B1-F0 mouse melanoma cells were grown on cover slips and treated with 10 μmol/L COH-SR4 for 24 hours. TUNEL assay was carried out using Promega Fluorescence Detection Kit. Apoptotic cells showed green fluorescence. The data showed that treatment of COH-SR4 increased apoptosis in melanoma cells (FIG. 56). The pictures shown in the top panels were obtained from one sample, and the pictures shown in the bottom panels were obtained from another sample (FIG. 56).

Figure 57:
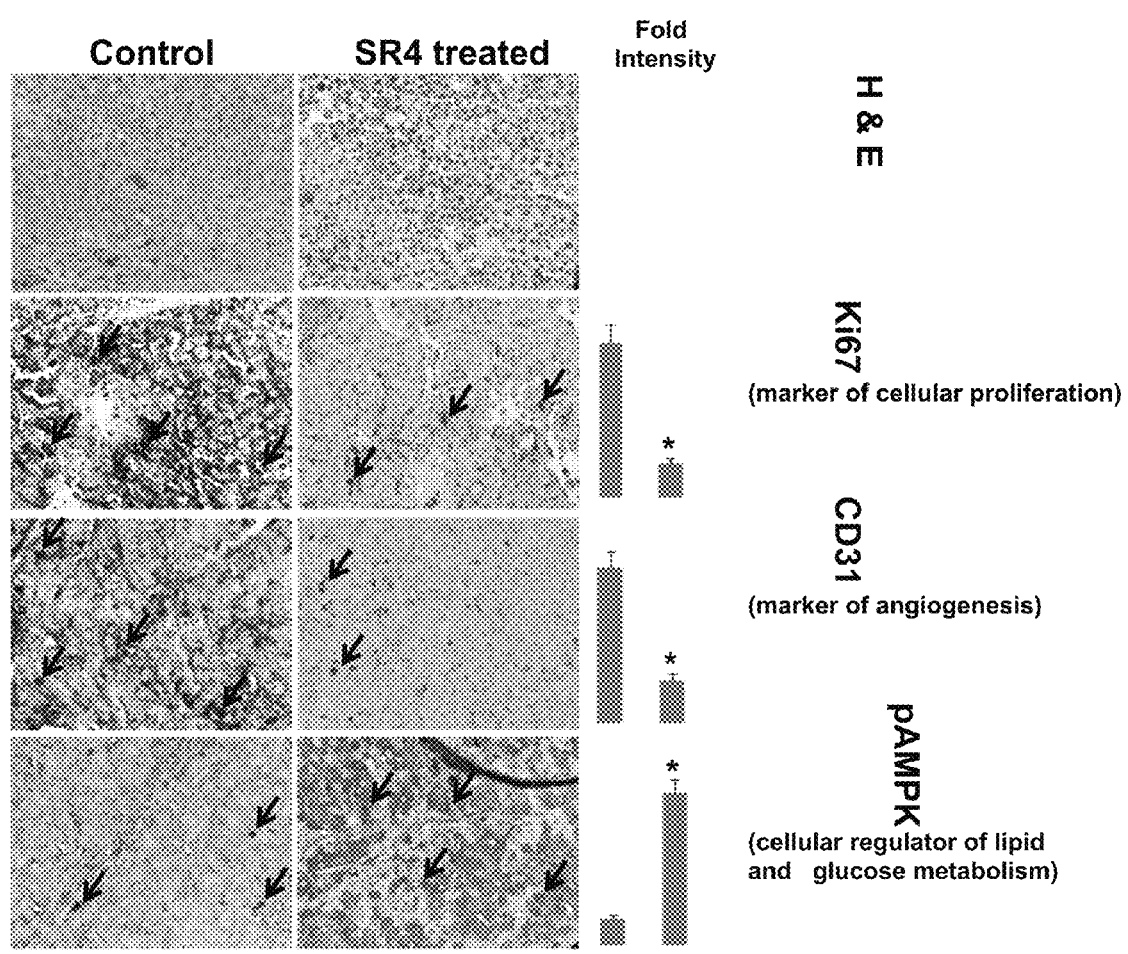
FIG. 57: Histopathologic analyses of effects of COH-SR4 in B16 mouse melanoma tumor section.
Figure 58:
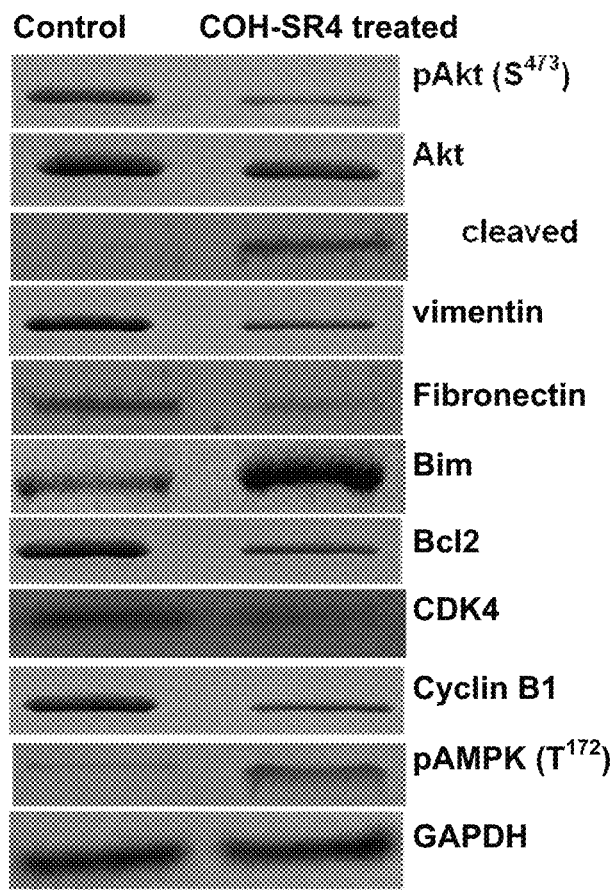
FIG. 58: Western-blot analyses of signaling proteins showing effects of COH-SR4 in B16 mouse melanoma tumor tissue lysates.

Example 15. Effects of COH-SR4 on Apoptosis in B16 Mouse Melanoma Tumor Section (FIGS. 57 and 58)

B16 melanoma bearing C57B mice tumor sections were treated without or with COH-SR4, and used for histopathologic analyses.

H&E stain, or hematoxylin and eosin stain, a general gross morphology stain were used. Hematoxylin had a deep blue-purple color and stained nucleic acids. Eosin was pink and stained proteins nonspecifically. In a typical tissue, nuclei were stained blue, whereas the cytoplasm and extracellular matrix had varying degrees of pink staining. The pink coloration in the control tumor cells indicated cell proliferation (FIG. 57)

IHC analyses for Ki-67 expression (marker of cellular proliferation), CD31 (angiogenesis marker), and pAMPK (cellular regulator of lipid and glucose metabolism) from tumors in mice of control and COH-SR4-treated groups were carried out. Statistical significance of difference was determined by two-tailed Student's t test. When COH-SR4-treated tumor sections were compared with the control, $p<0.001$. Immuno-reactivity was evident as a dark brown stain, whereas non-reactive areas displayed only the background color. Sections were counterstained with Hematoxylin (blue). Photomicrographs at 40× magnification were acquired using Olympus Provis AX70 microscope. Percent staining was determined by measuring positive immuno-reactivity per unit area. Arrows indicated the areas for positive staining for an antigen. The intensity of antigen staining was quantified by digital image analysis. Bars represented mean+S.E. (n=5); "*" means $p<0.001$ compared with control.

The results showed that treatment of COH-SR4 lowered cellular proliferation (decreased Ki67), lowered angiogenesis (decreased CD31) and increased cellular regulation of lipid and glucose metabolism (increased pAMPK) in melanoma tumors.

Western-blot analyses of signaling proteins in tumor tissue lysates in control and COH-SR4 treated groups were shown in FIG. 58. Crude fraction (about 50 μg) and WB with various antibodies were used. The densities of the COH-SR4 treated bands were divided by the corresponding bands in the control group, and summarized in Table 4 below.

TABLE 4

| | Ratio of proteins in COH-SR4 treated groups v. control groups | | | | | | | | |
|---|---|---|---|---|---|---|---|---|---|
| | pAkt | Akt | Vimentin | Fibronectin | Bim | Bcl2 | CDK4 | Cyclin B1 | pAMPK |
| COH-SR4 group/ Control Group | 0.32 | 0.84 | 0.39 | 0.22 | 5.8 | 0.39 | 0.29 | 0.32 | 3.1 |

Example 16. Effects of Oral Administration of COH-SR4 in In Vivo Syngeneic Mouse Model (FIGS. 59A-B~61)

C57B mice for syngeneic model were obtained from Harlan, Indianapolis, Ind. All animal experiments were carried out in accordance with a protocol approved by the Institutional Animal Care and Use Committee (IACUC). Ten 10-weeks-old mice were divided into two groups of 5 animals (treated with corn oil (vehicle), and COH-SR4 4 mg/kg body weight). All 10 animals were injected with $1\times10^6$ mouse melanoma cells (B16-F0) suspensions in 100 μL of PBS, subcutaneously into one flank of each mouse. At the same time, animals were randomized treatment groups as indicated in the figure. Treatment was started 10 days after the B16 melanoma cells implantation to see palpable tumor growth. Treatment consisted of 0.1 mg of COH-SR4/ mice in 200 μL corn oil by oral gavage alternate day. Control groups were treated with 200 μL corn oil by oral gavage alternate day. Animals were examined daily for signs of tumor growth, and body weights were recorded. Tumors were measured in two dimensions using calipers. Photographs of animals were taken at day 1, day 10, day 14, day 18, and day 20 after subcutaneous injection, are shown for all groups. Photographs of tumors were also taken at day 20.

Figure 59A:
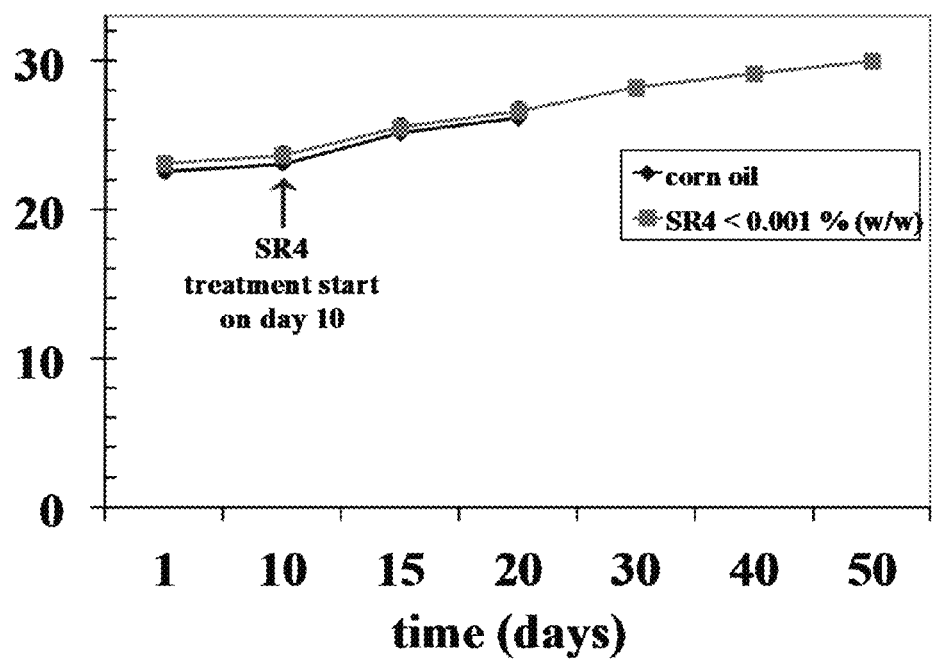
FIGS. 59A-59B: Effects of oral administrations of COH-SR4 in in vivo Syngeneic mouse model based on (FIG. 59A) changes of mice weight.
Figure 59B:
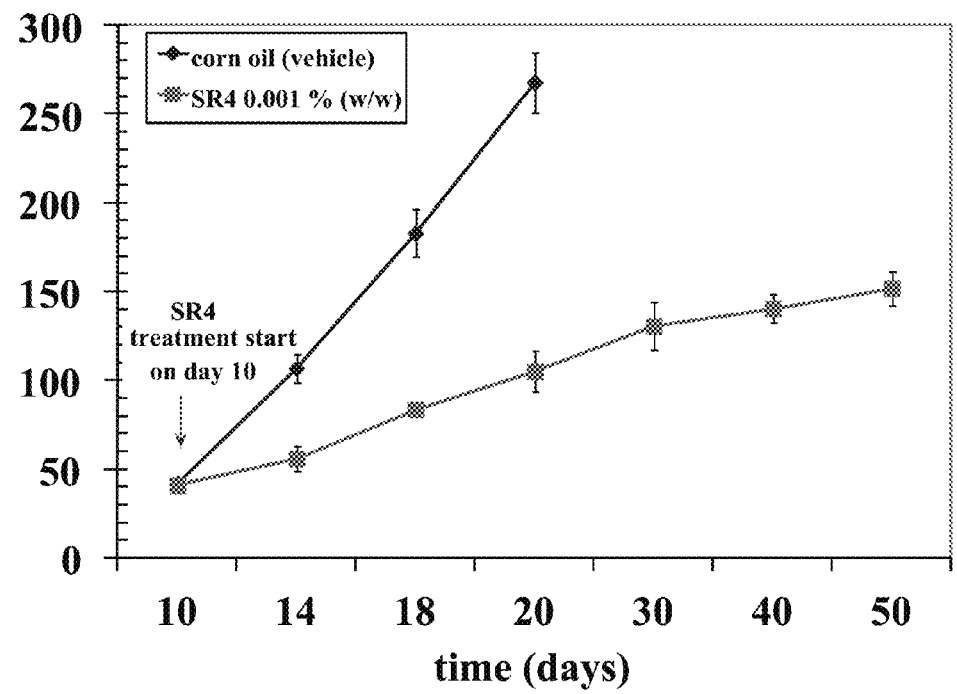
Figure 60:
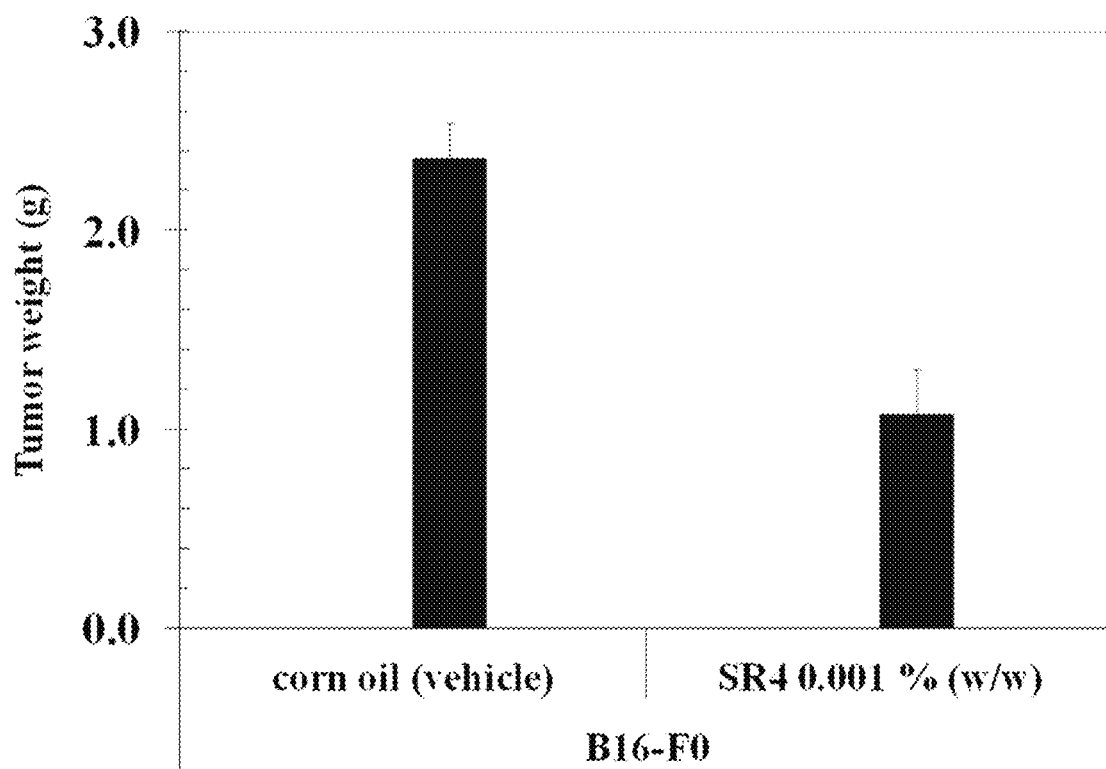
FIG. 60: Effects of oral administrations of COH-SR4 in in vivo Syngeneic mouse model based on changes of tumor weight.

Mice treated with COH-SR4 showed similar weights compared to mice treated with corn oil (FIG. 59A). The tumor cross-section areas in the mice treated with COH-SR4 were significantly smaller than that of the mice treated with corn oil (FIG. 59B). Tumor weights in the mice treated with COH-SR4 were significantly smaller than that of the mice treated with corn oil at day 20 (FIG. 60), "*" means p<0.001 for COH-SR4 treated group when compared to the control group.

Figure 61:
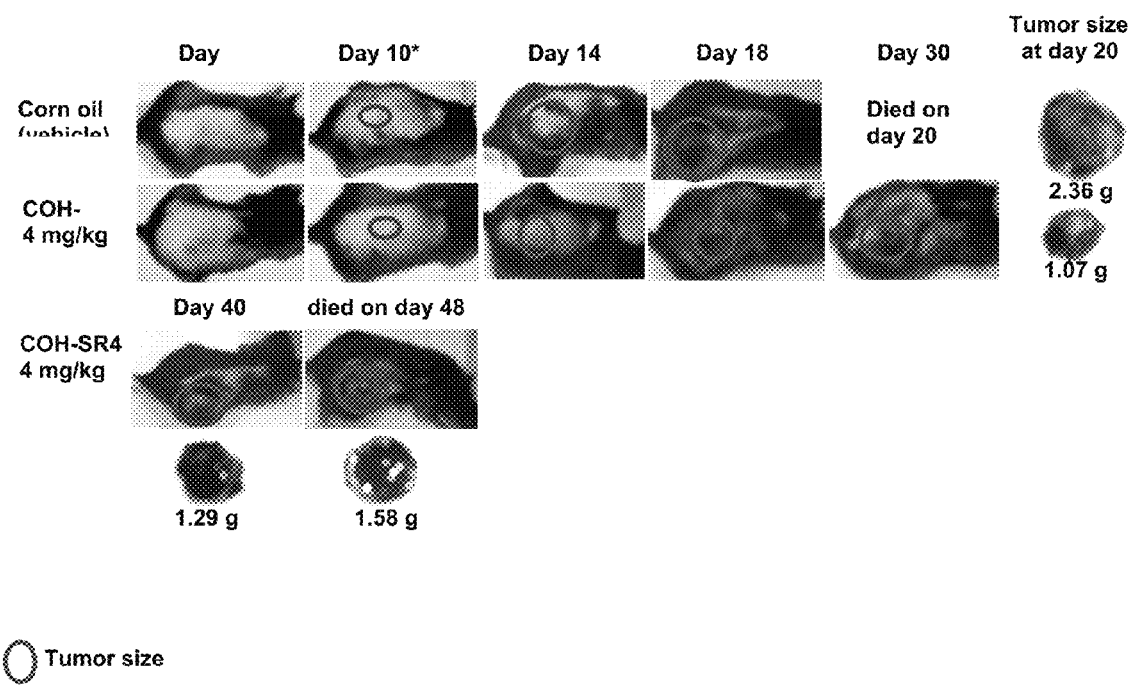
FIG. 61: Effects of oral administrations of COH-SR4 in in vivo Syngeneic mouse model.

Photos of tumor taken during the treatment are shown in FIG. 61, "*" indicates COH-SR4 treatment started alternate day by oral gavage after 10 days of B16-F0 cells implantation. Treatment of COH-SR4 elongated the life of the B16-F0 melanoma mice. Mice treated with corn oil only died on day 20, while mice treated with COH-SR4 at a dosage of 4 mg/kg died on day 48. The tumor size at day 20 in the mice treated with corn oil only was more than twice of that in the mice treated with COH-SR4. Thus, COH-SR4 was effective in treating melanoma in vivo.

Figure 62:
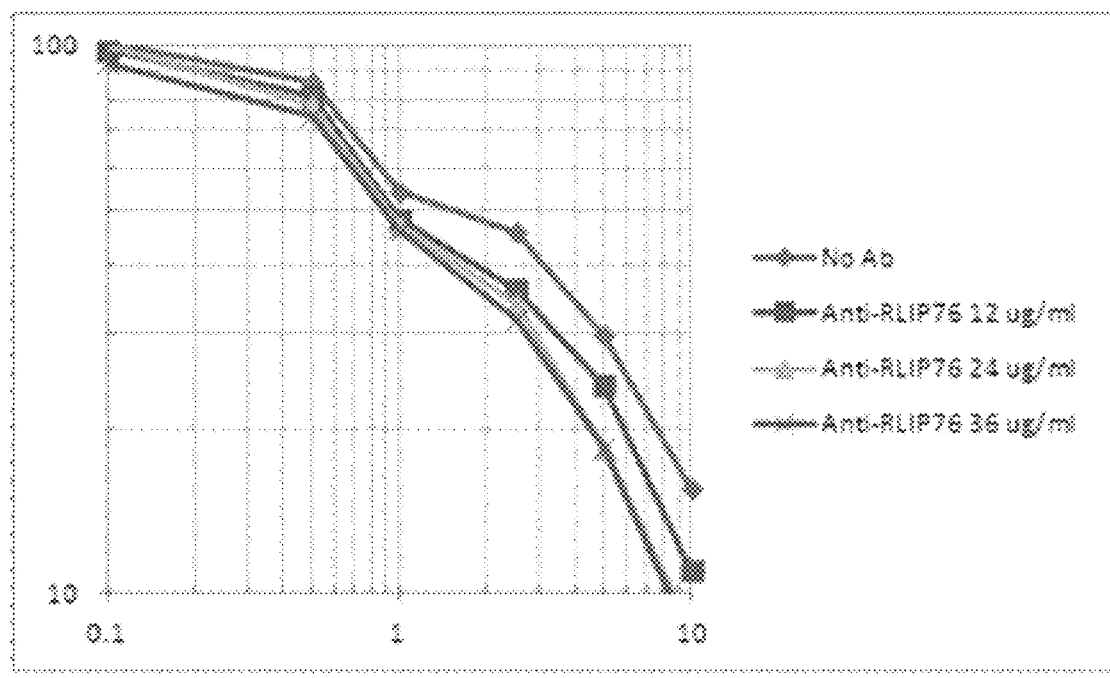
FIG. 62: Potentiating COH-SR4 cytotoxicity in B16F10 cells by anti-RLIP76 polyclonal antibodies (uM also represents μM in the figure).

Example 17. Treatment of Anti-RLIP76 Polyclonal Antibodies Increased COH-SR4 Cytotoxicities in B16F10 Cells (FIG. 62)

Anti-RLIP76 IgG potentiated the cytotoxicities of COH-SR4 in vitro. B16F10 cells were treated with various fixed doses of anti-RLIP76 polyclonal antibodies for 24 hours followed by treatment of various doses of COH-SR4 and MTT cell proliferation assay was performed after 48 hours. The data plotted in FIG. 62 were representative of at least 4 replicates and the standard deviations were also presented. Anti-RLIP76 IgG showed a dose-related increase of COH-SR4 cytotoxicities in B16F10 cells. The higher concentration of the anti-RLIP76 IgG was used, the more cytotoxic COH-SR4 was to the cells treated. Thus, treatment of COH-SR4 in combination with anti-RLIP76 IgG could be an effective way to treat cancer, and could be more effective compared to treatment with COH-SR4 alone.

Example 18. Effects of COH-SR4 on Melanoma Cell Proliferation, Clonogenic Potential and Apoptosis (FIGS. 65 A-D-67A-D)

Figure 65A:
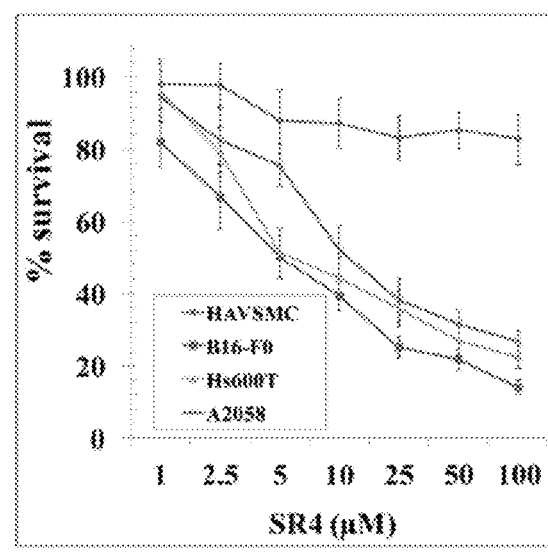
FIGS. 65A-65D: Anti-proliferative and pro-apoptotic effects of COH-SR4 in melanoma.
Figure 65B:
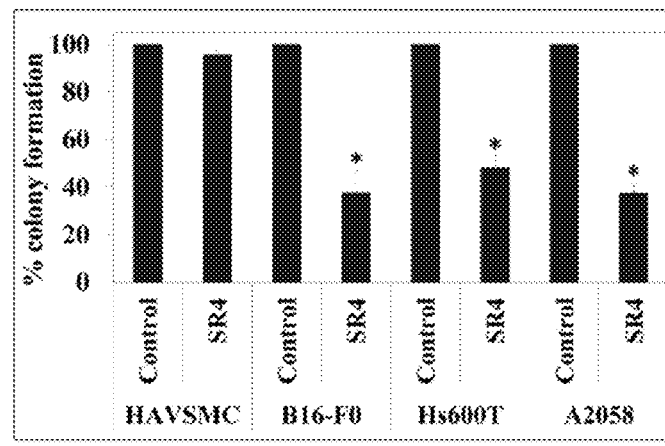
Figure 65C:
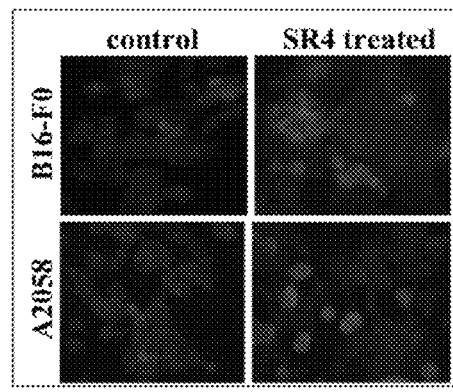
Figure 65D:
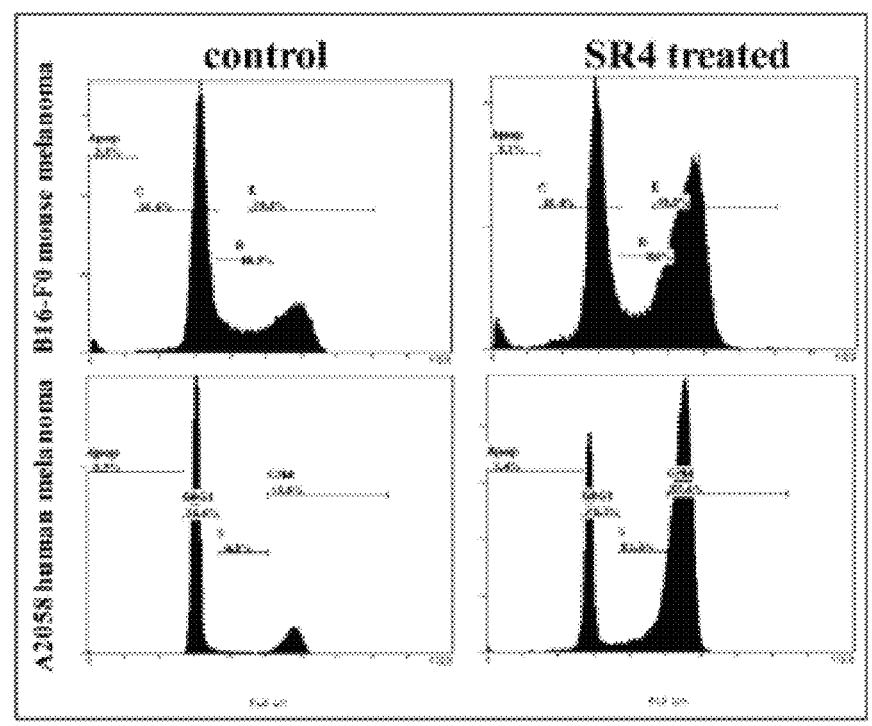

The extent of melanoma cell survival was analyzed by MTT assay following treatment with COH-SR4 for 96 h. The COH-SR4 treatment had a strong inhibitory effect on the survival of melanoma cells [$IC_{50}$: B16-F0 cell line-5±1 µM, Hs600T cell line-6±1 µM, and A2058 cell line-11±2 µM]. COH-SR4 did not cause any significant cytotoxicity in normal human aortic vascular smooth muscle cells (HAVSMC) (FIG. 65A, values presented as mean±standard deviation from two separate determinations with eight replicates each (n=16)). The anti-proliferative effects of COH-SR4 were further examined by colony formation assay as described in Materials and Methods. The COH-SR4 (10 µM) treatment resulted in 38±9%, 48±5% and 37±4% colony formation in B16-F0, Hs600T and A2058 melanoma cells. The COH-SR4 treatment did not significantly affect the colony forming ability of HAVSMC as the HAVSMC cells displayed 96±4% colony forming potential compared to respective untreated controls (FIG. 65B, *p<0.001 compared with control, n=3). The 10 µM of COH-SR4 treatment for 24 h induced apoptosis in B16-F0 and A2058 melanoma cells as determined by enhanced DNA fragmentation in TUNEL apoptotic assay (FIG. 65C, apoptotic cells showed green fluorescence.). The cytotoxicity of COH-SR4 in melanoma cells as evident by MTT, clonogenic survival and apoptotic assays revealed that COH-SR4 is a potential lead compound for melanoma. The anti-proliferative effect of COH-SR4 was further examined by fluorescence activated cell sorting (FACS) analysis (FIG. 65D, experiment repeated three times and similar results obtained). COH-SR4 treatment caused G2/M phase arrest in both B16-F0 mouse and A2058 human melanoma cells (~50% cells accumulated in G2 phase) (FIG. 65D).

Figure 66:
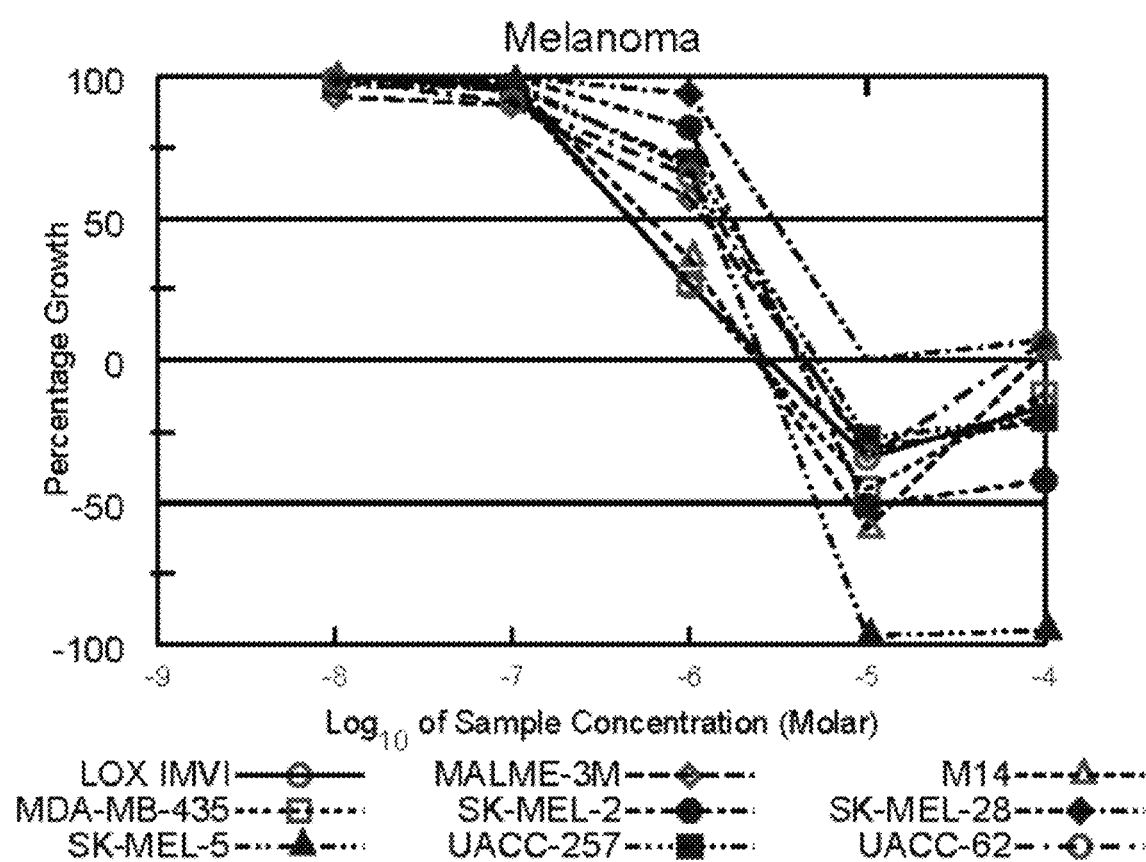
FIG. 66: Dose-dependent growth inhibition of various human (LOX-IMVI, Malme-3M, M14, MDA-MB-435, SK-MEL-2, SK-MEL-5, SK-MEL-28, UACC-257, and UACC-62) melanoma cell lines by COH-SR4 (NIH/NCI DTP60 screening data).

Also, independent cytotoxicity testing from the NCI-60 DTP Human Tumor Cell Line Screen further confirmed the potential anti-cancer activities of COH-SR4 against several melanoma cell lines (FIG. 66, NIH/NCI DTP60 screening data).

The anti-proliferative and pro-apoptotic effects of COH-SR4 were compared with those of elesclomol in melanoma. Melanoma cell survival was analyzed by MTT assay following treatment with COH-SR4. COH-SR4 treatment had a strong inhibitory effect on the survival of melanoma cells regardless of mutational status with $IC_{50}$ values in the range 1.2 µM-4.8 µM at 48 h, highly potent to elesclomol ($IC_{50}$ 5.8 to >20 µM), which is FDA approved drug for stage IV metastatic melanoma and a known regulator of OxPhos. The structure of elesclomol is shown below:

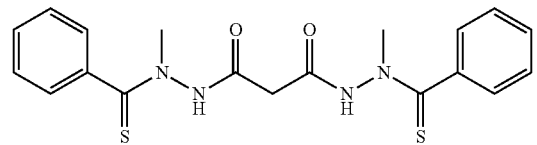

1-N′,3-N′-bis(benzenecarbonothioyl)-1-N′,3-N′-dimethylpropanedihydrazide (Elesclomol)

Figure 67C:
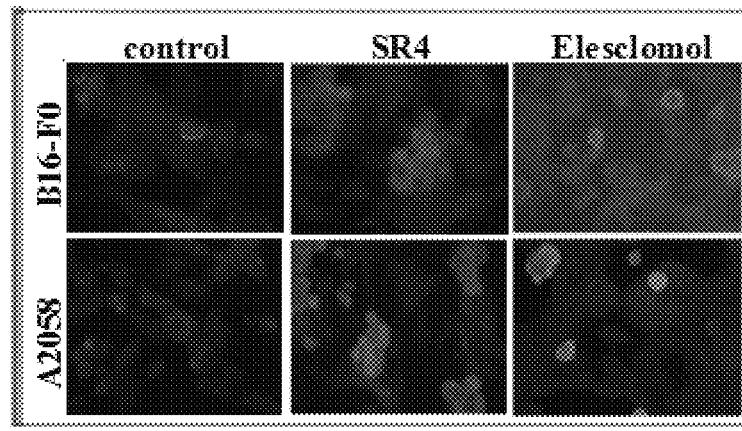
Figure 67D:
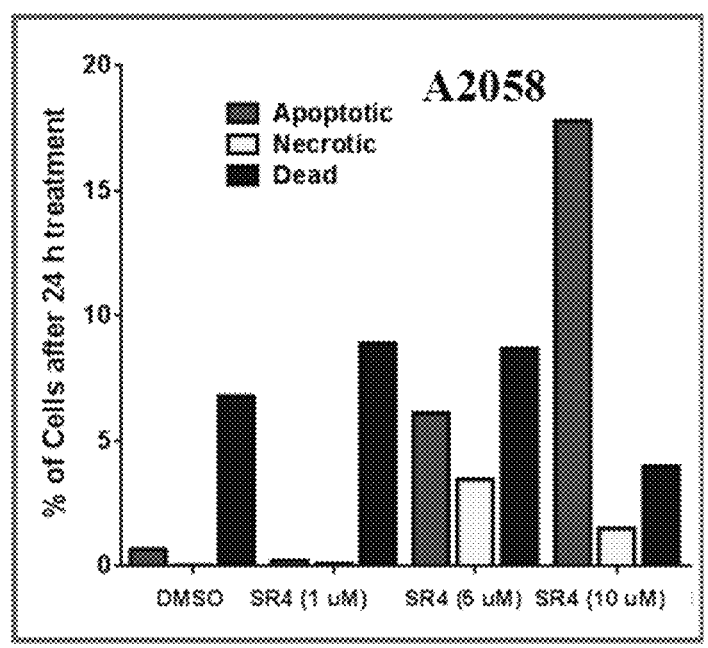

COH-SR4 did not cause any significant cytotoxicity in normal human aortic vascular smooth muscle cells (HAVSMC) and normal human dermal fibroblasts (NHDFs) as well as melanocytes (FIG. 67A, values presented as mean±SD from two separate determinations with eight replicates each (n=8-16)). COH-SR4 treatment also effectively inhibited clonogenic potential along with inducing apoptosis in melanoma. The COH-SR4 (5 µM) treatment resulted in 40±4%, 43±7%, 22±8%, 42±6%, and 48±6% colony formation in SK-Mel-31, A2058, SK-Mel-5, A375 and SK-Mel-2 melanoma cells. Elesclomol treatment did not significantly affect the colony forming ability of melanoma cells compared to COH-SR4. The COH-SR4 treatment did not significantly affect the colony forming ability of HAVSMC and NHDFs as the HAVSMC and NHDF displayed 95±4% and 97±3% colony forming potential compared to respective untreated controls (FIG. 67B, *p<0.001 compared with control (n=3)). The 5 µM of COH-SR4 and elesclomol treatment for 24 h induced apoptosis in B16-F0 and A2058 melanoma cells as determined by enhanced DNA fragmentation in TUNEL apoptotic assay. However, the effect of elesclomol was not potent (FIG. 67C, apoptotic cells showed green fluorescence.). Dual staining with annexin V and propidium iodide was used to quantify apoptosis and necrosis using flow-cytometry. COH-SR4 caused apoptosis in A2058 cells in a dose-dependent manner (FIG. 67D). Overall, data indicated that COH-SR4 administration will inhibit melanoma growth independent of genetic background or driver mutations.

Example 19. Effects of COH-SR4 on Melanoma Cell GST Activity and Cell Cycle Progression (FIGS. 68A-C)

GSTs are a class of phase II detoxifying enzymes, which mediate drug resistance by detoxifying administered chemotherapy drugs for efflux out of cells by transport proteins. The over-expression of GSTs is associated with malignant progression of many cancers including melanoma, lung and prostate cancers. GSTs mediate glutathione conjugation of toxic end products of lipid peroxidation like 4-hydroxy-2-nonenal (4-HNE) which eventually leads to buffering of tumor-toxic oxidative stress and favors tumor survival and proliferation in hypoxic environment. Hence, the effect of COH-SR4 was investigated on the enzymatic activity of GSTs towards 1-chloro 2,4-dinitro benzene (CDNB), a model substrate routinely used for GST activity.

GST activity towards 1-chloro 2,4-dinitro benzene (CDNB) and its inhibition by COH-SR4 was performed in 28000×g crude supernatant prepared from B16-F0, Hs600T and A2058 cells. Human liver purified GST was used as a control (inset). The inhibitory effect of COH-SR4 on GST was studied at a fixed concentration of GSH and CDNB (1 mM each) and varying concentrations of inhibitor. The enzymes were pre-incubated with the inhibitor for 5 min at 37° C. prior to the addition of the substrates. The COH-SR4 treatment inhibited the total GST activity to a significant extent in the B16-F0, Hs600T and A2058 melanoma cells (FIG. 68A). The ability of COH-SR4 to inhibit GST activity in melanomas represents a potential mechanism that contributes to decreased survival of melanoma cells following COH-SR4 treatment (FIG. 68A).

Figure 68A:
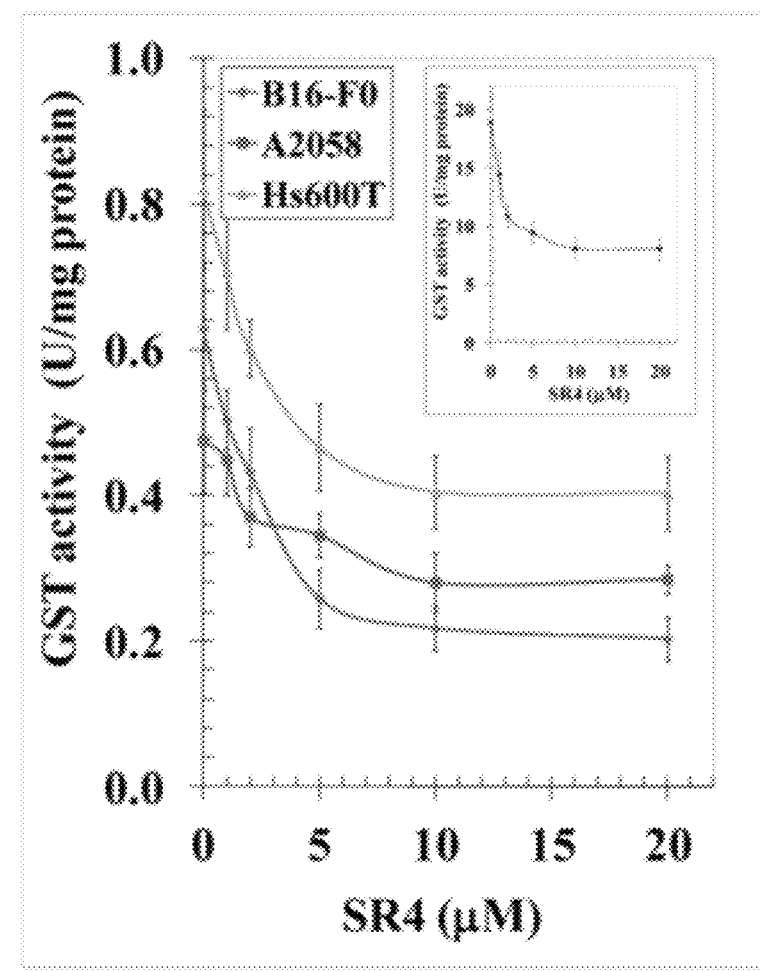
FIGS. 68A-68C: Effects of COH-SR4 on GST activity in melanoma.
Figure 68B:
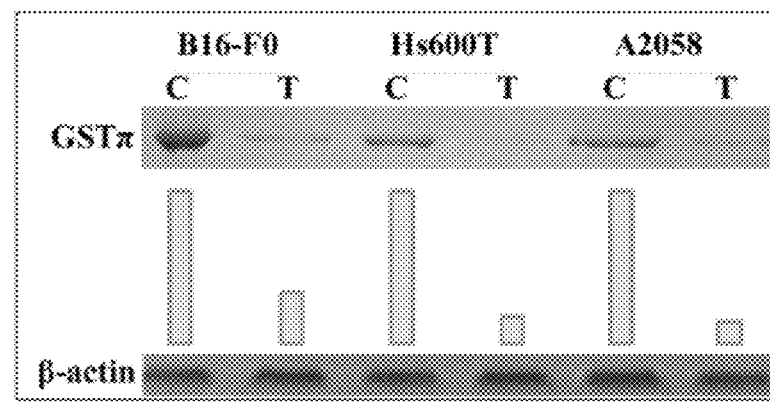
Figure 68C:
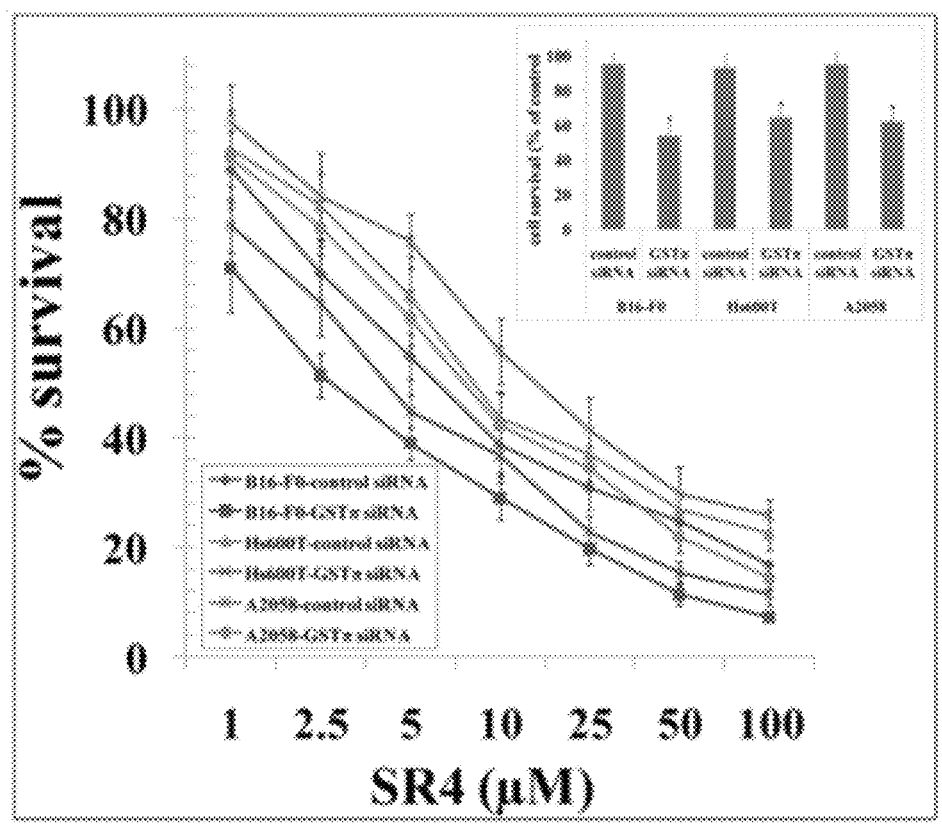
Figure 69A:
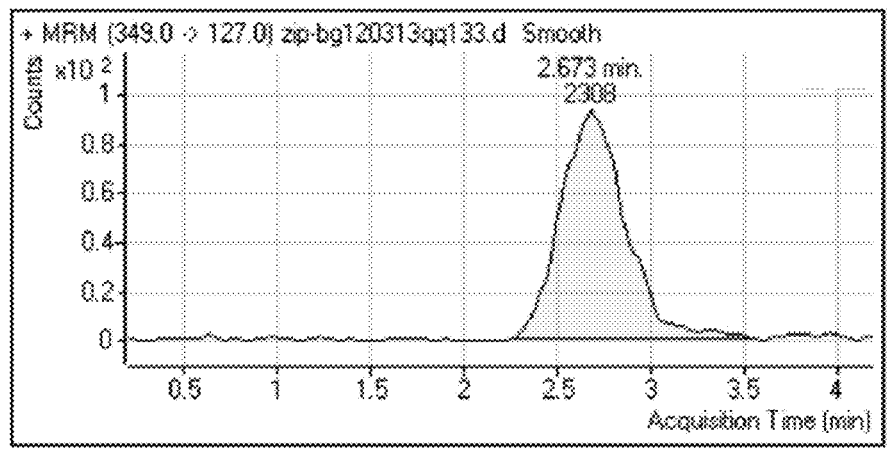
FIGS. 69A-69D: Measurement of serum levels of COH-SR4 in control and COH-SR4 treated mice.
Figure 69B:
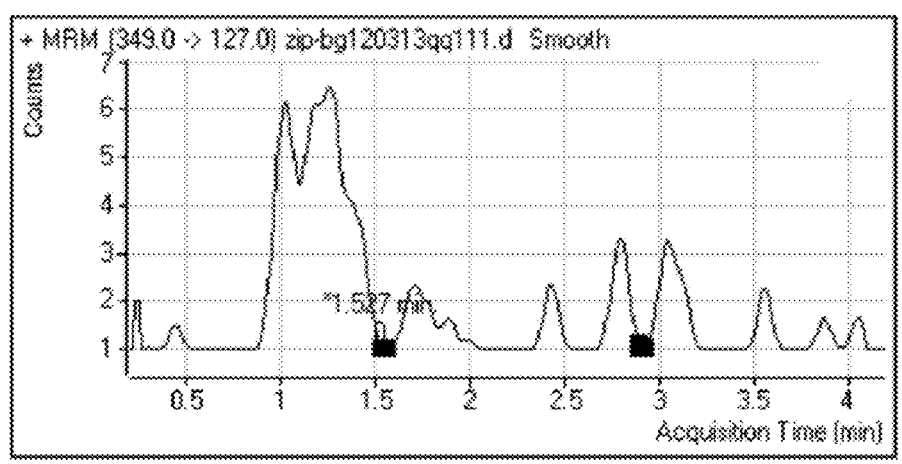
Figure 69C:
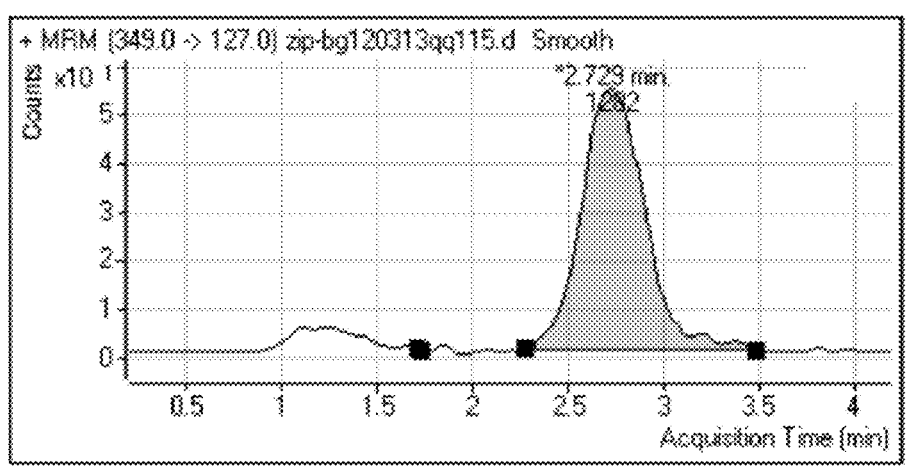
Figure 69D:
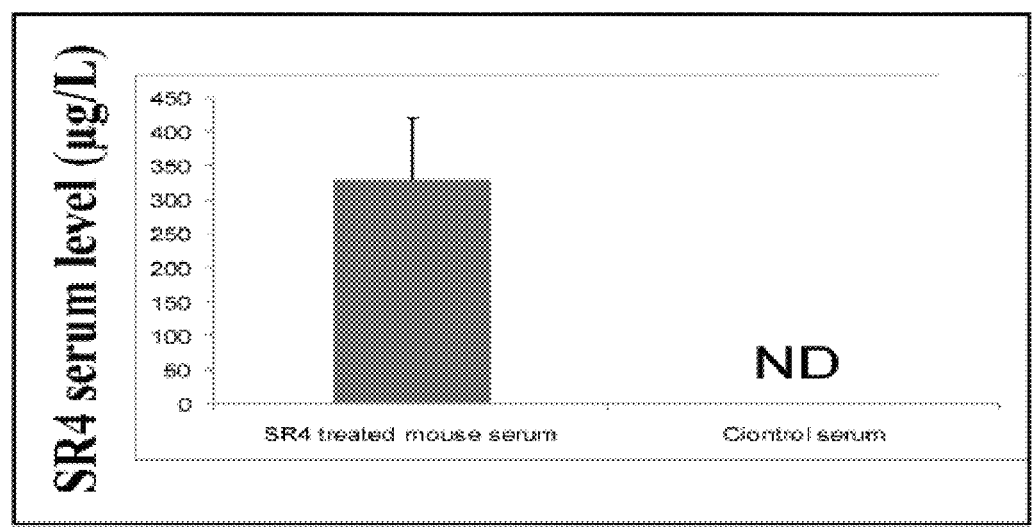

COH-SR4 treatment significantly decreased the GST activity in both mouse and human melanomas cells (FIG. 68A). Given the significant role of GSTπ in tumor progression, the impact of knock-down of GSTπ was further studied by transfection using GSTP1-1 siRNA in B16-F0, Hs600T and A2058 melanoma cells with Lipofectamine 2000 (Invitrogen). The knock-down of GSTπ was confirmed by Western-blot analyses (FIG. 68B). Membranes were stripped and reprobed for β-actin as a loading control. Results were quantified by scanning densitometry: C, control siRNA; T, GSTπ siRNA (FIG. 68B).

MTT assay in GSTπ siRNA transfected cells were performed 96 h after COH-SR4 treatment. The values are presented as mean±SD from two separate determinations with eight replicates each (n=16) (FIG. 68C). The MTT assay revealed that GSTπ-depletion itself decreased cell growth by ~35-46% (FIG. 68C inset, *p<0.01 compared to control), and sensitized to COH-SR4 significantly by decreasing the $IC_{50}$ to almost half (FIG. 68C, values are presented as mean±SD from two separate determinations with eight replicates each (n=16)). Taken together, these studies suggest that COH-SR4 targets GSTπ activity and that GSTπ inhibition further sensitizes to the growth inhibitory effects of COH-SR4 in melanoma.

Example 20. Analyses of COH-SR4 in Mice Serum (FIGS. 69A-D)

Next, the absorption of orally administered COH-SR4 in mice was assessed by LC-MS/MS analyses. C57 B mice were treated with 0.1 mg/mice (4 mg/kg b.w.) of COH-SR4 on alternate day for 8 weeks. The blood was collected within 2 h of the dosing on the final day of treatment and further processed for MS analyses as described in the methods section. LC-MS/MS analysis of COH-SR4 treated mice serum revealed that COH-SR4 was effectively absorbed after oral dosage and it reached a serum concentration of 342±44 μg/L (equivalent to 1±0.22 μM) (FIGS. 69A-69D).

Example 21. Analyses of Blood Chemistries in Control and COH-SR4 Treated Mice To evaluate the potential toxicity of COH-SR4 on animals, C57 B mice were treated with 0.1 mg/mice (4 mg/kg b.w.) of COH-SR4 or with vehicle on alternate day for 2 weeks (n=6). After the treatment period, blood and plasma/serum were isolated and analyzed. Oral administration of COH-SR4 showed no significant differences on key blood and metabolic profiles as compared with vehicle-treated mice. The plasma alanine transaminase (ALT) and alkaline phosphatase (ALP) were moderately higher in COH-SR4-treated mice (p<0.05), while the levels of two other liver enzymes; aspartate transaminase (AST) and lactate dehydrogenase (LDH) were similar with control mice (Table 5).

TABLE 5

Effects of COH-SR4 on some key metabolic parameters on C57B mice (mean ± SE)

| | Vehicle Control | COH-SR4 treated | P-value |
|---|---|---|---|
| CBC | | | |
| RBC (×10$^6$/uL) | 8.8 ± 0.1 | 8.7 ± 0.2 | 0.675 |
| WBC (×10$^3$/uL) | 9.1 ± 0.3 | 7.4 ± 0.9 | 0.219 |
| Platelets (×10$^3$/uL) | 1207 ± 71 | 1055 ± 124 | 0.350 |
| Hemoglobin (g/dL) | 14.0 ± 0.1 | 13.9 ± 0.4 | 0.818 |
| Hematocrit (%) | 41.2 ± 0.1 | 41.0 ± 0.7 | 0.737 |
| Plasma/Serum | | | |
| Glucose (mg/dL) | 336.3 ± 14.8 | 304.2 ± 21.1 | 0.249 |
| Creatinine (mg/dL) | 0.2 ± 0.0 | 0.2 ± 0.0 | 1.000 |
| Albumin (g/dL) | 2.4 ± 0.1 | 2.4 ± 0.1 | 1.000 |
| ALT (units/L) | 63.3 ± 2.4 | 73.3 ± 2.4 | 0.042 |
| AST (units/L) | 54.0 ± 1.2 | 48.0 ± 3.0 | 0.140 |
| ALP (units/L) | 81.3 ± 4.1 | 119.3 ± 2.4 | 0.001 |
| LDH (units/L) | 943.3 ± 138.0 | 822.7 ± 56.0 | 0.463 |
| Triglycerides (mg/dL) | 94.6 ± 1.3 | 78.7 ± 2.4 | 0.004 |
| Cholsterol (mg/dL) | 92.0 ± 3.5 | 82.0 ± 0.1 | 0.114 | n = 6 mice in each group

Example 22. Effective Targeting of Tumor Progression by COH-SR4 Using In Vivo Models of Syngeneic and Nude Mouse Melanoma (FIGS. 63 and 64 and 70A-C-72A-B)

Anti-Neoplastic Effect of COH-SR4 In Vivo on Melanoma Progression

Figure 70A:
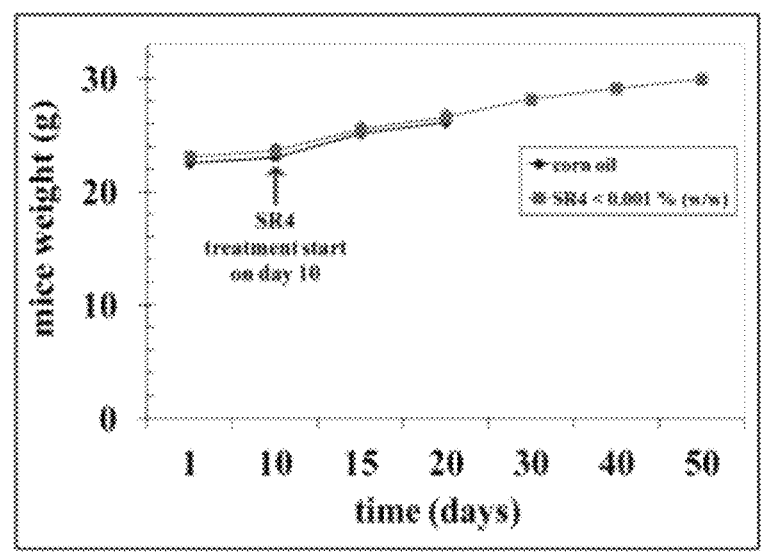
FIGS. 70A-70C: Effect of oral administration of COH-SR4 on melanoma progression in mice.
Figure 70A:
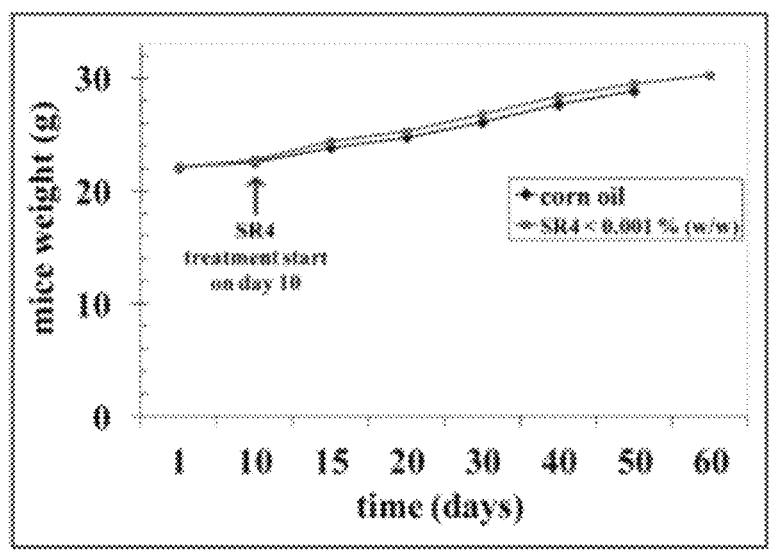
Figure 70B:
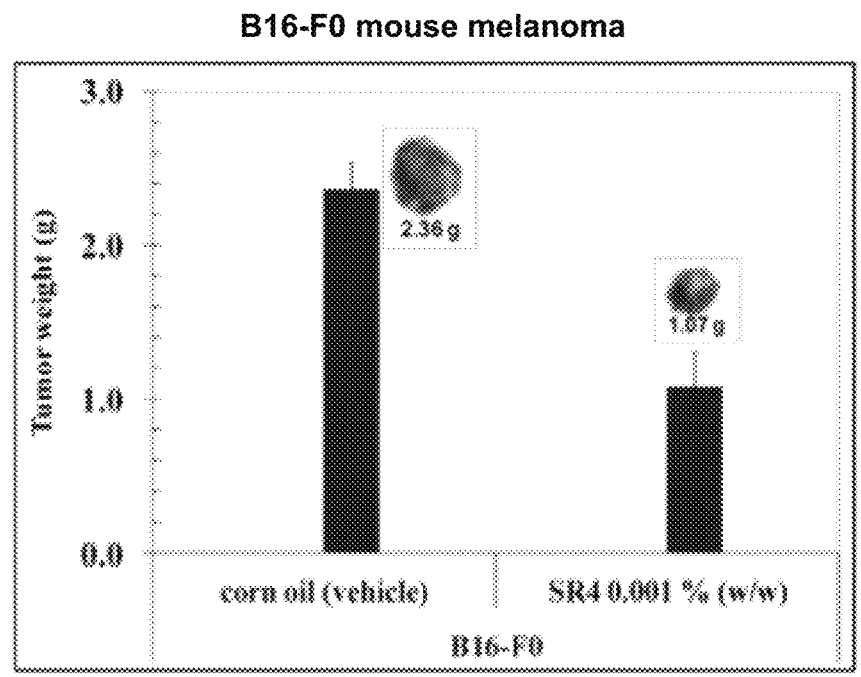
Figure 70B:
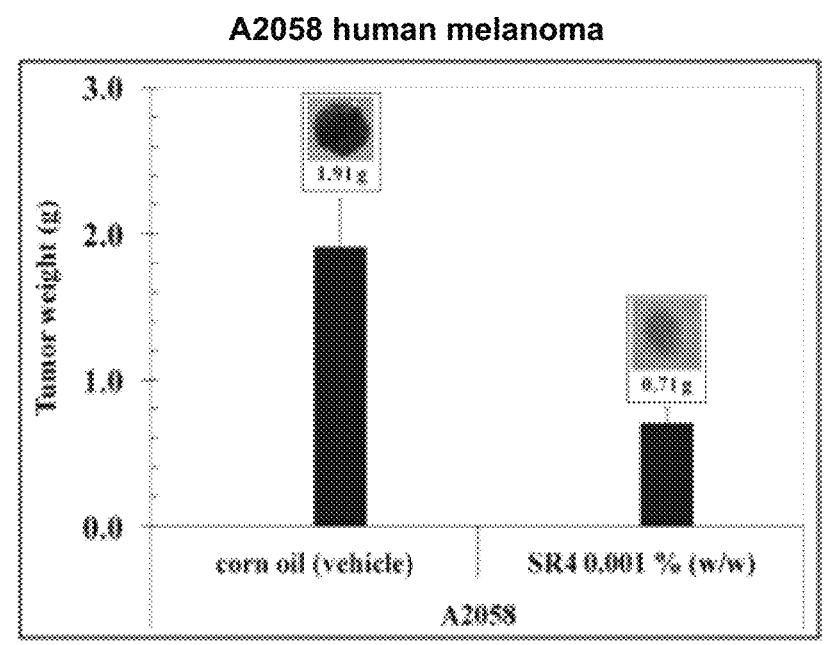
Figure 70C:
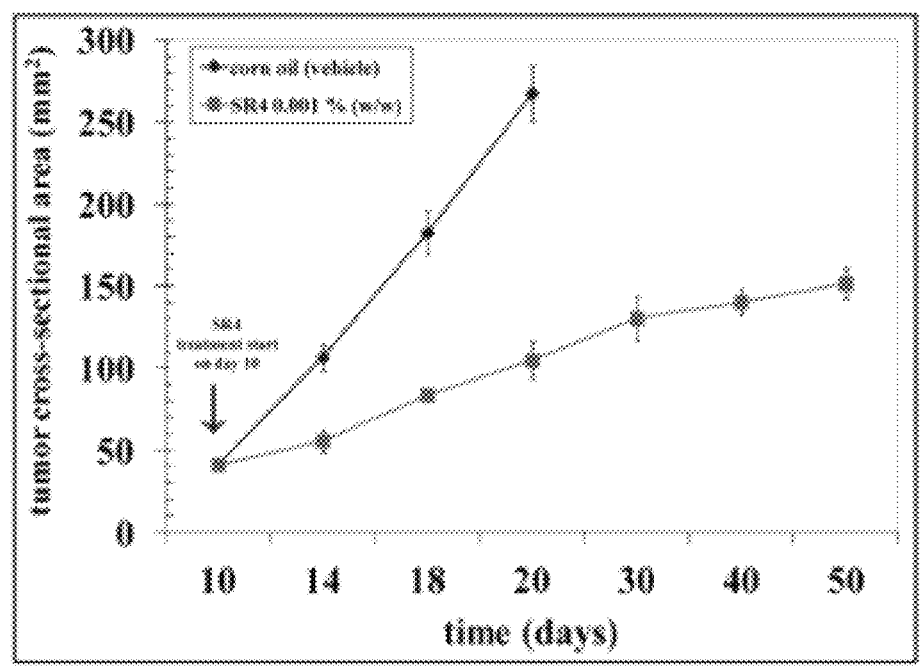
Figure 70C:
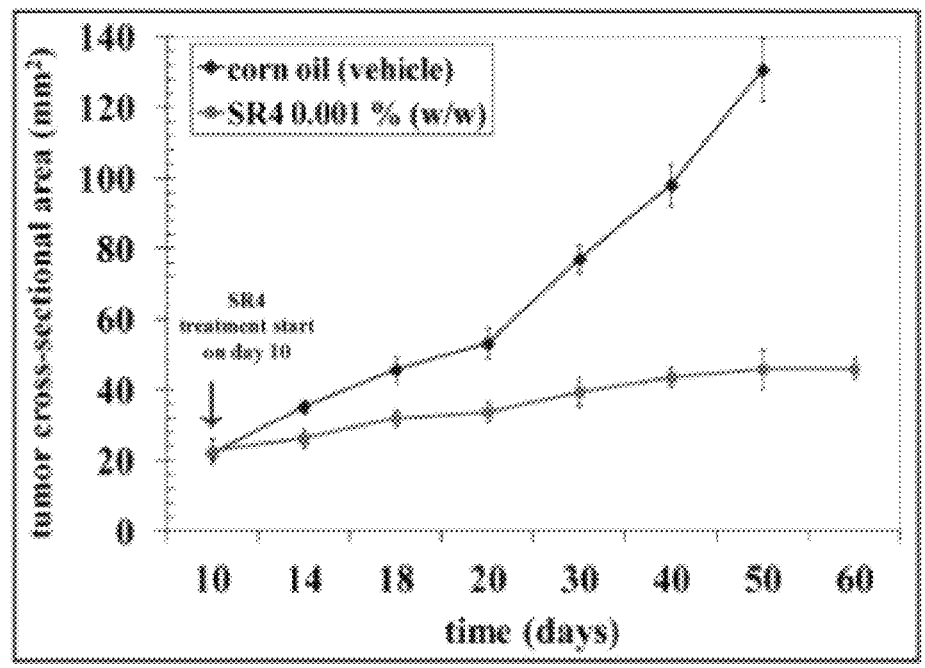
Figure 72A:
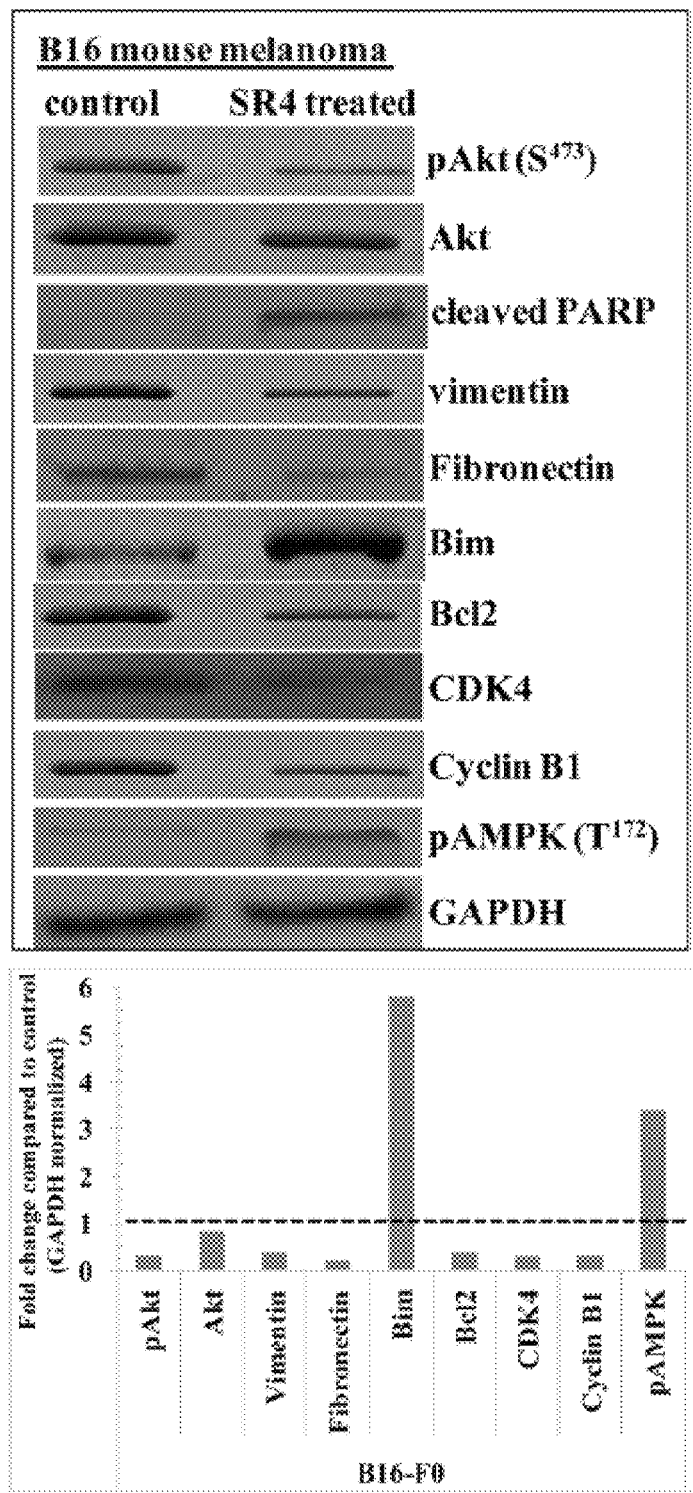
FIGS. 72A-72B: Effect of COH-SR4 on signaling proteins in vivo models of melanoma.
Figure 72B:
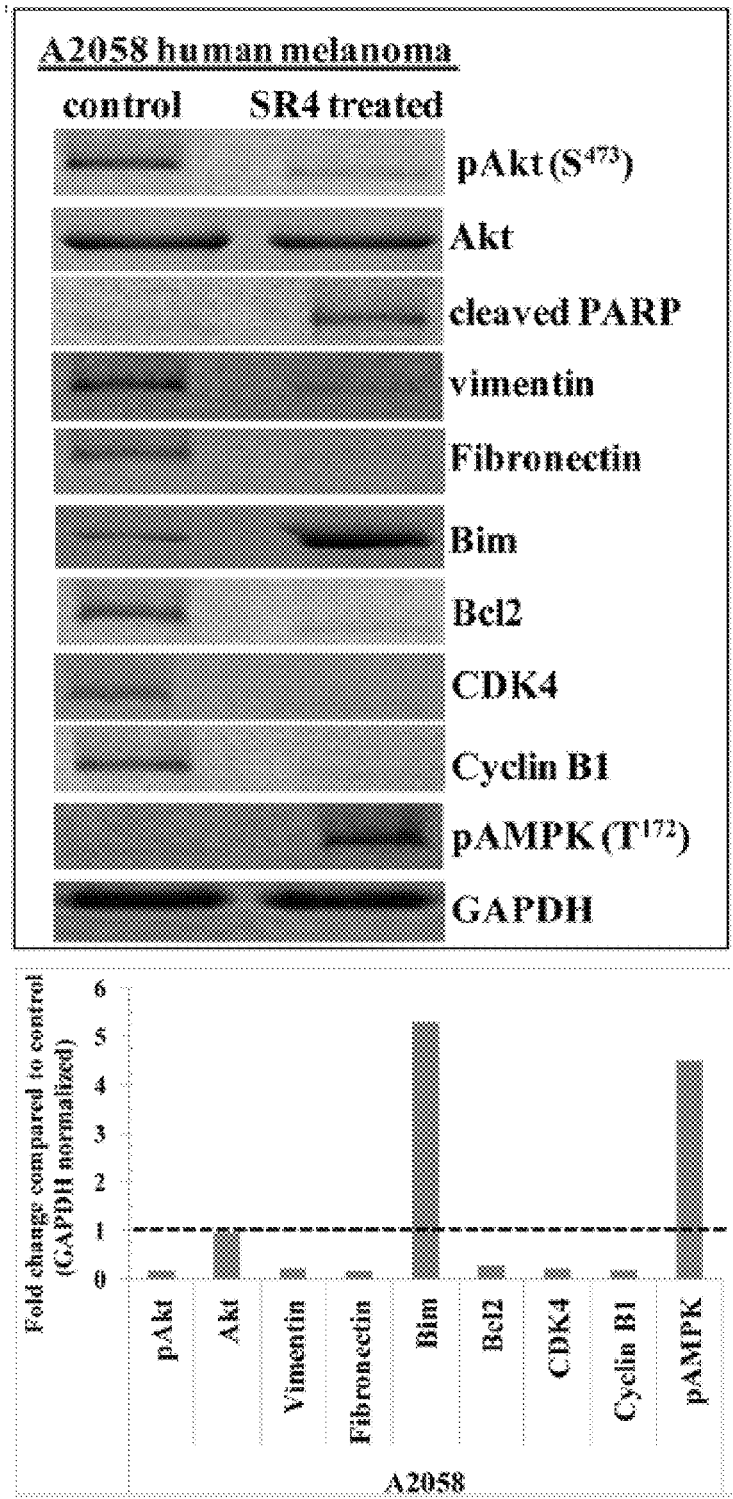

C57B mice (for syngeneic B16-F0 mouse melanoma model) and Hsd: Athymic nude nu/nu mice (for A2058 human melanoma mouse xenografts model), were used for testing the impact of oral administration of COH-SR4 on melanoma progression in vivo models. In each model, ten 10-weeks-old mice were divided into two groups of 5 animals (treated with corn oil (vehicle), and COH-SR4 compound (4 mg/kg b.w.). All animals were injected with 2×10$^6$ melanoma cells suspensions in 100 μL of PBS, subcutaneously into one flank of each mouse. Treatment was started 10 days after the implantation of melanoma cells. Treatment consisted of 0.1 mg of COH-SR4/mice in 200 μL corn oil by oral gavage on alternate days. Control groups were treated with 200 μL corn oil by oral gavage alternate day. Animals were examined daily for signs of tumor growth and body weights were recorded. The COH-SR4 treatment was tolerated well by the mice without any weight loss compared with age-matched controls (FIG. 70A). Animals were examined daily for signs of tumor growth. Tumors were measured in two dimensions using calipers. Photographs of animals were taken at day 1, day 10, day 14, day 18, day 20, day 30, day 40, and day 51 after subcutaneous injection for all groups (FIGS. 63 and 64, the circles indicate the tumor sizes; and the * indicates that COH-SR4 treatment started alternate days by oral gavage after 10 days of B16-F0 and A2058 cells implantation, respectively.). Weights and photographs of tumors were also taken at day 20 (for syngeneic model), and at day 51 (for xenograft model) (FIG. 70B). The COH-SR4 treatment resulted in significant reduction in the tumor burdens in the treated groups [B16-F0 syngeneic melanoma model: 2.36±0.2 g vs. 1.07±0.2 g in control and COH-SR4 treated groups, respectively on day 20. A2058 human melanoma xenograft model: 1.91±0.3 g vs. 0.7±0.1 g in control and treated and groups, respectively, on day 51] (FIG. 70B). Tumors were measured in two dimensions using calipers and time-course analysis of tumor regression was performed during the study. The time course analyses of COH-SR4 treatment revealed a substantial inhibition of tumor progression in both syngeneic and xenografts models of melanoma whereas uncontrolled growth was observed in untreated controls (FIG. 70C). In parallel xenografts studies, 20 mg/kg b.w. COH-SR4 was used to see the better regression and any toxicity. Higher dosage of COH-SR4 caused no further improvement in tumor regression and no toxicity was observed (FIG. 64). The COH-SR4 treated animals with B16-F0 melanoma survived for 50±5 days, while all animals treated with vehicle only were censored by day 20±2. The COH-SR4 treated animals with A2058 melanoma were still alive at 88 days, while all animals treated with vehicle only were censored by day 51±3. These results indicated that COH-SR4 administration inhibited melanoma growth and prolonged survival without causing side effects.

Impact of COH-SR4 on the Markers of Proliferation and Angiogenesis

Following the in vivo animal studies, the histopathological examination of paraffin-embedded tumor xenograft sections by H&E staining revealed that COH-SR4 reduces the number of tumor blood vessels and restores the normal morphology when compared with controls (FIGS. 71A-71B). Immuno-histochemistry analyses for Ki-67, CD31, and pAMPK expression from tumors in mice of control and COH-SR4-treated groups were carried out. Statistical significance of difference was determined by two-tailed Student's t test, p<0.001, COH-SR4-treated compared with control. Immuno-reactivity was evident as a dark brown stain, whereas non-reactive areas displayed only the background color. Sections were counterstained with Hematoxylin (blue). Percent staining was determined by measuring positive immuno-reactivity per unit area. Arrows represent the area for positive staining for an antigen. COH-SR4 treatment decreased the levels of proliferation marker, Ki 67 and angiogenesis marker, CD31 as revealed by ABC staining. AMPK is a critical cellular protein which senses the low energy status of cells and its activation inhibits cell growth and proliferation. COH-SR4 treatments resulted in increase in the levels of phosphorylated AMPK (pAMPK) in tumor sections which provides corroborative evidence for the induction of anti-tumor effects in in vivo models of melanoma.

Effect of COH-SR4 on the Expression of Tumor Proteins

The COH-SR4 treated groups had high levels of the cleaved PARP compared to untreated controls, which is in accordance with the observed apoptotic effects of COH-SR4 in vitro melanoma cultures. Akt is a critical signaling protein that transduces the proliferative signals from upstream integrins and growth factor receptors. The COH-SR4 treatments resulted in an increase in the levels of PARP cleavage along with decrease in the levels of Akt and pAkt ($S^{473}$). The cellular levels of vimentin and fibronectin determine the extent of migration and proliferation in melanoma cells. COH-SR4 treatments lead to decreases in the expression of vimentin and fibronectin which are associated with invasive progression of melanomas. COH-SR4 treated groups had an enhanced expression of pro-apoptotic protein Bim along with a parallel decrease in the levels of anti-apoptotic protein Bcl2. The expression of cell cycle regulatory proteins CDK4 and Cyclin B1 was decreased following COH-SR4 treatment. The results regarding G2/M phase arrest was observed consequent to COH-SR4 treatment are in accordance with some of the published studies which indicate that that anti-cancer compounds such as apigenin and thimerosal which also cause inhibition of CDK4 along with cyclin B1. In accordance with the histopathological examination, the levels of pAMPK ($T^{172}$) were enhanced in COH-SR4 treated groups compared to controls in both B16-F0 and A2058 melanoma (FIGS. 72A-72B, bar diagrams representing the fold change in the levels of proteins as compared to controls as determined by densitometry; dotted lines representing no significant change as observed with control.). Thus, COH-SR4 represents a novel candidate for the further development of mono and combinatorial therapies to effectively target aggressive and therapeutically refractory melanomas.

Example 23. COH-SR4 Targets Mitochondrial Respiration Via Uncoupling and Disrupts the Mitochondrial Membrane Potential and Promotes Mitochondria Membrane Swelling (FIGS. 73A-G)

Figure 73A:
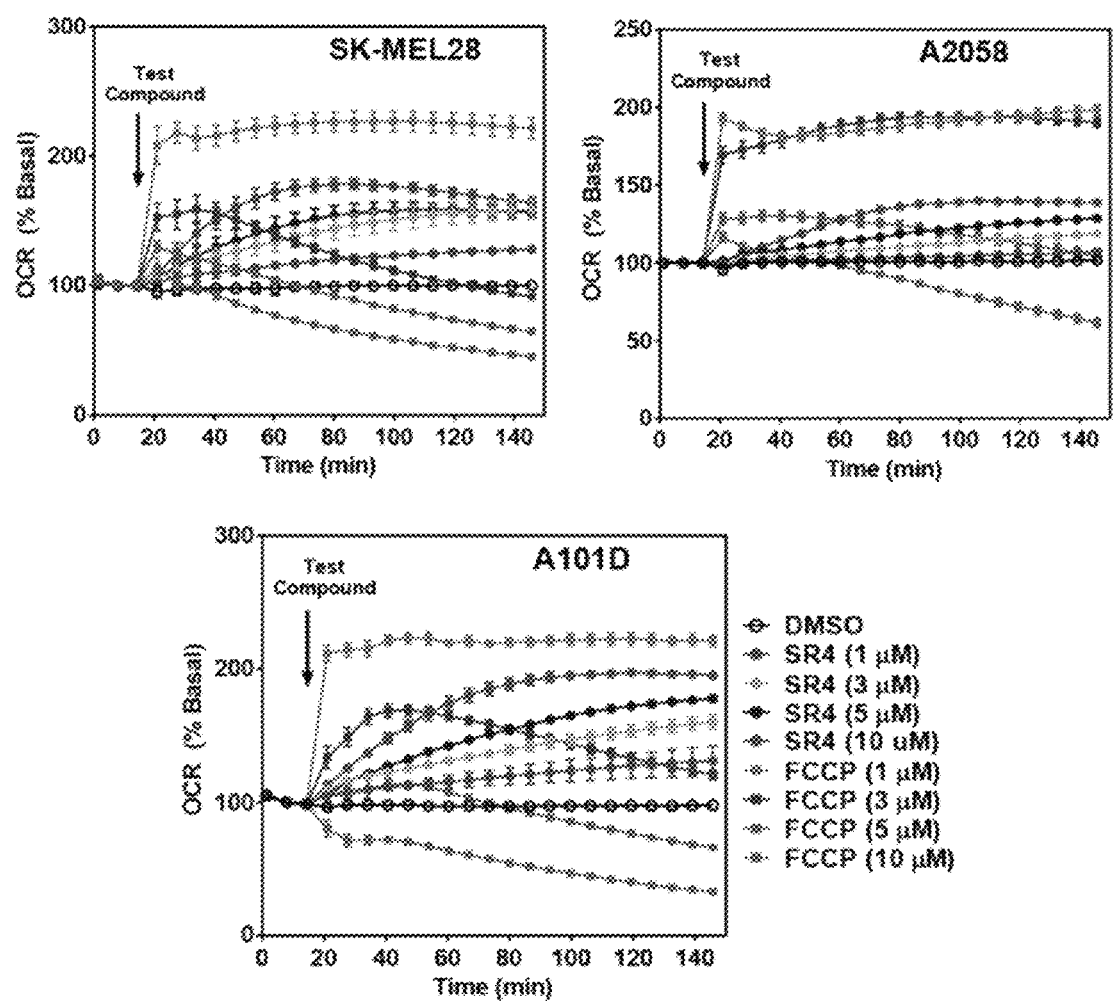
FIGS. 73A-73G: Mitochondrial effects of COH-SR4 as compared to the uncoupler FCCP.
Figure 73B:
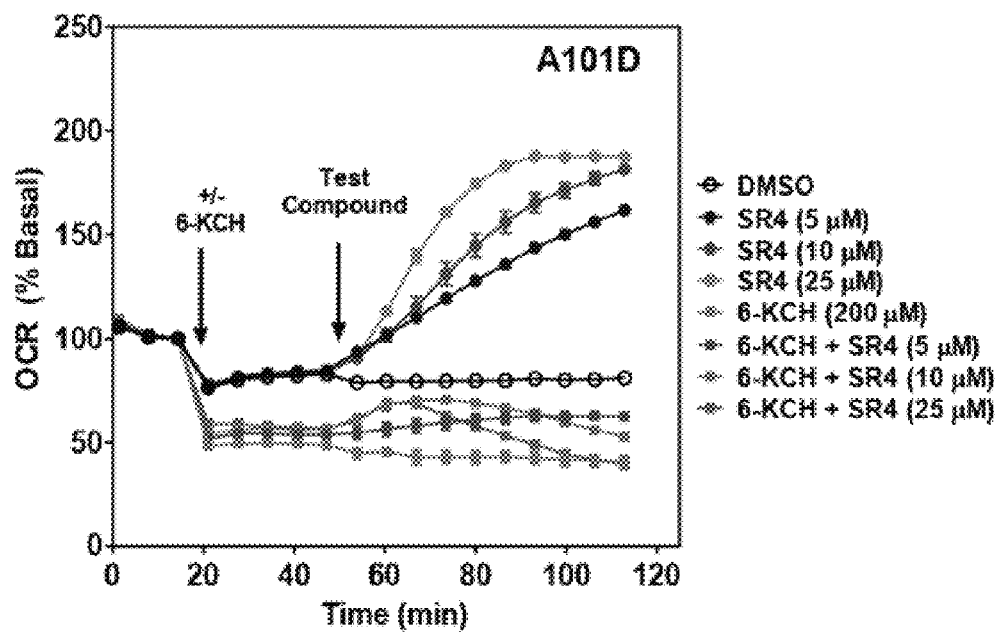
Figure 73C:
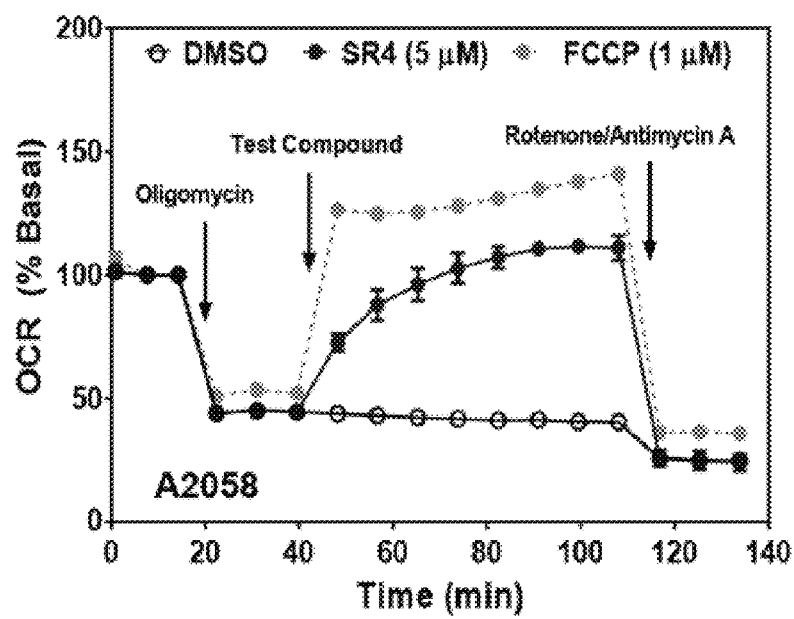
Figure 73D:
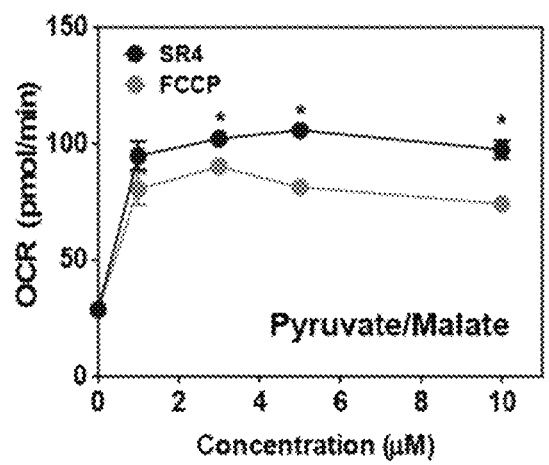

The importance of mitochondria as oxygen sensors as well as producers of ATP and ROS has recently become a focal point of cancer research. However, in the case of melanoma, little information is available to what extent cellular bioenergetics processes contribute to the progression of the disease and related to it, whether OxPhos has a prominent role in advanced melanoma. The data disclosed herein shows that cellular bioenergetics and, in particular, mitochondrial functions played an important role in this disease. Without being bound by a specific mechanism, as COH-SR4 indirectly activated AMPK in cancer cells as well as normal cells (3T3-L1 adipocytes, C2C12 myocytes) via increased AMP:ATP ratio, COH-SR4 may target the mitochondria and cellular bioenergetics. Using the Seahorse XF$^e$ 96 flux analyzer, the "real time" effects of COH-SR4 were followed on several human melanoma cells. Increased oxygen consumption rate (OCR) is one of the consequences of uncoupling, and as shown in FIG. 73A, COH-SR4 increased OCR in a time-dependent and dose-dependent manner in three human melanoma cell lines. Compared with the prototype uncoupler FCCP which caused an abrupt increase in OCR at the lower concentration and decreases OCR at higher (>3 µM) concentrations, COH-SR4 at higher concentrations (up to 25 µM) was able to maintain uncoupled respiration at a high rate in these cells. After measuring the basal respiration rate, COH-SR4 (1-10 µM) or the prototypical uncoupler FCCP (1-10 uM) was introduced into one of the injection ports of the Seahorse XFe96 flux analyzer and incubated with cells. OCR was continuously monitored for 2 h. Mitochondria recoupler 6-KCH (200 µM) was added to the assay system prior to injection of COH-SR4 (5 µM)

as shown by arrows and OCR of A101D cells were monitored (FIG. 37B). Cells were sequentially treated with ATP synthase inhibitor oligomycin (1 μM), the indicated concentrations of COH-SR4 or FCCP, and rotenone (1 μM) plus antimycin A (1 μM) as shown by arrows (FIG. 37C). Pre-treatment of cells with the mitochondria recoupler 6-KCH abolished the uncoupling effects of COH-SR4 (FIG. 73B), but the compound is fully capable of increasing OCR in the presence of the ATP synthase inhibitor oligomycin (FIG. 73C). Thus, COH-SR4 may be an uncoupler of mitochondrial respiration.

Figure 73E:
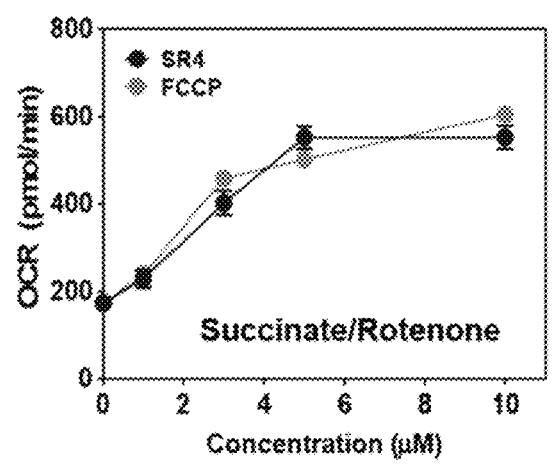

To further verify that COH-SR4 acted directly on mitochondrial respiration, OCR was measured in freshly isolated mouse liver mitochondria and treated them with either COH-SR4 or FCCP. Both COH-SR4 and FCCP dose-dependently increased OCR of mitochondria respiring on pyruvate and malate (FIG. 73D), as well as succinate-rotenone (FIG. 73E). OCR values in said figures are representative rates of n=6-8 wells per treatment from 2-3 separate experiments.

Figure 73F:
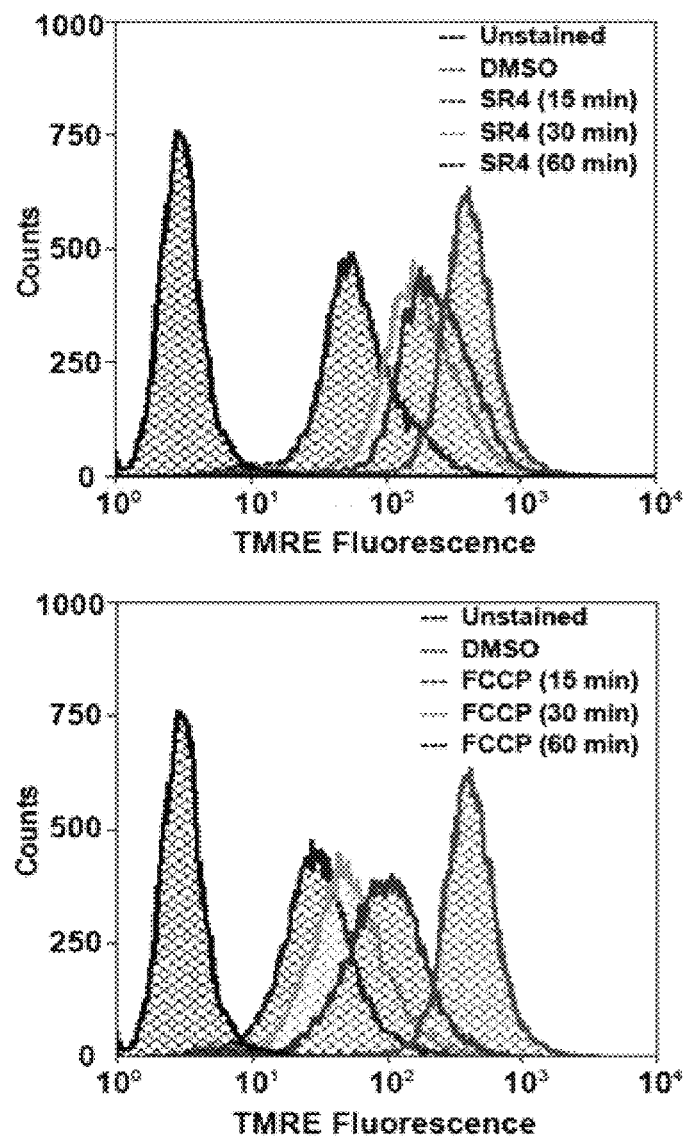

Increasing proton leak into mitochondria was expected to induce mitochondrial depolarization. Both 5 μM COH-SR4 and 5 μM FCCP induced mitochondrial membrane depolarization in a time-dependent manner in A2058 cells as measured by TMRE fluorescence (FIG. 73F).

Figure 73G:
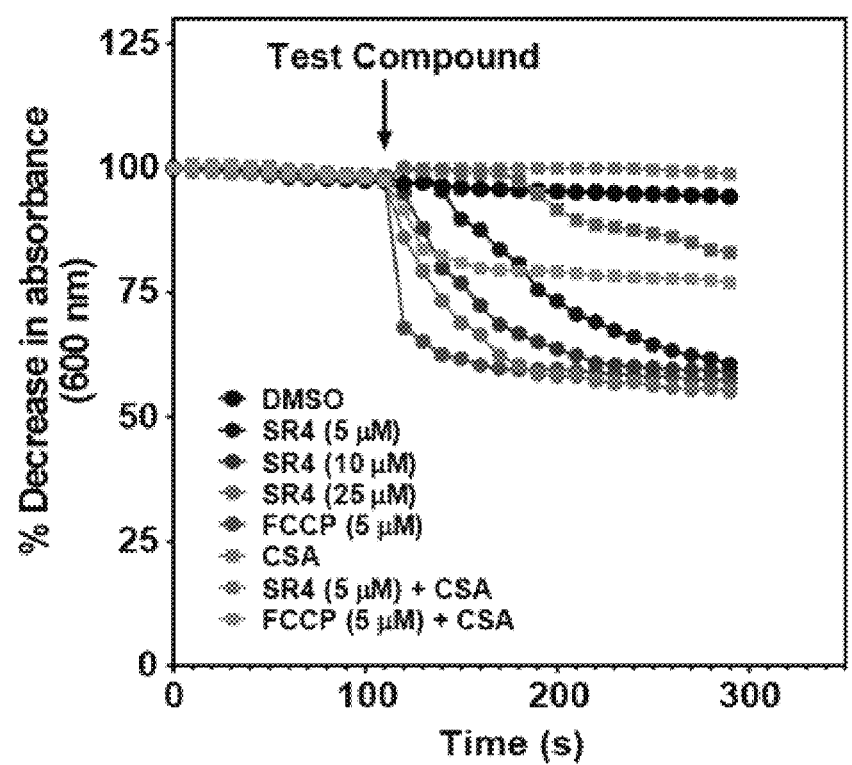

To further characterize COH-SR4-mediated uncoupling, mitochondrial swelling assays (an indirect measure of MPT opening) were performed in potassium acetate buffer treated with K+ ionophore valinomycin. 101D cells were preloaded with the 200 nM of the fluorescent dye TMRE for 15 min, rinsed once with media, then treated with either 5 μM COH-SR4 or FCCP from 0-60 min. After incubation, cells were then rinsed with PBS and the overall fluorescence was analyzed by flow cytometry ($488_{ex}/572_{em}$). Mitochondrial membrane swelling was detected as decrease in absorbance at 600 nm following the addition of COH-SR4 or FCCP alone or in the presence of cysclosporin A (CSA, 1 μM) on isolated mouse liver mitochondria respiring on succinate (10 mM) in the presence of rotenone (1 μM) and valinomycin (5 μM) in potassium acetate buffer. As shown in FIG. 73G, mitochondrial swelling was observed in the presence of either COH-SR4 or the classical protonophore FCCP. Arrow indicates time of addition of test compounds into the mitochondria suspension. These results suggest that COH-SR4 could be functioning as a protonophore uncoupler.

To verify that COH-SR4 acts directly on mitochondrial respiration, OCR in mitochondrial DNA-depleted ($p^0$) A2058 cells was measured, as well as freshly isolated mouse liver mitochondria and treated with either COH-SR4 or FCCP. Both compounds failed to increase OCR in A2058 $p^0$ cells compared with wild-type A2058 (data not shown). Collectively, these results provide convincing evidence that COH-SR4 is a bona fide mitochondrial uncoupler.

Figure 74A:
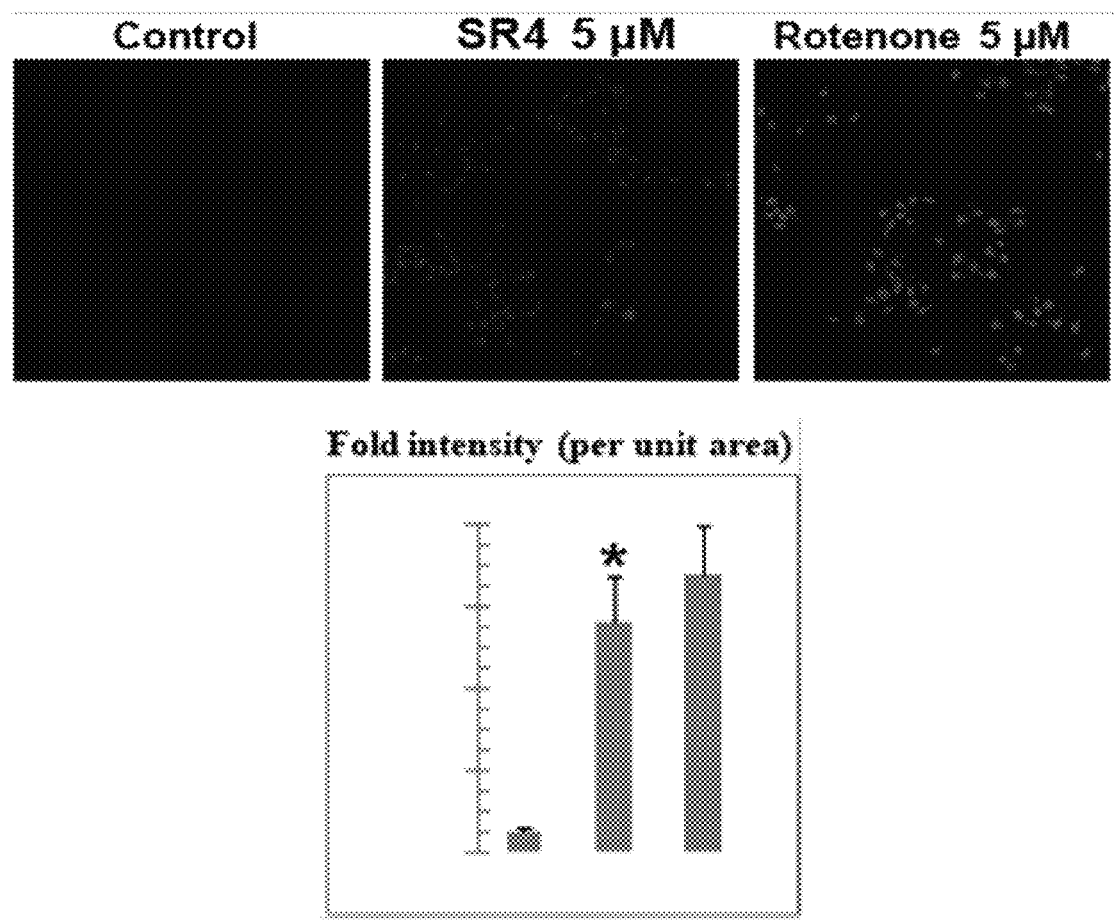
FIGS. 74A-74B: COH-SR4 induced mitochondrial ROS formation.
Figure 74B:
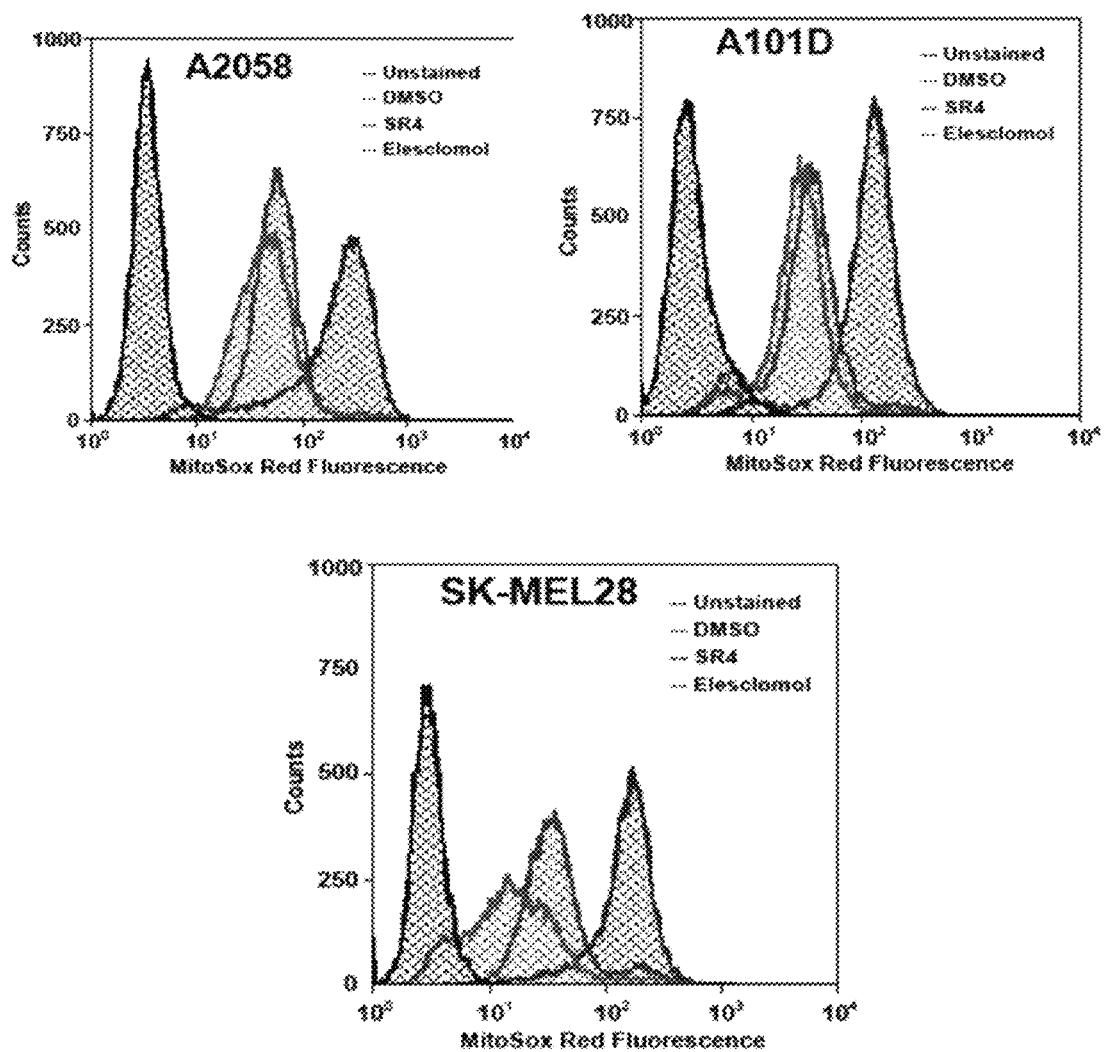

Example 24. COH-SR4 Stimulates Mitochondrial ROS Production in Melanoma (FIGS. 74A-B)

Redox imbalance has a central role in melanomagenesis. Melanoma cells have increased levels of GSH and related enzymes, which may play a role in chemoresistance. As shown in the foregoing examples, COH-SR4 treatment resulted in inhibition of GST activity in melanoma cells, which could lead to increased levels of intracellular ROS formation. Thus, any further increase in cellular ROS production will be detrimental to melanoma proliferation and growth. Using the mitochondrial superoxide probe MitoSox Red, it is shown that COH-SR4 induced ROS production in A2058, A101D and SK-Mel-28 melanoma cells similarly as rotenone, a mitochondria complex 1 inhibitor, but more potent than elesclomol (FIGS. 74A and 74B).

Mitochondrial ROS was measured by MitoSox Red according to the manufacturer's instructions (Molecular Probes, CA). The intensity of fluorescence was quantified by digital analysis of images obtained from confocal microscopy using Image Pro Premiere software (Media Cybernetics Inc., Bethesda, Md.) (A2058, FIG. 74A) or by flow cytometry (FIG. 74B). Cells were treated with either 5 μM of COH-SR4, rotenone (mitochondrial complex 1 inhibitor) or elesclomol for 1 h. *Results represent fold increase of ROS generation over control and are expressed as mean±SD from three independent experiments.

Figure 75A:
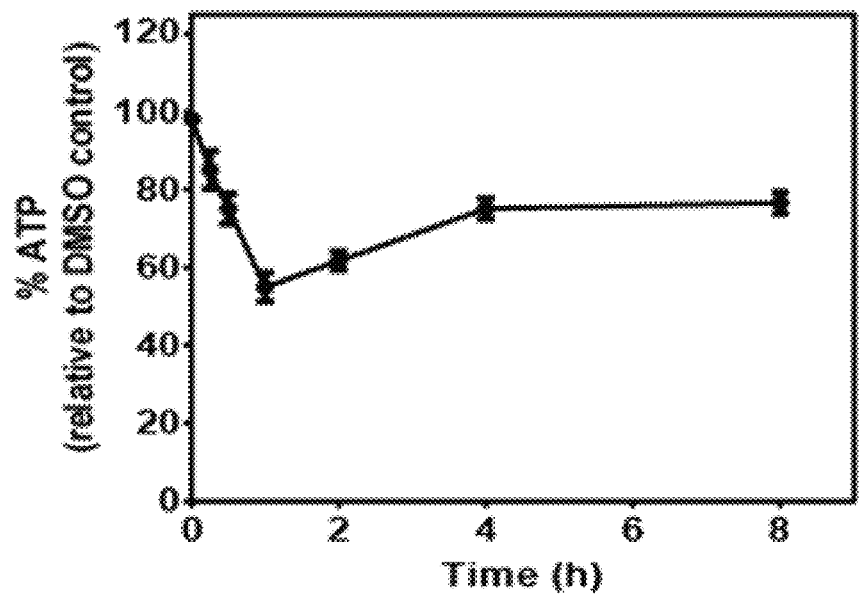
FIGS. 75A-75B: COH-SR4 decreased intracellular ATP production in melanoma.
Figure 75B:
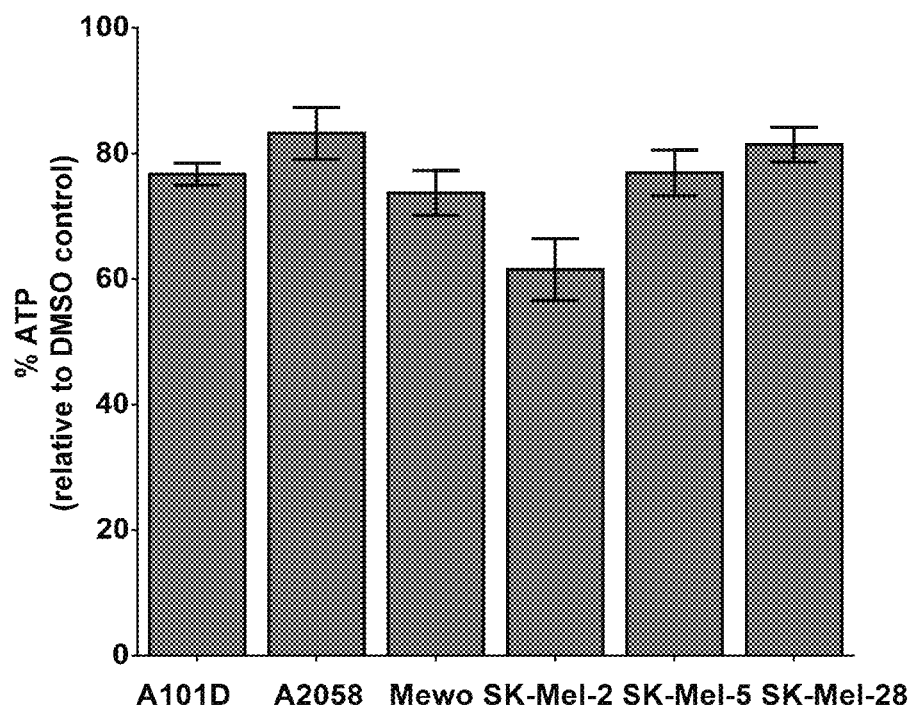

Example 25. COH-SR4 Decreased Intracellular ATP Levels and Activates AMPK in Melanoma Cells Regardless of Driver Mutations/Genetic Background (FIGS. 75A-B)

One of the consequences of mitochondria uncoupling is decrease intracellular ATP production, leading to increased AMP:ATP ratio and triggering activation of the energy-sensitive enzyme AMPK. It has been previously shown that COH-SR4 indirectly activates AMPK in a time- and dose-dependent manner in both HepG2 cells and 3T3-adipocytes. As disclosed herein, treatment of melanoma cells with COH-SR4 also resulted in decreased ATP production. For example, treatment of COH-SR4 resulted in a rapid decline (less than 1 h) in intracellular ATP production in SK-MEL2 as assayed by a sensitive ATP luminescence kit (FIG. 75A). Almost similar decrease in ATP production was observed in other human melanoma cells treated with COH-SR4 (FIG. 75B). As a consequence of this ATP depletion from COH-SR4 treatment, a dose- and time-dependent activation of AMPK, regardless of BRAF, NRAS and LKB1 mutation was observed in several human melanoma cell lines. In melanomas, mutation rates for BRAF NRAS and LKB1 are 50-70%, 5-30%, and 10%, respectively. Studies also demonstrated that in 3T3-cells, human lung cancer and hepatocarcinoma that COH-SR4 inhibited the mTOR pathway as a consequence of AMPK activation. AMPK activation may cause a cell cycle arrest associated with stabilization of p53 and the cyclin-dependent kinase inhibitors $p21^{WAF1}$ and $p27^{CIP1}$. AMPK may also inhibit the mechanistic target-of-rapamycin complex-1 (mTORC1) by phosphorylating its upstream regulator TSC2 (tuberous sclerosis complex 2) and its regulatory subunit raptor, and thus may inhibit translation of many proteins required for rapid cell growth, including hypoxia-inducible factor-1α (HIF1α). The uncoupler FCCP has also been shown to activate the AMPK-mTOR pathway.

Figure 76A:
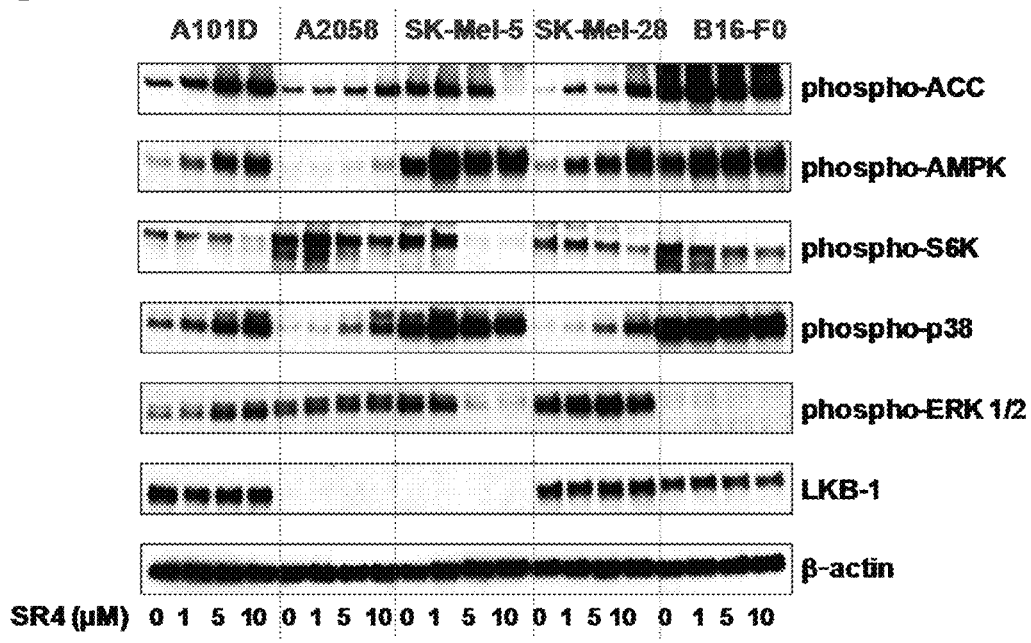
FIGS. 76A-76B: Dose- and time-dependent effects of COH-SR4 on AMPK-mTOR and MAPK/ERK signaling pathways in melanoma cell lines of different driver mutations/genetic background (A101D, A2056, SK-Mel-5, SK-Mel-28 and B16-F0).

Example 26. COH-SR4 Modulated MAPK/ERK Signaling in Melanoma Cells (FIGS. 76A-B)

Figure 76B:
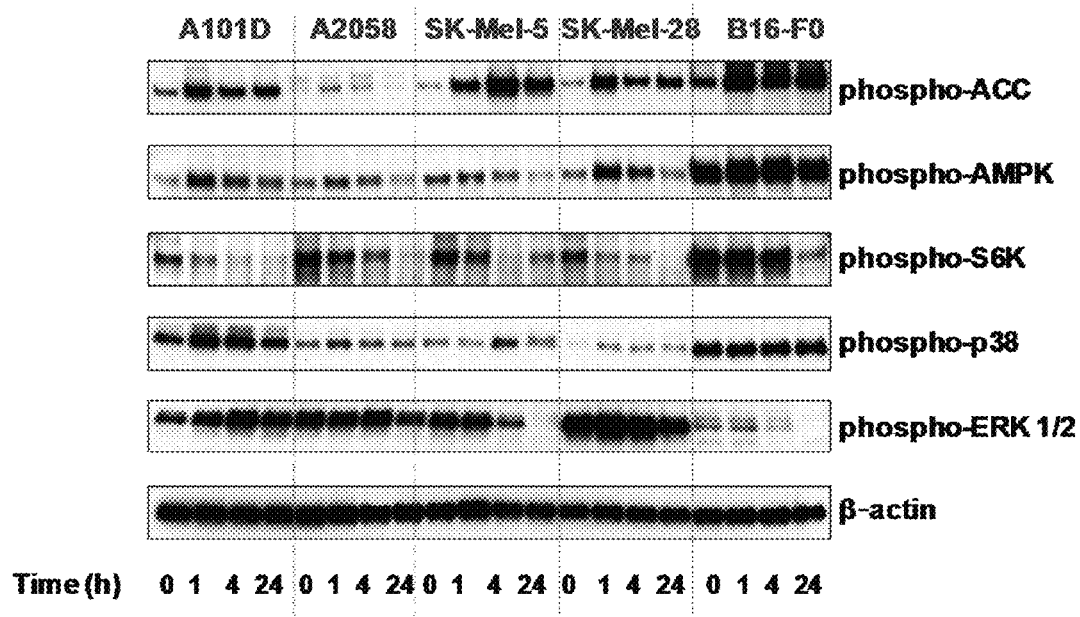

To investigate whether COH-SR4 affected the MAPK/ERK signaling pathway in human melanoma, the phosphorylation levels of p38 MAPK ($T^{180}/Y^{182}$), ERK1/2 ($T^{202}/Y^{204}$), and pJNK ($T^{183}/Y^{185}$), in A101D, A2058, SK-Mel-5, SK-MEL-28 and B16-F0 melanoma cells were examined after COH-SR4 treatment at various doses (0-10 μM) (FIG. 76A) or at a dose of 5 μM at various time points (0-24 h) (FIG. 76B). Total proteins were isolated and analyzed by Western blotting. COH-SR4 treatments resulted in a dose- and time dependent increase in the levels of phosphorylation of p38 MAPK ($T^{180}/Y^{182}$) and ERK1/2 ($T^{202}/Y^{204}$) (FIGS. 76A-76B), but not JNK (data not shown) in most of the melanoma cell lines tested. Altogether, these data show that the effects of COH-SR4 are consistent across diverse human melanoma cells and include inhibition of signaling pathways that are involved in cell adhesion, migration, and invasion, suggesting that COH-SR4 could be a lead compound to develop anticancer therapeutic agents for aggressive malignant melanoma treatment.

Figure 77A:
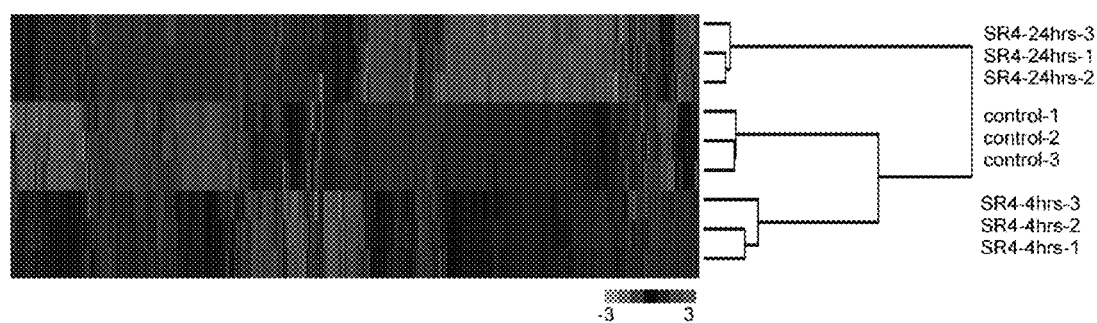
FIGS. 77A-77C: COH-SR4 associated differential gene expression and corresponding gene ontology in melanoma.
Figure 77B:
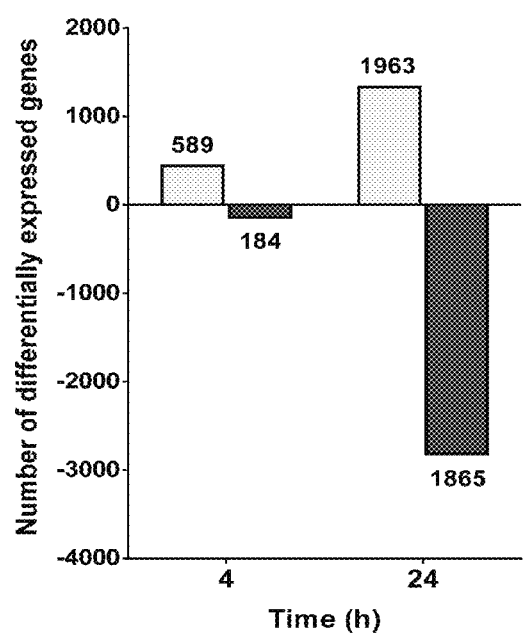
Figure 77C:
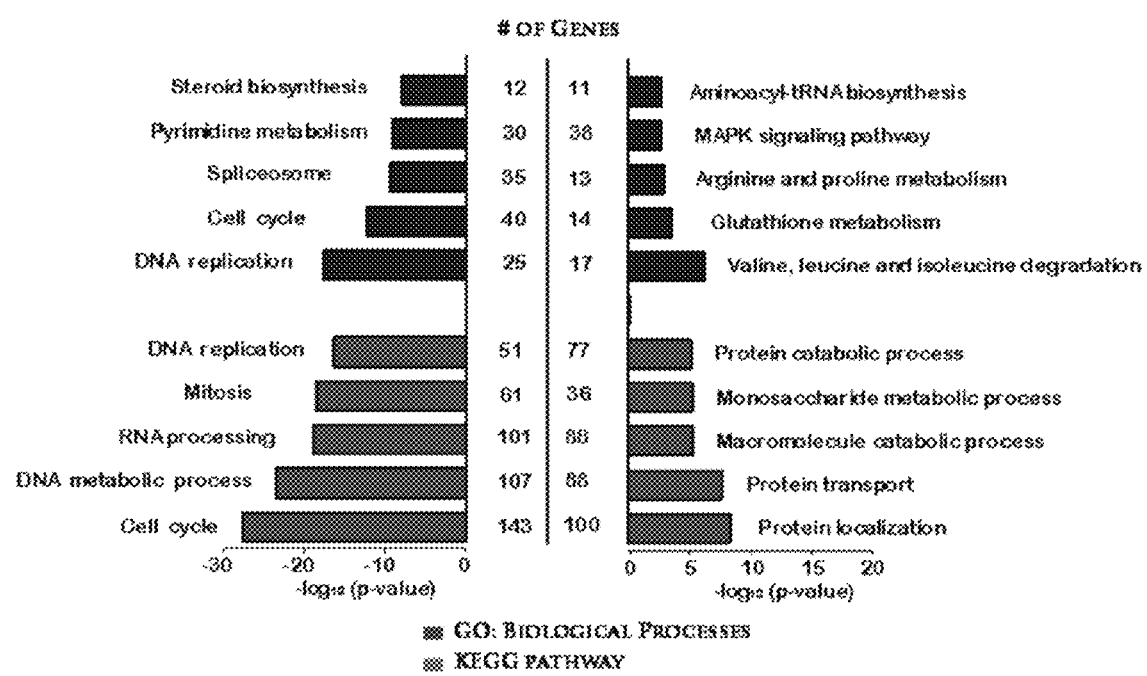

Example 27. RNA-Sequence Data Reveals COH-SR4 Targets a Number of Genes Involved in Mitochondrial Functions in Melanoma (FIGS. 77A-C)

A preliminary RNA-sequence analysis on B16-F0 melanoma cells was performed where COH-SR4-induced differential gene expression was quantified at 4 and 24 h post treatment and analyzed for functional enrichment by gene ontology (GO). B16-F0 melanoma cells were treated with COH-SR4 for 4 h or 24 h. Heirarchical sample clustering map analysis of COH-SR4-treated and untreated sample replicates showed tight clustering (FIG. 77A). Differentially expressed genes subsequent to COH-SR4 treatment were displayed within the heat map. Log 2 transformed RPKM values were used for clustering using dChIP. Genes were mean-centered and average linkage method was used for clustering. Samples sub-cluster according to biological replicate. Differential gene expression was identified from standard Partek workflow (Partek Genomics Suite version 6.6, Partek) using ANOVA, with step-up false discovery rate multiple testing correction p value <0.05 and requiring a >1.5-fold change between each time point and control samples. Results showed 773 (589 upregulated, 184 downregulated) and 3828 genes (1963 upregulated, 1865 downregulated) were differentially expressed by exposure to COH-SR4 for 4 and 24 h, respectively (FIG. 77B) Gene ontology for the 24 h COH-SR4 treatment for the up- or down-regulated genes was analyzed for functional enrichment using the Database for Annotation, Visualization, and Integrated Discovery (DAVID; version 6.7) Databases included GOTERM_BP_FAT (biological process), and the Kyoto Encyclopedia of Genes and Genomes (KEGG_PATHWAY). The top 5 ontology results for each data base examined as ranked by p-value (EASE score) are provided for differentially expressed genes 24 h following COH-SR4 treatment (FIG. 77C). Consistent with COH-SR4-mediated induction of cell toxicity and inhibition of cell proliferation in B16-F0 melanoma cells, the highest ranked biological process ontology terms were upregulation of protein and amino acid metabolism and MAPK signaling, concomitant with downregulation of cell cycle, DNA replication and RNA processing, which are more likely associated with cellular response to energy depletion and ROS production induced by COH-SR4 (FIGS. 77A-C). Taken together, COH-SR4 treatment uncoupled mitochondrial OxPhos, promoted loss of membrane potential, induced ROS production and MAPK signaling, activated AMPK and inhibited mTOR, leading to cell cycle arrest and apoptosis in melanoma cells, suggesting COH-SR4 targeting the mitochondria and may have clinical potential for advanced melanoma.

Example 28. Impact of COH-SR4 Treatment In-Vitro on Human Lung Cancer Cell Survival, Clonogenic Potential and Apoptosis (FIGS. 78A-D)

Figure 78A:
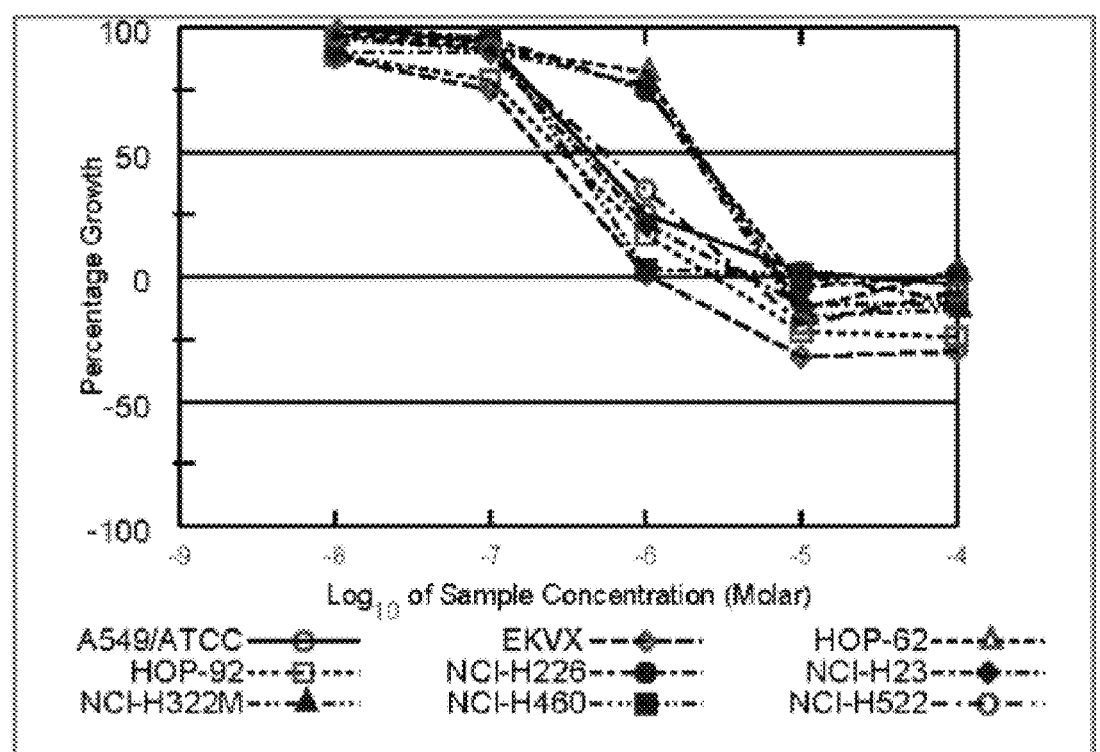
FIGS. 78A-78D: Anti-proliferative and pro-apoptotic effects of COH-SR4 in lung cancer.
Figure 78B:
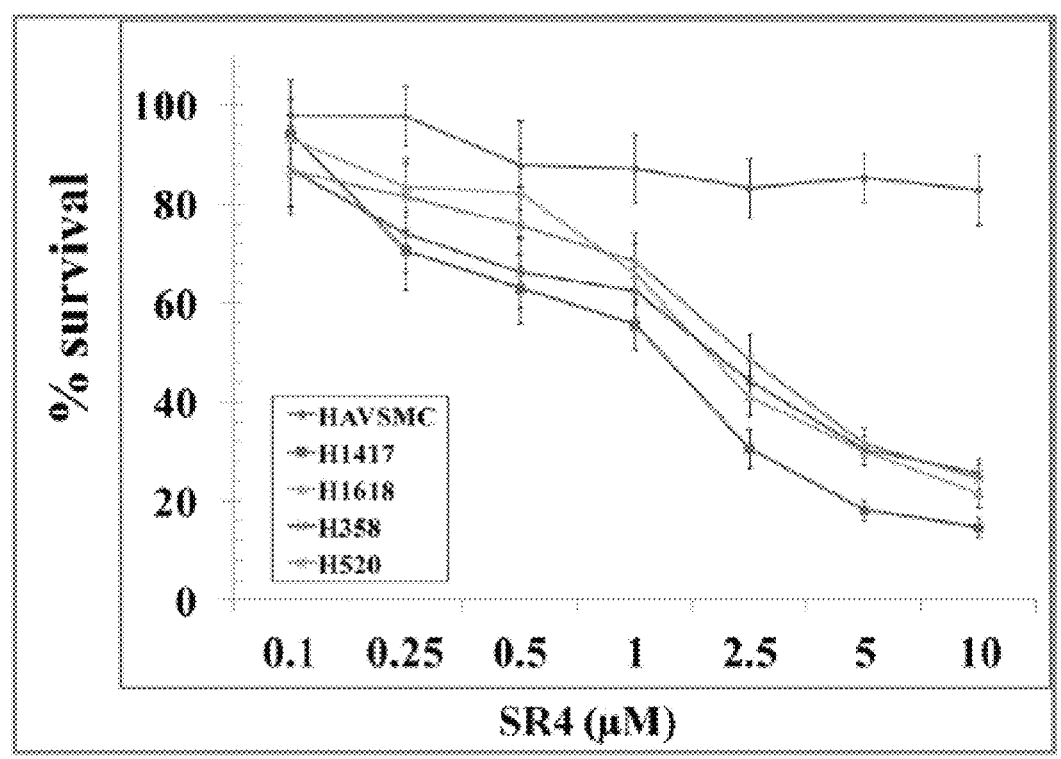
Figure 78C:
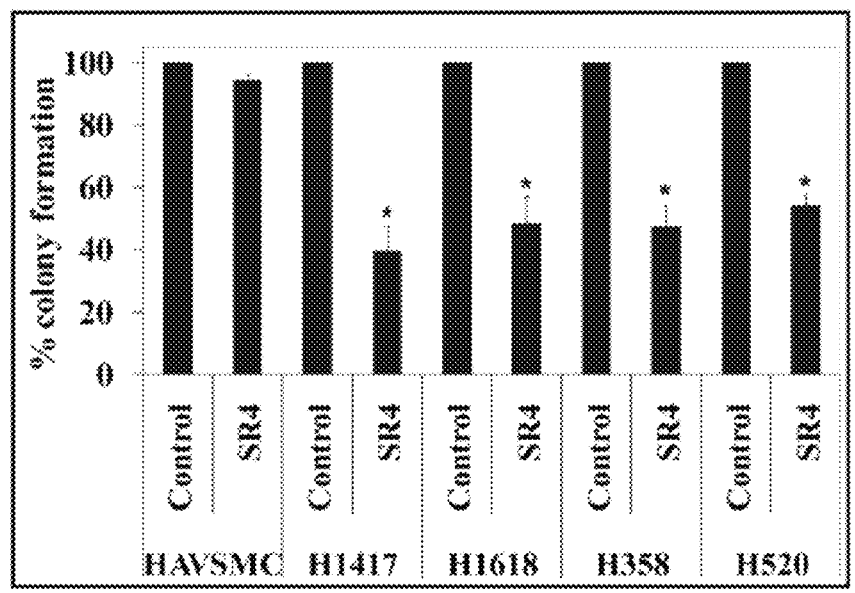
Figure 78D:
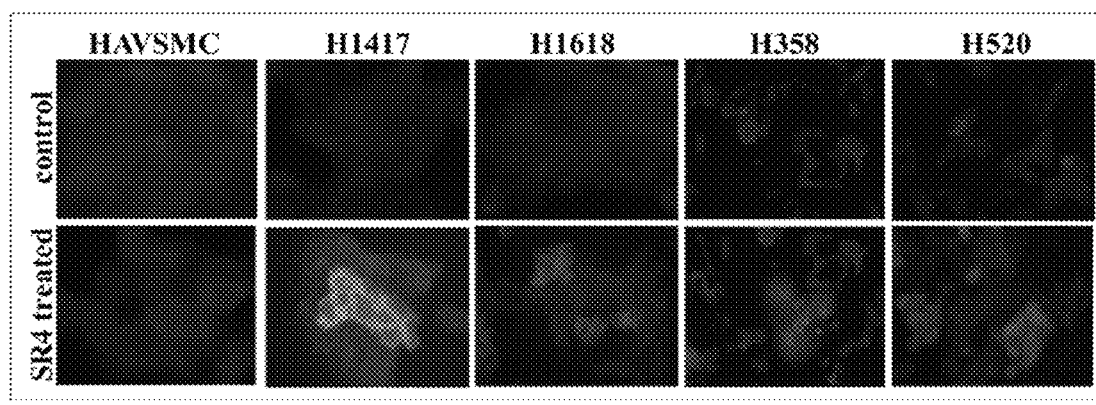

The effect of COH-SR4 was first examined in a NCI panel of cancer cell lines, the results of which indicated good activity of COH-SR4 towards lung cancer (FIG. 78A). The activity of COH-SR4 was confirmed in various lung cancer cell lines after 48 h treatment using MTT assay, and $IC_{50}$ was determined. Values are presented as mean±SD from two separate determinations with eight replicates each (n=16) (FIG. 78B). The COH-SR4 treatment exerted a significant inhibitory effect on the survival of lung cancer cells [$IC_{50}$: H1417 cells-1.2±0.2 µM, H1618 cells-1.5±0.2 µM, H358 cells-2.1±0.2 µM and H520 cells-2.4±0.3 µM]. Unexpectedly, COH-SR4, at concentrations effective in inhibiting the survival of lung cancer cell lines, did not exert any significant cytotoxicity in normal HAVSMC. Following initial screening for the anticancer activity of COH-SR4, the effect of COH-SR4 on clonogenic potential was studied. Standard colony-forming assay was performed and the colonies were counted using Innotech Alpha Imager HP. The COH-SR4 (1.5 µM) treatment resulted in 39±8%, 48±9%, 47±7% and 54±5% colony formation in H1417, H1618, H358 and H520 lung cancer cells, respectively (FIG. 78C). In accordance with MTT assay, the 1.5 µM COH-SR4 treatment did not result in significant inhibition of colony formation in normal HAVSMC (FIG. 78C). The effect of COH-SR4 on induction of apoptosis was further investigated. For TUNEL apoptosis assay, cells were grown on cover-slips and treated with 1.5 µM COH-SR4 for 24 h. TUNEL assay was performed using Promega fluorescence detection kit and examined using Zeiss LSM 510 META laser-scanning fluorescence microscope with filters 520 and 620 nm. Photographs taken at identical exposure at ×40 magnification are presented. The 1.5 µM COH-SR4 treatment for 24 h induced apoptosis in all the lung cancer cell lines as determined by TUNEL assay (FIG. 78D). These studies showed that the COH-SR4 induced anti-proliferative and pro-apoptotic effects in lung cancer cells.

Example 29. Effect of COH-SR4 on Cell Cycle Progression and GST Activity in Human Lung Cancer (FIGS. 79A-B and 80A)

Figure 79A:
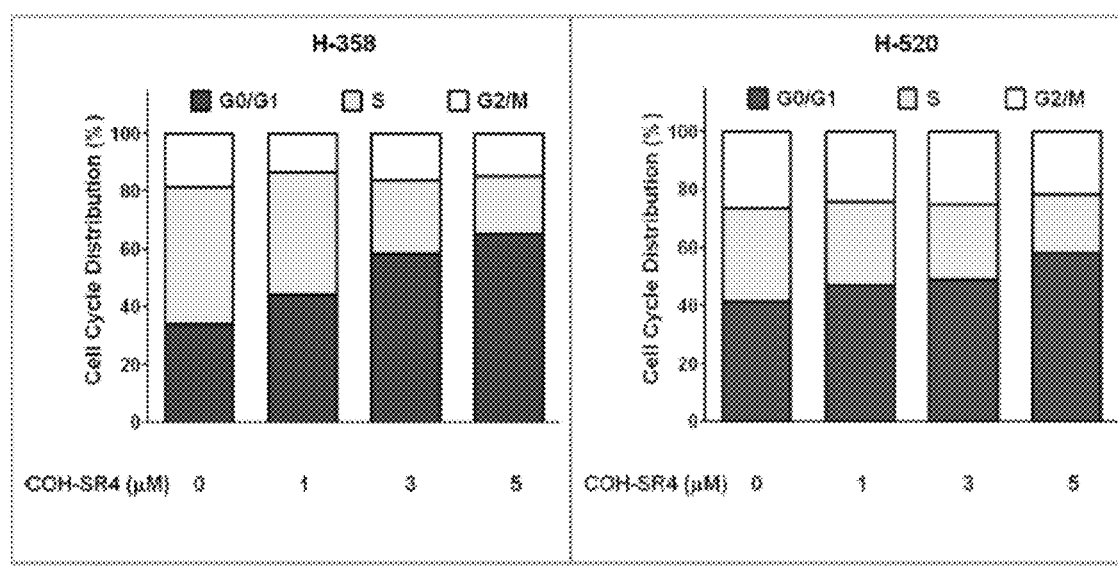
FIGS. 79A-79B: COH-SR4 induced G0/G1 cell cycle arrest and GST inactivation in lung cancer.
Figure 79B:
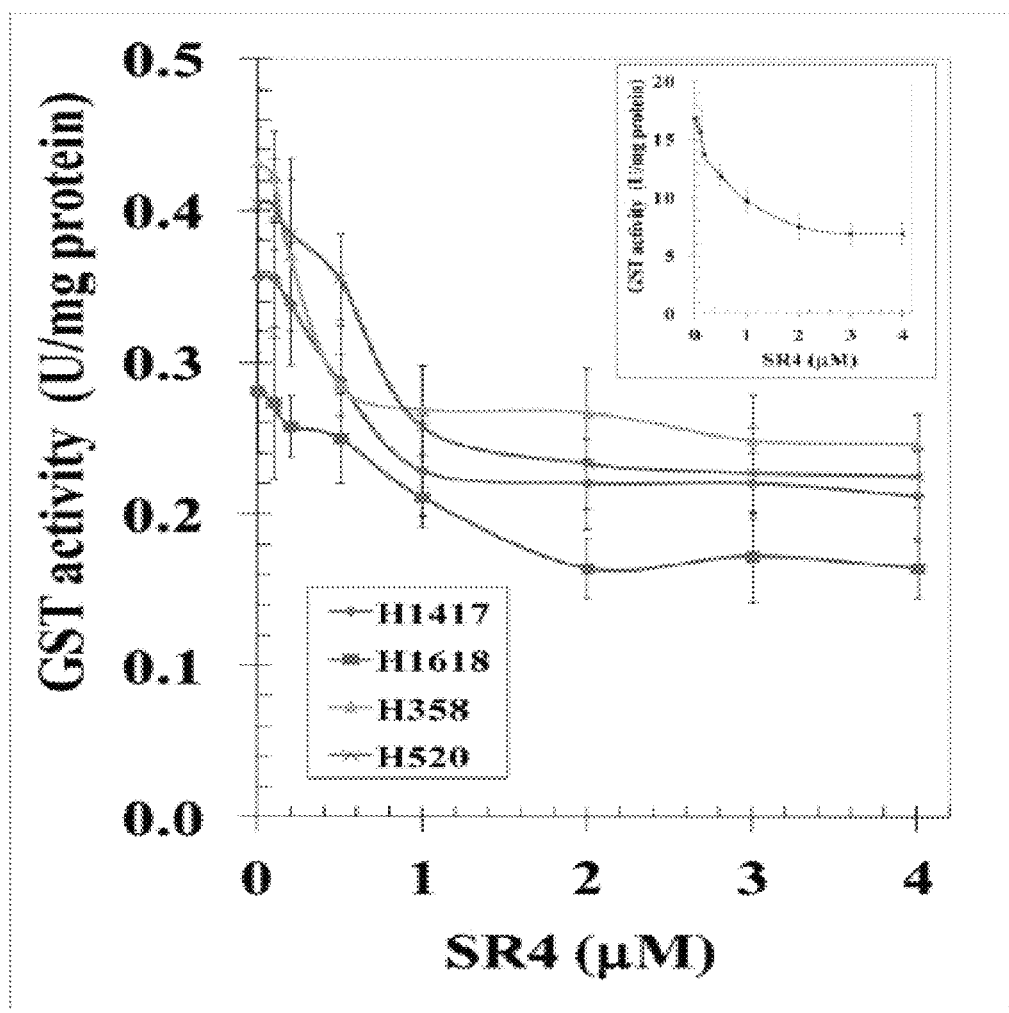
Figure 80A:
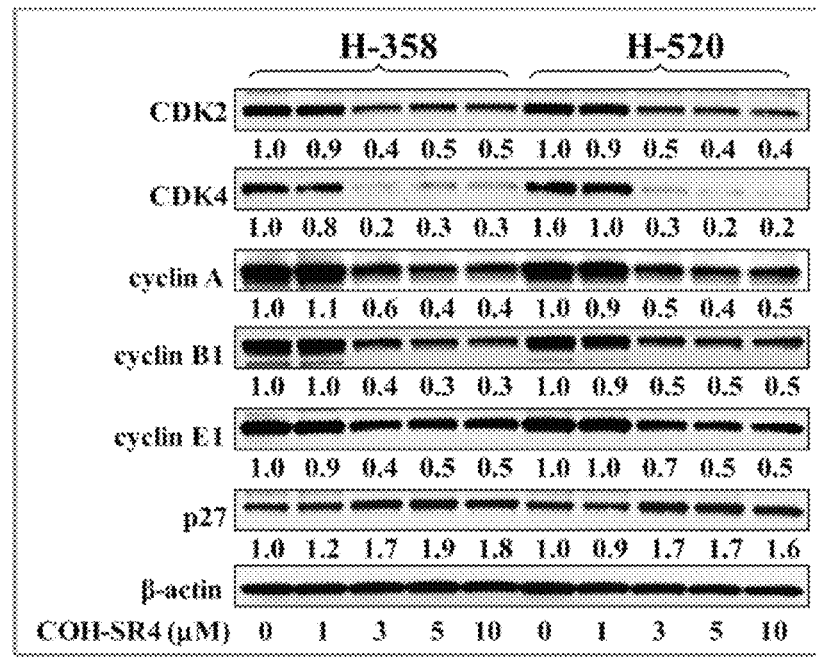
FIGS. 80A-80D: Western-blot analyses on the effects of COH-SR4 on cell survival proteins and cell signaling pathways in lung cancer cells.

Treatment with COH-SR4 induced G0/G1 phase arrest in a concentration dependent manner in H-358 and H-520 cells, thereby providing corroborative evidence for the anti-proliferative and pro-apoptotic effects of COH-SR4 in lung cancer (FIG. 79A). In the context of the elevation of GSTs in lung cancer, the impact of COH-SR4 on the catalytic activity of GSTs towards 1-chloro 2,4-dinitro benzene (CDNB), a model substrate used for GST activity was analyzed. GST activity towards 1-chloro 2,4-dinitro benzene (CDNB) and its inhibition by COH-SR4 was performed in 28000×g crude supernatant prepared from H1417, H1618, H520 and H358 cells. The inhibitory effect of COH-SR4 on GST was studied at a fixed concentration of GSH and CDNB (1 mM each) and varying concentrations of inhibitor. The enzymes were pre-incubated with the inhibitor for 5 min at 37° C. prior to the addition of the substrates. The experiment was repeated three times and similar results were obtained. The COH-SR4 treatment inhibited the total GST activity to a significant extent in said lung cancer cells (FIG. 79B). Human liver purified GST was used as a control (FIG. 79B, inset). GSTs are a class of phase II detoxifying enzymes, which regulate detoxification of administered chemotherapy drugs for further efflux out of cells by transport proteins. The GST inhibition leads to accumulation of toxic end-products of lipid peroxidation due to decreased efflux of GS-HNE which also reinforces the GST inhibition by feedback inhibition. The over-expression of GSTs is a common phenomenon associated with malignant progression of many cancers including lung cancer, melanomas skin and prostate cancers.

It was shown that the glutathione-conjugate transport by the MAP transporter RLIP76 is essential for the clathrin-dependent ligand-receptor endocytosis (CDE) which in turn regulates the activation of intracellular signaling cascades. The effect of COH-SR4 on downstream signaling proteins of significance for cellular proliferation and survival was further investigated. Western-blot results of cell cycle regulator proteins confirmed that COH-SR4 induces cell cycle arrest in H358 and H520 lung cancer cells. After 24 h treatment, COH-SR4 decreased the protein levels of CDK2, CDK4, cyclin A, cyclin B1 and cyclin E1. In addition, the protein level of p27, a potent CDK inhibitor of cyclin E- and cyclin A-CDK2 complexes involved in G1 arrest, was up-regulated by COH-SR4 (FIG. 80A). Based on these results, COH-SR4 treatment modulated the level of proteins active during S and G2 phases of the cell cycle, confirming the results of FACS analysis indicating G1 arrest induced by COH-SR4.

Example 30. Effect of COH-SR4 on AMPK-mTOR Signaling Pathway in Lung Cancer (FIGS. 80B-80D)

Figure 80B:
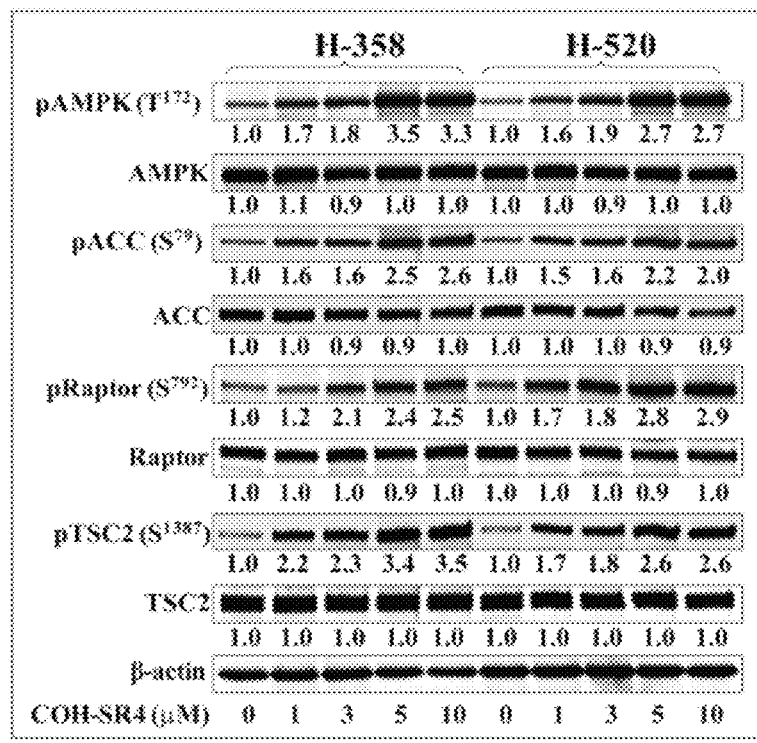
Figure 80C:
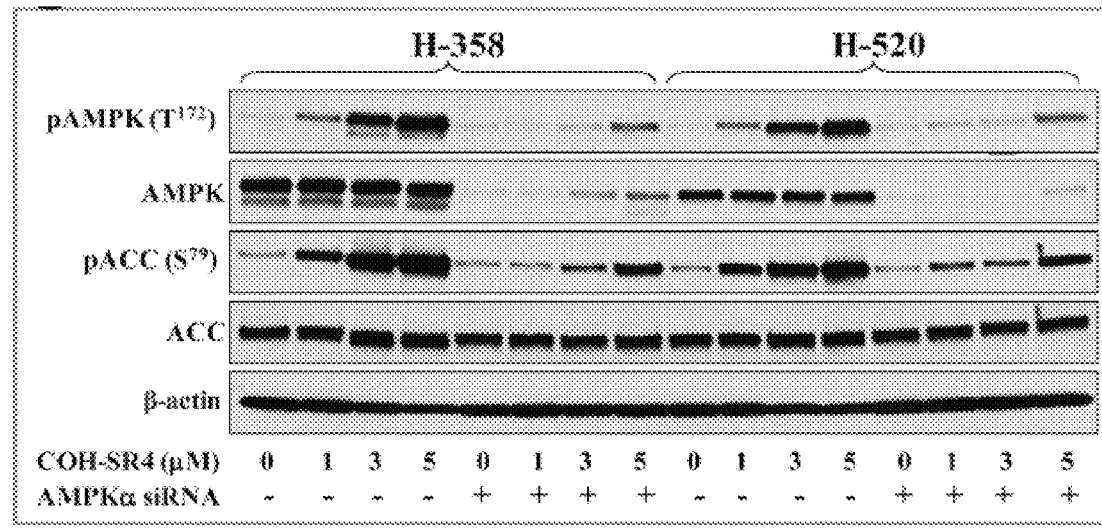
Figure 80D:
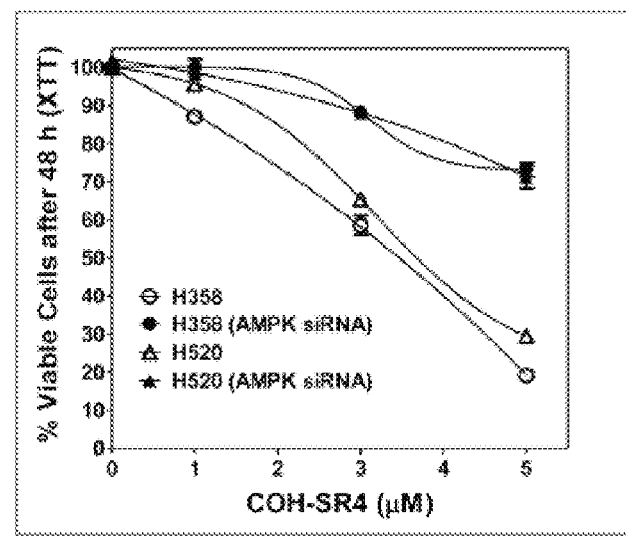

COH-SR4 treatment resulted in increased phosphorylation of AMPK (pAMPK) along with an increase in phosphorylation of down-stream target ACC, the mTOR binding partner Raptor and the tumor suppressor TSC2 (FIG. 80B). AMPK was knocked down by siRNA and assessed the impact on COH-SR4-induced cytotoxicity. The knock-down of AMPK resulted in significant reversal in the cytotoxicity of COH-SR4 in both H358 and H520 cells (FIGS. 80C and 80D). Thus, the in-vitro analyses of critical signaling proteins of cell proliferation further supported the anti-cancer effects of COH-SR4 in lung cancer cells.

Example 31. Anti-Tumor Effect of COH-SR4 In-Vivo on Lung Cancer Progression (FIGS. 81A-D)

Figure 81A:
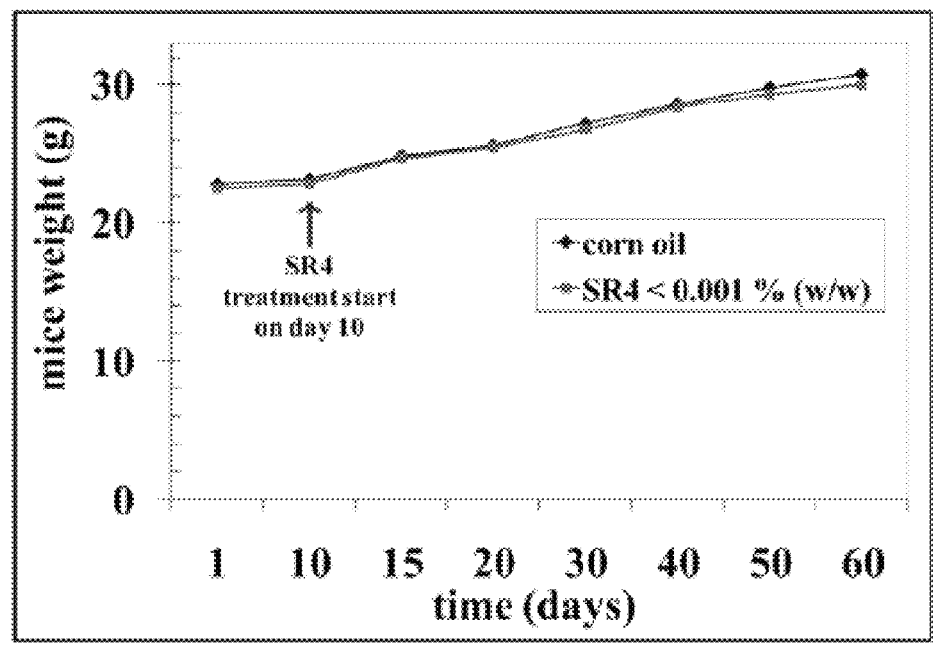
FIGS. 81A-81D: Effects of oral administration of COH-SR4 on progression of lung cancer xenografts in mice.
Figure 81B:
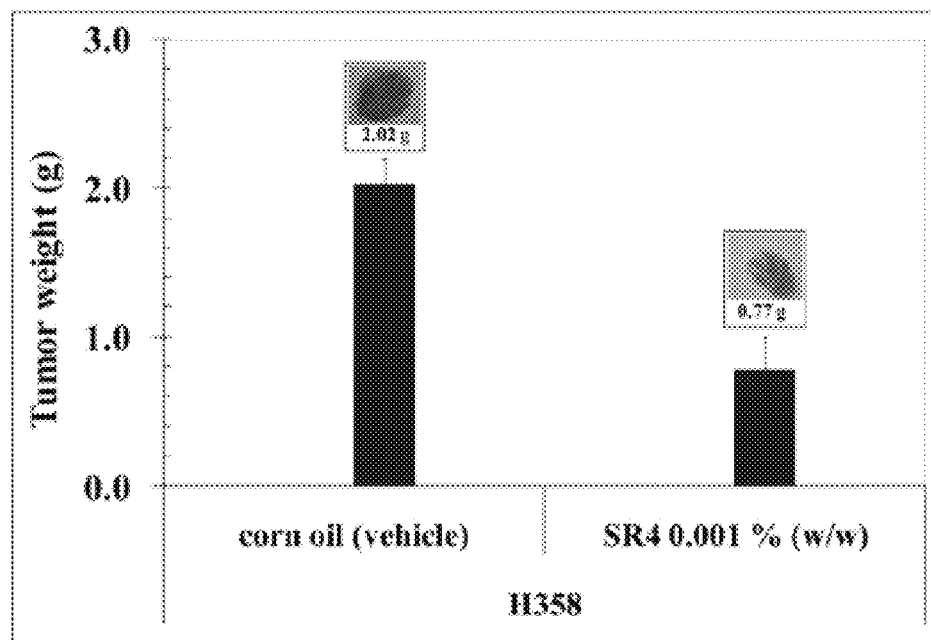
Figure 81C:
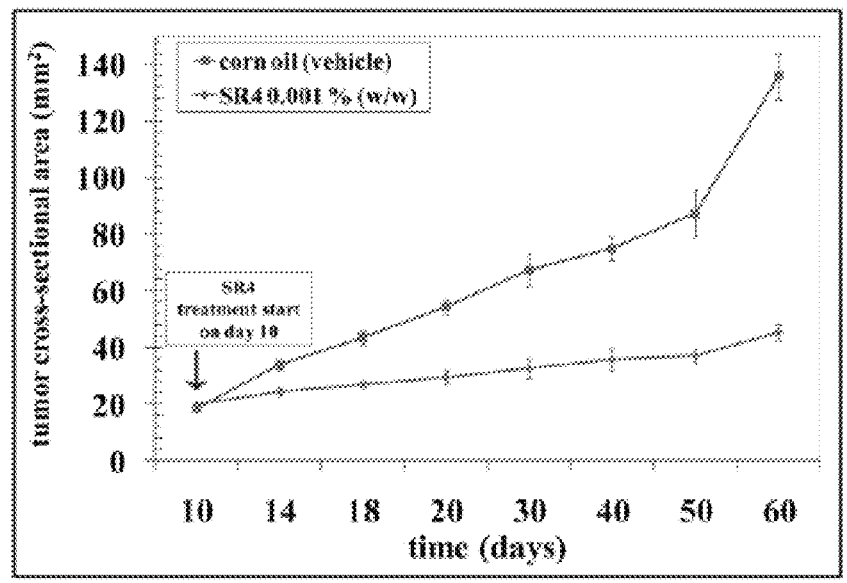
Figure 81D:
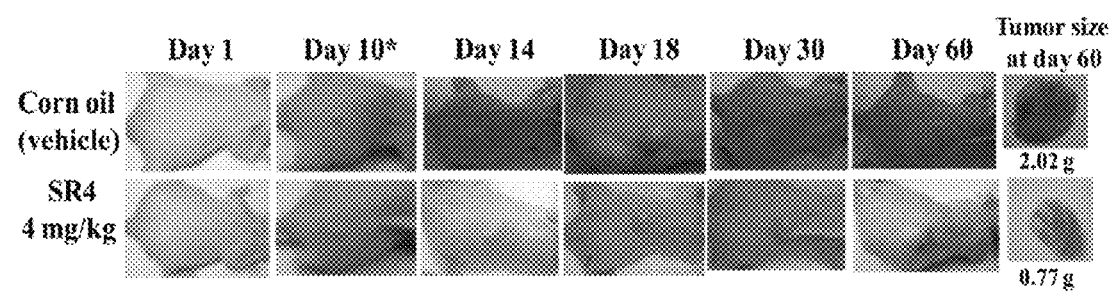

Hsd: Athymic nude nu/nu mice obtained from Harlan, Indianapolis, Ind. were used for the oral administration of COH-SR4 on lung cancer progression in in-vivo xenograft model. Twelve 10-weeks-old mice were divided into two groups of 6 animals (treated with corn oil (vehicle), and COH-SR4 4 mg/kg b.w.). All animals were subcutaneously injected with $2 \times 10^6$ H358 cells in 100 µL of PBS into one flank of each mouse. Treatment was started 10 days after the implantation of cells to see palpable tumor growth. Treatment consisted of 0.1 mg (4 mg/kg b.w.) of COH-SR4/mice in 200 µL corn oil by oral gavage alternate day. Control groups were treated with 200 µL corn oil by oral gavage alternate day. Animals were examined daily for signs of tumor growth and body weights were recorded. The 0.1 mg of COH-SR4 treatment was well tolerated by the mice and did not result in significant change in animal body weight or any signs of overt toxicity (FIG. 81A). Tumors were measured in two dimensions using calipers. The COH-SR4 treatment resulted in significant reduction in the tumor burdens in the treated groups [2.02±0.3 g vs. 0.77±0.2 g in control and COH-SR4 treated groups, respectively, weights and photographs of the final tumor taken on day 60] (FIG. 81B). Tumors were measured in two dimensions using calipers and time-course analysis of tumor regression revealed a substantial inhibition of tumor progression (FIG. 81C). Photographs of animals were taken at day 1, day 10, day 14, day 18, day 30 and day 60 after subcutaneous injection, are shown for all groups (FIG. 81D). The absorption of orally administered COH-SR4 in mice was assessed. HPLC analysis of 4 mg/kg COH-SR4 treated mice serum revealed that COH-SR4 was effectively absorbed after oral dosage and it reached a serum concentration of 1.1±0.3 µM.

Figure 82A:
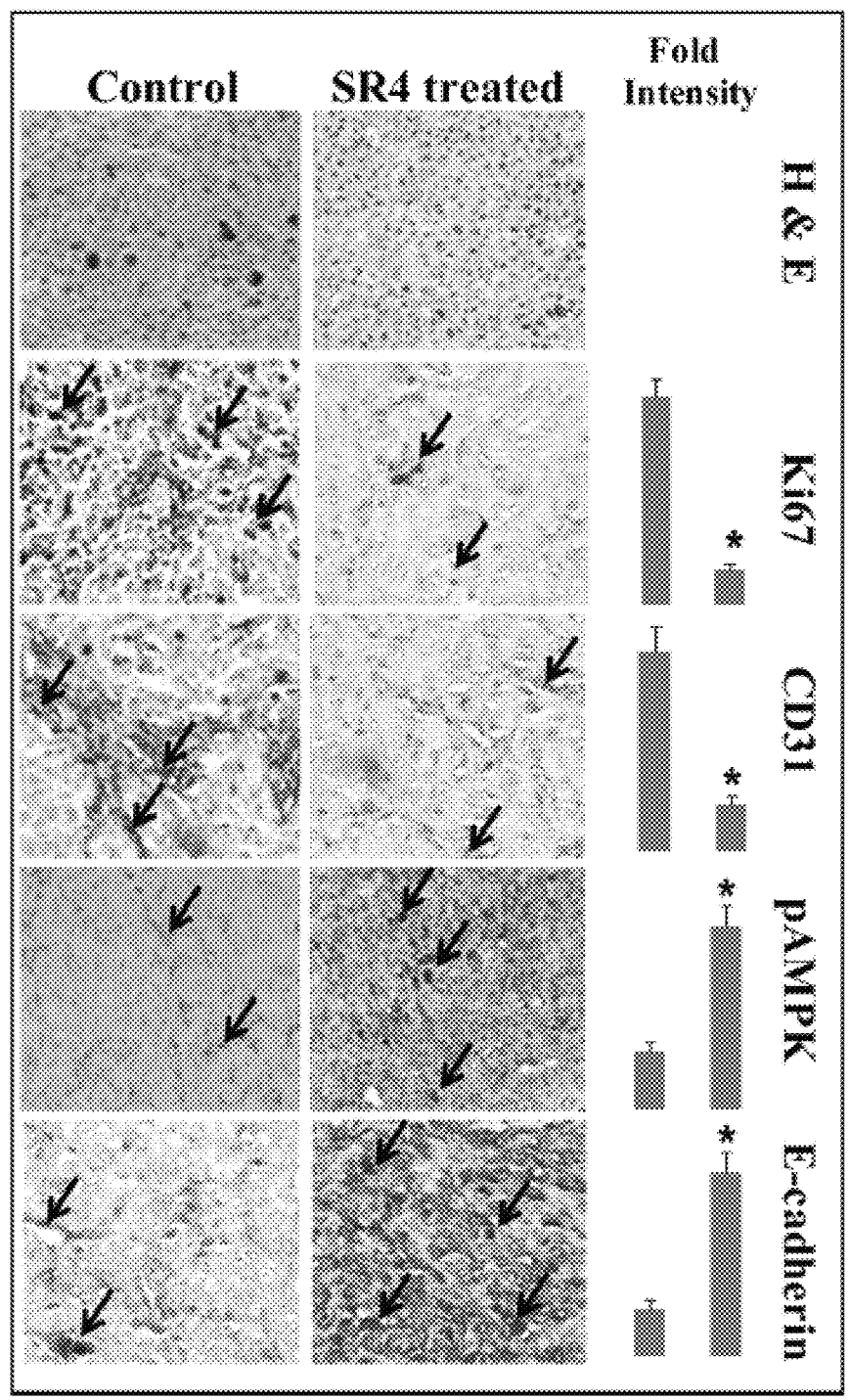
FIGS. 82A-82B: Histopathologic and Western-blot analyses of resected tumors in sections of lung tissues of xenograft mice after COH-SR4 treatment.

Example 32. Histopathological Examination of Control and COH-SR4 Treated Tumors (FIG. 82A)

Control and COH-SR4 treated tumor sections obtained from the in-vivo animal studies of Example 31 were used for histopathologic analyses. The histopathological examination of paraffin-embedded tumor xenograft sections by H&E staining revealed that COH-SR4 reduced the number of tumor blood-vessels and restored the normal morphology when compared to controls (FIG. 82A). Arrows represent the area for positive staining for an antigen. Bars represent means with 95% confidence intervals (n=5). Asterisks denote statistically significant differences (p<0.001) compared with control by two-sided Student's t test. Statistical significance of difference was determined following image analyses as described in methods section. COH-SR4 treatment decreased the levels of proliferation marker Ki67, and angiogenesis marker CD31 as revealed by ABC staining. COH-SR4 treatments increased the levels of pAMPK and normal differentiation marker E-cadherin, which provides corroborative evidence for the induction of anti-tumor effects using in-vivo models of lung cancer (FIG. 82A).

Figure 82B:
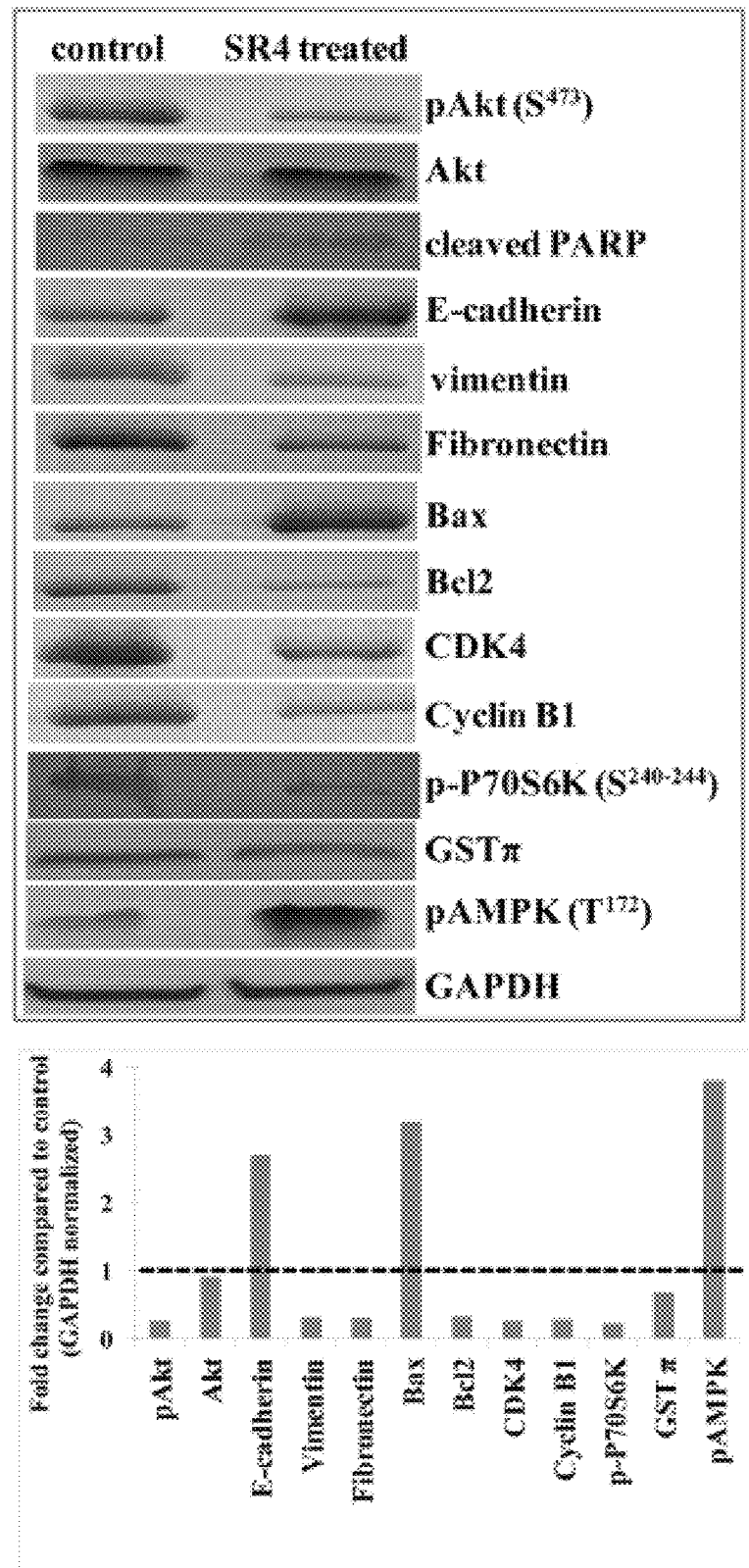

Example 33. Effect of COH-SR4 on Tumor Signaling Pathways in Lung Cancer (FIG. 82B)

The effect of COH-SR4 on signaling pathways of relevance to lung cancer progression was further analyzed by Western-blots of lysates from resected tumors (as described in Example 31). GAPDH was used as internal control. The bar diagrams (FIG. 82B) represent the fold change in the levels of proteins as compared to the controls as determined by densitometry. Dotted line represents no significant change observed when compared to the controls. The COH-SR4 treated groups had high levels of cleaved-PARP compared to the untreated controls, which reinforces the finding of apoptotic effect as observed in-vitro by TUNEL assay. Akt is a signaling protein that transduces the proliferative signals from upstream integrins and growth factor receptors. The COH-SR4 treatments increased the levels of PARP cleavage along with decreased levels of pAkt ($S^{473}$). The activated AMPK transduces signals through mTOR pathway. In accordance with decreased levels of pAkt ($S^{473}$), the levels of pP70S6K were decreased in COH-SR4 treated groups compared to controls. The cellular levels of vimentin and fibronectin determine the extent of migration and proliferation in lung cancer cells. COH-SR4 treated tumor tissue lysates were analyzed to test the impact of long term COH-SR4 treatment in vivo on GST expression and activity. Western blot analyses of tumor tissues revealed a decrease in the levels of GSTπ in COH-SR4 treated groups compared to the controls. The total GST activity as measured by activity towards CDNB as a substrate, in COH-SR4 treated tumor tissue lysates was lower compared to the controls [control, 0.32±0.03 U/mg protein; COH-SR4 treated, 0.21±0.05 U/mg protein; (n=3)]. COH-SR4 treatment decreased the expression of vimentin and fibronectin which were associated with invasive progression of lung cancer. COH-SR4 treated groups had an enhanced expression of pro-apoptotic protein Bax along with a parallel decrease in the levels of anti-apoptotic protein Bcl2. The expression of cell cycle regulatory proteins CDK4, which is a critical determinant of $KRAS^{G12V}$ induced lung tumor formation, and Cyclin B1 were also decreased following COH-SR4 treatment. Also, the normal epithelial marker E-cadherin showed increased expression following COH-SR4 treatment. In accordance with the in-vitro Western-blot analyses and in-vivo histopathological examination, the levels of pAMPK ($T^{172}$) were enhanced in COH-SR4 treated groups compared to controls in tumor tissue lysates (FIG. 82B).

Example 34. Effect of COH-SR4 on Uncoupling OXPHOS in Treating Diabetes and/or Obesity (FIGS. 83A-C)

Strategies to prevent and treat obesity aim to decrease energy intake and/or increase energy expenditure. To increase energy expenditure, two key intracellular targets may be considered: (1) mitochondrial oxidative phosphorylation (OXPHOS), the major site of ATP production, and (2) AMP-activated protein kinase (AMPK), the master regulator of cellular energy homeostasis.

Uncouplers of OXPHOS reduce the proton gradient across the mitochondrial inner membrane, creating a futile cycle of nutrient oxidation without generating energy.

Figure 83A:
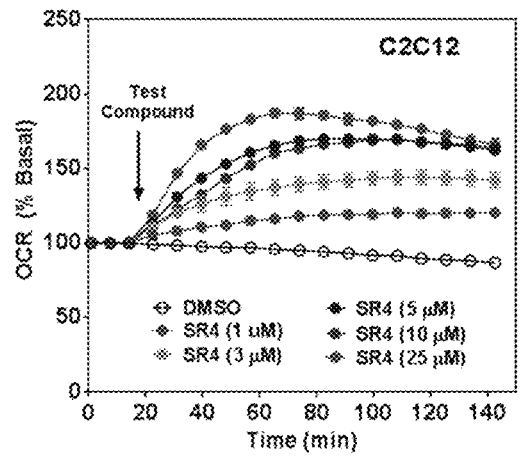
FIGS. 83A-83C: Mitochondrial uncoupling effects of COH-SR4 in mouse adipocytes, myotubes and human HepG2 liver cells.
Figure 83B:
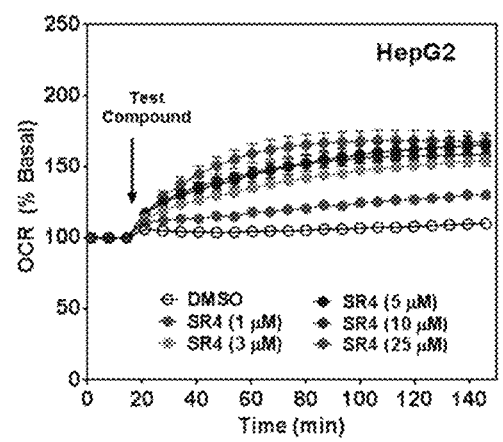
Figure 83C:
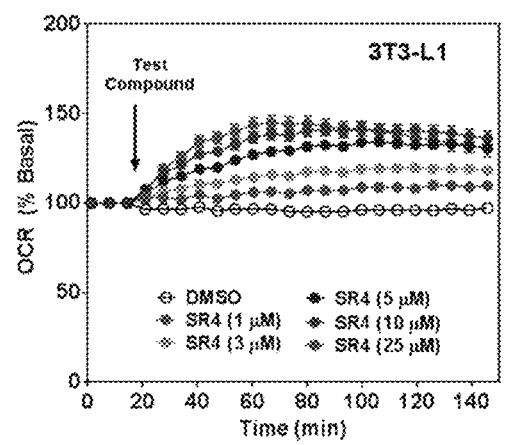

FIGS. 83A-C demonstrates the uncoupling effects of COH-SR4 in mouse myotubes and adipocytes, and human HepG2 liver carcinoma cells. COH-SR4 dose- and time dependently increased the OCR in mouse C2C12 (FIG. 83A), HepG2 (FIG. 83B), and 3T3-L1 cells (FIG. 83C). OCR in these figures are representative rates of n=6-8 wells/treatment/experiment from 2-3 separate experiments.

Example 35. Effect of COH-SR4 on Activating AMPK in Treating Diabetes and/or Obesity (FIGS. 84A-G)

Figure 84A:
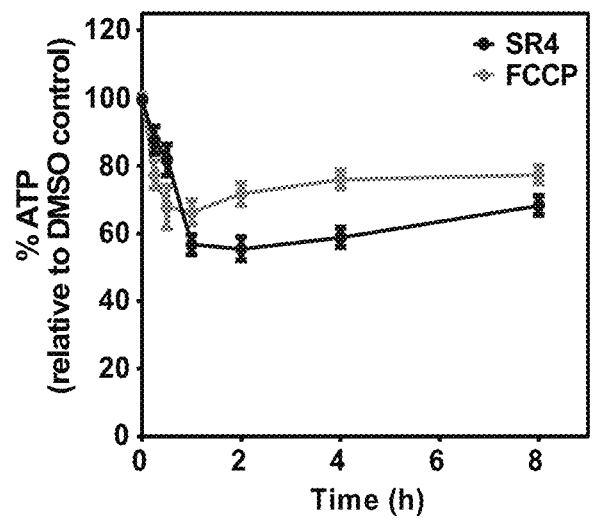
FIGS. 84A-84G: COH-SR4 decreased cellular ATP production and modulates AMPK-ACC signaling.
Figure 84B:
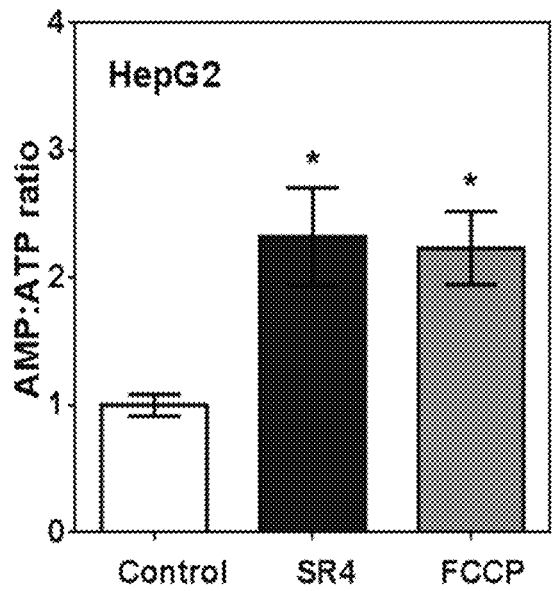
Figure 84C:
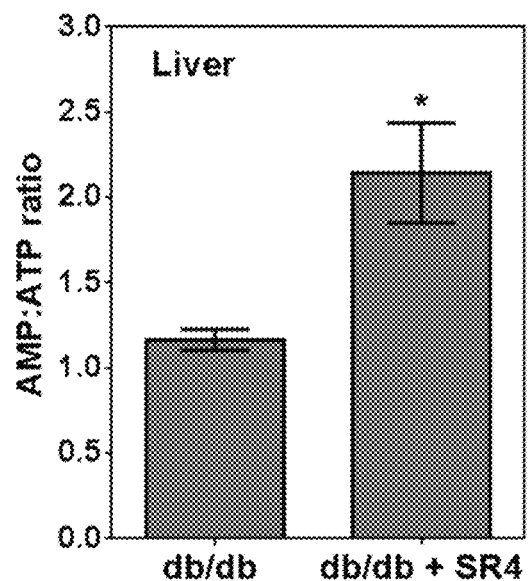

FIGS. 84A-G demonstrates that mitochondrial uncoupling by COH-SR4 decreased intracellular ATP levels, increased AMP:ATP ratio and activated AMPK in cells and tissues. Total intracellular ATP production in cells treated with either 5 µM COH-SR4 or 5 µM FCCP was measured by bioluminescence assay and expressed as percentage of time-matched vehicle (DMSO) control (FIG. 84A). Intracellular AMP: ATP ratios increased in HepG2 liver carcinoma cells following 1 h treatment with either 5 µM COH-SR4 or 5 µM FCCP (FIG. 84B) and in liver of db/db mice treated with COH-SR4 (5 mg/kg B.W.) for 5 weeks (FIG. 84C). All data represented are mean±SEM, *P<0.05.

Figure 84D:
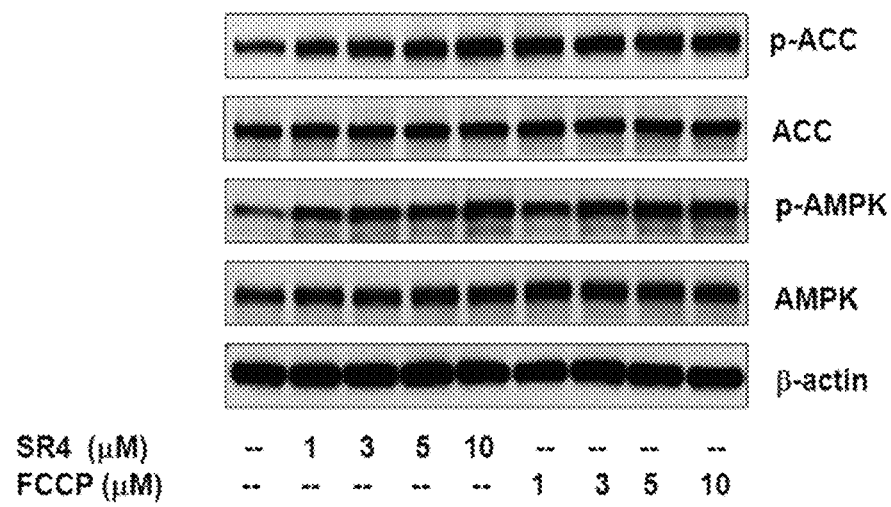
Figure 84E:
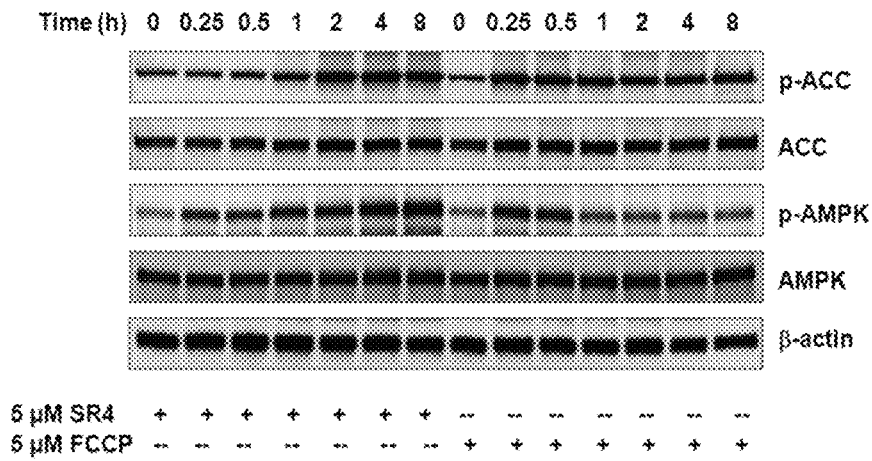
Figure 84F:
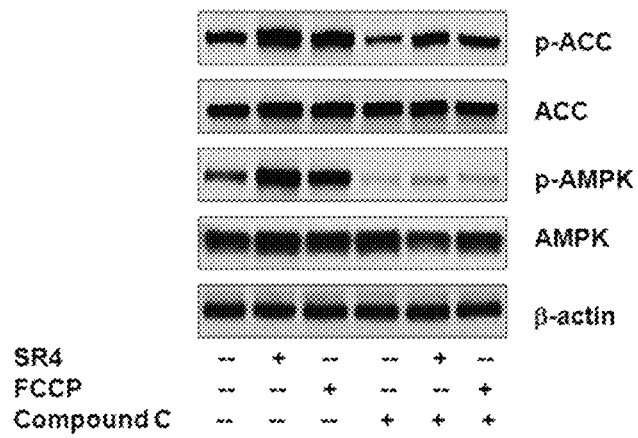
Figure 84G:
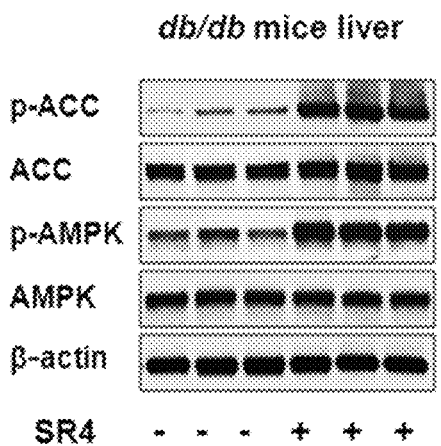

Western blots showed dose- and time-dependent modulation of AMPK-ACC signaling pathways in HepG2 cells (FIGS. 84D and 84E). Treatment with the AMPK inhibitor Compound C (20 µM) diminished AMPK activation and ACC phosphorylation by either uncoupler COH-SR4 or FCCP (FIG. 84F). Increased AMPK and ACC phosphorylations were also observed in liver of db/db mice treated with COH-SR4 for 5 weeks (FIG. 84G).

Example 36. Metabolic Effects of COH-SR4 on HFD Obese Mice and Db/Db Mice (FIGS. 85A-N)

Figure 85A:
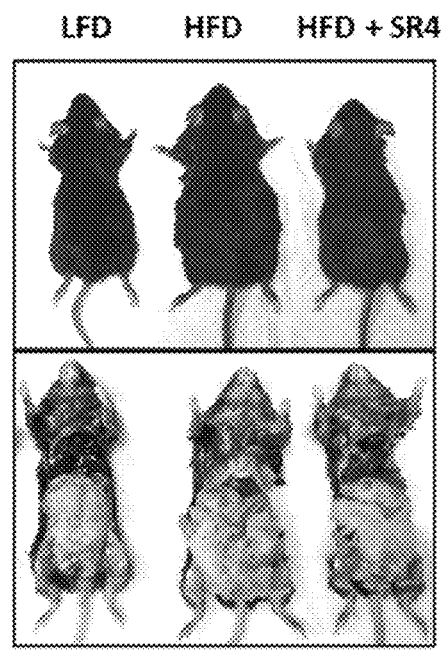
FIGS. 85A-85N show metabolic effects of COH-SR4 in high fat diet (HFD)-induced obese mice.
Figure 85B:
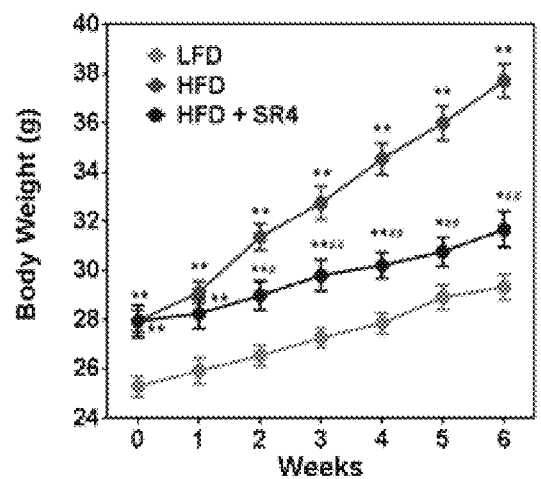
FIG. 85B: Six weeks of COH-SR4 treatment resulted in decreased body weight.
Figure 85C:
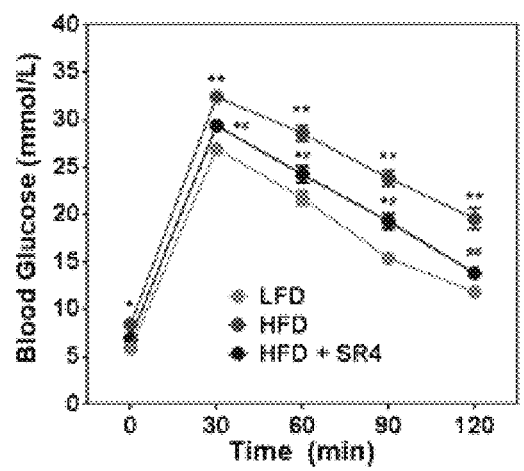
FIG. 85C: Six weeks of COH-SR4 treatment resulted in improved glucose tolerance.
Figure 85D:
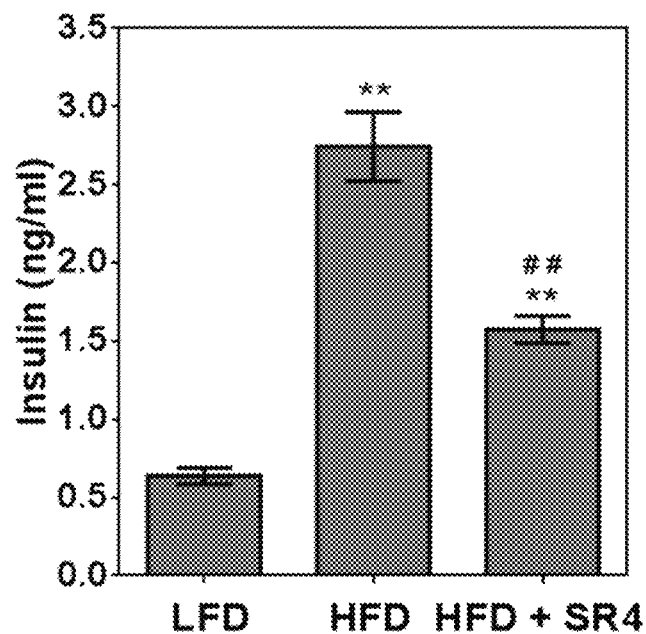
FIG. 85D: Six weeks of COH-SR4 treatment resulted in lower plasma insulin concentration.
Figure 85E:
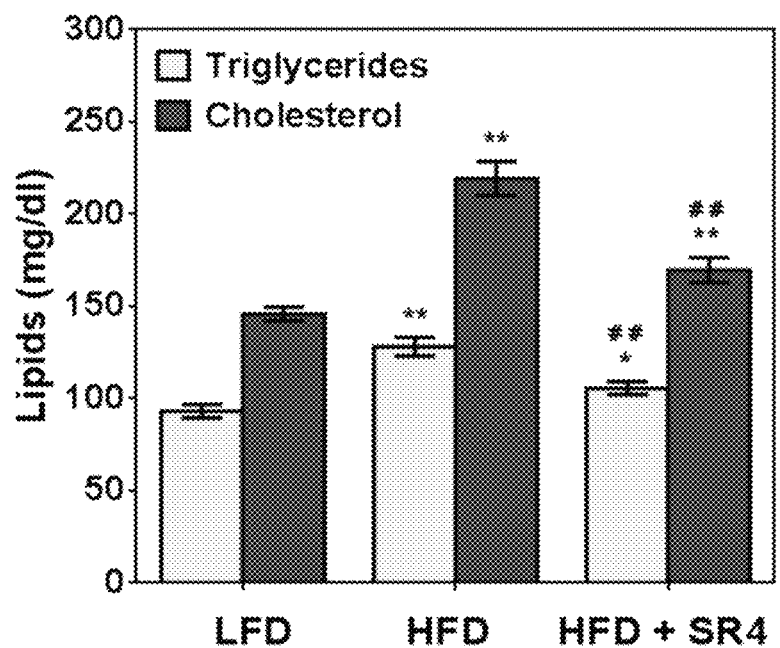
FIG. 85E: Six weeks of COH-SR4 treatment reduced plasma lipids.
Figure 85F:
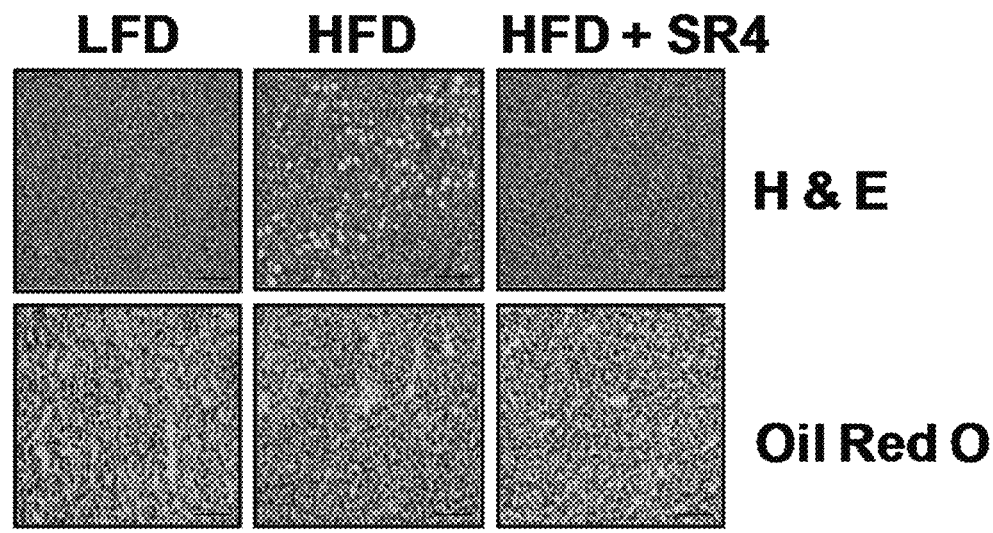
FIG. 85F: Representative histological image of mouse livers showing COH-SR4 reduced hepatic steatosis in HFD mice.
Figure 85G:
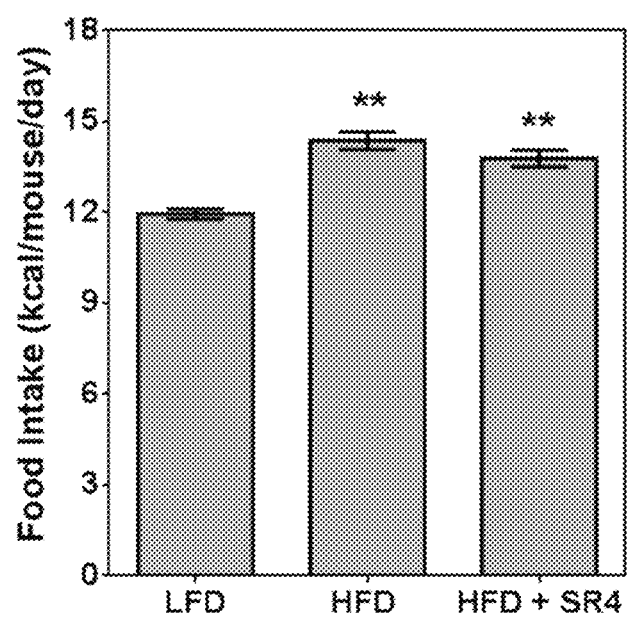
FIG. 85G: Food intake of each treatment group showed no significant differences between control and COH-SR4-treated HFD mice.
Figure 85H:
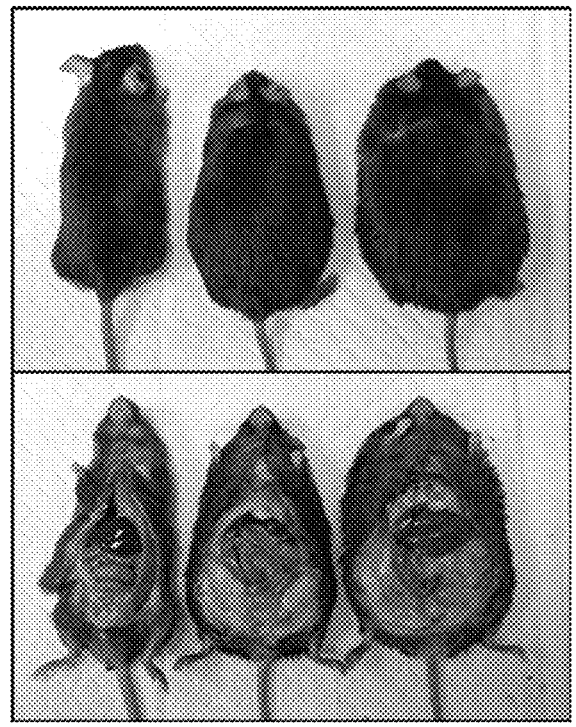
Figure 85I:
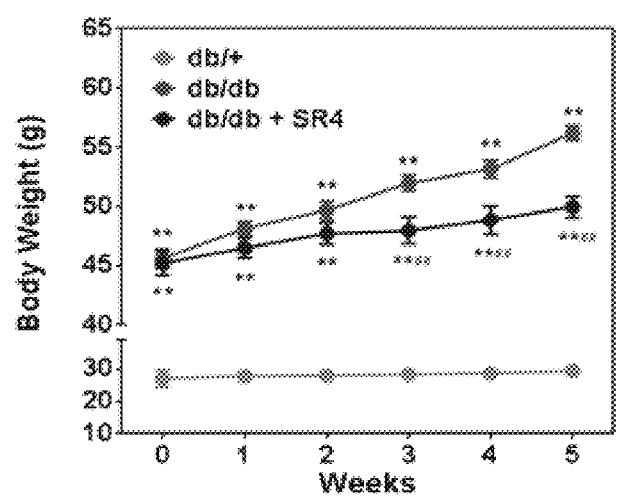
Figure 85J:
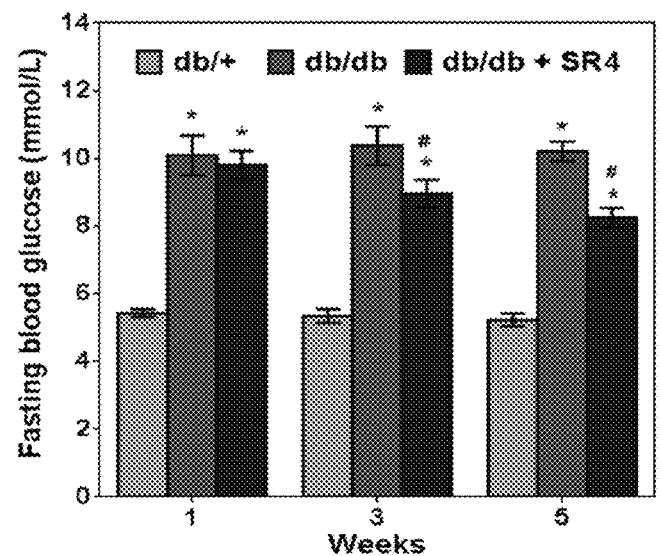
Figure 85K:
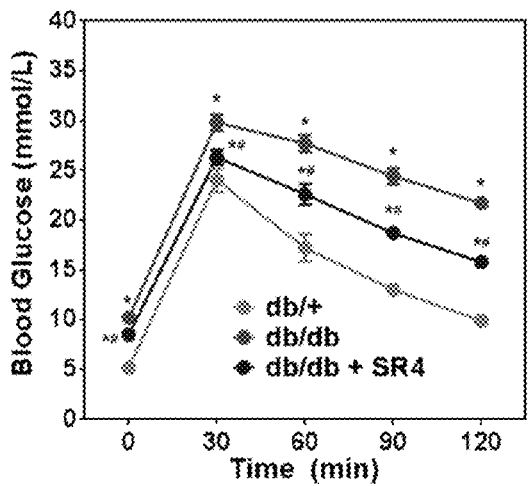
Figure 85L:
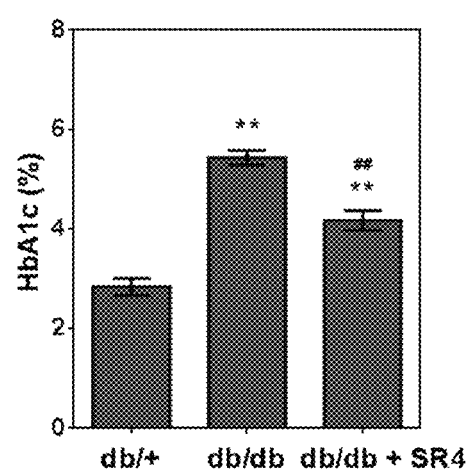
Figure 85M:
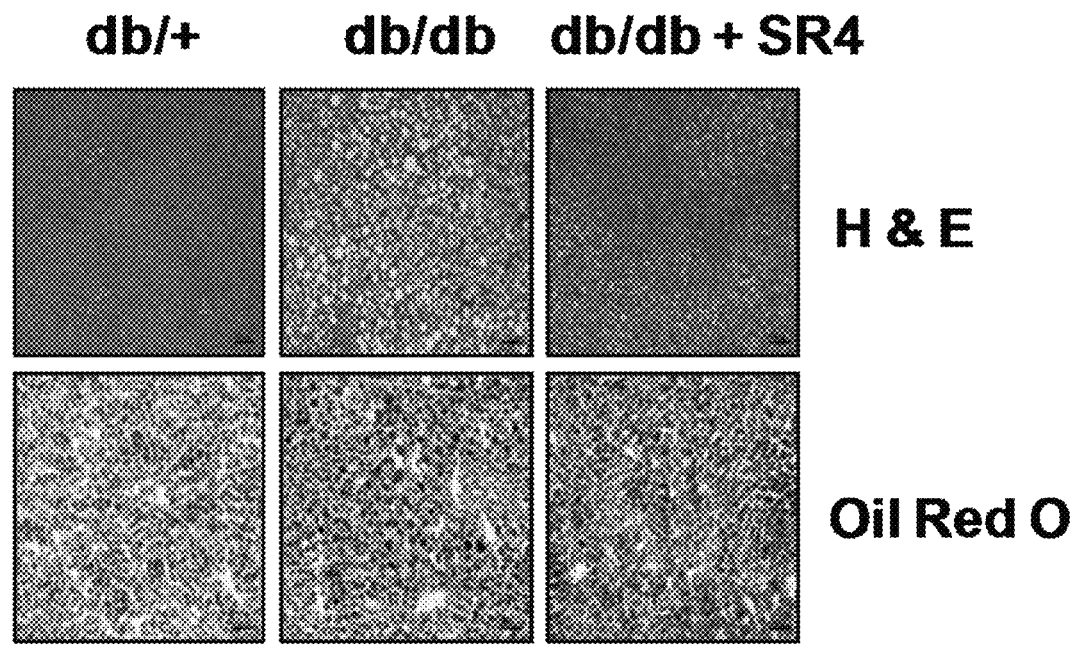
Figure 85N:
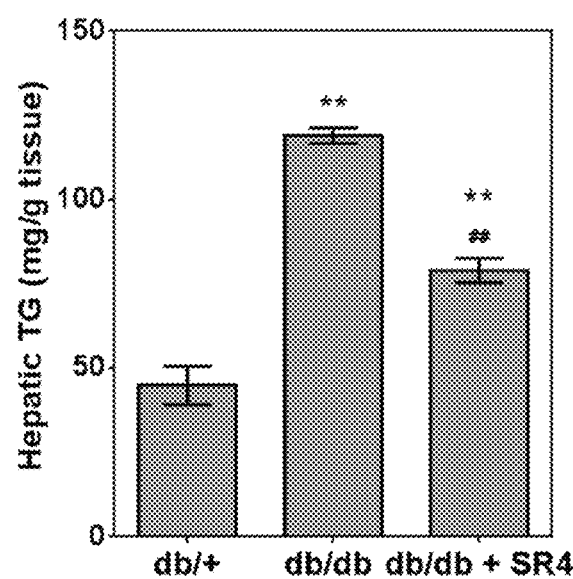

FIGS. 85A-N demonstrated that COH-SR4 treatment reduced body weight, improved glycemic control and insulin sensitivity, and prevented dyslipidemia and hepatic steatosis in both HFD obese mice and Type 2 diabetes db/db mice. FIGS. 85A-85G showed metabolic effects of COH-SR4 in HFD obese mice, and FIGS. 85H-85N showed metabolic effects of COH-SR4 in db/db mice. All data represented are mean±SEM. *P<0.05, **P<0.01 vs. LFD or db/+; #P<0.05, ##P<0.01 vs. HFD or db/db. n=12 animals per group for HFD mice. LFD=low fat diet (lean), HFD=high fat diet (obese). n=8 animals per group for db/db mice.

Representative mice in each treatment group (LFD, HFD, and HFD treated with COH-SR4 (HFD+SR4)) depicted gross images of whole body shape (top) and abdominal fat (bottom) (FIG. 85A). Six weeks of COH-SR4 treatment resulted in decreased body weight (FIG. 85B), improved glucose tolerance (FIG. 85C), and lower plasma insulin concentration (FIG. 85D) and significantly reduced plasma lipids (FIG. 85E). Histological analysis using Oil Red O and H&E stainings of mouse livers revealed massive hepatic steatosis in HFD-fed mice, whereas mice that were fed an HFD and given COH-SR4 showed little hepatic lipid accumulation (FIG. 85F). No significant difference in food intake between control and COH-SR4-treated HFD mice were observed (FIG. 85G).

Representative mice in each treatment group (db/+, db/db, db/db treated with COH-SR4 (db/db+SR4)) depicted gross images of whole body shape (top) and abdominal fat (bottom) (FIG. 85H). Five weeks of COH-SR4 treatment resulted in decreased body weight (FIG. 85I), improved fasting blood glucose (FIG. 85J) and glucose tolerance (FIG. 85K), and lower HbA1c levels (FIG. 85L). COH-SR4 also reduced hepatic triglycerides (FIG. 85M) and steatosis (FIG. 85N) as revealed by Oil Red O staining and H&E stainings.

Example 37. Gene Expression Analyses of HFD Obese Mice and Db/Db Mice Treated with COH-SR4 (FIGS. 86A-D)

Figure 86A:
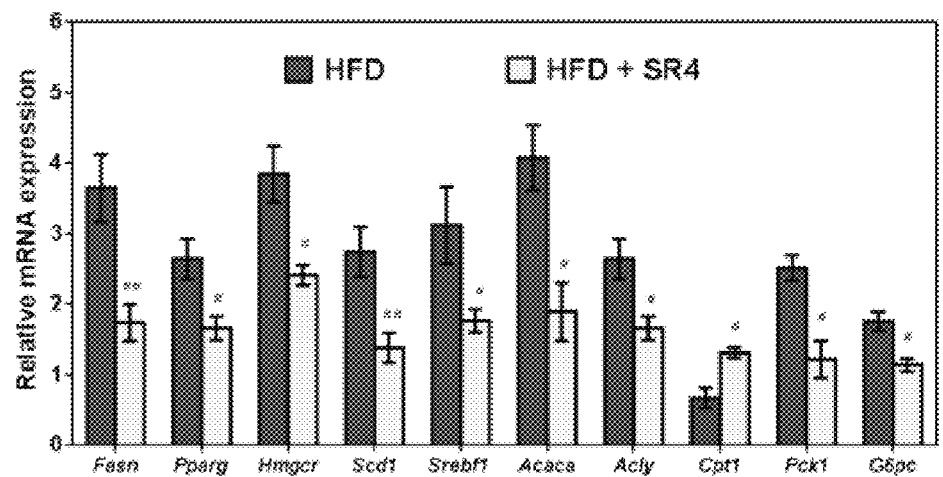
FIGS. 86A-86D: Gene expression analyses of livers of HFD obese and db/db mice treated with COH-SR4.
Figure 86B:
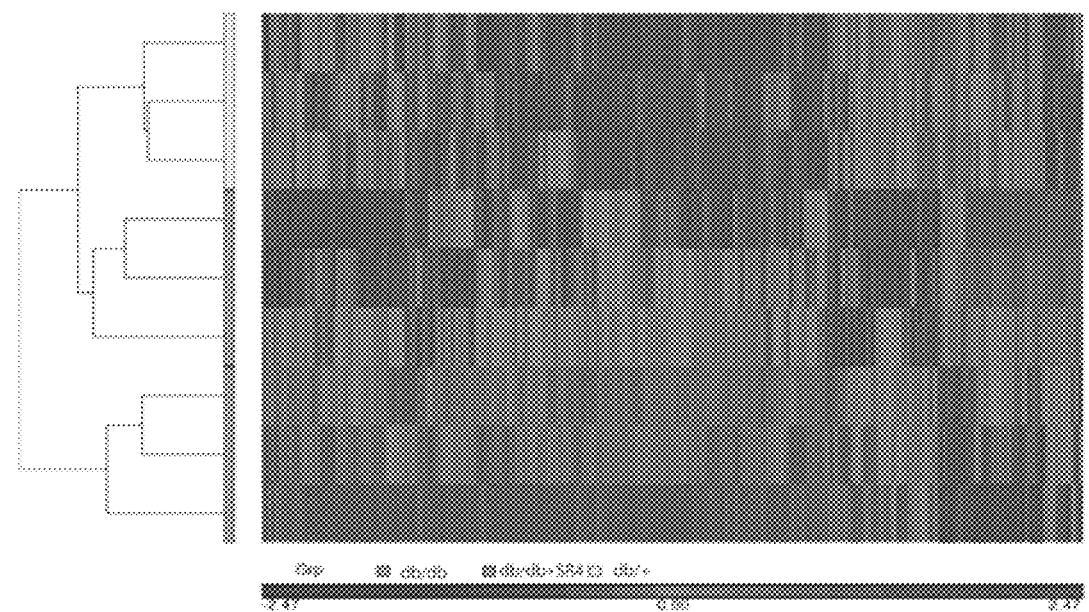
Figure 86C:
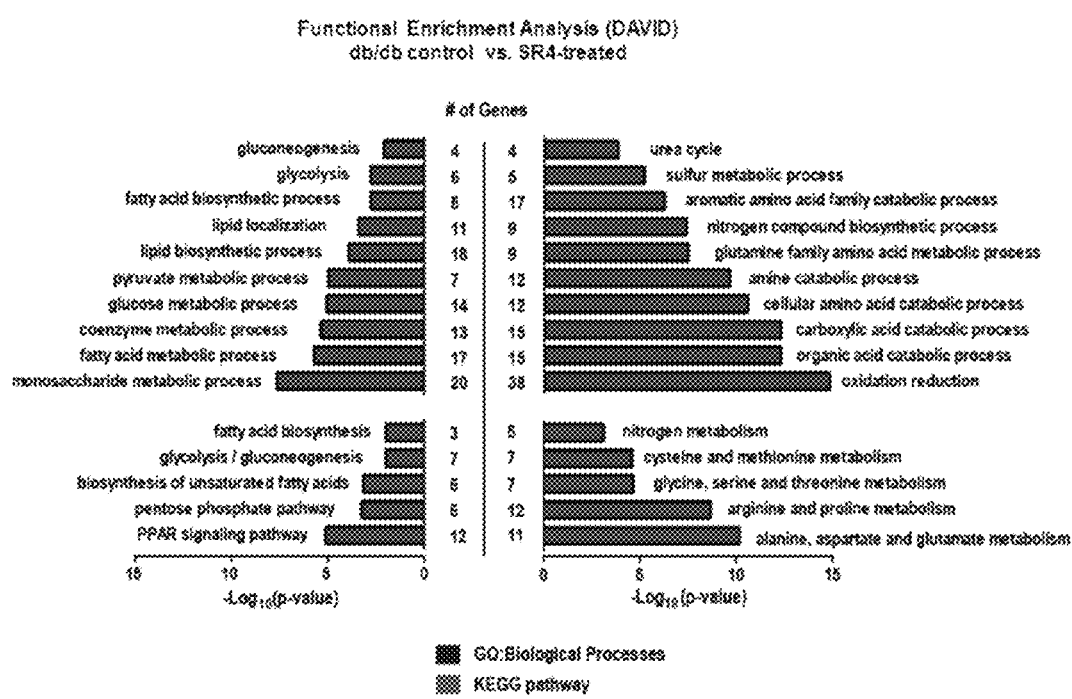
Figure 86D:
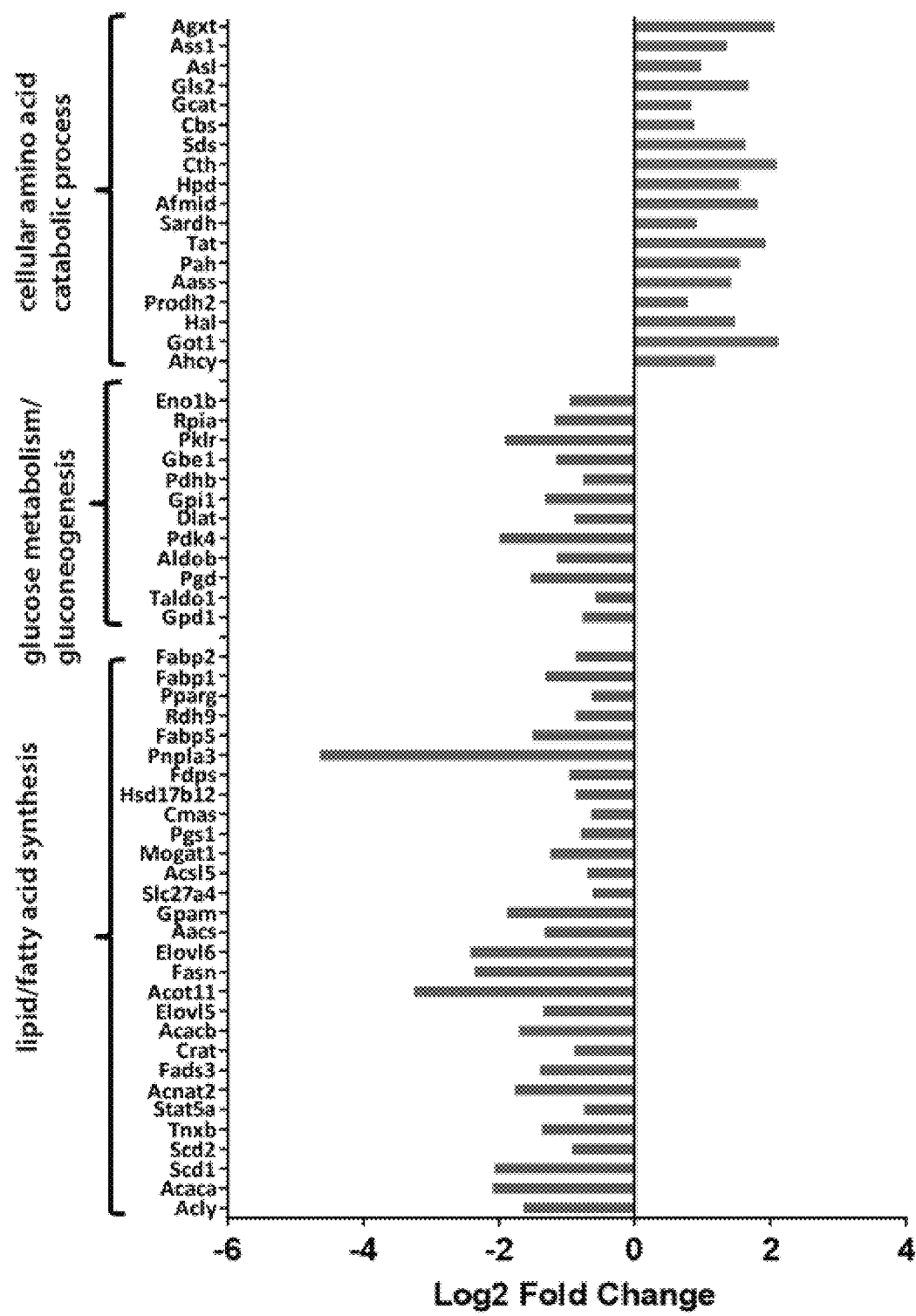

COH-SR4 treatment downregulated hepatic lipogenesis and glucose metabolic pathways, while upregulating amino acid metabolism (FIGS. 86A-D). Total RNA was isolated from liver of control animals and HFD obese or db/db mice treated with vehicle or COH-SR4 (as described in Example 35). Relative mRNA expression (mean±SEM) of lipogenic and gluconeogenic genes were determined using real time RT-PCR and quantified using the comparative Ct method (FIG. 86A, #P<0.05, ##P<0.01 vs. HFD). Hierarchical clustering of COH-SR4-treatment associated differential gene expression was shown in FIG. 86B. Functional enrichment analysis using DAVID showed top biological processes and pathways affected by COH-SR4 (FIG. 86C). Key hepatic genes associated with lipid/fatty acid synthesis and glucose and amino acid metabolism regulated by COH-SR4 in db/db mice are shown in FIG. 86D.

The references cited supra and the references listed below are herein incorporated by reference in their entireties:
1. Adler v. Zin Z., et al., regulation of JNK signaling by GSTP. EMBO J. 1999, 18:1321-1324.
2. Al-Hajj M, Wich M S., et al., 2003, PNAS, 100:3983-3498.
3. Ali-Osman F, Brunner J M, et al., Prognostic significance of Glutathione S-transferase P expression and subcellular localization in human gliomas. Clin. Cancer Res., 3:2253-2261, 1997.
4. Auld, C. A., Fernandes, K. M., and Morrison, M. A., J. Cell. Physiol. 211:101-111 (2007).
5. Badva, A., Dabbs, D. J. et al., Modern Pathology, 2011: 24: 157-167.
6. Barwixk M, Wiggins C, The current epidemiology of cutaneous malignant melanoma, Front. Biosci. 11:1244-1254, 2000.
7. Booch, A., Eroles, P. et al., 2010 Cancer Treat Rev. 36:206-215.

8. Boyle J. G., Logan, P J., et al 2011 Diabetologia 54: 1799-1809.
9. Bray, G. and Bellanger, T., Endocrine 29:109-117 (2006).
10. Bray, G. A. and Tartaglia L. A., Nature, 404:672-677 (2000).
11. Bruserud, O., Gjertsen, B. T., Huanga, T., The Oncologist 5:454-462 (2000).
12. Carra, A., De Pasquale, F. et al., 2006, Plant Cell Tissue Organ Culture, 87:41-48.
13. Chao, R W., Wang, X., et al., 2008, Stem Cells 2008, 26:364-371.
14. CHOU, TING-CHAO. Theoretical Basis, Experimental Design, and Computerized Simulation of Synergism and Antagonism in Drug Combination Studies PHARMACOLOGICAL REVIEWS Vol. 58, No. 3, 2006.
15. Cool, B., Tinkler, B., et al; 2005, Cell Metabolism 3:403-416.
16. Davies, G. F., Ross, A. R. et al., Cancer Letters Cancer Lett. 288:236-250 (2010).
17. de Ferranti, S. and Mozaffarian, D., Clinical Chemistry 54:945-955 (2008).
18. DeAngelis L M (2001). Brain tumors. N Engl J Med 344, 114-123.
19. Doyle, B. T., O'Neill, A. J., Fitspatrick J. M., Wtason R. W. G., Apoptosis 9:345-352 (2004).
20. Fernandes, K. M., Auld, C. A., Hopkins, R. G., and Morrison, R. F., J. Cell. Biochem. 105:913-921.
21. Fischer H, Gottschlich R, Seelig A. Blood-brain barrier permeation molecular parameters governing passive diffusion J Membr Biol 165:201 211 1998.
22. Fogarly S, Hardie DG, 2010 Biochem, Biophys. Acta, 1804: 581-591.
23. Gaspar J. Kitange, et al. Induction of MGMT expression is associated with temozolomide resistance in glioblastoma xenografts. Neuro Oncol (June 2009) 11 (3): 281-291.
24. Shchepinova et al., Biochim. Biophys. Acta 1837: 149-158 (2014).
25. Kenwood et al., Mol. Metab. 3: 114-123 (2014).
26. Guihua Huanga, Na Zhanga, Xiuli Bia and Mingjin Doub. Solid lipid nanoparticles of temozolomide: Potential reduction of cardial and nephric toxicity. International Journal of Pharmaceutics. volume 355, Issues 1-2, 1 May 2008, Pages 314-320.
27. Gupta P B, Chaffer C L, Weinberg R A. NaT. Med. 15:1010-1012 (2009).
28. Gupta, P B., Onder, T T., Jiang, G., Tao, K., Kuperwasser, C., Weinberg, R A., 2009, Cell, 138: 645-659.
29. Hansen L A, Sigman C C, Andreola F, Ross S A, Kelloff G J, De Luca L M. Carcinogenesis 21:01271-1279 (2000).
30. Hardie D G, 2010, Gene and Development 25:1895-1908.
31. Hatzivassiiiou, G. T., Zhao, F. et al., Cancer Cell 8:311-321 (2005).
32. Hayes J D, and Pulford D J., The glutathione S-transferase superfamily; regulation of GST and the contribution of isoenzymes to cancer chemotherapeutics and drug resistance. Crit. Rev. biochem. Mol. Biol., 30:445-600, 1995.
33. Hayes J D, Flanagan J U, Jowsey I R, Glutathione transferase, Anu. Rev. Pharmacol. Toxicol., 2005, 45:51-88.
34. Heitz, D., Erxleben, et al., 2006, J Proteome Res. 5:2283-2293.
35. Hurt, H. M. and Farrar, W. L., Mol Interv. 8:140-142 (2008).
36. "Inhibitors Reduce Staphylococcus aureus Hemolytic Activity and Protect Cultured Endothelial Cells from Lysis," ANTIMICROBIAL AGENTS AND CHEMOTHERAPY, August 2002, p. 2333-2336 Vol. 46, No. 8.
37. Jacoby W B, the glutathione S-transferase: a group of multi-functional detoxification proteins. Adv. enzymol. Mol. biol., 46: 383-414, 1978.
38. Kim J Y, Mercer S E, et al., the stress activated protein Kinase p38 alpha and JNK1 stabilize p21 (CIP) by phosphorylation. J. Bio. Chem., 277: 29792-22802, 2000.
39. Kim, S., Park, H., Lee, M., et al., Biochem. Biophys. Res. Comm. 327:108-113 (2008).
40. Kim, S. N., Choy, H. Y., Kim, Y. K., Arch. Pharm. Res. 32:535-541 (2009).
41. Laborde E, Glutathione transferases as mediators of signaling pathways involved in cell proliferation and cell death. Cell Death and differentiation 2010, 171373-1380.
42. Lapidot, T., Sirard, C., et al., 1994, Naturi. 367:645-648.
43. Lee G., Fryer D., et al, 2002, J. Brol. Chem., 277:25226-25232.
44. Leszczyniecka M, Roberts T, Dent P, Grant S, Fisher P B. Pharmacol Ther. 9:105-56 (2001).
45. Li Fang Yu, Bei-Ying Qiu, et al., 2010, Current topics in Medicine Chemistry 54:3101-3110.
46. Li, J. J., Wang. H. et al., Bioorganie & Medicinal Letters 17:3208-3211 (2007).
47. Linos E, Swetta, S., et al., increasing burden of melanoma in the United States. J. Invest. Derm., 8: 2009.
48. Liu, H., Patel, M R., et al., 2010, PNAS, 107: 18115-18126.
49. Lopez-bergami P, Huang c., et al., Rewired Erk-JNK signaling pathways in melanoma. Cancer Cell, 11; 447-460, 2007.
50. Lowe S W, Lin A W, Appoptosis in cancer. Carcinogenesis, 21: 485-493, 2000.
51. Lyon R P, Hill J J, atkins W M, Novel class of bivalent glutathione stransferase inhibitors. Biochemistry 2003, 42; 10418-10428.
52. Mannervik g, Castro V M., et al., Expression of class P1 glutathione transferase in human malignant melanoma cells. Carcinogenesis 1987, 8:1929-1932.
53. Mol Cancer Ther 2009; 8(12). December 2009.
54. Nowak, D, Stewart D, Koeffler H P Blood, 113:3655-3665 (2009).
55. Ofra Benny and Pouya Pakneshan. Novel technologies fantiangiogenic drug delivery in the brainCell Adh Migr. 2009 April-June; 3(2): 224-229.
56. Petrie, K., Zellent, A., Waxman, S., Current opinion in Hematology 16:84-91 (2009).
57. Pilch, P. F. and Bergenhem, N., Mol. Pharmacol. 70:779-785 (2006).
58. Pipeline insight: Cancer Overview-gastrointestinal, skin, sarcoma. Data monitor pharmaceutical report; 118-123, 2008.
59. Prat A., Perou, C. M., Molecular Oncology; 2001: (1): 5-23.
60. Proctor, R. A., et al., Two Diarylurea Electron Transport PSA-is expressed on the surface of NSCs: Marina Quartu, #1 Maria Pina Serra, #1 Marianna Boi, 1 Viviana Ibba, 1 Tiziana Melis, 1 and Marina Del Fiacco#1 BMC Neurosci. 2008; 9: 108.
61. Rahbar, S., Lalezari, I. U.S. Pat. No. 6,337,350.
62. Rahbar, S., Lalezari, I. U.S. Pat. No. 6,589,994.
63. Rahbar, S., Lalezari, I. U.S. Pat. No. 6,605,642.
64. Rahbar, S., Lalezari, I. U.S. Pat. No. 6,693,106.
65. Rahbar, S., Lalezari, I. U.S. Pat. No. 6,787,566.
66. Rahbar, S., Lalezari, I. U.S. Pat. No. 7,030,133.

67. Rahbar, S., Figarola, J., U.S. Pat. No. 7,320,988.
68. Rahbar, S., Figarola, J., U.S. Pat. No. 7,652,037.
69. Rathmell, J. C., Newgard, C. B., Science 324:1021-1022 (2009).
70. Ricci, A., Bertoletti, C., 2009, Plant Biology 14:262-272.
71. Ricci, A., Carra, A. et al., 2005 J Plant Growth Regul., 23:261-268.
72. Riester, D., Hildmann, C., Appl. Microbiol Biotechnol. 75:499-514 (2007).
73. Roy, R., Willan, P., Clarke, R., Farnie, G., Breast Cancer Res. 18:12 Suppl 1:05 (2010).
74. Sell S, Crit Rev Oncol Hematol 5: 1-28. (2004).
75. Shea T C, Kelley S L, Henner W D, Identification of an anionic form of glutathione transferase present in many human tumors and human tumors cell lines. Cancer Res., 1988, 48:527-533.
76. Steven R, et al. Pharmacokinetic assessment of novel anti-cancer drugs using spectral analysis and positron emission tomography: A feasibility study. Cancer Chemother Pharmacol. 42, 183, 1998.
77. Stupp et al., N Engl J Med 2007; 352:987-996.
78. Tew K D, Monks A, et al., Glutathione associated enzymes in the human cell line of the National Cancer Institute Drug screening Program. Mol. Pharmacol., 1996, 50:149-159.
79. Van Lenten, L. and G. Ashwell, 1 mM NaIo4 selectively oxidizes sialic acid. J. Biol. Chem. 246, 1889 (1971).
80. Wald, D. N., Verraaat, H. M. et al., Cancer Research 68:4369-4376 (2008).
81. Wang W, Guan K L. 2009, Acta Physiol (Oxf). 196:55-63.
82. Waxman D, Glutathione s-transferase: role in alkylating agent resistance and possible target for modulation chemotherapy-a review, Cancer res., 50: 6449-6454, 1990.
83. Wellen, E. K., Hatzivassiliou, G. el al., Science 324: 1076-108 (2009).
84. William M. Pardridge. The Blood-Brain Barrier: Bottleneck in Brain Drug Development. NeuroRx. 2005. 2(1): 3-14.
85. Yu L F, Qiu B Y, Nan F J, Li J. 2010, Curr Top Med Chem. 10:397-410.
86. Yun H, Ha J. 2011, Expert Opin Ther Pat. 21: 983-1005.
87. Zhuang, Y., Miskimins, W. K., 2008, J. Molecular Signaling 3:18.
88. Figarola J L, Weng Y, Lincoln C, Home D, Rahbar S. Invest New Drugs 2012, 30:1413-1425.
89. Nicholls D G, Darley-Usmar V M, Wu M, Jensen P B, Rogers G W, Ferrick D A. J Vis Exp 2010; 46:e2511.
90. Rogers G W, Brand M D, Petrosyan S, Ashok D, Elorza A A, Ferrick D A, et al. PLoS One. 2011; 6:e21746.
91. Singhal S S, Yadav S, Drake K, Singhal J, Awasthi S. J Biol Chem 2008; 283:19714-19729.
92. Huang da W, Sherman B T, Lempicki R A. Nucleic Acids Res 2009; 37:1-13.
93. Schmittgen T D, Livak K J. Nat Protoc 2008; 3:1101-1118.
94. Spitzer M, Wildenhain J, Rappsilber J, Tyers M. Nature Methods 2014; 11:121-122.

The invention claimed is:

1. A method of treating a cancer in a subject in need thereof, comprising administering to the subject a pharmaceutical composition comprising a therapeutically effective amount of 1,3-bis (3,5-dichlorophenyl) urea (COH-SR4), a salt thereof, or stereoisomers thereof, wherein the cancer is selected from the group consisting of melanoma, and lung cancer.

2. The method of claim 1, wherein the cancer is melanoma.

3. The method of claim 2, wherein the melanoma is metastatic melanoma.

4. The method of claim 1, wherein the cancer is lung cancer.

5. The method of claim 4, wherein the lung cancer is non-small cell lung cancer.

6. The method of claim 1, wherein the lung cancer is metastatic lung cancer.

7. The method of claim 2, wherein the pharmaceutical composition further comprising one or more second anti-cancer agents selected from the group consisting of TMZ, SN38, CPT-11, and 5-FU.

8. The method of claim 1, further comprising administering chemotherapy to the subject.

9. The method of claim 2, further comprising administering chemotherapy to the subject.

10. The method of claim 4, further comprising administering chemotherapy to the subject.

11. The method of claim 1, wherein the pharmaceutical composition is administered by topical administration, mucosal administration, oral administration, nasal administration, vaginal administration, rectal administration, parenteral administration, transdermal administration, intravenous injection, subcutaneous administration, intramuscular injection, inhalation, or ophthalmic administration.

12. The method of claim 2, wherein the pharmaceutical composition is administered by topical administration, mucosal administration, oral administration, nasal administration, vaginal administration, rectal administration, parenteral administration, transdermal administration, intravenous injection, subcutaneous administration, intramuscular injection, inhalation, or ophthalmic administration.

13. The method of claim 4, wherein the pharmaceutical composition is administered by topical administration, mucosal administration, oral administration, nasal administration, vaginal administration, rectal administration, parenteral administration, transdermal administration, intravenous injection, subcutaneous administration, intramuscular injection, inhalation, or ophthalmic administration.

14. The method of claim 1, wherein the pharmaceutical composition is administered at a daily dose of about 0.005 to about 25 mg/kg, about 0.01 to about 10 mg/kg, or about 0.05 to about 1 mg/kg, body weight of COH-SR4, a salt thereof, or stereoisomers thereof.

15. The method of claim 2, wherein the pharmaceutical composition is administered at a daily dose of about 0.005 to about 25 mg/kg, about 0.01 to about 10 mg/kg, or about 0.05 to about 1 mg/kg, body weight of COH-SR4, a salt thereof, or stereoisomers thereof.

16. The method of claim 4, wherein the pharmaceutical composition is administered at a daily dose of about 0.005 to about 25 mg/kg, about 0.01 to about 10 mg/kg, or about 0.05 to about 1 mg/kg, body weight of COH-SR4, a salt thereof, or stereoisomers thereof.

* * * * *